United States Patent [19]

Thompson

[11] Patent Number: 4,655,817

[45] Date of Patent: Apr. 7, 1987

[54] HERBICIDAL ORTHO-HETEROCYCLIC PYRAZOLESULFONAMIDES

[75] Inventor: Mark E. Thompson, Wilmington, Del.

[73] Assignee: E. I. Du Pont de Nemours and Company, Wilmington, Del.

[21] Appl. No.: 756,538

[22] Filed: Jul. 22, 1985

Related U.S. Application Data

[63] Continuation-in-part of Ser. No. 671,072, Nov. 13, 1984, abandoned.

[51] Int. Cl.[4] .................. C07D 405/14; C07D 417/14; C07D 419/14; A01N 47/36

[52] U.S. Cl. .......................................... 71/90; 71/91; 71/92; 71/93; 544/3; 544/253; 544/278; 544/209; 544/212; 544/320; 544/324; 544/331; 544/332; 548/268

[58] Field of Search ............... 71/90, 92, 91; 544/320, 544/324, 331, 332, 3, 258, 278; 548/268

[56] References Cited

FOREIGN PATENT DOCUMENTS 111442 6/1984 European Pat. Off. ................ 71/90

*Primary Examiner*—Robert Gerstl

[57] ABSTRACT

Herbicidally active pyrazolesulfonamide compounds having an ortho cyclic saturated or partially saturated group which includes a carbonyl or sulfonyl radical having utility as herbicides and plant growth regulants.

48 Claims, No Drawings

HERBICIDAL ORTHO-HETEROCYCLIC PYRAZOLESULFONAMIDES

RELATED APPLICATION

This application is a continuation-in-part of my co-pending application Ser. No. 671,072 filed Nov. 13, 1984 now abandoned.

BACKGROUND OF THE INVENTION

European Patent Application (EP-A) No. 83,975 (published July 20, 1983) discloses herbicidal benzene-sulfonamides of formula

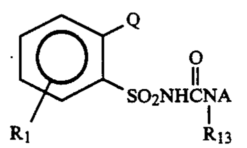

wherein

Q is selected from various five or six-membered aromatic or partially unsaturated heterocyclic rings containing 2 or 3 heteroatoms selected from O, S or NR.

EP-A-85,476 (published Aug. 10, 1983) discloses herbicidal benzenesulfonamides of formulae

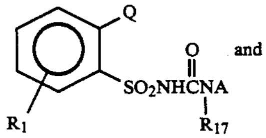

and

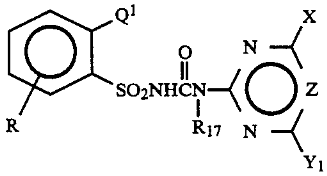

wherein

Q is selected from various 5-membered aromatic heterocycles, and their dihydro and tetrahydro analogs, which contain one heteroatom selected from O, S or NR, or Q is a saturated or partially unsaturated 6-membered ring containing one heteroatom selected from O or S; and $Q^1$ is a 6-membered aromatic heterocycle containing one to three N atoms.

South African Patent Application No. 83/8416 (published May, 1984) discloses herbicidal benzenesulfonamides of formula

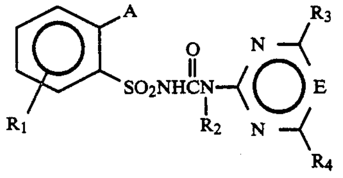

wherein

A is an unsaturated or only partially saturated 5- or 6-membered heterocyclic ring system which is bonded through a carbon atom and contains 1, 2 or 3 heteroatoms.

No. EP-A-95,925 (published Dec. 7, 1983) discloses herbicidal pyrazolesulfonamides in which the group adjacent to the sulfonamide moiety may be selected from H, $C_1$–$C_3$ alkyl, F, Cl, Br, $NO_2$, $OR_{16}$, $CO_2R_{23}$, $S(O)_nR_{24}$ or $SO_2NR_{19}R_{20}$.

No. EP-A-87,780 (published Sept. 7, 1983) claims pyrazole sulfonamides of general formula

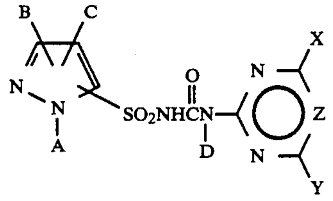

wherein

A is H, $C_1$–$C_8$ alkyl or optionally substituted phenyl;

B and C are independently H, halogen, $NO_2$, $C_1$–$C_8$ alkyl, $CO_2R$, etc.; and D is H or $C_1$–$C_8$ alkyl.

No. EP-A-96,003 (published Nov. 28, 1983) discloses herbicidal compounds of general formula

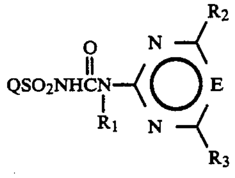

wherein $R_1$ is H or $C_1$–$C_3$ alkyl; and

Q is an unsubstituted or substituted five-membered heterocyclic radical which is bound by way of a carbon atom and which contains 2 or 3 identical or different heteroatoms.

Unexamined Japanese Patent Application No. 9,013,778 (priority July 15, 1982) filed by Nihon Noyaku describes herbicidal pyrazolesulfonamides with halo, alkyl and alkoxycarbonyl substituents.

European Publication No. 116,518 (published 8/22/84; Swiss priority 2/4/83) discloses herbicidal sulfonylureas of the formula

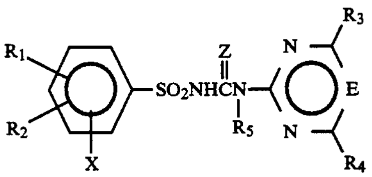

where, in part,

X is $—NR_6R_7$, $—N(SO_2R_9)_2$ or

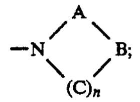

A is —CO—, $—SO_2—$, $—CONR_{23}—$ or $—CO_2—$;

B is $C_1$–$C_4$ alkylene or $C_2$–$C_4$ alkenylene;

C is —CO—, $CR_{21}R_{22}$ or —$SO_2$—; and
n is 0 or 1.

SUMMARY OF THE INVENTION

This invention pertains to novel compounds of Formula I, agriculturally suitable compositions containing them and their method of use as general and/or selective preemergent and/or postemergent herbicides or plant growth regulants.

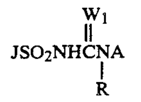

I wherein

J is

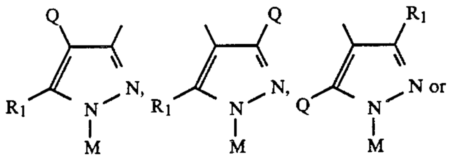

J-1 J-2 J-3

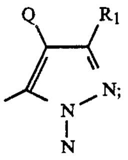

J-4

$W_1$ is O or S;

R is H or $CH_3$;

$R_1$ is H, $C_1$–$C_3$ alkyl, $C_1$–$C_3$ haloalkyl, halogen, nitro, $C_1$–$C_3$ alkoxy, $SO_2NR^IR^{II}$, $C_1$–$C_3$ alkylthio, $C_1$–$C_3$ alkylsulfinyl, amino, $C_1$–$C_3$ alkylsulfonyl, $CO_2R^{III}$, $C_1$–$C_3$ haloalkoxy, $C_1$–$C_3$ haloalkylthio, $CH_2CN$, $CH_2OCH_3$, or $CH_2SCH_3$;

$R^I$ is H, $C_1$–$C_4$ alkyl, $C_2$–$C_3$ cyanoalkyl, methoxy or ethoxy;

$R^{II}$ is H, $C_1$–$C_4$ alkyl or $C_3$–$C_4$ alkenyl; or $R^I$ and $R^{II}$ may be taken together as —$(CH_2)_3$—, —$(CH_2)_4$—, —$(CH_2)_5$— or —$CH_2CH_2OCH_2CH_2$—;

$R^{III}$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, $C_5$–$C_6$ cycloalkyl, $C_4$–$C_7$ cycloalkylalkyl or $C_2$–$C_4$ alkoxyalkyl;

M is H, $C_1$–$C_4$ alkyl, $C_3$–$C_4$ alkenyl, $C_3$–$C_4$ alkynyl, phenyl, phenyl substituted with Cl, $NO_2$, $CH_3$ or $OCH_3$, $C_2$–$C_3$ alkoxycarbonyl, $C_1$–$C_3$ alkylsulfonyl or $SO_2NR_4R_5$;

Q is

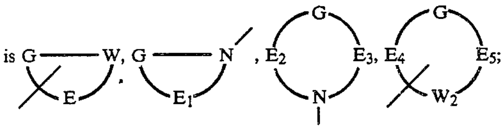

$Q_1$ $Q_2$ $Q_3$ $Q_4$

G is C=O or $SO_2$;

W is O, S, $CHR_2$ or $NR_3$;

$W_2$ is O, S, $SO_2$, $CHR_2$ or $NR_3$;

$R_2$ is H, $C_1$–$C_2$ alkyl, Cl, F, or Br;

$R_3$ is H, $C_1$–$C_4$ alkyl, $C_1$–$C_4$ haloalkyl, $C_2$–$C_4$ alkoxyalkyl, $C_2$–$C_4$ cyanoalkyl, $C_3$–$C_4$ alkenyl or $C_3$–$C_4$ alkynyl;

E and $E_1$ are independently $C_3$–$C_4$ alkylene, $C_3$–$C_4$ alkenylene or $C_4$ alkenyldienyl;

$E_2$ and $E_4$ are independently $C_1$–$C_2$ alkylene or $C_2$ alkenylene;

$E_3$ and $E_5$ independently are $C_2$–$C_3$ alkylene or $C_2$–$C_3$ alkenylene; and E, $E_1$, $E_2$, $E_3$, $E_4$ and $E_5$ may optionally be substituted by 1–4 groups selected from $C_1$–$C_4$ alkyl, $C_1$–$C_4$ alkoxy, $C_1$–$C_4$ alkenyl, OH, halogen or $C_1$–$C_4$ haloalkoxy; further, when W is O, $CHR_2$ or $NR_3$, one of the carbon atoms of E may be in the form of a carbonyl group, and when $W_2$ is O, $CHR_2$ or $NR_3$, one of the carbon atoms of $E_4$ or $E_5$ may be in the form of a carbonyl group, provided that said carbonyl groups are not bonded directly to G;

A is

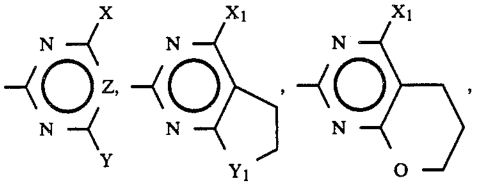

A-1 A-2 A-3

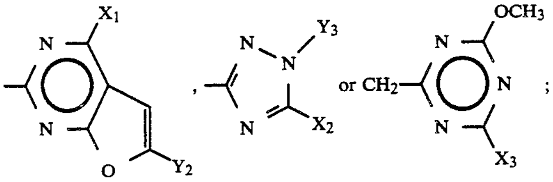

A-4 A-5 A-6

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_3$–$C_5$ cycloalkyl, $C_2$–$C_4$ alkynyl, $C(O)R_6$,

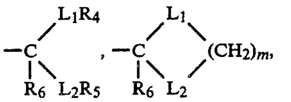

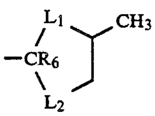

or $N(OCH_3)CH_3$;

m is 2 or 3;

$L_1$ and $L_2$ are independently O or S;

$R_4$ and $R_5$ are independently $C_1$–$C_2$ alkyl;

$R_6$ is H or $CH_3$;

Z is CH or N;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$;

$Y_3$ is $CH_3$, $CH_2CH_3$ or $CH_2CF_3$; and $X_3$ is $CH_3$ or $OCH_3$;

and their agriculturally suitable salts; provided that a. when G is $SO_2$, then W is O, $CHR_2$ or $NR_3$;

b. when $E_2$ or $E_4$ is $C_2$ alkylene or $C_2$ alkenylene then $E_3$ or $E_5$ is $C_2$ alkylene or $C_2$ alkenylene;

c. when X is Cl, F, Br or I, then Z is CH and Y is $OCH_3$, $OC_2H_5$, $N(OCH_3)CH_3$, $NHCH_3$, $N(CH_3)_2$ or $OCF_2H$;

d. when M is other than H, alkyl, alkenyl, alkynyl or phenyl, optionally substituted, then $R_1$ is H, alkyl, haloalkyl or halogen;

e. when X or Y is $OCF_2H$, then Z is CH;

f. when the total number of carbon atoms of X and Y is greater than four, then the number of carbons of $R_1$ is less than or equal to two and the number of carbons of Q is less than or equal to eight; and g. when $W_1$ is S, then R is H, A is A-1, and Y is $CH_3$, $OCH_3$, $OC_2H_5$, $CH_2OCH_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or

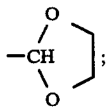;

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers; $C_1$ alkenyl means as exocyclic double bond.

Alkynyl denotes straight chain or branched alkynes, e.g., ethynyl, 1-propynyl, 2-propynyl and the different butynyl isomers.

The term "halogen", either alone or in compound words such as "haloalkyl", denotes fluorine, chlorine, bromine or iodine.

In terms such as $C_2$–$C_3$ alkylthioalkyl, the specified number of carbon atoms is meant to define the total number of carbon atoms in that substituent group. For example, $C_2$–$C_3$ alkylthioalkyl would designate $CH_2SCH_3$, $CH_2SC_2H_5$, $CH_2CH_2SCH_3$ or $CH(CH_3)SCH_3$, and $C_2$–$C_5$ alkoxyalkoxy would represent $OCH_2OCH_3$ through $O(CH_2)_4OCH_3$ or $OCH_2O(CH_2)_3CH_3$ and the various structural isomers embraced therein.

$C_4$–$C_7$ cycloalkylalkyl means cyclopropylmethyl through cyclopropylbutyl or cyclohexylmethyl.

Alkylsulfonyl denotes methylsulfonyl, ethylsulfonyl and the different propylsulfonyl isomers.

Alkylthio, alkylsulfinyl, alkylamino, etc. are defined in an analogous manner.

Alkylene denotes methylene ($-CH_2-$), ethylene ($-CH_2CH_2-$), propylene or butylene; alkenylene denotes $-CH{=}CH-$, $-CH{=}CHCH_2-$, $-CH{=}CHCH_2CH_2-$ or $-CH_2CH{=}CHCH_2-$; and alkenyldienyl denotes $-CH{=}CH-CH{=}CH-$.

Preferred for reasons of increased ease of synthesis and/or greater herbicidal efficacy are:

1. Compounds of Formula I where
   $W_1$ is O; and
   R is H;
2. Compounds of Preferred 1 where
   $R_1$ is H, Cl, Br, $CH_3$, or $OCF_2H$;
   M is $C_1$–$C_3$ alkyl;
   X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$; and
   Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH{=}CH_2$, $OCH_2C{\equiv}CH$, $CH_2OCH_2CH_3$, $OCH_2CH_2OCH_3$, $CH_2SCH_3$, $C(O)R_6$,

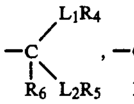 , 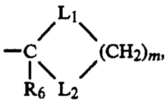 , 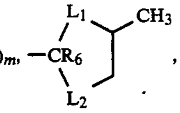 , $OCF_2H$, $SCF_2H$, cyclopropyl, $C{\equiv}CH$ or $C{\equiv}CCH_3$;
3. Compounds of Preferred 2 where Q is $Q_1$;
4. Compounds of Preferred 2 where Q is $Q_2$;
5. Compounds of Preferred 2 where Q is $Q_3$;
6. Compounds of Preferred 2 where Q is $Q_4$;
7. Compounds of Preferred 2 where Q is

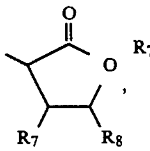
Q-1

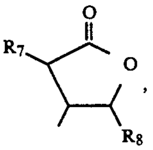
Q-2

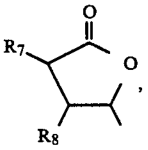
Q-3

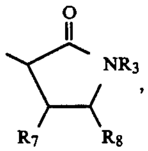
Q-4

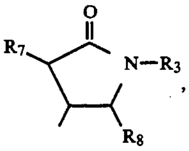
Q-5

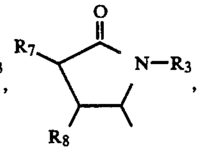
Q-6

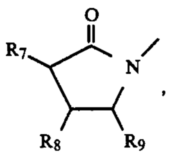
Q-7

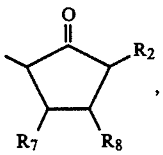
Q-8

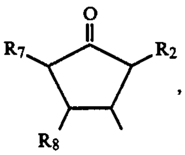
Q-9

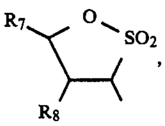
Q-10

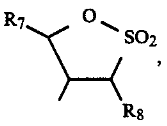
Q-11

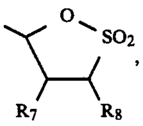
Q-12

-continued
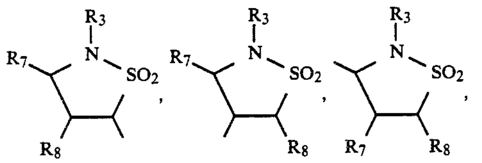
Q-13, Q-14, Q-15,
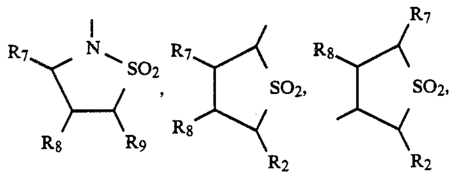
Q-16, Q-17, Q-18,
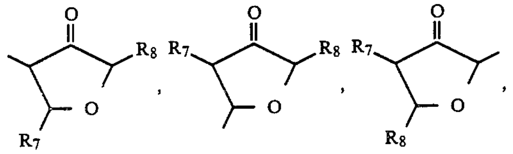
Q-19, Q-20, Q-21,
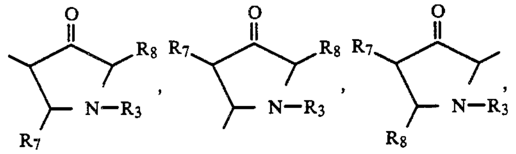
Q-22, Q-23, Q-24,
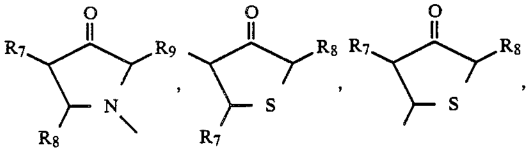
Q-25, Q-26, Q-27,
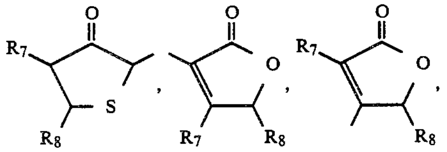
Q-28, Q-29, Q-30,
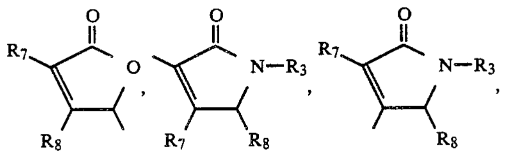
Q-31, Q-32, Q-33,
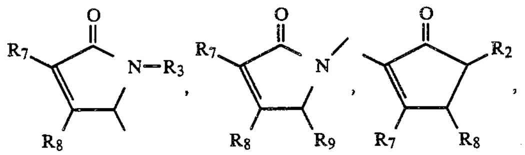
Q-34, Q-35, Q-36,
-continued
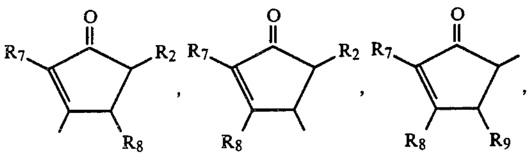
Q-37, Q-38, Q-39,
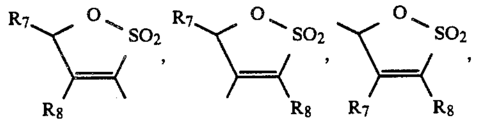
Q-40, Q-41, Q-42,
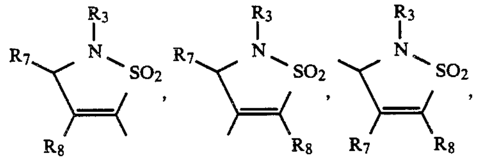
Q-43, Q-44, Q-45,
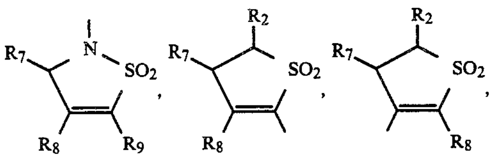
Q-46, Q-47, Q-48,
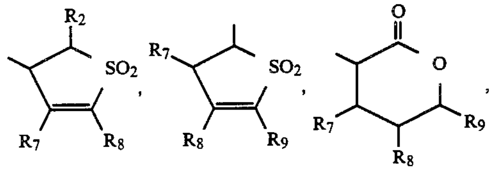
Q-49, Q-50, Q-51,
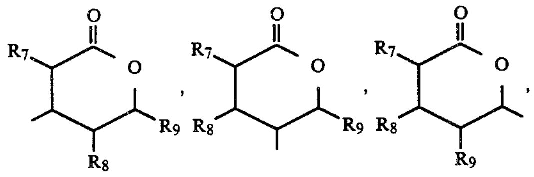
Q-52, Q-53, Q-54,
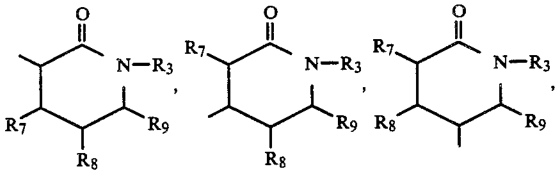
Q-55, Q-56, Q-57,
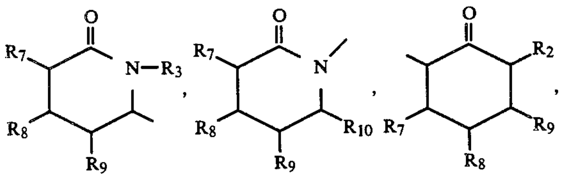
Q-58, Q-59, Q-60, -continued
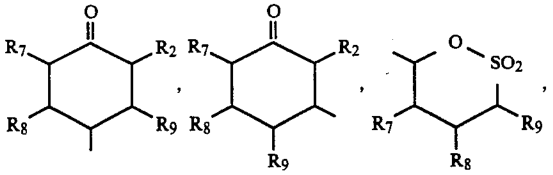
Q-61 Q-62 Q-63
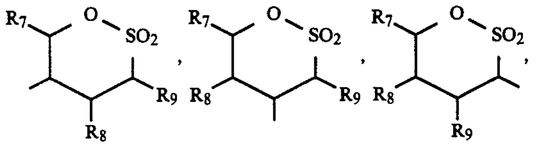
Q-64 Q-65 Q-66
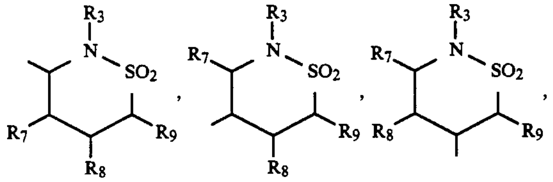
Q-67 Q-68 Q-69
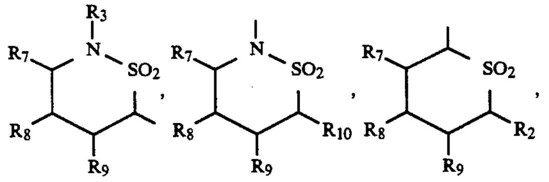
Q-70 Q-71 Q-72
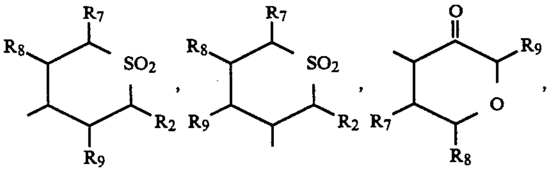
Q-73 Q-74 Q-75
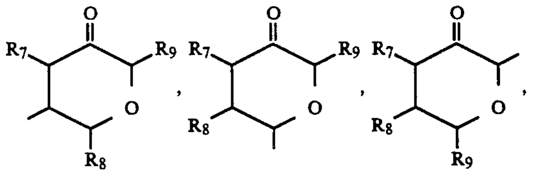
Q-76 Q-77 Q-78
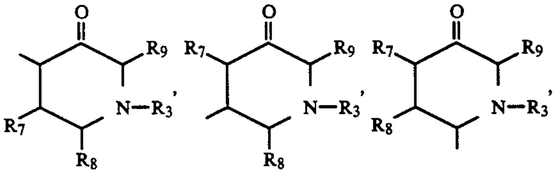
Q-79 Q-80 Q-81
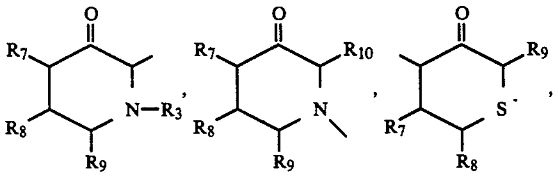
Q-82 Q-83 Q-84
-continued
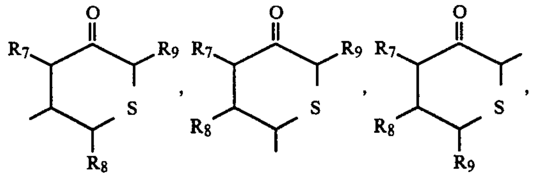
Q-85 Q-86 Q-87
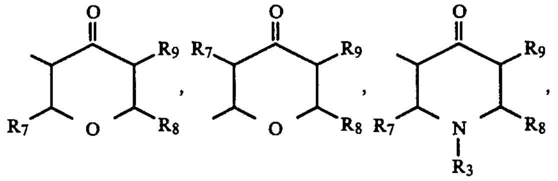
Q-88 Q-89 Q-90
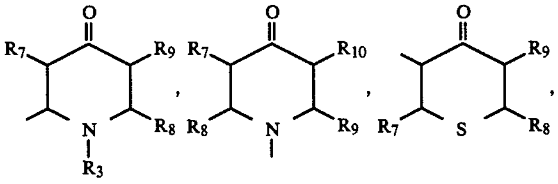
Q-91 Q-92 Q-93
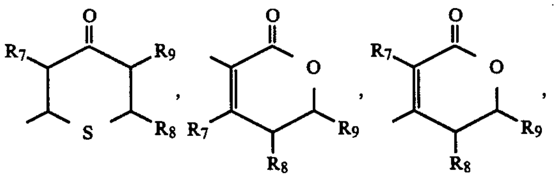
Q-94 Q-95 Q-96
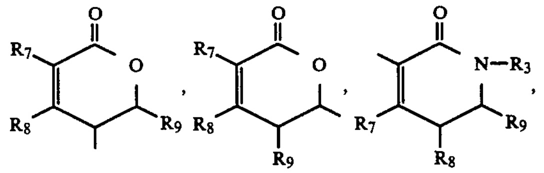
Q-97 Q-98 Q-99
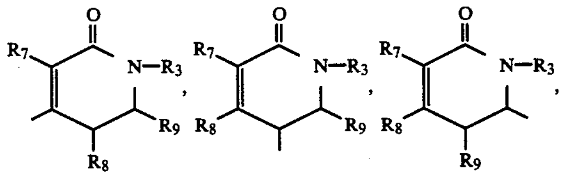
Q-100 Q-101 Q-102
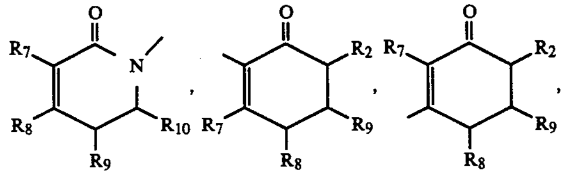
Q-103 Q-104 Q-105
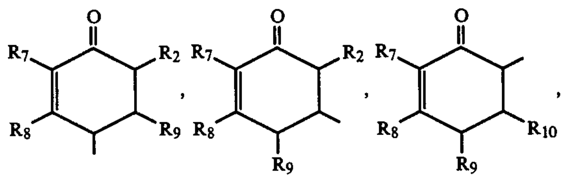
Q-106 Q-107 Q-108

-continued
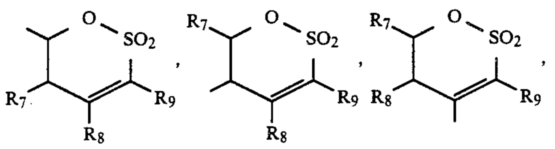
Q-109 Q-110 Q-111
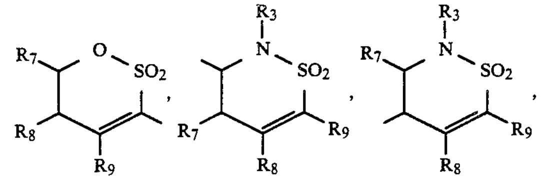
Q-112 Q-113 Q-114
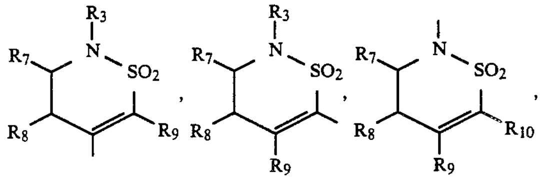
Q-115 Q-116 Q-117
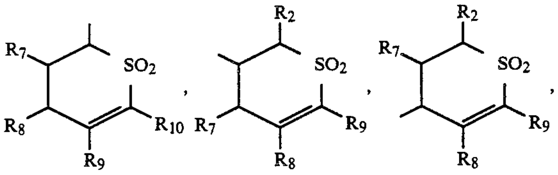
Q-118 Q-119 Q-120
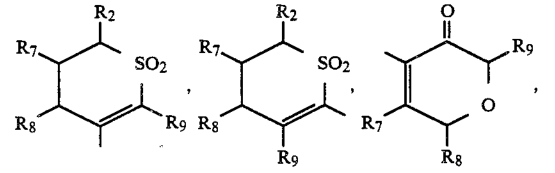
Q-121 Q-122 Q-123
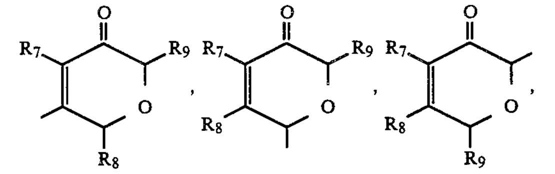
Q-124 Q-125 Q-126
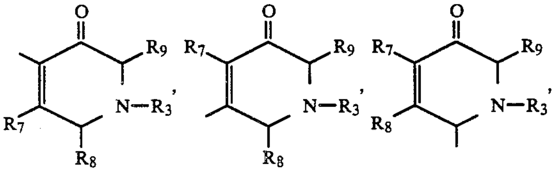
Q-127 Q-128 Q-129
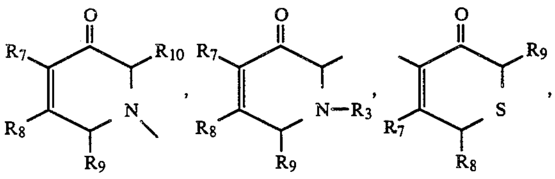
Q-130 Q-131 Q-132
-continued
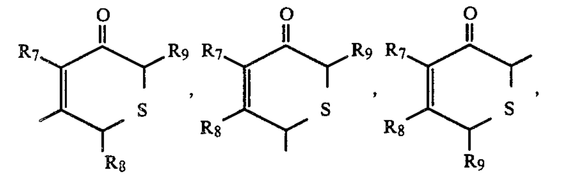
Q-133 Q-134 Q-135
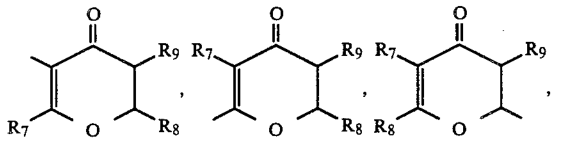
Q-136 Q-137 Q-138
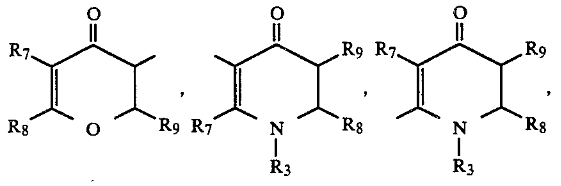
Q-139 Q-140 Q-141
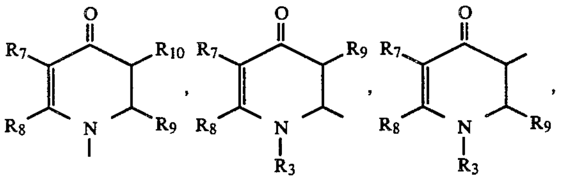
Q-142 Q-143 Q-144
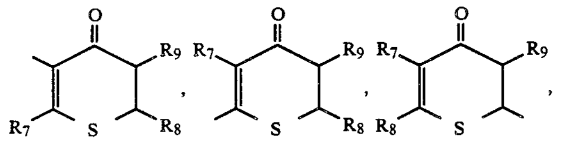
Q-145 Q-146 Q-147
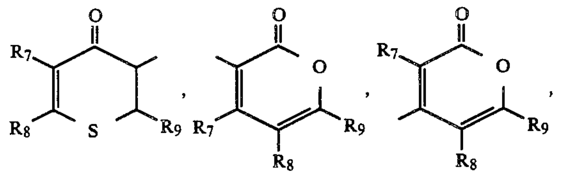
Q-148 Q-149 Q-150
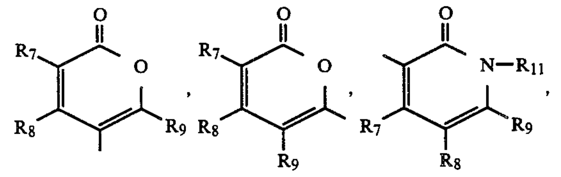
Q-151 Q-152 Q-153
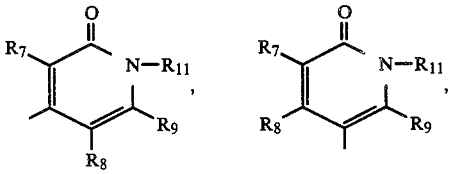
Q-154 Q-155

-continued

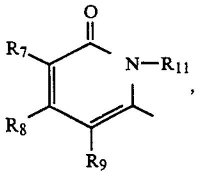, 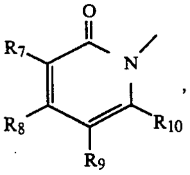, 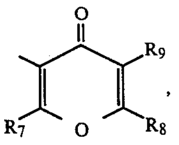,

Q-156 Q-157 Q-158

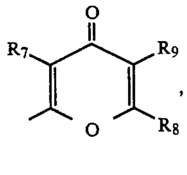, 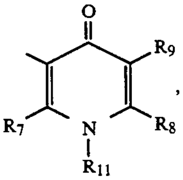, 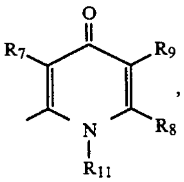,

Q-159 Q-160 Q-161

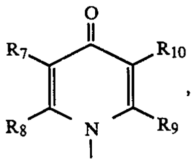, 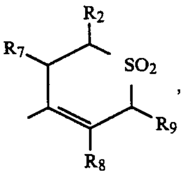, 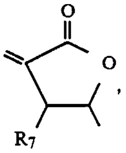,

Q-162 Q-163 Q-164

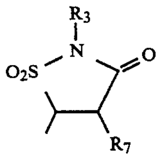 or 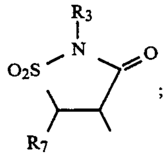 ;

Q-165 Q-166

$R_7$, $R_8$, $R_{10}$ are independently H or $CH_3$; and
$R_{11}$ is H, $CH_3$ or $CH_2CH_3$;

8. Compounds of Preferred 7 where
$R_1$ is H, $CH_3$ or Cl; and
Y is $CH_3$, $OCH_3$, $C_2H_5$, $OC_2H_5$, $CH_2OCH_3$, $NHCH_3$, $CH(OCH_3)_2$ or cyclopropyl;
9. Compounds of Preferred 8 where
$R_2$ is H or $CH_3$; and
$R_3$ is H, $CH_3$ or $C_2H_5$;
10. Compounds of Preferred 9 where
A is A-1; and
X is $CH_3$, $OCH_3$, Cl or $OCF_2H$;
11. Compounds of Preferred 10 where Q is Q-1;
12. Compounds of Preferred 10 where Q is Q-2;
13. Compounds of Preferred 10 where Q is Q-3;
14. Compounds of Preferred 10 where Q is Q-4;
15. Compounds of Preferred 10 where Q is Q-5;
16. Compounds of Preferred 10 where Q is Q-6;
17. Compounds of Preferred 10 where Q is Q-7;
18. Compounds of Preferred 10 where Q is Q-8;
19. Compounds of Preferred 10 where Q is Q-9;
20. Compounds of Preferred 10 where Q is Q-10;
21. Compounds of Preferred 10 where Q is Q-11;
22. Compounds of Preferred 10 where Q is Q-12;
23. Compounds of Preferred 10 where Q is Q-13;
24. Compounds of Preferred 10 where Q is Q-14;
25. Compounds of Preferred 10 where Q is Q-15;
26. Compounds of Preferred 10 where Q is Q-16;
27. Compounds of Preferred 10 where Q is Q-17;
28. Compounds of Preferred 10 where Q is Q-18;
29. Compounds of Preferred 10 where Q is Q-19;
30. Compounds of Preferred 10 where Q is Q-20;
31. Compounds of Preferred 10 where Q is Q-21;
32. Compounds of Preferred 10 where Q is Q-22;
33. Compounds of Preferred 10 where Q is Q-23;
34. Compounds of Preferred 10 where Q is Q-24;
35. Compounds of Preferred 10 where Q is Q-25;
36. Compounds of Preferred 10 where Q is Q-26;
37. Compounds of Preferred 10 where Q is Q-27;
38. Compounds of Preferred 10 where Q is Q-28;
39. Compounds of Preferred 10 where Q is Q-29;
40. Compounds of Preferred 10 where Q is Q-30;
41. Compounds of Preferred 10 where Q is Q-31;
42. Compounds of Preferred 10 where Q is Q-32;
43. Compounds of Preferred 10 where Q is Q-33;
44. Compounds of Preferred 10 where Q is Q-34;
45. Compounds of Preferred 10 where Q is Q-35;
46. Compounds of Preferred 10 where Q is Q-36;
47. Compounds of Preferred 10 where Q is Q-37;
48. Compounds of Preferred 10 where Q is Q-38;
49. Compounds of Preferred 10 where Q is Q-39;
50. Compounds of Preferred 10 where Q is Q-40;
51. Compounds of Preferred 10 where Q is Q-41;
52. Compounds of Preferred 10 where Q is Q-42;
53. Compounds of Preferred 10 where Q is Q-43;
54. Compounds of Preferred 10 where Q is Q-44;
55. Compounds of Preferred 10 where Q is Q-45;
56. Compounds of Preferred 10 where Q is Q-46;
57. Compounds of Preferred 10 where Q is Q-47;
58. Compounds of Preferred 10 where Q is Q-48;
59. Compounds of Preferred 10 where Q is Q-49;
60. Compounds of Preferred 10 where Q is Q-50;
61. Compounds of Preferred 10 where Q is Q-51;
62. Compounds of Preferred 10 where Q is Q-52;
63. Compounds of Preferred 10 where Q is Q-53;
64. Compounds of Preferred 10 where Q is Q-54;
65. Compounds of Preferred 10 where Q is Q-55;
66. Compounds of Preferred 10 where Q is Q-56;
67. Compounds of Preferred 10 where Q is Q-57;
68. Compounds of Preferred 10 where Q is Q-58;
69. Compounds of Preferred 10 where Q is Q-59;
70. Compounds of Preferred 10 where Q is Q-60;
71. Compounds of Preferred 10 where Q is Q-61;
72. Compounds of Preferred 10 where Q is Q-62;
73. Compounds of Preferred 10 where Q is Q-63;
74. Compounds of Preferred 10 where Q is Q-64;
75. Compounds of Preferred 10 where Q is Q-65;
76. Compounds of Preferred 10 where Q is Q-66;
77. Compounds of Preferred 10 where Q is Q-67;
78. Compounds of Preferred 10 where Q is Q-68;
79. Compounds of Preferred 10 where Q is Q-69;
80. Compounds of Preferred 10 where Q is Q-70;
81. Compounds of Preferred 10 where Q is Q-71;
82. Compounds of Preferred 10 where Q is Q-72;
83. Compounds of Preferred 10 where Q is Q-73;
84. Compounds of Preferred 10 where Q is Q-74;
85. Compounds of Preferred 10 where Q is Q-75;
86. Compounds of Preferred 10 where Q is Q-76;
87. Compounds of Preferred 10 where Q is Q-77;
88. Compounds of Preferred 10 where Q is Q-78;
89. Compounds of Preferred 10 where Q is Q-79;
90. Compounds of Preferred 10 where Q is Q-80;
91. Compounds of Preferred 10 where Q is Q-81;
92. Compounds of Preferred 10 where Q is Q-82;
93. Compounds of Preferred 10 where Q is Q-83;
94. Compounds of Preferred 10 where Q is Q-84;
95. Compounds of Preferred 10 where Q is Q-85;
96. Compounds of Preferred 10 where Q is Q-86;
97. Compounds of Preferred 10 where Q is Q-87;
98. Compounds of Preferred 10 where Q is Q-88;
99. Compounds of Preferred 10 where Q is Q-89;

100. Compounds of Preferred 10 where Q is Q-90;
101. Compounds of Preferred 10 where Q is Q-91;
102. Compounds of Preferred 10 where Q is Q-92;
103. Compounds of Preferred 10 where Q is Q-93;
104. Compounds of Preferred 10 where Q is Q-94;
105. Compounds of Preferred 10 where Q is Q-95;
106. Compounds of Preferred 10 where Q is Q-96;
107. Compounds of Preferred 10 where Q is Q-97;
108. Compounds of Preferred 10 where Q is Q-98;
109. Compounds of Preferred 10 where Q is Q-99;
110. Compounds of Preferred 10 where Q is Q-100;
111. Compounds of Preferred 10 where Q is Q-101;
112. Compounds of Preferred 10 where Q is Q-102;
113. Compounds of Preferred 10 where Q is Q-103;
114. Compounds of Preferred 10 where Q is Q-104;
115. Compounds of Preferred 10 where Q is Q-105;
116. Compounds of Preferred 10 where Q is Q-106;
117. Compounds of Preferred 10 where Q is Q-107;
118. Compounds of Preferred 10 where Q is Q-108;
119. Compounds of Preferred 10 where Q is Q-109;
120. Compounds of Preferred 10 where Q is Q-110;
121. Compounds of Preferred 10 where Q is Q-111;
122. Compounds of Preferred 10 where Q is Q-112;
123. Compounds of Preferred 10 where Q is Q-113;
124. Compounds of Preferred 10 where Q is Q-114;
125. Compounds of Preferred 10 where Q is Q-115;
126. Compounds of Preferred 10 where Q is Q-116;
127. Compounds of Preferred 10 where Q is Q-117;
128. Compounds of Preferred 10 where Q is Q-118;
129. Compounds of Preferred 10 where Q is Q-119;
130. Compounds of Preferred 10 where Q is Q-120;
131. Compounds of Preferred 10 where Q is Q-121;
132. Compounds of Preferred 10 where Q is Q-122;
133. Compounds of Preferred 10 where Q is Q-123;
134. Compounds of Preferred 10 where Q is Q-124;
135. Compounds of Preferred 10 where Q is Q-125;
136. Compounds of Preferred 10 where Q is Q-126;
137. Compounds of Preferred 10 where Q is Q-127;
138. Compounds of Preferred 10 where Q is Q-128;
139. Compounds of Preferred 10 where Q is Q-129;
140. Compounds of Preferred 10 where Q is Q-130;
141. Compounds of Preferred 10 where Q is Q-131;
142. Compounds of Preferred 10 where Q is Q-132;
143. Compounds of Preferred 10 where Q is Q-133;
144. Compounds of Preferred 10 where Q is Q-134;
145. Compounds of Preferred 10 where Q is Q-135;
146. Compounds of Preferred 10 where Q is Q-136;
147. Compounds of Preferred 10 where Q is Q-137;
148. Compounds of Preferred 10 where Q is Q-138;
149. Compounds of Preferred 10 where Q is Q-139;
150. Compounds of Preferred 10 where Q is Q-140;
151. Compounds of Preferred 10 where Q is Q-141;
152. Compounds of Preferred 10 where Q is Q-142;
153. Compounds of Preferred 10 where Q is Q-143;
154. Compounds of Preferred 10 where Q is Q-144;
155. Compounds of Preferred 10 where Q is Q-145;
156. Compounds of Preferred 10 where Q is Q-146;
157. Compounds of Preferred 10 where Q is Q-147;
158. Compounds of Preferred 10 where Q is Q-148;
159. Compounds of Preferred 10 where Q is Q-149;
160. Compounds of Preferred 10 where Q is Q-150;
161. Compounds of Preferred 10 where Q is Q-151;
162. Compounds of Preferred 10 where Q is Q-152;
163. Compounds of Preferred 10 where Q is Q-153;
164. Compounds of Preferred 10 where Q is Q-154;
165. Compounds of Preferred 10 where Q is Q-155;
166. Compounds of Preferred 10 where Q is Q-156;
167. Compounds of Preferred 10 where Q is Q-157;
168. Compounds of Preferred 10 where Q is Q-158;
169. Compounds of Preferred 10 where Q is Q-159;
170. Compounds of Preferred 10 where Q is Q-160;
171. Compounds of Preferred 10 where Q is Q-161;
172. Compounds of Preferred 10 where Q is Q-162;
173. Compounds of Preferred 10 where Q is Q-163;
174. Compounds of Preferred 10 where Q is Q-164;
175. Compounds of Preferred 10 where Q is Q-165;
176. Compounds of Preferred 10 where Q is Q-166.

Specifically Preferred for reasons of greatest ease of synthesis and/or greatest herbicidal efficacy are:

N-[(4,6-dimethoxypyrimidin-2-yl)aminocarbonyl]-1-methyl-4-(tetrahydro-2-oxofuran-3-yl)pyrazole-3-sulfonamide;

N-[(4-methoxy-6-methyltriazin-2-yl)aminocarbonyl]-1-methyl-4-(tetrahydro-2-oxofuran-3-yl)pyrazole-3-sulfonamide; and N-[4,6-dimethoxypyrimidin-2-yl)aminocarbonyl]-1-methyl-4-(3-oxo-1-cyclohexenyl)-1H-pyrazole-5-sulfonamide, m.p. 175°-182° C. (dec).

DETAILED DESCRIPTION OF THE INVENTION

Synthesis

Compounds of Formula I can be synthesized by one or more of the methods shown below in Equations 1, 2 and 3.

Equation 1 depicts the reaction of sulfonyl isocyanates 11 with the appropriate heterocyclic amines of Formula III to give the desired sulfonylureas I.

Equation 1

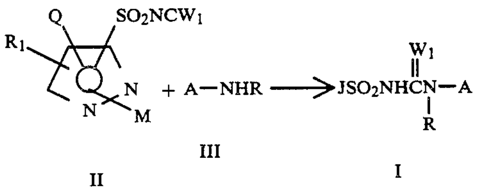

wherein

J is J-1 to J-4, $R_1$, Q, R, M, $W_1$ and A are as previously defined.

The nature of the substituent when M=H and its chemical compatibility with the wide variety of reactions and reaction conditions described throughout this disclosure must be taken into account to perform many of the transformations. The selection of a suitable aromatic amino protecting group also must take into account the nature of other substituents in the molecules. The selection of an appropriate protecting group fulfilling the aforementioned requirements is obvious to one skilled in the art. For a compilation of references describing the wide variety of protecting groups available for aromatic amines. see T. W. Greene, "Protective Groups in Organic Synthesis", pp. 218-287, John Wiley and Sons, Inc., New York, 1981.

The reaction of Equation 1 is best carried out in an inert aprotic solvent such as methylene chloride, tetrahydrofuran, acetonitrile or xylene at a temperature between 0° and 90° C. A catalytic amount of 1,4-diazabicyclo[2.2.2]octane (DABCO) may be used to accelerate the reaction. In the cases in which the products are insoluble in the reaction solvent, they may be isolated by simple filtration. When the products are soluble, they can be isolated by evaporation of the solvent and trituration of the residue with solvents such as 1-chlorobutane, diethyl ether or ethyl acetate, and filtration.

Compounds of Formula I can also be prepared as shown below in Equation 2 by treating sulfonamides of Formula IV with the methyl ester of a pyrimidine or triazine carbamic acid of Formula V in the presence of an equimolar quantity of trimethylaluminum.

Equation 2

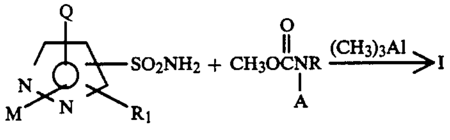

IV V wherein

J is J-1 to J-4, $R_1$, Q, R, M, and A are as previously defined.

The reaction of Equation 2 is best carried out at temperatures between 25° and 83° C. in a solvent such as methylene chloride or 1,2-dichloroethane for 12 to 96 hours under an inert atmosphere, as taught in European Patent Application (EP-A) No. 84,244 (published July 27, 1983). The products of Formula I are most conveniently isolated by acidifying the reaction solution with dilute aqueous hydrochloric acid, and extraction with a suitable solvent such as methylene chloride or ethyl acetate. If necessary, purification can be achieved by recrystallization or column chromatography. The methyl carbamates V can be synthesized by treatment of the corresponding heterocyclic amines of Formula III with dimethyl carbonate or methyl chloroformate in the presence of a base such as sodium hydride or pyridine.

Alternatively, compounds of Formula I can be prepared as shown below in Equation 3 by the reaction of sulfonamides IV with the phenyl ester of the appropriate carbamic acid, VI, in the presence of an equimolar quantity of a tertiary amine base such as 1,8-diazabicyclo[5.4.0]undec-7-ene (DBU).

Equation 3

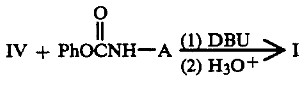

VI wherein

J is J-1 to J-4, $R_1$, Q, A, M and R are as previously defined.

The reaction shown in Equation 3 is best carried out at about 25° C. in a suitable solvent such as dioxane or acetonitrile for 1-2 hours under an inert atmosphere as described in European Patent Application No. 70,804 (published Jan. 26, 1983). The desired products of Formula I can be most conveniently isolated by acidifying the reaction solution with dilute aqueous hydrochloric acid. In certain cases, the products are insoluble and may be filtered. Alternatively, the aqueous layer can be extracted with a solvent such as methylene chloride or ethyl acetate. Drying and evaporation of the solvent then affords the desired products. The phenyl carbamates VI can be synthesized by treatment of the corresponding heterocyclic amines of Formula III with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12-36 hours.

A judicious choice of the appropriate methods for preparing compounds of Formula I must take into account the nature of the substituents Q, M and $R_1$, and their chemical compatibility with the reaction conditions of Equations 1-3. Such a decision would be obvious to one who is skilled in the art.

Sulfonyl isocyanates of Formula IIa can be prepared as shown in Equation 4 by the reaction of sulfonamides of general structure IV with phosgene in the presence of n-butyl isocyanate and a catalytic amount of 1,4-diazabicyclo[2.2.2]octane (DABCO).

Equation 4

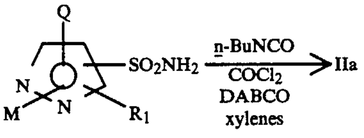

IV wherein

M, Q, and $R_1$ are as previously defined, and $W_1$=O.

The reaction shown in Equation 4 is best carried out according to the procedure described in U.S. Pat. No. 4,238,621.

Alternatively, sulfonyl isocyanates IIa can be prepared via phosgenation of the preformed n-butylureas of Formula VII as represented in Equation 5.

Equation 5

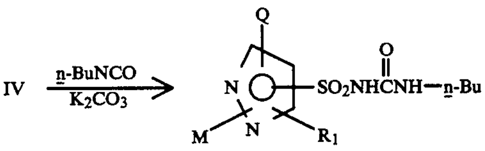

VII

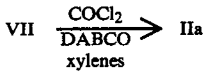

wherein

M, Q, and $R_1$ are as previously defined.

The compounds of Formula VII are conveniently prepared by stirring a mixture of the appropriate sulfonamides IV, anhydrous potassium carbonate, and n-butyl isocyanate in a suitable solvent such as acetone or methyl ethyl ketone at 25° to 80° C. until all of the isocyanate has reacted. The products are isolated by quenching in dilute aqueous hydrochloric acid and recrystallizing the insoluble solid. The n-butylureas VII are then treated with phosgene and a catalytic amount of DABCO in refluxing xylenes or chlorobenzene in a manner analogous to that described in Equation 4.

Another, somewhat milder, method for the preparation of sulfonyl isocyanates IIa is shown in Equation 6. Treatment of sulfonamides of Formula IV with thionyl chloride gives intermediate N-sulfinylsulfonamides VIII, which afford sulfonyl isocyanates IIa upon exposure to phosgene in the presence of a catalytic amount of pyridine.

Equation 6

IV 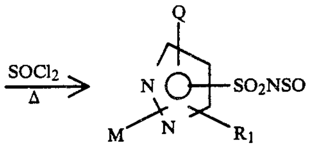

VIII

VIII $\xrightarrow[\text{cat. pyridine, toluene, } \Delta]{COCl_2}$ IIa wherein

M, Q, and $R_1$ are as previously defined.

The reaction of Equation 6 can best be performed according to the procedure of H. Ulrich, B. Tucker and A. Sayigh, *J. Org. Chem.*, 34, 3200 (1969).

Sulfonyl isothiocyanates of Formula II, where $W_1$ is S, can be prepared according to the method described by K. Hartke, *Arch. Pharm.*, 299, 174 (1966).

A judicious choice of the appropriate method for preparing compounds of Formula II must take into account the nature of the substituents Q, M, and $R_1$, and their chemical compatibility with the reaction conditions of Equations 4–6. Such a decision would be obvious to one skilled in the art.

The requisite sulfonamides of Formula IV can be synthesized by one or more of the methods shown below in Equations 7, 8 and 9.

Equation 7 depicts the reaction of sulfonyl chlorides of Formula IX with ammonia to give sulfonamides of Formula IVa.

Equation 7

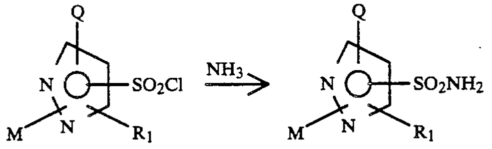

IX IVa wherein

M, Q, and $R_1$ are as previously defined.

The amination of Equation 7 is most conveniently effected by adding at least two molar equivalents of either anhydrous ammonia or concentrated ammonium hydroxide to a solution of the sulfonyl chloride IX in a suitable solvent such as diethyl ether, tetrahydrofuran, or methylene chloride at temperatures between −30° and 25° C. The desired sulfonamides of Formula IVa are isolated either by filtration, in which case the by-product ammonium chloride is removed by washing with water, or extraction into a suitable organic solvent such as methylene chloride or ethyl acetate. Drying and evaporation of the solvent then affords the products IVa, which are usually sufficiently pure to be carried directly on to the next step.

Sulfonamides of Formula IVb can be prepared as shown in Equation 8 by treatment of the corresponding N-t-butylsulfonamides X with an appropriate acid such as trifluoroacetic (TFA), polyphosphoric (PPA), or p-toluenesulfonic acid (p-TSA).

Equation 8

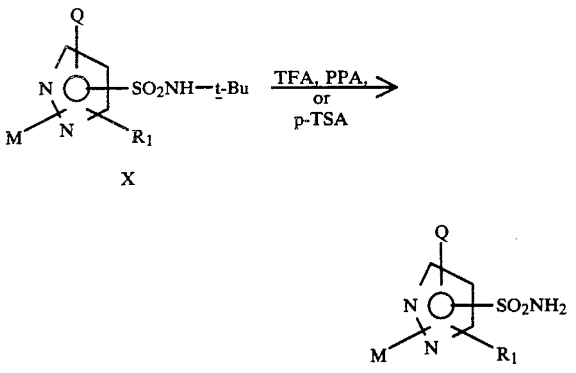

X

IVb wherein

M, Q, and $R_1$ are as previously defined.

The reaction of Equation 8 is most conveniently carried out by stirring a solution of the compound of Formula X in excess trifluoroacetic acid (approximately 0.3M) at about 25° C. for 1–24 hours. The desired sulfonamides of Formula IVb are then isolated by removal of the volatiles in vacuo and crystallization from a suitable solvent such as diethyl ether, 1-chlorobutane, or ethyl acetate. Alternatively, the N-t-butylsulfonamides of Formula X can be treated with a catalytic amount of p-toluenesulfonic acid monohydrate in a solvent such as toluene or xylenes at reflux temperature for 1–6 hours. The desired products are then isolated in a manner analogous to the one described above. For use of polyphosphoric acid in the deprotection of N-t-butylsulfonamides, see J. G. Lombardino, *J. Org. Chem.*, 36, 1843 (1971); for use of trifluoroacetic acid, see J. D. Catt and W. L. Matier, *J. Org. Chem.*, 39, 566 (1974).

Alternatively, sulfonamides of Formula IVa, where Q is Q-1, can be synthesized via the two-step procedure represented below in Equation 9(a) exemplified with the pyrazolothiazin-1,1-dioxides of Formula XI. In a similar fashion, sulfonamides of Formula IVd, where Q is Q-51, can be prepared via the two-step procedure shown in Equation 9(b) starting from the same compound XI.

Equation 9

(a)

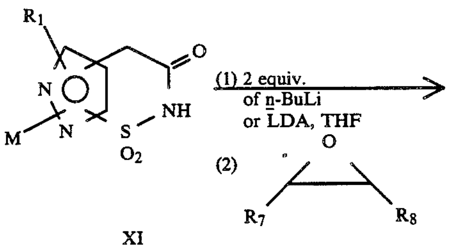

XI

-continued

Equation 9

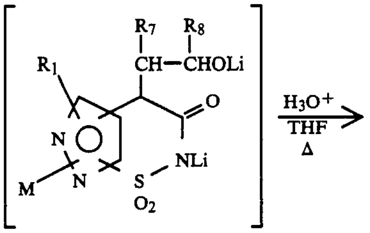

XII

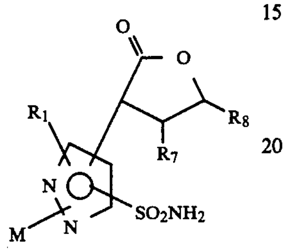

IVc (b)

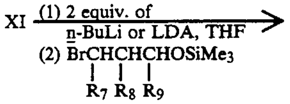

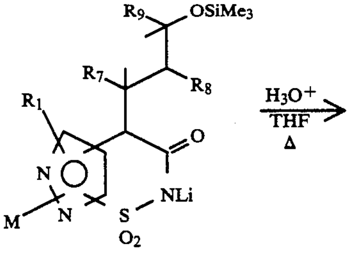

XIII

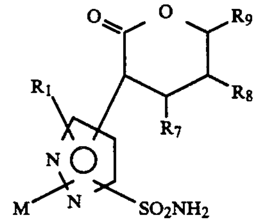

IVd wherein

M, $R_1$, $R_7$, $R_8$, and $R_9$ are as previously defined.

Equation 9(a)

The transformation shown above in Equation 9(a) can be conveniently carried out by adding a suitable base such as n-butyllithium (n-BuLi) or lithium diisopropylamide (LDA) to a solution of the compound of general structure XI in a solvent such as tetrahydrofuran at −78° C. under an inert atmosphere. To ensure complete dianion formation, the reaction mixture is typically allowed to warm to about −30° C. over a period of 0.5 to 1 hour, and is then recooled and treated with the appropriate epoxide. After being stirred overnight at −78° to 25° C., the reaction solution is acidified with dilute aqueous hydrochloric acid and the water layer extracted with a suitable solvent such as diethyl ether or methylene chloride. Drying and evaporation of the organic extracts affords a crude residue which is immediately dissolved in an organic solvent such as tetrahydrofuran, and heated at reflux temperature in the presence of a mineral acid such as hydrochloric acid for 1 to 4 hours. The desired products of Formula IVc are isolated by extraction into an organic solvent such as diethyl ether or methylene chloride. Drying and evaporation of the organic extracts affords the crude sulfonamides IVc, which are typically purified by silica gel chromatography; elution is achieved with an appropriate solvent system such as 40–80% ethyl acetate-hexanes containing 1% methanol.

Equation 9(b)

The transformation depicted in Equation 9(b) is carried out in a manner analogous to the one described for Equation 9(a), except that a protected bromoalkanol is employed in the reaction with the dianions of pyrazolothiazin-1,1-dioxides XI to give intermediates of Formula XIII. These compounds are then treated with aqueous acid as described above to afford the desired sulfonamides of Formula IVd, which can be purified by column chromatography if necessary.

The pyrazolothiazin-1,1-dioxides XI can be prepared as shown below in Equation 10 by treatment of sulfonamides of Formula XIV with aqueous sodium hydroxide.

Equation 10

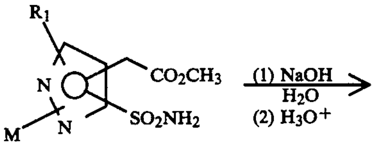

XIV

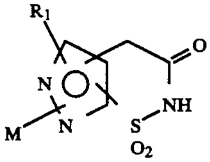

XI wherein

M and $R_1$ are as previously defined.

The ring-closure reaction shown in Equation 10 can be effected by stirring a solution of the compound of Formula XIV in excess 10% aqueous sodium hydroxide at about 25° C. for 1–12 hours. The products of Formula XI are then isolated by acidifying the cooled (0°–10° C.) reaction mixture with concentrated hydrochloric acid, and filtration. These compounds are generally sufficiently pure to be carried directly on to the next step.

The requisite sulfonamides of Formula XIV can be synthesized by methods which are obvious to one skilled in the art.

Sulfonyl chlorides of Formula IX can be prepared by one or more of the methods shown below in Equations 11, 12 and 13.

Equation 11 depicts the diazotization of appropriately substituted aminopyrazole derivatives of Formula XV and subsequent coupling with sulfur dioxide in the presence of either cupric or cuprous chloride to give the desired products of Formula IXa.

Equation 11

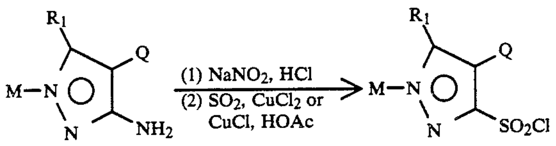

XV IXa wherein

M, Q, and $R_1$ are as previously defined.

The reaction of Equation 11 is accomplished by treating a solution of the substituted aminopyrazole XV in concentrated hydrochloric acid with a solution of sodium nitrite in water at $-5°$ to $5°$ C. After being stirred for 10–30 minutes at about 0° C., the solution is added to a mixture of excess sulfur dioxide and a catalytic amount of cupric chloride or cuprous chloride in glacial acetic acid at about 10° C. The temperature is maintained at about 10° C. for ½–1 hour, then raised to 25° C. and stirred for 2–24 hours. This solution is then poured into a large excess of ice-water. The desired sulfonyl chlorides IXa can be isolated by filtration, or by extraction into a solvent such as diethyl ether or methylene chloride, followed by drying and evaporation of the solvent.

Sulfonyl chlorides of Formula IXb can be prepared as shown in Equation 12(a) by metal-halogen exchange of appropriately substituted bromopyrazoles XVIa, where K is Br, and trapping with sulfuryl chloride.

Equation 12(a)

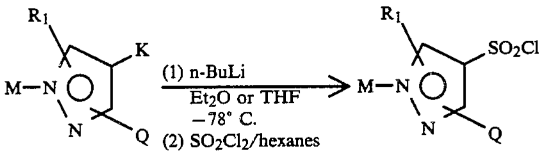

XVIa IXb wherein

M, Q and $R_1$ are as previously defined, and K is Br.

The lithiation shown in Equation 12(a) is best carried out according to the procedure of S. H. Bhattacharya, et al., *J. Chem. Soc.* (*C*), 1265 (1968).

Sulfonyl chlorides of Formula IXc can be prepared as shown in Equation 12(b) by lithiation of appropriately substituted pyrazoles XVIb, where K is H, and trapping with sulfuryl chloride.

Equation 12(b)

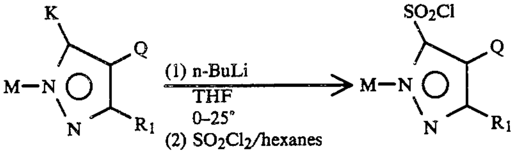

XVIb IXc wherein

M, Q and $R_1$ are as previously defined, and K is H.

The lithiation shown in Equation 12(b) is best carried out according to the procedures of R. Hüttel and M. E. Schön, *Liebigs Ann. Chem.*, 625, 55 (1959). Lithiation reactions of heterocycles, including pyrazoles, are discussed in H. W. Gschwend and H. R. Rodriguez, "Org. Reactions", 1, 1, Wiley & Sons, Inc., New York, 1979.

Sulfonyl chlorides of Formula IXd can be prepared as shown in Equation 12(c) by chlorosulfonation of appropriately substituted pyrazole carboxylic acid esters, acetamidopyrazoles, or pyrazoles of Formula XVIc where K is $CO_2CH_3$, $NHCOCH_3$ or H.

Equation 12(c)

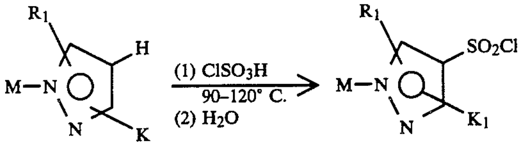

XVIc IXd wherein

M and $R_1$ are as previously defined,

K is $CO_2CH_3$, $NHCOCH_3$ or H, and $K_1$ is COOH, $NH_2$ or H.

The reaction of Equation 13 can be accomplished by adding the appropriate pyrazole XVIc at 0° C. to 25° C. to chlorosulfonic acid and heating the resulting solution at 90° C. to 120° C. for 2 to 24 hours. The reaction is carried out in the presence of at least 10 molar equivalents of chlorosulfonic acid. The desired sulfonyl chlorides of Formula IXd can be isolated by pouring the reaction solution on ice followed by extraction into a solvent such as diethyl ether or methylene chloride, followed by drying and evaporation of the solvent.

Alternatively, compounds of Formula IX can be prepared via oxidative chlorination of the appropriate thioethers of Formula XVId, where K is $SR_{12}$, as represented in Equation 13.

Equation 13

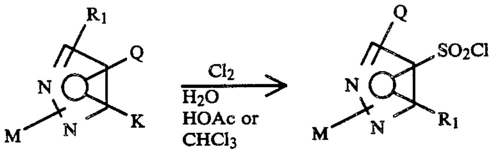

XVId IX wherein

M, Q, and $R_1$ are as previously defined, K is $SR_{12}$, and $R_{12}$ is $C_2$–$C_4$ alkyl or benzyl.

The reaction of Equation 13 can be accomplished by treating a solution of the thioether XVIb in a suitable solvent such as chloroform or methylene chloride; in some cases, it is advantageous to use acetic acid as solvent. The reaction is carried out in the presence of at least 2.5 equivalents of water and at least 3 molar equivalents of chlorine at 0°–30° C. for 1 to 5 hours. The products can be isolated by removal of the solvent in vacuo and are generally sufficiently pure to be carried directly on to the next step.

A judicious choice of the appropriate method for preparing compounds of Formula IX must take into account the nature of the substituents Q, M, and $R_1$, and their chemical compatability with the reaction conditions of Equations 11-13. Such a decision would be obvious to one who is skilled in the art.

Sulfonamides of Formulas XVIIa and XVIIb can be prepared as shown in Equations 14(a) and 14(b) by hydrogenolysis of the benzyl ethers XVIIIa and XVIIIb, followed by lactonization under acidic conditions.

Equation 14

(a)

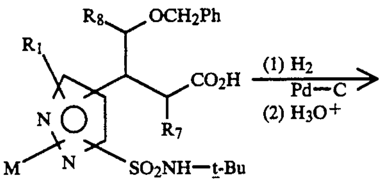

XVIIIa

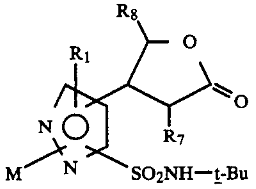

XVIIa (b)

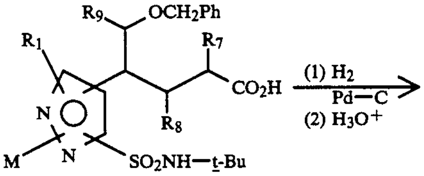

XVIIIb

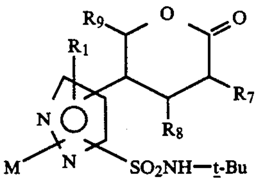

XVIIb wherein

M, $R_1$, $R_7$, $R_8$ and $R_9$ are as previously defined.

The hydrogenolysis of benzyl ethers to generate alcohols as shown in the first step of Equations 14(a) and 14(b) is well precedented in the literature and can be accomplished by subjecting compounds of Formulas XVIIIa and XVIIIb to a hydrogen atmosphere in the presence of a suitable catalyst such as palladium-on-carbon. For relevant references, see C. H. Heathcock and R. Ratcliffe, *J. Am. Chem. Soc.*, 93, 1746 (1971), and A. M. Felix, et al. *J. Org. Chem.*, 43, 4194 (1978). The second step represented above in Equations 14(a) and 14(b) involves the formation of 5 or 6-membered ring lactones from the corresponding 5 or 6-hydroxy carboxylic acids, an extremely facile cyclization which often occurs spontaneously. This lactonization process can be aided by heating the hydroxy acids in the presence of a suitable acid such as hydrochloric or sulfuric acid. For a discussion of this reaction and useful references, see J. March, "Advanced Organic Chemistry", 2nd Ed., McGraw-Hill Book Co., New York, 1977, pp. 363-365.

Alternatively, sulfonamides of Formual XVIIa can be synthesized via iodolactonization of the appropriate unsaturated carboxylic acids of Formula XIX, followed by reductive cleavage of the carbon-iodine bond as shown in Equation 15.

Equation 15

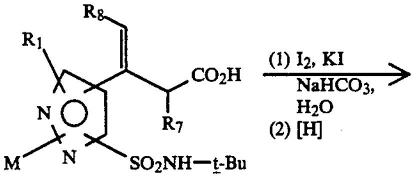

XIX

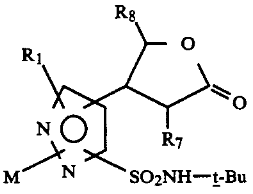

XVIIa wherein

M, $R_1$, $R_7$ and $R_8$ are as previously defined.

The first step of the reaction of Equation 15 can be accomplished according to the procedure of J. Klein, *J. Am. Chem. Soc.*, 81, 3611 (1959). The intermediate iodolactones obtained from this reaction are then treated with a suitable reducing agent such as hydrogen over Raney nickel catalyst (see reference cited above) or zinc in acetic acid as described by C. Heathcock, et al., *J. Am. Chem. Soc.*, 92, 1326 (1970).

Sulfonamides of Formula XVIIc can be conveniently prepared as shown below in Equation 16, by a two-step procedure analogous to that shown in Equations 14(a) and 14(b) except that the starting carboxylic acids are those of Formula XVIIIc.

Equation 16

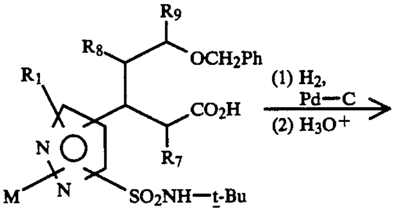

XVIIIc

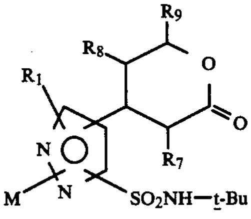

XVIIc wherein

M, $R_1$, $R_7$, $R_8$, and $R_9$ are as previously define

The transformation shown above in Equation 16 can be effected in a manner identical to that described for Equations 14(a) and 14(b).

Sulfonamides of Formulas XVIId and XVIIe can be synthesized by the three-step sequence of reactions outlined below in Equations 17(a) and 17(b) which involves: (1) addition of the dianions of suitable N-t-butyl pyrazolesulfonamides of Formula XXa to the appropriate β- or γ-formyl esters to give hydroxy esters XXIa and XXIb, (2) saponification of the esters XXIa and XXIb to afford the corresponding γ- or δ-hydroxy carboxylic acids, and (3) acid-induced lactonization.

Equation 17

(a)

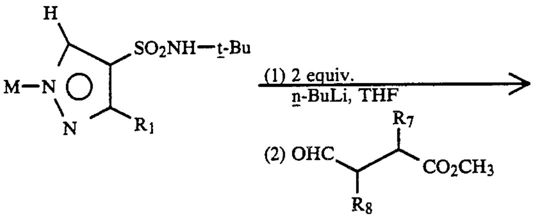

XXa

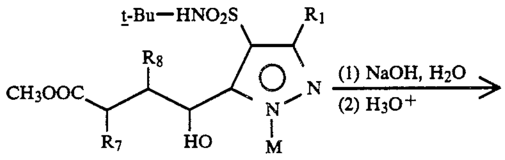

XXIa

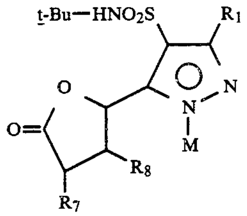

XVIId (b)

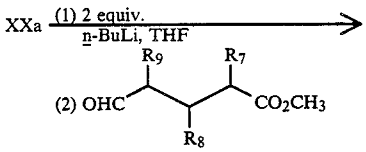

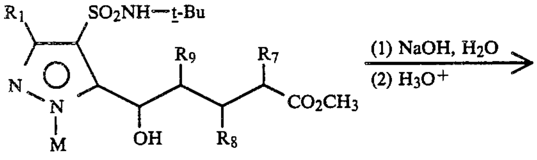

XXIb

-continued

Equation 17

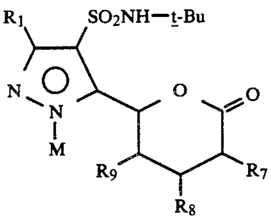

XVIIe wherein

M, $R_1$, $R_7$, $R_8$, and $R_9$ are as previously defined.

The first step of Equations 17(a) and 17(b) can be carried out by treating the appropriate N-t-butylpyrazolesulfonamide XXa with n-butyllithium in a solvent such as tetrahydrofuran at 0°–25° C. according to the procedure of J. G. Lombardino, *J. Org. Chem.*, 36, 1843 (1971). Addition of suitably substituted β- or γ-formyl esters to these dianions affords the hydroxy esters of Formulas XXIa and XXIb. Saponification of these hydroxy esters can be most easily accomplished by treatment with excess aqueous sodium hydroxide solution at about 25° C. for 1–6 hours. The desired products are obtained by acidifying with concentrated hydrochloric acid (ice-water cooling) and either filtration or extraction into a suitable organic solvent such as methylene chloride, diethyl ether, or ethyl acetate. These γ- and δ-hydroxy carboxylic acids may the spontaneously cyclize to give the desired products of Formulas XVIId and XVIIe; if not, lactonization may be achieved in a manner identical to that described for Equation 14 above.

Sulfonamides of Formulas XVIIf and XVIIg can be prepared by the three-step sequence of reactions outlined in Equations 17(c) and 17(d) which involves essentially the same transformations as depicted in Equations 17(a) and 17(b).

Equation 17

(c)

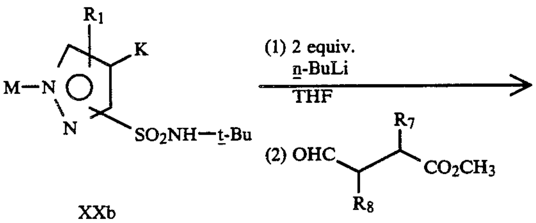

XXb

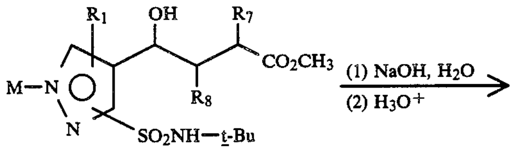

XXIc

-continued
Equation 17

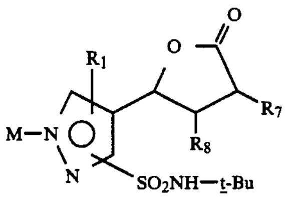

XVIIf (d)

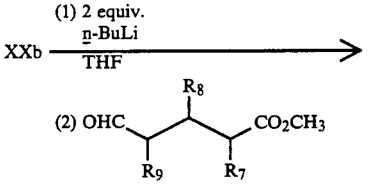

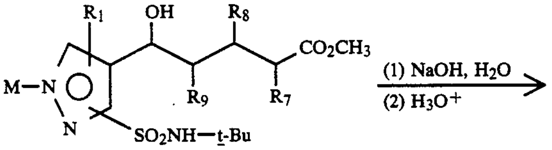

XXId

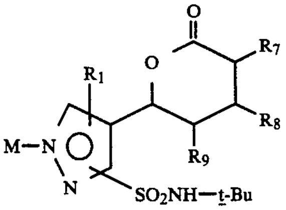

XVIIg wherein

M, $R_1$, $R_7$, $R_8$ and $R_9$ are as previously defined, and K is Br.

The N-t-butylsulfonamide dianions are best prepared according to the procedure of S. H. Bhattacharya, et al., *J. Chem. Soc.* (*C*), 1265 (1968). The saponification or lactonization steps are carried out in the same fashion as for Equations 17(a) and 17(b).

Alternatively, sulfonamides of Formula XVIIh can be prepared by iodolactonization of the appropriate unsaturated carboxylic acids of Formula XXII, followed by reductive cleavage of the carbon-iodine bond as shown in Equation 18.

Equation 18

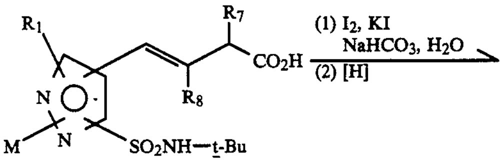

XXII

-continued
Equation 18

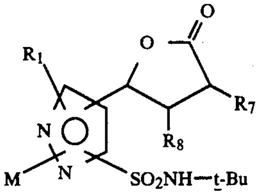

XVIId wherein

M, $R_1$, $R_7$ and $R_8$ are as previously defined.

The transformation shown in Equation 18 above can be achieved in a manner identical to that described for Equation 15.

Sulfonamides of Formula XVIIi can also be synthesized by a Baeyer-Villiger reaction on the appropriately substituted cyclopentanones XXIII as depicted in Equation 19.

Equation 19

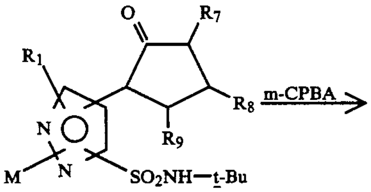

XXIII

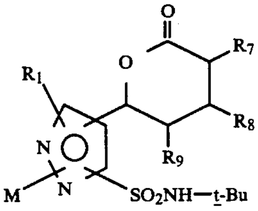

XVIIi wherein

M, $R_1$, $R_7$, $R_8$, and $R_9$ are as previously defined.

The oxidation shown in Equation 19 can be carried out by treating a solution of the ketone XXIII in a suitable solvent such as chloroform or methylene chloride with m-chloroperoxybenzoic acid (m-CPBA) according to the methods described by S. L. Friess, *J. Am. Chem. Soc.*, 71, 2571 (1949), and S. L. Friess and P. E. Frankenburg, ibid., 74, 2679 (1952). For a review of the Baeyer-Villiger reaction, refer to C. H. Hassall, *Org. Reactions*, 9, 73 (1957).

It should be recognized that removal of the tert-butyl protecting group from compounds of Formulas XVIIa-XVIIe by one of the methods described above in Equation 8 will furnish the primary sulfonamides of Formula IVb, where Q is Q-2, Q-3, Q-52, Q-53 and Q-54, which can then be converted to compounds of Formula I with the corresponding Q substituents.

Compounds of Formula XXIV(a-g) can be prepared by treatment of the corresponding lactones IVc, XVIIa, XVIIh, IVd, XVIIc, XVIIb and XVIIi, respectively, with ammonia or the appropriate primary amine, $R_3NH_2$, as shown below in Equation 20.

Equation 20
(a)
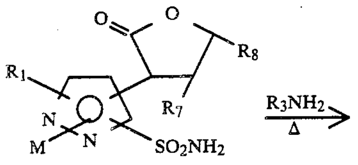
IVc
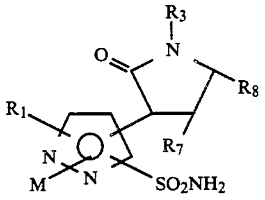
XXIVa
(b)
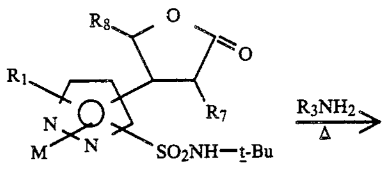
XVIIa
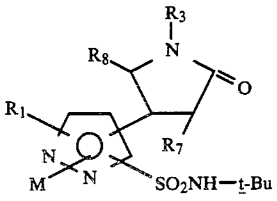
XXIVb
(c)
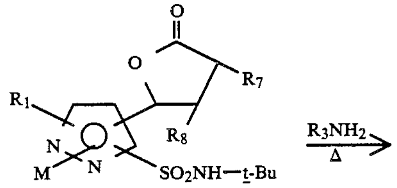
XVIIh
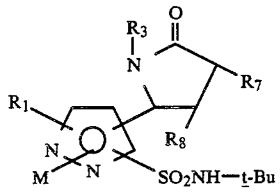
XXIVc
-continued
Equation 20
(d)
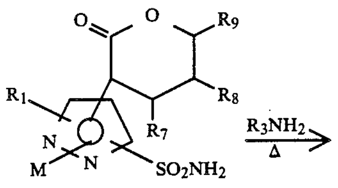
IVd
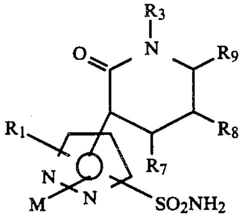
XXIVd
(e)
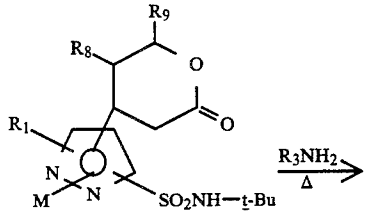
XVIIc
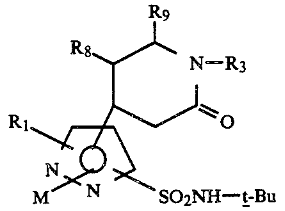
XXIVe
(f)
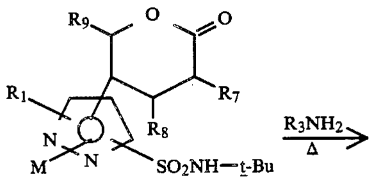
XVIIb
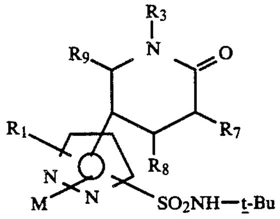
XXIVf -continued Equation 20

(g)

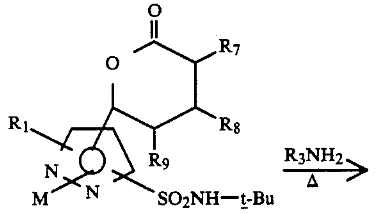

XVIIi

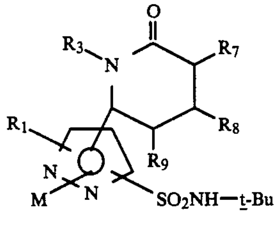

XXIVq wherein

M, $R_1$, $R_3$, $R_7$, $R_8$ and $R_9$ are as previously defined.

The conversion of lactones to lactams as shown in Equations 20(a)-20(g) is a well-known process and can be effectively carried out according to the procedures of Scott and Kearse, *J. Org. Chem.*, 5, 598 (1940), and Jones, et al., *J. Am. Chem. Soc.*, 48, 181 (1926); 49, 2528 (1927).

Lactams of Formulas XXIVh and XXIVi can be prepared as shown below in Equation 21 by an intramolecular N-actylation reaction of aminopyrazole derivatives of Formulas XXVa and XXVb.

Equation 21

(a)

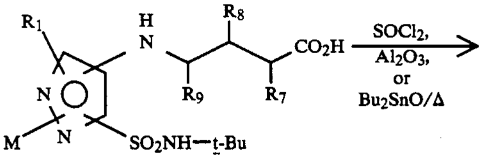

XXVa

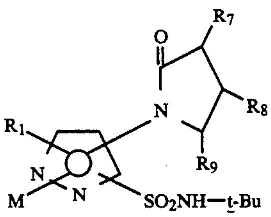

XXIVh (b)

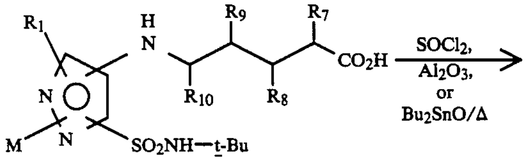

XXVb

-continued

Equation 21

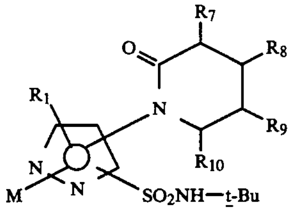

XXIVi wherein

M, $R_1$, $R_7$, $R_8$, $R_9$ and $R_{10}$ are as previously defined.

The reaction represented in Equations 21(a) and 21(b) can be accomplished by one or more of the following procedures: (1) treatment of compounds of Formulas XXVa and XXVb with thionyl chloride at reflux temperature to give intermediate acid chlorides which rapidly undergo cyclization (for related methods, see Kent and McElvain, *Org. Syntheses*, 25, 7 (1945); A. P. Martinez, et al., *J. Org. Chem.*, 26, 4501 (1961); W. B. Weaver and W. M. Whaley, *J. Am. Chem. Soc.*, 69, 515, 1144 (1947); and F. Falk. *J. Prakt. Chem.*, 15, 228 (1962)); (2) reaction of compounds of Formulas XXVa and XXVb with alumina or silica as described by A. Bladë-Font. *Tetrahedron Lett.*, 21, 2443 (1980); and (3) treatment of compounds XXVa and XXVb with dibutylthin oxide as described by K. Steliou, et al., *J. Am. Chem. Soc.*, 102, 7578 (1980).

Subsequent treatment of N-t-butylsulfonamides of Formulas XXIVb, c and e-i according to one of the methods described in Equation 8 will furnish the primary sulfonamides of Formula IVb, where Q is Q-5, Q-6, Q-55, Q-56, Q-57, Q-58 and Q-59, which can then be converted to compounds of Formula I with the corresponding substituents.

Ketones of Formulas XXIIIa and XXIIIb can be prepared via the two-step sequence of reactions shown below in Equation 22, starting from the appropriate olefins of Formulas XXVIa and XXVIb.

Equation 22

(a)

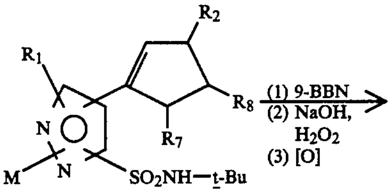

XXVIa

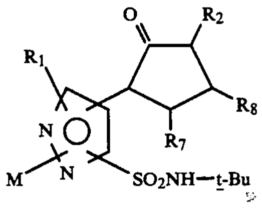

XXIIIa

-continued

Equation 22

(b)

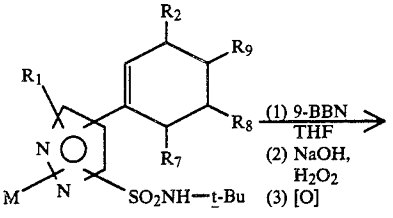

XXVIb

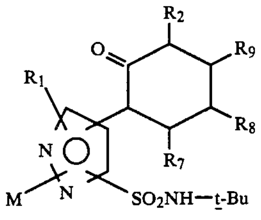

XXIIIb wherein

M, $R_1$, $R_2$, $R_7$, $R_8$ and $R_9$ are as previously defined.

The first step shown in Equations 22(a) and 22(b) above involves treating olefins of Formulas XXVIa and XXVIb with 9-borabicyclo[3.3.1]nonane (9-BBN) in a suitable solvent such as tetrahydrofuran, followed by an oxidative workup with basic hydrogen peroxide to generate intermediate secondary alcohols. For details of this procedure, see. E. F. Knights and H. C. Brown, *J. Am. Chem. Soc.*, 90, 5280, 5281 (1968). The oxidation of these intermediate secondary alcohols to afford the desired products of Formulas XXIIIa and XXIIIb can be accomplished by any one of numerous methods; e.g., with chromium trioxide in aqueous sulfuric acid (E. R. H. Jones, et al., *J. Chem. Soc.*, 2548 (1953)), chromium trioxide-pyridine (G. I. Poos, G. E. Arth, R. E. Beyler and L. H. Sareff, *J. Am. Chem. Soc.*, 75, 422 (1953)), or pyridinium chlorochromate (E. J. Corey and T. L. Suggs, *Tetrahedron Lett.*, 2647 (1975)).

The requisite olefins of Formulas XXVI(a–d) can be synthesized by the two-step sequence of reactions represented in Equations 23(a–d), starting from the appropriate N-t-butylpyrazolesulfonamides of Formula XXa.

Equation 23

(a)

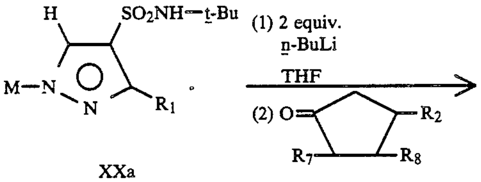

XXa

-continued

Equation 23

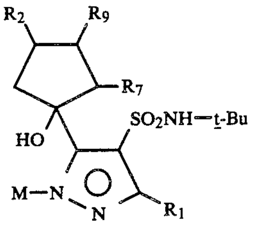

XXVIIa

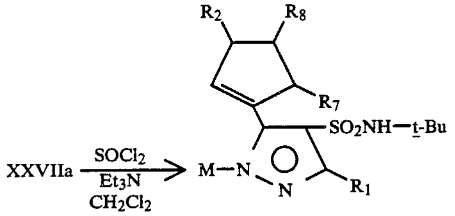

XXVIa (b)

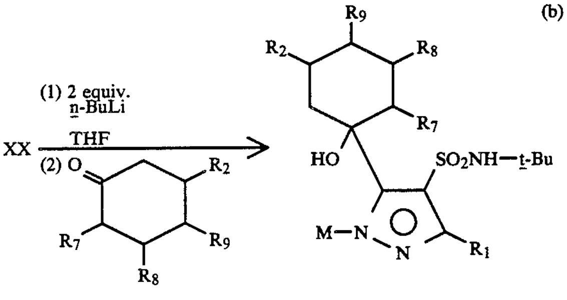

XXVIIb

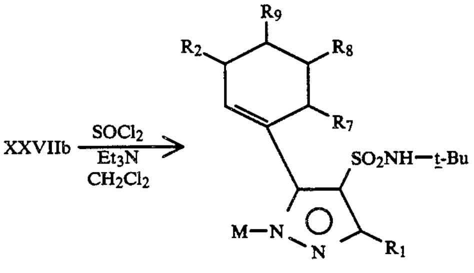

XXVIb (c)

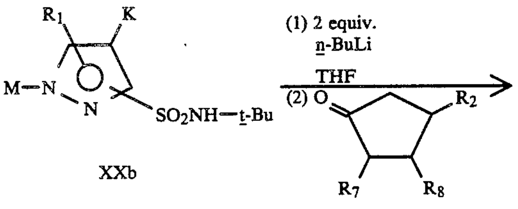

XXb

-continued

Equation 23

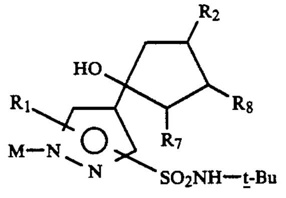

XXVIIc

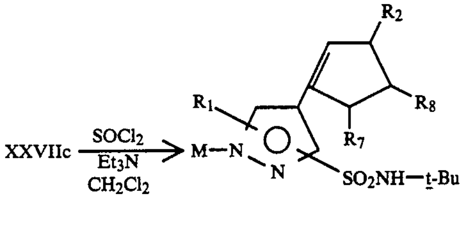

XXVIc (d)

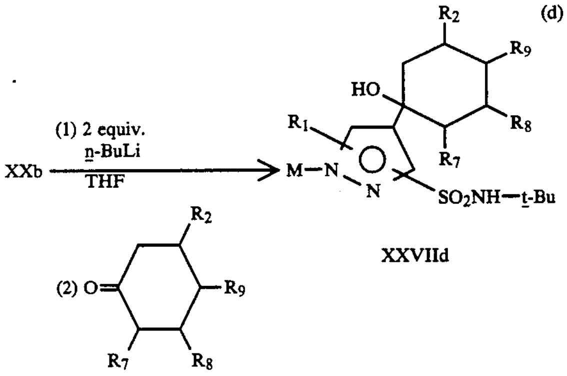

XXVIId

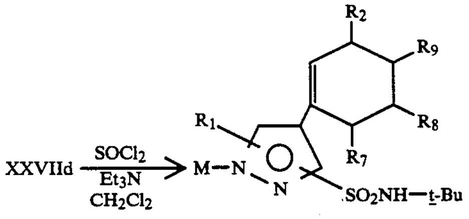

XXVId wherein

M, $R_1$, $R_2$, $R_7$, $R_8$ and $R_9$ are as previously defined, and K is Br.

The first step of Equations 23(a–d) can be carried out as described for Equations 12(a) and 17. Addition of the appropriate cycloalkanone derivatives to the dianions of sulfonamides XXa and XXb, and subsequent aqueous acid workup gives intermediate alcohols of Formulas XXVII(a–d). The second step depicted in Equations 23(a–d) involves treatment of the alcohols XXVII(a–d) with thionyl chloride in the presence of a suitable acid scavenger such as triethylamine at 0°–25° C. to give the olefins of Formulas XXVI(a–d), respectively. For a detailed description of this standard dehydration method, refer to Linstead and Meade, *J. Chem. Soc.*, 942 (1934), or Cook and Lawrence, *J. Chem. Soc.*, 1637 (1935).

The requisite olefins of Formulas XXVIe and XXVIf can be synthesized by a Wittig induced intramolecular cyclization represented in Equations 23(e,f).

Equation 23

(e)

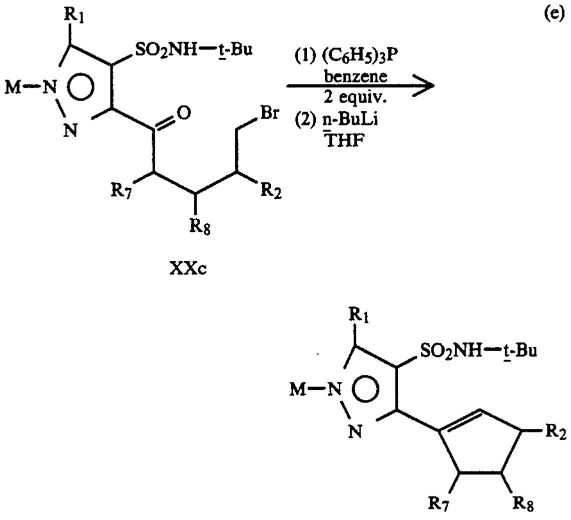

XXc

XXVIe (f)

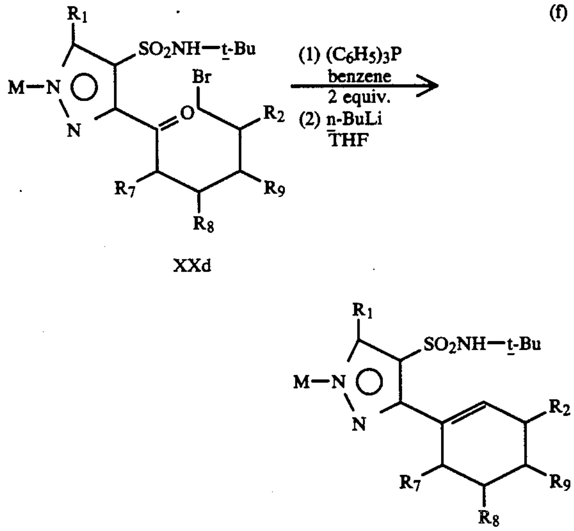

XXd

XXVIf wherein

M, $R_1$, $R_7$, $R_8$, and $R_9$ areas previously defined.

The intramolecular cyclization depicted in Equations 23(e,f) is most effectively carried out by treating compounds of Formulas XXc and XXd with two equivalents of a suitable base such as n-butyl lithium. For a discussion of Wittig induced intramolecular cyclizations, refer to H. O. House, "Modern Synthetic Reactions", 2nd Ed., W. A. Benjamin, Inc., New York, 1972, pp. 697–698 and references cited therein.

Ketones of Formulas XXIII(c–f) can be most conveniently synthesized by a process somewhat related to that of Equation 23, except that α,β-unsaturated cycloalkenones are employed in the reaction with dianions of N-t-butylpyrazolesulfonamides XXa and XXb instead of cycloalkanones. The result is a 1,4-addition to give the desired products of Formulas XXIII(c–f) as shown below in Equation 24.

Equation 24

(a)

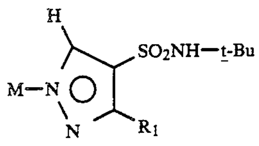

XXa

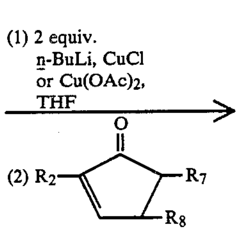

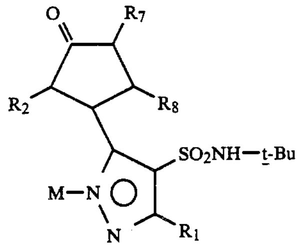

XXIIIc (b)

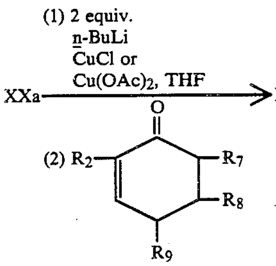

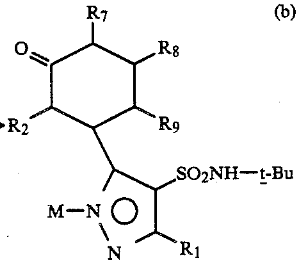

XXIIId (c)

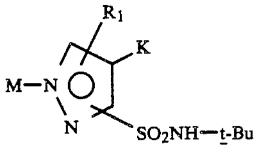

XXb

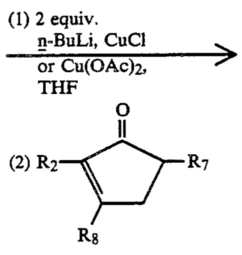

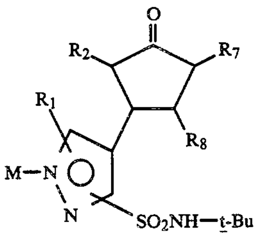

XXIIIe

-continued

Equation 24

(d)

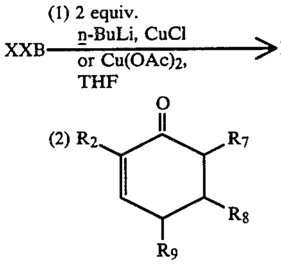

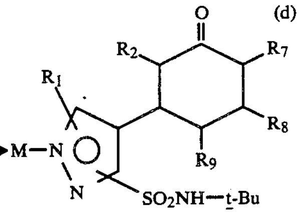

XXIIIf wherein

M, $R_1$, $R_2$, $R_7$, $R_8$ and $R_9$ are as previously defined, and K is Br.

The first step shown in Equations 24(a–d) involves the formation of N-t-butylpyrazolesulfonamide dianions as described for Equations 17 and 12(a). However, in the case of the reactions shown above in Equation 24, a suitable copper ion catalyst such as cuprous chloride or cupric acetate is added to form aryl copper reagents, which then undergo a conjugate addition to substituted cycloalkenones to generate the desired products of Formulas XXIII(c–f) after aqueous workup. Such as transformation is well precedented in the literature; for relevant examples, see Gorlier, Harmon, Levisalles and Wagnon, *Chem. Comm.*, 88 (1973); Posner, *Org. Reactions* 19, 1 (1972); or House *Acc. Chem., Res.*, 9, 59 (1976).

Ketones of Formulas XXIII(g,h) can be synthesized by a Dieckmann condensation followed by hydrolysis and decarboxylation as depicted in Equations 24(e,f).

Equation 24

(e)

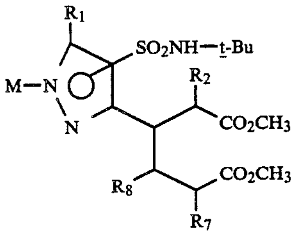

XXd

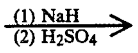

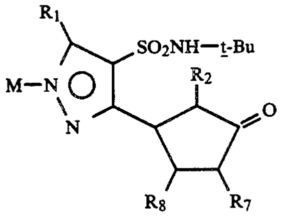

XXIIIg

-continued

Equation 24

(f)

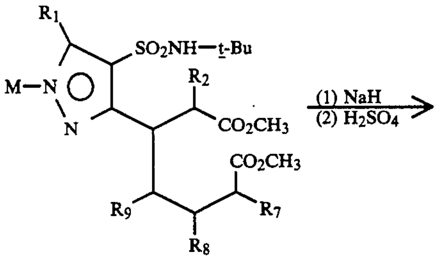

XXe

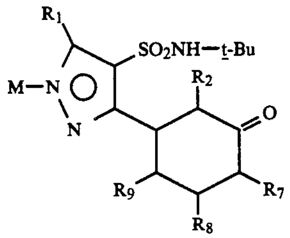

XXIIIh wherein

M, $R_1$, $R_2$, $R_7$, $R_8$, and $R_9$ are as previously defined.

The Dieckmann condensation is well precedented in the literature; for a review of this reaction see Schaefer and Bloomfield, *Org. Reactions,* 15, 1 (1967).

Ketones of Formula XXIIIi, where $R_8$ is H, can be synthesized in a straightforward manner via the three-step sequence of reactions shown in Equation 25 involving: (a) selective reduction of esters of Formula XXVIII to aldehydes of Formula XXIX, (b) base-induced aldol condensation and dehydration to give enones of Formula XXX, and (c) selective reduction of the olefinic bond of enones XXX to provide the desired products.

Equation 25

(a)

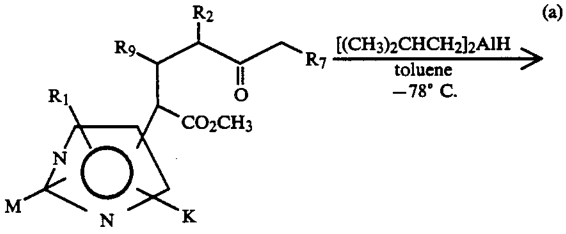

XXVIII

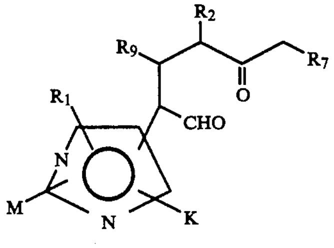

XXIX

-continued

Equation 25

(b)

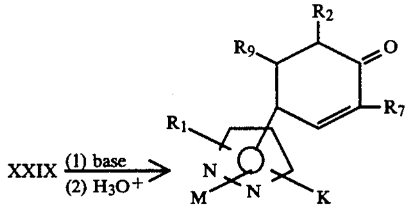

XXX (c)

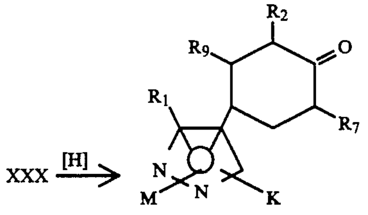

XXIIIi wherein

M, $R_1$, $R_2$, $R_7$, $R_8$, and $R_9$ are as previously defined, K is Br, H, or $SR_{12}$, and $R_{12}$ is $C_2$–$C_4$ alkyl or benzyl.

The selective reduction of carboxylic esters, such as those of Formula XXVIII, to the corresponding aldehydes of Formula XXIX as shown in Equation 25(a) can be achieved with diisobutylaluminum hydride (DIBAL) at low temperatures as described by E. J. Corey, K. C. Nicolaou and T. Toru, *J. Am. Chem. Soc.,* 97, 2287 (1975). The intramolecular aldol condensation depicted in Equation 25(b) is effectively carried out by treating the compounds of Formula XXIX with a catalytic amount of a suitable base such as sodium methoxide or potassium tert-butoxide. Subsequent aqueous acid workup results in dehydration of the intermediate aldols to give the enones of Formula XXX. Alternatively, the aldol condensation can be achieved under conditions of acid catalysis, in which case the enones XXX are obtained directly. For a comprehensive review of this well-known reaction, see A. T. Nielsen and W. J. Houlihan, *Org. Reactions,* 16, 1 (1968). Equation 25(c) represents a selective reduction of the olefinic bond of α,β-unsaturated ketones XXX, and can be accomplished by any one of several methods. Two such methods are catalytic hydrogenation (see H. O. House, "Modern Synthetic Methods", 2nd Ed., W. A. Benjamin, Inc., Menlo Park, 1972, pp. 26–28), and dissolving metal reduction with lithium in liquid ammonia (H. O. House, ibid, pp. 174–176).

Ketones of Formula XXIIIh, where $R_8$ is as defined in the Summary of the Invention, can be easily synthesized by the 1,4-conjugate addition of appropriate cuprate reagents to enones of Formula XXX, as shown below in Equation 26.

Equation 26

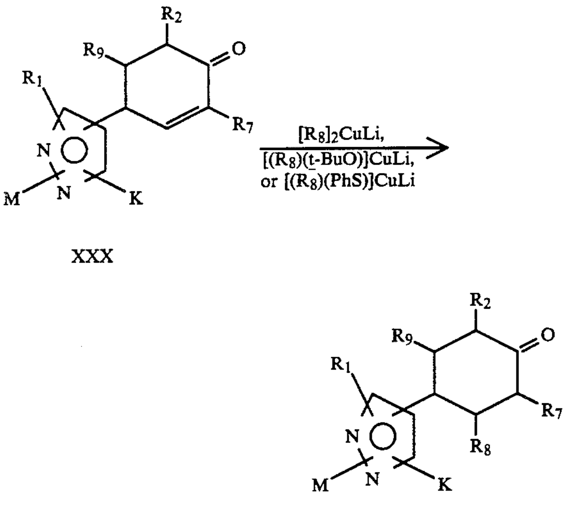

XXX

XXIIIh wherein

M, $R_1$, $R_2$, $R_7$, $R_8$ and $R_9$ are as previously defined, K is Br, H, or $SR_{12}$, and $R_{12}$ is $C_2$–$C_4$ alkyl or benzyl.

The 1,4-conjugate addition reaction of Equation 26 can be conveniently carried out according to the procedure described by House, Respess and Whitesides, *J. Org. Chem.*, 31, 3128 (1966) when the copper reagent is of the form [$R_8$]$_2$CuLi. For use of "mixed" copper reagents, see Posner and Whitten, *Tetrahedron Lett.*, 1815 (1973) (for the reagent [($R_8$)(t-BuO)]CuLi), or Posner, Whitten and Sterling, *J. Am. Chem. Soc.*, 95, 7788 (1973) (for the reagent [($R_8$)(PhS)]CuLi).

It should be recognized that compounds of Formulas XXIIIg and XXIIIh can be treated according to one or more of the methods described in Equations 11–13 to afford the corresponding sulfonyl chlorides of Formula IX, where Q is Q-61. Similarly, removal of the tert-butyl group from compounds of Formulas XXIIIa–d by one or more of the procedures outlined in Equation 8 will furnish the primary sulfonamides of Formula IV, where Q is Q-8, Q-9, Q-60 or Q-62, which can then be converted to compounds of Formula I with the corresponding Q substituents.

The requisite aminopyrazole derivatives of Formulas XXVa and XXVb can be prepared in a straightforward fashion by N-alkylation of compounds of Formula XXXI with the appropriate γ or δ-bromo esters, followed by saponification of the intermediate compounds of Formulas XXXIIa and XXXIIb, as shown below in Equation 27.

Equation 27

(a)

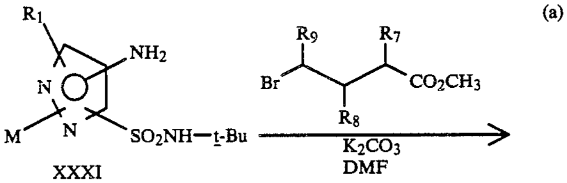

XXXI

-continued

Equation 27

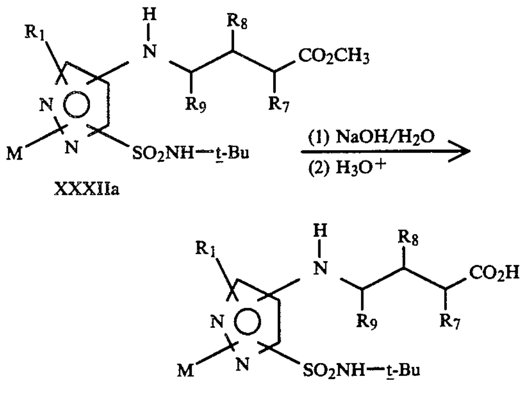

XXXIIa

XXVa (b)

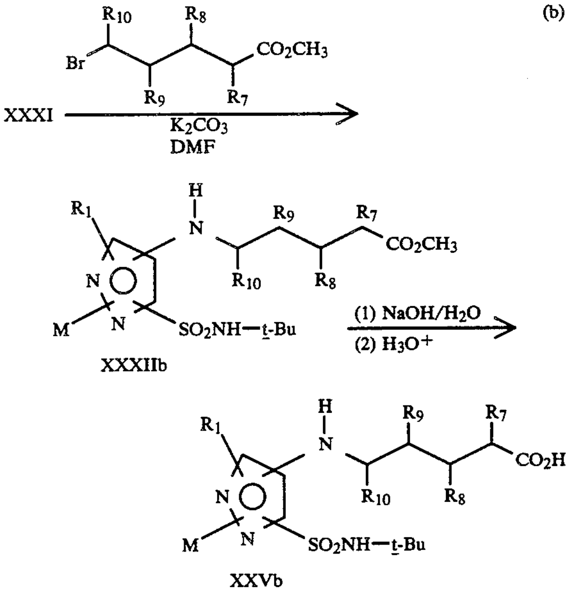

XXXI

XXXIIb

XXVb wherein

M, $R_1$, $R_7$, $R_8$, $R_9$ and $R_{10}$ are as previously defined.

The first step of Equations 27(a) and 27(b) is achieved by stirring a mixture of the aniline derivative XXXI and the appropriate γ- or δ-bromo ester together in the presence of an excess of a suitable base such as anhydrous potassium carbonate in a polar solvent such as N,N-dimethylformamide at temperatures of 25°–110° C. until all of the aminopyrazole derivative has been consumed. The intermediate compounds of Formulas XXXIIa and XXXIIb can then be isolated by pouring the reaction mixture into ice-water, neutralizing by the addition of dilute aqueous mineral acid, and either filtration or extraction into a suitable organic solvent such as diethyl ether, methylene chloride, or ethyl acetate. These compounds of Formulas XXXIIa and XXXIIb are then treated with excess dilute aqueous sodium hydroxide solution at about 25° C. for 1–6 hours. Acidification with concentrated hydrochloric acid (ice-water cooling) followed by either filtration or extraction as described above and removal of the solvent in vacuo affords the desired aminopyrazole derivatives of Formulas XXVa and XXVb.

The 4-amino-N-t-butylpyrazolesulfonamides of Formula XXXIa can be prepared from the appropriate 4-nitropyrazolesulfonyl chlorides XXXIVa by treatment with tert-butylamine, followed by reduction of the nitro group as depicted in Equation 28a.

Equation 28

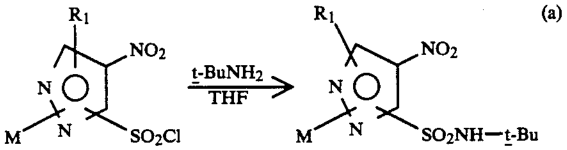

XXXIVa XXXIII

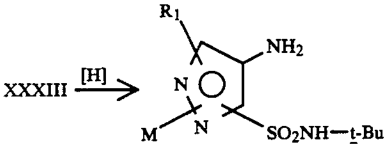

XXXIa wherein

M and $R_1$ are as previously defined.

The first step of Equation 28a is effected by adding a solution of the appropriate nitropyrazolesulfonyl chloride XXXIVa in a suitable solvent such as tetrahydrofuran or methylene chloride to a solution of excess tert-butylamine in the same solvent at about 0° C. After being stirred at 0°–25° C. for 2 to 24 hours, the reaction mixture is washed with water, and the organic layer dried and evaporated to give the desired intermediates of Formulas XXXIII and XXXIa. Intermediates of Formula XXXIII are generally sufficiently pure for reduction of nitro functionality to the corresponding 4-aminopyrazole derivatives XXXIa.

A wide variety of methods exist for effecting the reduction of aromatic nitro groups to the corresponding aromatic amino derivatives. One of the more common procedures involves treating the nitro compounds of Formula XXXIII with a slight excess of stannous chloride dihydrate in concentrated hydrochloric acid at temperatures between 25° and 80° C. Reduction can be accomplished with iron powder in glacial acetic acid as described by Hazlet and Dornfeld, *J. Am. Chem. Soc.*, 66, 1781 (1944), and by West, *J. Chem. Soc.*, 127, 494 (1925). For a general review, see Groggins in "Unit Processes in Organic Synthesis", McGraw-Hill Book Co., New York, 1947, pp. 73–128.

The 3(5)-amino-N-t-butylpyrazolesulfonamides of Formula XXXIb can be prepared by chlorosulfonation of the 3(5)-acetamidopyrazoles of Formula XVIc, followed by treating the intermediate 3(5)-aminopyrazole-4-sulfonyl chloride IXd with tert-butylamine as depicted in Equation 28(b).

Equation 28b

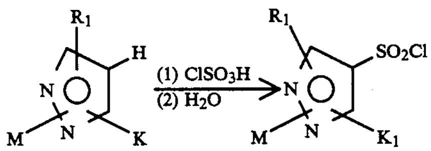

XVIc IXd

-continued

Equation 28b

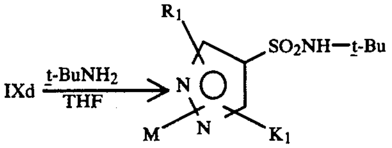

XXXIb wherein

M and $R_1$ are as previously defined,

K is $NHCOCH_3$; and $K_1$ is $NH_2$.

The chlorosulfonation step shown in Equation 28(b) can be effected by the procedure described for Equation 12(c). The second step of Equation 28(b) is carried out in an identical manner to the procedure described previously for Equation 28(a).

A judicious choice of the appropriate method for preparing compounds of Formula XXXIa and XXXIb must take into account the nature of the substituents M and $R_1$, and their chemical compatibility with the reaction conditions of Equations 28(a) and 28(b). Such a decision would be obvious to one who is skilled in the art.

The requisite unsaturated carboxylic acids of Formula XXII can be conveniently synthesized by dehydration of the appropriate hydroxy esters of Formula XXIa, followed by saponification as shown in Equation 29.

Equation 29

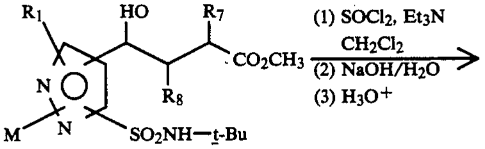

XXIa

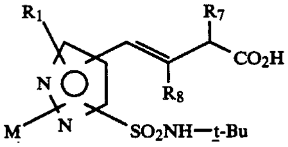

XXII wherein

M, $R_1$, $R_7$ and $R_8$ are as previously defined.

The first step of Equation 29, dehydration of alcohols of Formula XXIa to give the corresponding olefins, can be carried out in a manner identical to that described for the second step in Equations 23(a–d). The saponification shown in Equations 29 (steps 2 and 3) can be accomplished as described for the second step in Equations 17(a) and 17(b).

The carboxylic esters of Formula XXVIIi can be prepared by treatment of the anions derived from pyrazoylacetic esters of Formula XXXV with the appropriate α,β-unsaturated ketones as shown below in Equation 30.

Equation 30

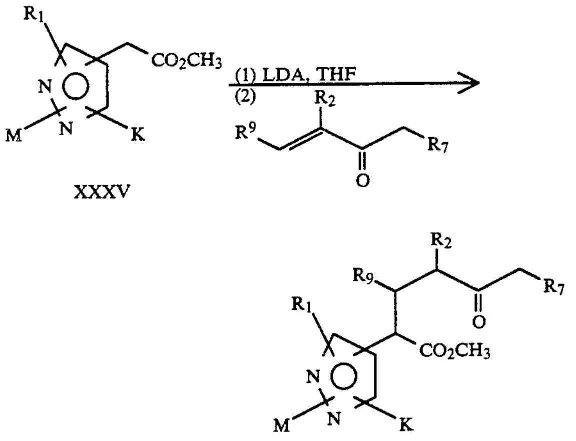

XXXV

XXVIII wherein

M, $R_1$, $R_2$, $R_7$ and $R_9$ are as previously defined, K is Br, H, or $SR_{12}$, and $R_{12}$ is $C_2$-$C_4$ alkyl or benzyl.

The reaction of Equation 30 is conveniently carried out by adding a solution of the pyrazoylacetic ester XXXV in a suitable solvent such as tetrahydrofuran to a solution of a strong base such as lithium diisopropylamide (LDA) at −78° to 0° C. under an inert atmosphere. The mixture is stirred at temperatures below 0° C. for 0.5-1 hour to ensure complete anion formation and is then treated with an equimolar quantity of the appropriately substituted, α,β-unsaturated ketones, which are prone to undergo reaction in a 1,4-conjugate manner. For a compilation of references dealing with this type of reaction, see Bergmann, Ginsburg, and Pappo, *Org. Reactions,* 10, 179 (1959).

The requisite N-t-butylpyrazolesulfonamides of Formulas XVIIIa, XVIIIb, XVIIIc, and XIX can all be synthesized from common pyrazoleacetic esters of Formula XXXVI via a sequence of reactions that entails the same seven basic processes. Equation 31 outlines this sequence of reactions leading to compounds of Formula XVIIIa (where $R_7$ is H): (a) alkylation of the anion derived from the appropriate pyrazoylacetic esters of Formula XXXVI with aldehydes of Formula $R_8CHO$ to give β-hydroxy pyrazoylacetic esters of Formula XXXVII, (b) protection of the alcohol with a suitable protecting group such as the benzyl ether of Formula XXXVIII, (c) reduction of the esters of Formula XXXVIII to afford primary alcohols of Formula XXXIX, (d) conversion of the hydroxyl group to a good leaving group such as the alkyl bromide of Formula XL, (e) conversion of the ortho substituent K to a N-t-butylsulfamoyl group by one of the methods described previously, (f) displacement of the bromides of Formula XLI to give the corresponding nitriles of Formula XLII, and (g) hydrolysis of the nitriles XLII to afford the carboxylic acids of Formula XVIIIa, where $R_7$ is H.

Equation 31

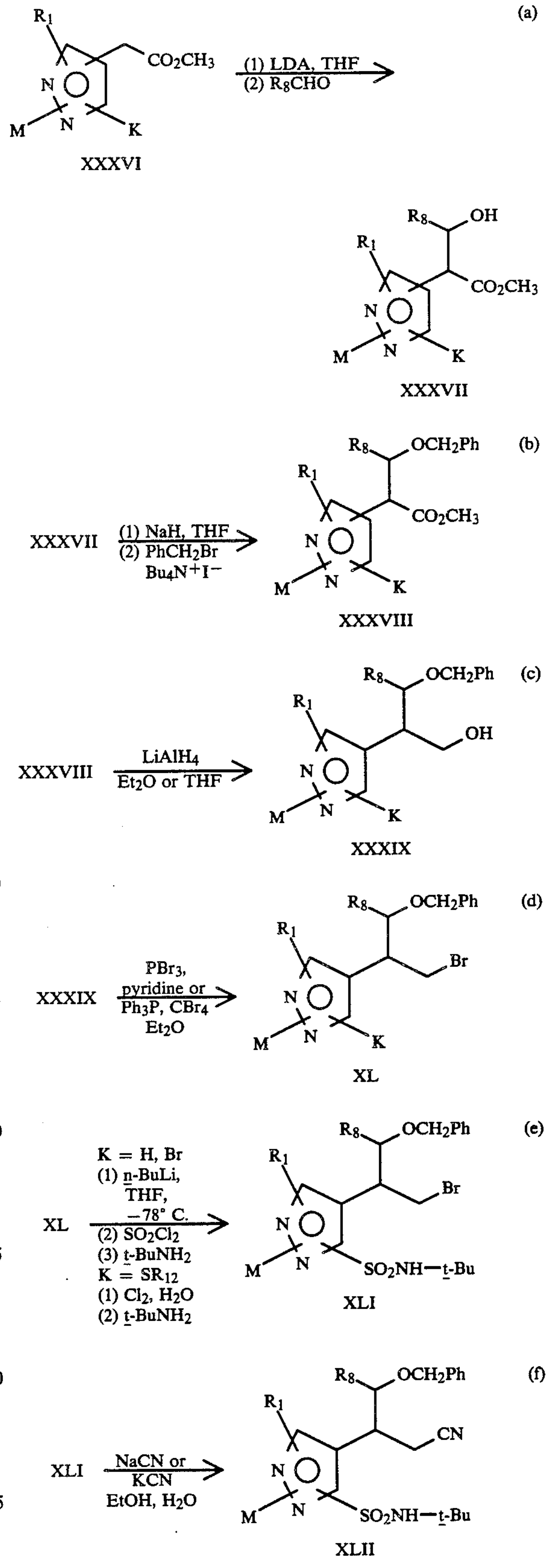

XXXVI

XXXVII

XXXVIII

XXXIX

XL

XLI

XLII

-continued

Equation 31

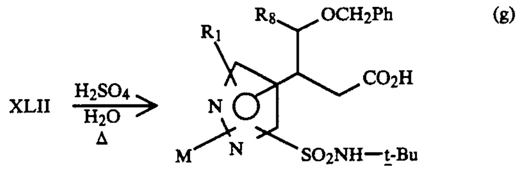

XLII

XVIIIa ($R_7$ = H)

wherein

M, $R_1$ and $R_8$ are as previously defined, K is H, Br or $SR_{12}$, and $R_{12}$ is $C_2$–$C_4$ alkyl or benzyl.

Equation 31(a)

Anions of pyrazoylacetic esters of Formula XXXVI can be formed as shown in Equation 31(a) by treatment with a suitable base such as lithium diisopropylamide (LDA). For a description of this procedure, see Equation 30. Other methods for the preparation and reaction of aliphatic ester enolates have been described by M. W. Rathke, *J. Am. Chem. Soc.*, 92, 3222 (1970), M. W. Rathke and D. F. Sullivan, ibid., 95, 3050 (1973), and M. W. Rathke and A. Lindert, *ibid.*, 93, 2318 (1971). Addition of the appropriate aldehydes of structure $R_8CHO$ to these anions gives the desired β-hydroxy esters XXXVII.

Equation 31(b)

The reaction of Equation 31(b) is accomplished by formation of the sodium alkoxide of alcohols XXXVII with sodium hydride, and treatment with benzyl bromide in the presence of a phase-transfer catalyst such as tetrabutylammonium iodide. For a description of this procedure, see S. Czernecki, C. Georgoulis and C. Provelenghiou, *Tetrahedron Lett.*, 3535 (1976).

Equation 31(c)

The reduction of carboxylic esters such as those of Formula XXXVIII with lithium aluminum hydride as shown in Equation 31(c) is a well-known process and can be carried according to the procedures described by Gaylord, "Reduction with Complex Metal Hydrides", Interscience Publishers, Inc., New York, 1956, pp. 391–531.

Equation 31(d)

The transformation shown in Equation 31(d) can be achieved by one or more of the following procedures: treatment of alcohols of Formula XXXIX with phosphorus tribromide in pyridine (Shone, et al., *J. Am. Chem. Soc.*, 58, 585 (1936)), or with triphenyl phosphine-carbon tetrabromide (Lee and Downie, *Tetrahedron*, 23, 2789 (1967); Hooz and Gilani, *Can. J. Chem.*, 46, 86 (1968)).

Equation 31(e)

Compounds of Formula XL, where K is H or Br, can be converted to the corresponding sulfonyl chlorides as described for Equations 12a and 12b. Treatment of these sulfonyl chlorides in a manner identical to that described in Equation 28 then affords the desired products of Formula XLI. Compounds of Formula XL, where K is $SR_{12}$, are efficiently converted to the corresponding sulfonyl chlorides in a manner identical to that described in Equation 13.

Equation 31(f)

The nucleophilic displacement reaction depicted in Equation 31(f) can be accomplished by treating bromides of Formula XLI with sodium or potassium cyanide according to the procedure of J. R. Ruhoff, *Org. Syntheses*, Coll. Vol. II, 292 (1943).

Equation 31(g)

Nitriles of Formula XLII can be conveniently converted to the corresponding acids of Formula XVIIIa, where $R_7$ is H, by treatment with sulfuric acid in the presence of water as described by Adams and Thal, *Org. Syntheses*, Coll. Vol. I, 436 (1941), and Wenner, *J. Org. Chem.*, 15, 548 (1950).

Compounds of Formula XVIIIa, where $R_7$ is other than H, can be conveniently prepared from the corresponding unsubstituted acids of Formula XVIIIa, where $R_7$=H, by formation of the O,α-dianion and subsequent trapping with the appropriate electrophile as shown in Equation 32.

Equation 32

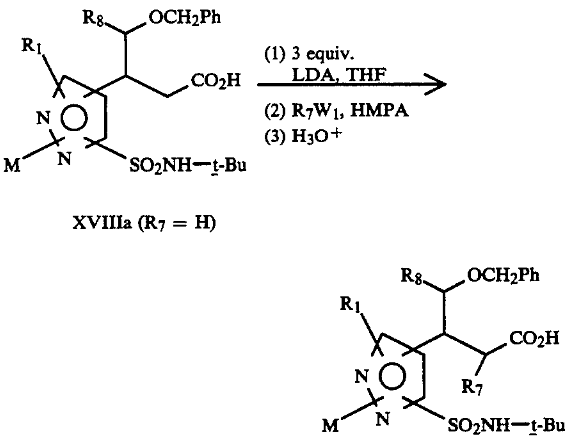

XVIIIa ($R_7$ = H)

XVIIIa wherein

M, $R_1$, $R_7$ and $R_8$ are as defined above except $R_7$ is other than H, and $W_1$ is Cl, Br or I.

The alkylation of Equation 32 can be accomplished in a manner analogous to that described in Equation 31(a), except that 3 equivalents of a strong base such as LDA are required, and an electrophile of Formula $R_7W_1$, where $R_7$ is other than H and $W_1$ is Cl, Br, or I, is used to trap the enolate in lieu of an aldehyde. For relevant references, see. J. C. Stowell, "Carbanions in Organic Synthesis", John Wiley and Sons, Inc., New York, 1979, pp 157–161.

As mentioned above, N-t-butylpyrazolesulfonamides of Formulas XVIIIb, XVIIIc, and XIX can all be synthesized from the appropriate pyrazoylacetic esters of Formula XXXVI in multi-step reaction schemes analogous to that described in Equation 31 for compounds of Formula XVIIIa. The minor modifications in reaction conditions necessary to achieve these syntheses would be obvious to one who is skilled in the art.

Butenolides of Formula XLIIIa can be prepared as shown below in Equation 33 by oxidation of the α-phenylthioethers XLIVa and subsequent thermolytic elimination.

Equation 33

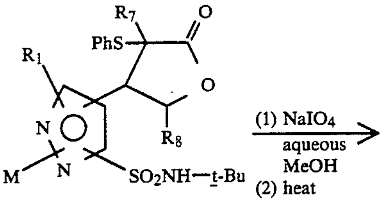

XLIVa

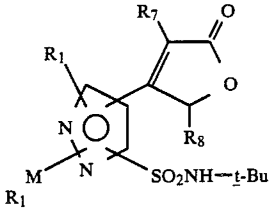

XLIIIa wherein

M, $R_1$, $R_7$ and $R_8$ are as previously defined.

The reactions of Equation 33 can be carried out according to the procedure of B. M. Trost and T. N. Salzmann, *J. Am. Chem. Soc.*, 95, 6840 (1973).

The requisite α-phenylthioethers XLIVa are readily obtained by treatment of the corresponding lactone of Formula XVIIa with a suitable base to generate the enolate, followed by trapping with diphenyl disulfide or phenylsulfenyl chloride as outlined in Equation 34.

Equation 34

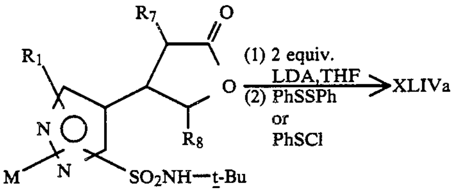

XVIIa wherein

M, $R_1$, $R_7$ and $R_8$ are as previously defined.

The α-alkylation of lactone enolates is a well-known process and can be successfully carried out according to G. H. Posner and G. L. Loomis, *Chem. Comm.*, 892 (1972), and K. Iwai, et al., *Chem. Letters*, 385 (1974). For use of diphenyl disulfide as the electrophile, see the reference cited for Equation 33. In the case of N-t-butylpyrazolesulfonamides of Formula XVIIa, it is necessary to use two molar equivalents of base. The first equivalent of base removes the acidic N-H proton, and the second equivalent forms the lactone enolate.

By using processes analogous to those described above in Equations 33 and 34, or modifications thereof, it is possible for one skilled in the art to prepare α,β-unsaturated lactones of Formulas XLIIIb-XLIIIe from the appropriate saturated precursors of Formulas XVIIb-XVIIe as represented in Equations 35(a-d).

Equation 35

(a)

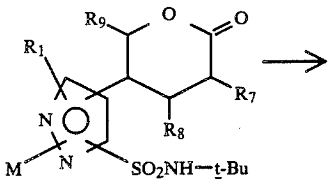

XVIIb

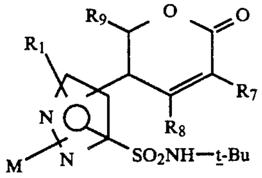

XLIIIb (b)

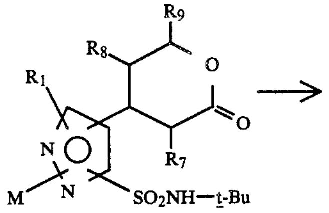

XVIIc

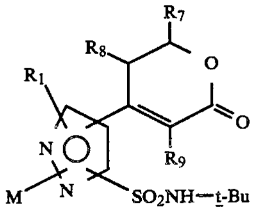

XLIIIc (c)

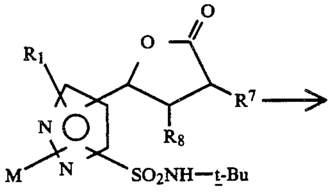

XVIId

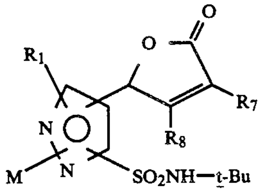

XLIIId

-continued

Equation 35

(d)

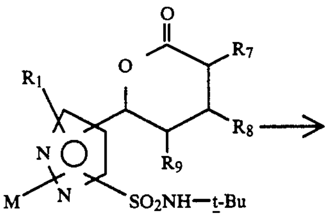

XVIIe

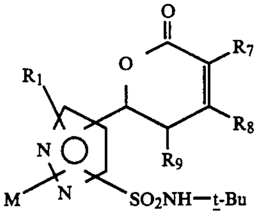

XLIIIe wherein

M, $R_1$, $R_7$, $R_8$ and $R_9$ are as previously defined.

An alternative route to the lactones of Formula XLIIIe above where $R_8$ is $C_1$–$C_4$ alkyl and $R_9$ is H involves the addition of the dienolates of the substituted crotonate esters of Formula XLIIIf to the aldehyde XLIIIg according to the procedure of R. W. Dagger and C. H. Heathcock, *J. Org. Chem.*, 45, 1181 (1980), as shown in Equation 35e. Aldehyde XLIIIg can be synthesized by the addition of N,N-dimethylformamide (DMF) to the dianions of the Formula XXa and XXb.

Equation 35e

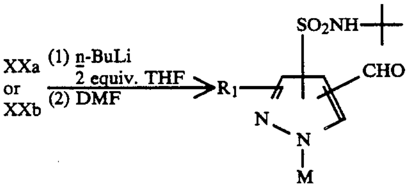

XLIIIq

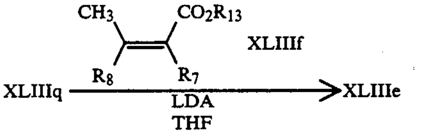

wherein

K, M, $R_1$ and $R_7$ are as previously defined, $R_8$ and $R_{13}$ are $C_1$–$C_4$ alkyl, and $R_9$ is H.

In a similar fashion, which is obvious to one skilled in the art, the lactams of Formulas XXIVa–XXIVi, where $R_3$ is other than H, can be converted to the corresponding $\alpha,\beta$-unsaturated lactams of Formulas XLVa–XLVe as outlined in Equations 36(a–i).

Equation 36

(a)

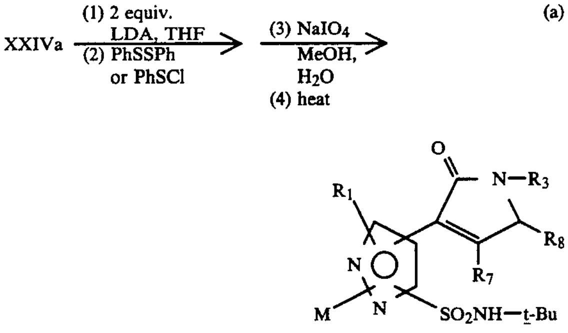

XLVa (b)

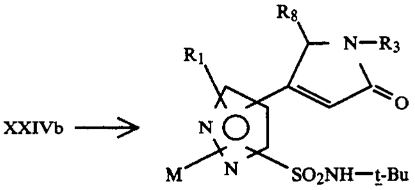

XLVb (c)

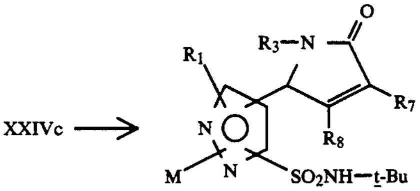

XLVc (d)

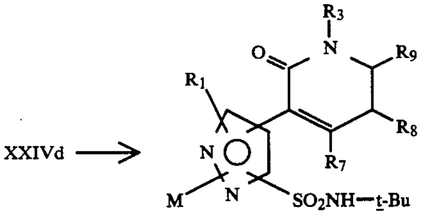

XLVd (e)

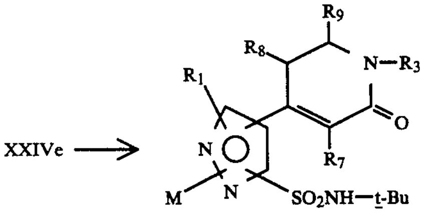

XLVe (f)

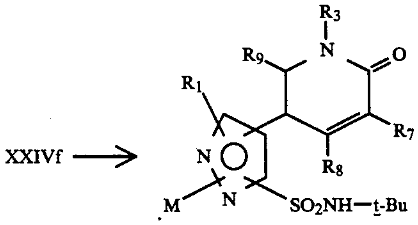

XLVf

-continued

Equation 36

(g)

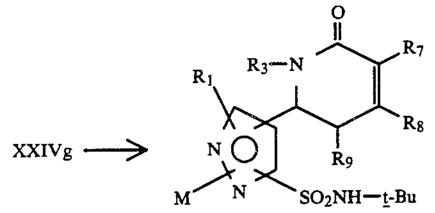

XLVg (h)

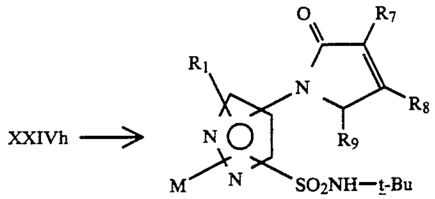

XLVh (i)

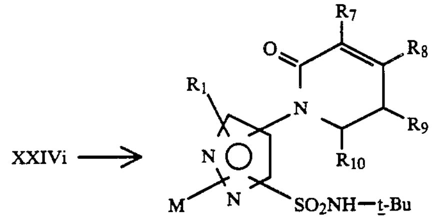

XLVi wherein

M, $R_1$, $R_3$, $R_7$, $R_8$, $R_9$ and $R_{10}$ are as previously defined except $R_3$ is other than H.

Unsaturated lactams of Formulas XLVa–XLVg, where $R_3$ is H, can be prepared by methods similar to those described in Equation 36. However, it is necessary to use one extra equivalent of a base such as lithium diisopropylamide (LDA) to generate the N, α-dianions XLVI, which can then be treated with diphenyl disulfide or phenylsulfenyl chloride in a manner identical to that described above to afford the desired products of Formulas XLVa–XLVg, where $R_3$ is H. Equation 37 depicts this procedure as it applies to the preparation of lactams of Formula XLVa ($R_3$=H) from the appropriate saturated precursor of Formula XXIVa.

Equation 37

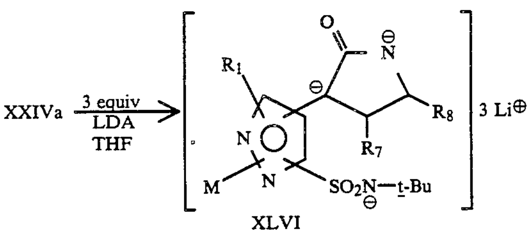

XLVI

-continued

Equation 37

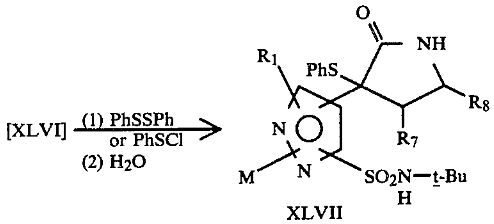

XLVII

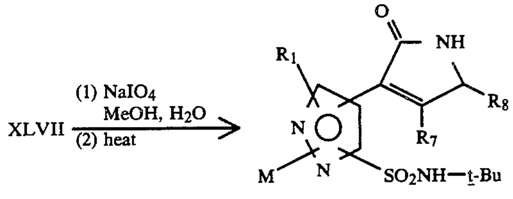

XLVa ($R_3$ = H)

wherein

M, $R_1$, $R_7$ and $R_8$ are as previously defined.

For procedures dealing with the formation and alkylation of lactam α-anions such as those described in Equation 36, see P. A. Zoretic and F. Barcelos, *Tetrahedron Lett.,* 529 (1977), or B. M. Trost and R. A. Kunz, *J. Org. Chem.,* 39, 2475 (1974).

The method shown in Equation 37 can be applied to the synthesis of unsaturated lactams of Formulas XLVb–XLVg, where $R_3$ is H. For a relevant reference, see J-P. Deprés, A. E. Greene and P. Crabbe, *Tetrahedron Lett.,* 2191 (1978).

Removal of the tert-butyl protecting group from compounds of Formula XLIIIa–XLIIIg and XLVa–XLVi by one or more of the procedures described in Equation 8 will give the primary sulfonamides of Formula IVb, where Q is Q-29, Q-30, Q-31, Q-32, Q-33, Q-34, Q-35, Q-95, Q-96, Q-97, Q-98, Q-99, Q-100, Q-101, Q-102, or Q-103. These sulfonamides can then be converted to compounds of Formula I with the corresponding substituents.

Enones of Formulas XLVIIIa and XLVIIIb can be conveniently prepared as shown below in Equation 38 by an intramolecular aldol condensation of the appropriate carbonyl compounds of Formulas XLIXa and XLIXb.

Equation 38

(a)

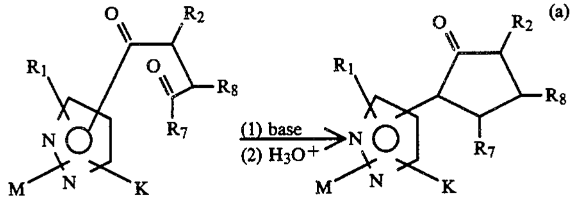

XLIXa XLVIIIa

-continued

Equation 38

(b)

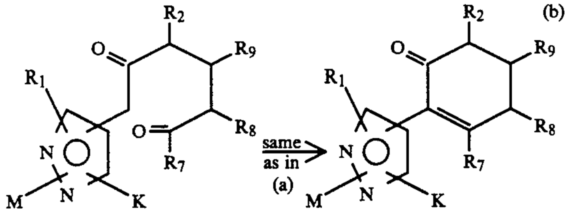

XLIXb XLVIIIb wherein

M, $R_1$, $R_2$, $R_7$, $R_8$ and $R_9$ are as previously defined, K is H, Br, or $SR_{12}$, and $R_{12}$ is $C_2$–$C_4$ alkyl or benzyl.

The aldol condensation depicted in Equations 38(a) and 38(b) can be carried out in a manner analogous to that described for Equation 25(b).

In a similar fashion, enones of Formulas XLVIIIc–XLVIIIi can be prepared from the appropriate carbonyl compounds of Formulas XLIXc–XLIXi as outlined below in Equations 39(a–g).

Equation 39

(a)

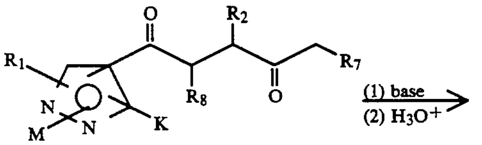

XLIXc

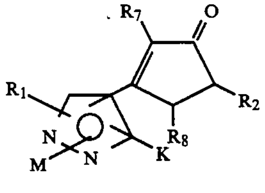

XLVIIIc (b)

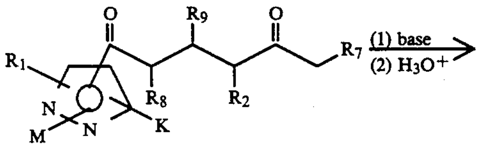

XLIXd

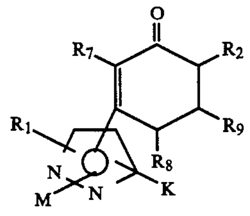

XLVIIId

-continued

Equation 39

(c)

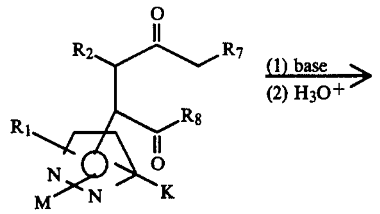

XLIXe

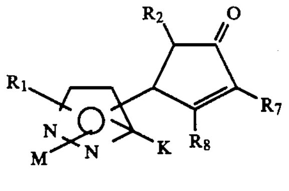

XLVIIIe (d)

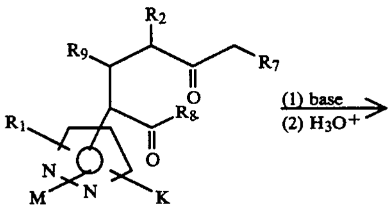

XLIXf

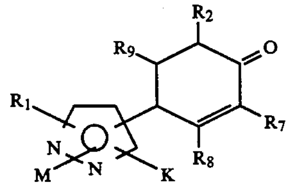

XLVIIIf (e)

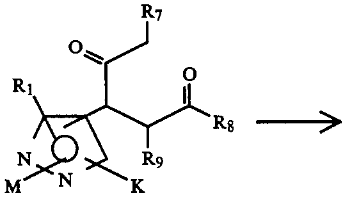

XLIXg

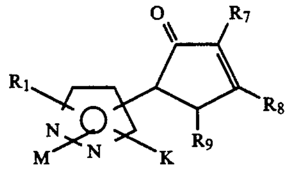

XLVIIIg

-continued

Equation 39

(f)

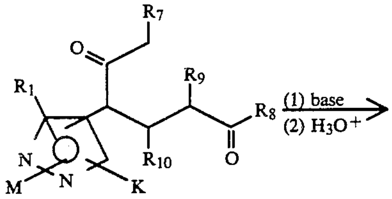

XLIXh

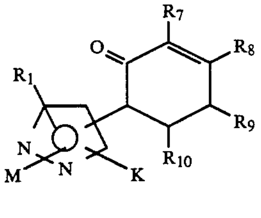

XLVIIIh (g)

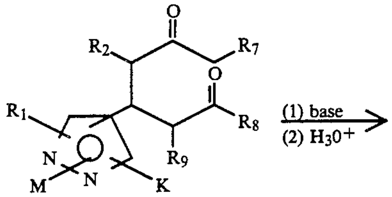

XLIXi

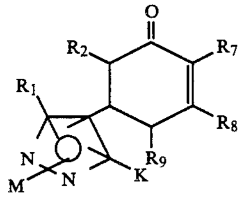

XLVIIIi wherein

M, $R_1$, $R_2$, $R_7$, $R_8$ and $R_9$ are as previously defined, K is H, Br, or $SR_{12}$, and $R_{12}$ is $C_2$–$C_4$ alkyl or benzyl.

An alternate route to the enones of Formula XLVIIIc and XLVIIId above is depicted in Equation 39h. The addition of 3-ethoxy-2-cyclohexenone or 3-ethoxy-2-cyclopentenone of Formula XLVIIIs and XLVIIIt respectively, to the dianions of sulfonamides of Formula XXa and XXB, followed by mild acid hydrolysis during workup affords the desired enones directly.

Equation 39h

XXa or XXb (1) n-BuLi, 2.0 equiv. THF (2) XLVIIIs or XLVIIIt (3) $H_3O^{\oplus}$ → XLVIIId or XLVIIIc -continued Equation 39h

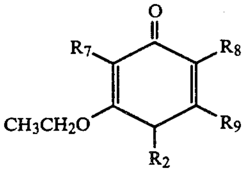

XLVIIIs

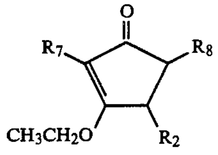

XLVIIIt wherein

M, $R_1$, $R_2$, $R_7$, $R_8$ and $R_9$ are as previously defined, and K is $SO_2NH$-t-Butyl or $SO_2NHSi(Me)_2$-t-Butyl.

Alternatively, many of the enones of Formulas XLVIIIj–XLVIIIr can be prepared from the corresponding saturated ketones of Formulas XXIIIa–XXIIIf via treatment with the appropriate base to form the α-carbanions, trapping with diphenyl disulfide or phenylsulfenyl chloride, and subsequent oxidative elimination. This sequence is depicted below in Equation 40 for the preparation of enones XLVIIIj or XLVIIIp from ketones of Formula XXIIIa or XXIIIa'.

Equation 40

(a)

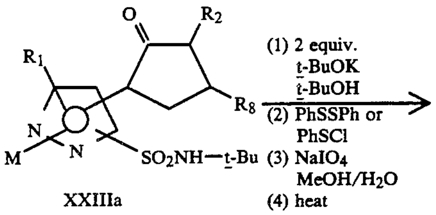

XXIIIa

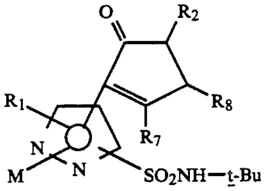

XLVIIIj (b)

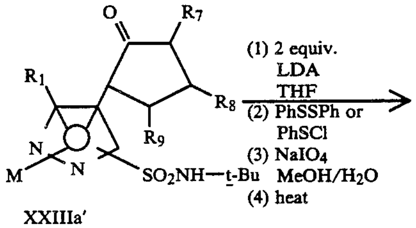

XXIIIa'

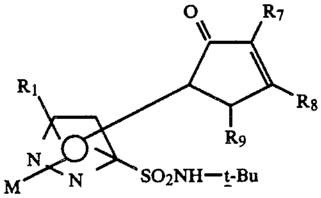

XLVIIIp wherein

M, $R_1$, $R_2$, $R_7$, $R_8$ and $R_9$ are as previously defined.

Equation 40(a)

The transformation shown above in Equation 40(a) can be effectively carried out by treating ketones of Formula XXIIIa with two molar equivalents of a strong base such as potassium tert-butoxide (t-BuOK) in a suitable solvent such as t-butanol under an inert atmosphere at 0°-25° C. Such conditions are conducive to formation of the more stable, or thermodynamic, enolates. These anions are then treated in a manner analogous to that described in Equations 33 and 34.

Equation 40(b)

The transformation shown above in Equation 40(b) can be effectively carried out by treating ketones of Formula XXIIIa' with two molar equivalents of a hindered base such as lithium diisopropylamide (LDA) in a suitable solvent such as tetrahydrofuran at low temperature (−78° C.) under an inert atmosphere. Such conditions are conducive to formation of the less stable, or kinetic, enolates. These anions are then treated in a manner analogous to that described in Equations 33 and 34.

For a discussion of the optimal conditions required for selectively generating thermodynamic or kinetic enolates, see J. C. Stowell, "Carbanions in Organic Synthesis", John Wiley and Sons, Inc., New York, 1979, pp. 8-11, and references cited therein.

In a similar fashion, enones of Formulas XLVIIIk, XLVIIIl, XLVIIIm, XLVIIIn, XLVIIIo, XLVIIIq. and XLVIIIr can be prepared from the corresponding ketones of Formulas XXIIIb-XXIIIf by selection of the appropriate conditions for enolate formation.

The requisite carbonyl compounds of Formulas XLIXa-XLIVi can be prepared by methods obvious to one skilled in the art. The appropriately substituted pyrazolylacetic esters of Formula XXXVI will serve as useful precursors for most of the desired compounds of Formulas XLIXa-XLIXi, and can be transformed by methods similar to those described in Equation 31 or modifications thereof. Such methods would be obvious to one skilled in the art.

Sulfonamides of Formulas La and Lb can be prepared as shown in Equation 41 by treatment of compounds of Formulas LIa and LIb with base.

Equation 41

(a)

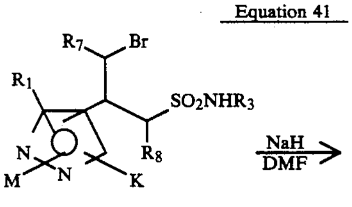

LIa

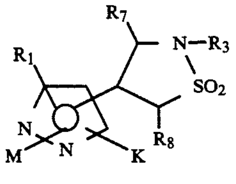

La

-continued

Equation 41

(b)

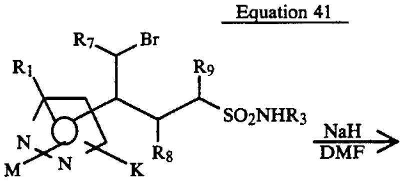

LIb

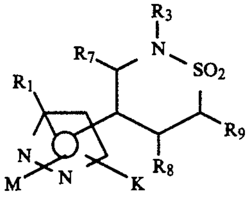

Lb wherein

M, $R_1$, $R_3$, $R_7$, $R_8$ and $R_9$ are as previously defined, K is Br, H, or $SR_{12}$, and $R_{12}$ is $C_2$-$C_4$ alkyl or benzyl.

The reactions of Equations 41(a) and 41(b) can be accomplished by adding a solution of sulfonamide LIa or LIb in a suitable solvent such as N,N-dimethylformamide (DMF) to a stirred suspension of a base such as sodium hydride at 0°-25° C. under an inert atmosphere. After being stirred at 25°-100° C. for several hours, or until all of the starting material has disappeared, the reaction mixture is cooled and poured into ice-water. The desired product of Formula La or Lb are then isolated by filtration or extraction with a suitable solvent such as diethyl ether, methylene chloride, or ethyl acetate, followed by drying and evaporation of the volatile components.

The sulfonamides of Formulas Lc-Lg can be synthesized in a manner identical to that described above in Equation 41 from the appropriate compounds of Formulas LIc-LIg as shown in Equations 42(a-e).

Equation 42

(a)

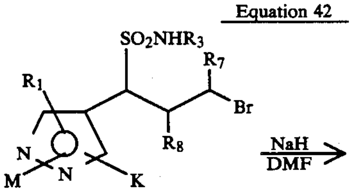

LIc

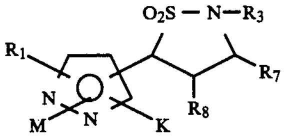

Lc (b)

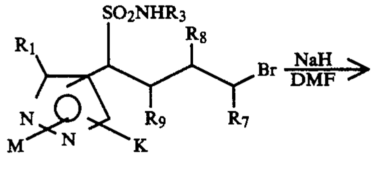

LId

-continued
Equation 42

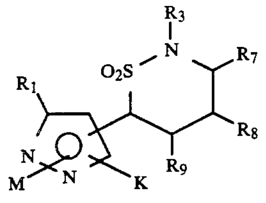

Ld (c)

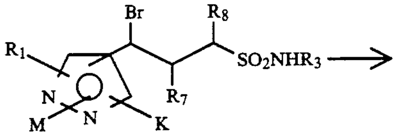

LIe

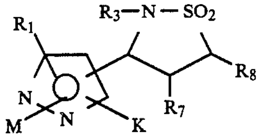

Le (d)

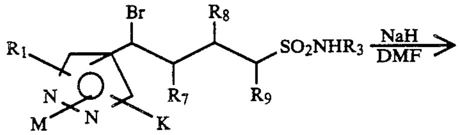

LIf

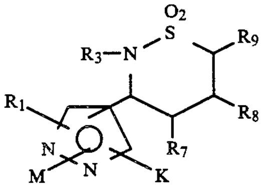

Lf (e)

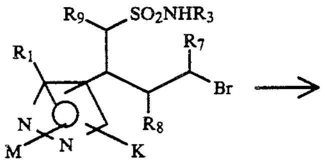

LIg

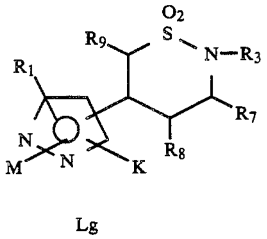

Lg wherein

M, $R_1$, $R_3$, $R_7$, $R_8$ and $R_9$ are as previously defined, K is Br, H, or $SR_{12}$, and $R_{12}$ is $C_2$–$C_4$ alkyl or benzyl.

Sulfonamides of Formulas Lh and Li can be synthesized from common aminopyrazoles via a sequence of reactions that entails the same four basic processes. Equation 43 outlines this sequence of reactions leading to compounds of Formulas Lh and Li: (a,e) reacting the appropriate aminopyrazoles of Formulas LIIa and LIIa' with protected δ- and γ-hydroxyalkyl sulfonyl chlorides to afford the sulfonamides of Formulas LIIb and LIIb', (b,f) deprotection of the hydroxyl protecting group to give the corresponding δ- and γ-hydroxysulfonamides of Formulas LIIc and LIIc', (c,g) conversion of the hydroxy group to a good leaving group such as the alkyl bromides of Formulas LIId and LIId', and (d,h) base promoted cyclization to afford the desired compounds of Formulas Lh and Li.

Equation 43

(a)

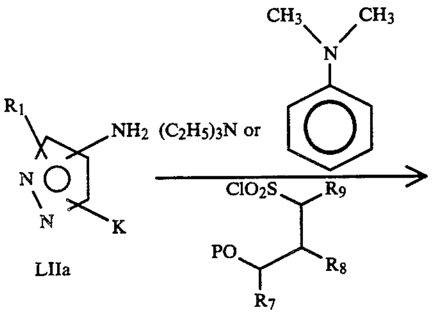

LIIa

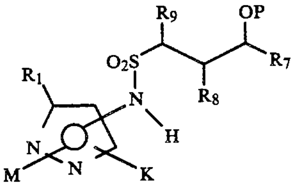

LIIb (b)

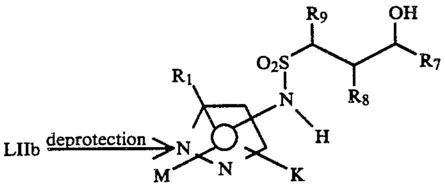

LIIc (c)

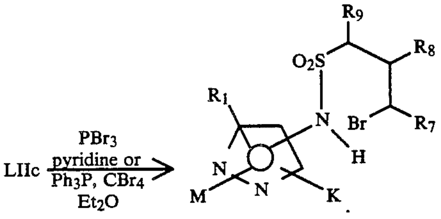

LIId

-continued

Equation 43

(d)

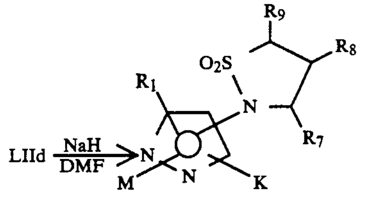

Lh (e)

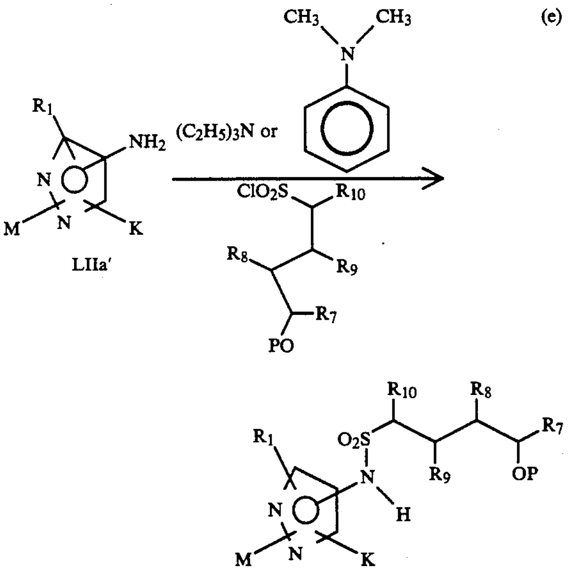

LIIa'

LIIb'

(f)

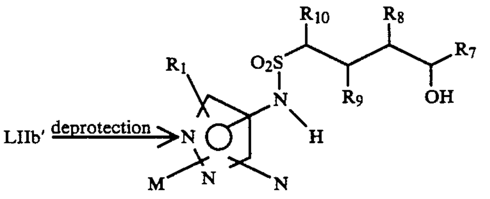

LIIc'

(g)

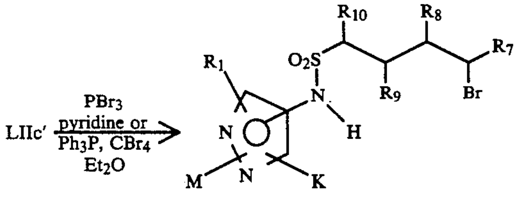

LIId'

(h)

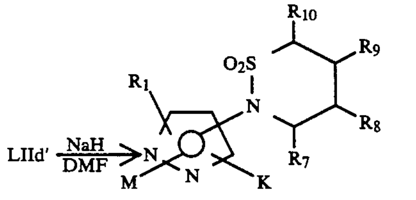

Li wherein

M, $R_1$, $R_7$, $R_8$, $R_9$, and $R_{10}$ are as previously defined,

K is H, Br, or $SR_{12}$, $R_{12}$ is $C_2$–$C_4$ alkyl or benzyl, and P is an appropriate alcohol protecting group such as benzyl, t-butyl, $Si(CH_3)_2(t\text{-}Bu)$, etc.

Equation 43(a,e)

The aminations of Equations 43a and 43e are most conveniently effected by adding the requisite sulfonyl chlorides to a solution of the aminopyrazoles LIIa and LIIa' in a suitable solvent such as diethyl ether, tetrahydrofuran, or methylene chloride containing at least two equivalents of an acid scavenger such as triethylamine or dimethylaniline at temperatures between 0° C. and 65° C. The desired sulfonamides of Formulas LIIb and LIIb' are isolated either by filtration, in which case the by-product triethylamine hydrochloride or dimethylaniline hydrochloride is removed by washing with water, or extraction into a suitable organic solvent such as methylene chloride or ethyl acetate. Drying and evaporation of the solvent then affords the products LIIb and LIIb', which are usually sufficiently pure to be carried directly onto the next step.

Equations 43(b,f)

The deprotection step, Equations 43b and 43f, involves removal of the hydroxyl protecting group to release an alcohol substituent. Selection of a suitable protecting group must take into account the nature of other substituents in the molecules and would be obvious to one skilled in the art. For a compilation of references describing the wide variety of protecting groups available for alcohols, see T. W. Greene, "Protective Groups in Organic Synthesis", John Wiley and Sons, New York, 1981, pp. 10–72.

Equations 43(c,g)

The third step shown, Equations 43c and 43g, involves the preparation of the desired products of Formulas LIId and LIId' from the corresponding alcohols with either phosphorous tribromide or triphenylphosphine-carbon tetrabromide. For relevant procedures, see Equation 31(d).

Equations 43(d,h)

The reactions shown in Equations 43(d) and 43(h) are most conveniently accomplished in a manner identical to that described for Equations 41(a) and 41(b).

The requisite compounds of Formulas LIa–Lig can be synthesized via the same basic four-step sequence of reactions. Equation 44 depicts this synthetic scheme for the preparation of sulfonamides LIa, starting from the appropriate alkyl bromides of Formula LVIIa as a representative example.

Equation 44

(a)

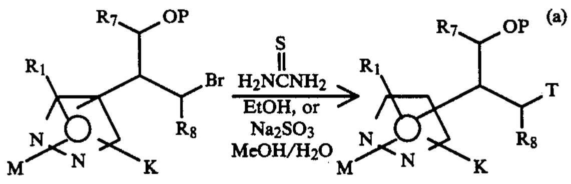

LVIIa

LVIa

(T = —SCNH$_2$.HBr, or —SO$_3$Na)

-continued

Equation 44

(b)

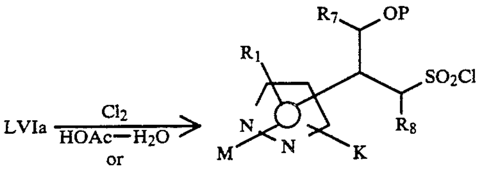

LVa (c)

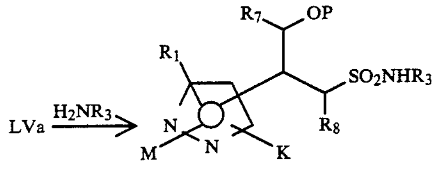

LIVa (d)

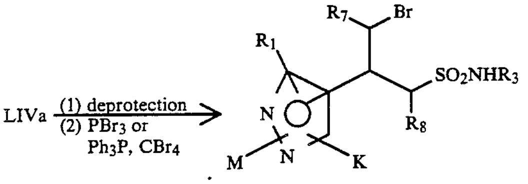

LIa wherein

M, $R_1$, $R_7$ and $R_8$ are as previously defined,

K is Br, H, or $SR_{12}$, $R_{12}$ is $C_2$–$C_4$ alkyl or benzyl, and

P is an appropriate alcohol protecting group such as $CH_2Ph$, t-butyl, $Si(CH_3)_2(t\text{-}Bu)$, etc.

Equation 44(a)

The displacement reaction of Equation 44(a) can be effected by treating the alkyl bromides of Formula LVIIa with either one molar equivalent of thiourea to give the corresponding isothiouronium salts LVIa, where T is $-SC(NH_2)=NH.HBr$, or with sodium sulfite to yield the sodium sulfonate salts LVIa, where T is $-SO_3Na$. For detailed procedures relating to the preparation of isothiouronium salts, see Urquhart, Gates and Connor, *Org. Syntheses,* 21, 36 (1941), or Vogel, *J. Chem. Soc.,* 1822 (1948). For the use of sodium sulfite in the preparation of sodium sulfonate salts, see Reed and Tarter, *J. Am. Chem. Soc.,* 57, 571 (1935), or Latimer and Bost, *J. Org. Chem.,* 5, 24 (1940).

Equation 44(b)

The choice of chlorination conditions to be employed in the reaction of Equation 44(b) depends upon the nature of the substituent T. When T is $-SC(NH_2)=NH.HBr$, the process can be effected with chlorine in an aqueous medium according to Johnson and Sprague, *J. Am. Chem. Soc.,* 58, 1348 (1936); 59, 1837, 2439 (1937). When T is $-SO_3Na$, the reaction can be carried out using phosphorous oxychloride according to the procedure of Westlake and Dougherty, *J. Am. Chem. Soc.,* 63, 658 (1941).

Equation 44(c)

The reaction shown in Equation 44(c) is conveniently accomplished in a manner identical to that described for Equation 7. For useful references, see Huntress and Carter, *J. Am. Chem. Soc.,* 62, 511 (1940), or Huntress and Autenrieth, *ibid.,* 63, 3446 (1941).

Equation 44(d)

The first step of Equation 44(d) involves removal of the hydroxyl protecting group to release an alcohol substituent. Selection of a suitable protecting group must take into account the nature of other substituents in the molecule and would be obvious to one skilled in the art. For a compilation of references describing the wide variety of protecting groups available for alcohols, see T. W. Greene, "Protective Groups in Organic Synthesis", John Wiley and Sons, Inc., New York, 1981, pp. 10–72. The second step shown in Equation 44(d) involves the preparation of the desired products of Formula LIa from the corresponding alcohols with either phosphorous tribomide or triphenylphosphine-carbon tetrabromide. For relevant procedures, see Equation 31(d).

The requisite alkyl bromides of Formula LVIIa, where $R_8$ is H, can be synthesized in a manner analogous to that described in Equation 31 for compounds of Formula XL. Alternatively, the alkyl bromides of Formula LVIIa, where $R_8$ is other than H, are conveniently obtained as shown in Equation 45, starting from the appropriate esters of Formula XXXVIIIa.

Equation 45

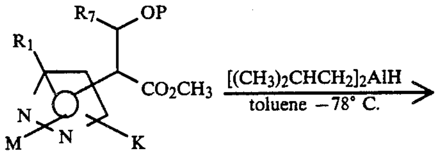

XXXVIIIa

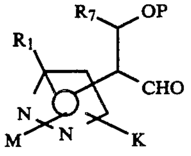

LIXa

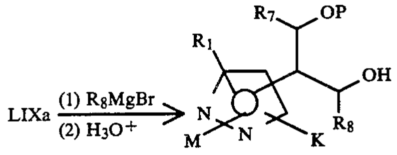

LIXb

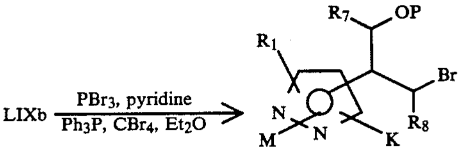

LVIIa wherein

M, $R_1$, $R_7$ and $R_8$ are as previously defined,

K is Br, H, or $SR_{12}$, $R_{12}$ is $C_2$–$C_4$ alkyl or benzyl, and

P is a protecting group as defined above in Equation 44.

The reduction of carboxylic esters such as those of Formula XXXVIIIa to the corresponding aldehydes with diisobutylaluminum hydride can be carried out as described in Equation 25(a). The second step of Equation 45 involves the addition of appropriate Grignard reagents, $R_8MgBr$, to aldehydes of Formula LIXa to afford the corresponding alcohols LIXb after aqueous workup. This is a well-known reaction and can be accomplished by following the procedures compiled in Patai, "The Chemistry of the Carbonyl Group", Vol. 1, Interscience Publishers, New York, 1969, pp. 621–693, or Kharasch and Reinmuth, "Grignard Reactions of Nonmetallic Substances", Prentice-Hall, Inc., Englewood Cliffs, N.J., 1954, pp. 138–528. The third step shown in Equation 45 involves the conversion of alcohols LIXb to the corresponding alkyl bromides LVIIa, and has been described in Equation 31(d).

Compounds of Formulas LIb-LIg can be prepared by methods analogous to those described in Equations 44 and 45 with suitable modifications which would be obvious to one skilled in the art.

Equation 46 depicts the intramolecular reaction of γ- and δ-hydroxysulfonyl chlorides of Formulas LXa and LXb to afford the sulfonates of Formulas LXIa and LXIb.

Equation 46

(a)

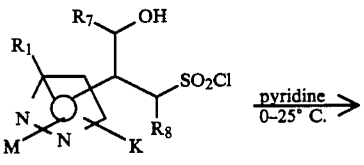

LXa

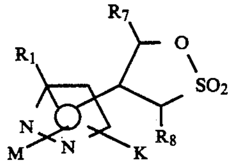

LXIa (b)

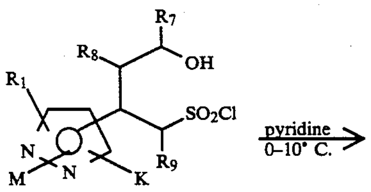

LXb

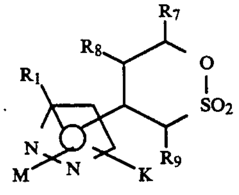

LXIb wherein

M, $R_1$, $R_7$, $R_8$ and $R_9$ are as previously defined, K is Br, H, or $SR_{12}$, and $R_{12}$ is $C_2$–$C_4$ alkyl or benzyl.

The cyclization shown in Equations 46(a) and 46(b) can be achieved according to the procedures of Tipson, *J. Org. Chem.*, 9, 235 (1944), Marvel and Sekera, *Org. Syntheses*, 20, 50 (1940), or Sekera and Marvel, *J. Am. Chem. Soc.*, 55, 346 (1933).

In a similar fashion, sulfonates of Formulas LXIc-LXIg can be prepared by base-induced cyclization of the appropriate or γ- or δ-hydroxysulfonyl chlorides of Formulas LXc-LXg, as shown below in Equations 47(a-e).

Equation 47

(a)

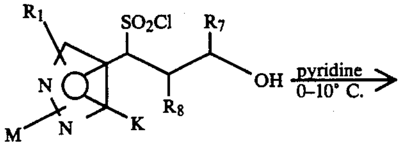

LXc

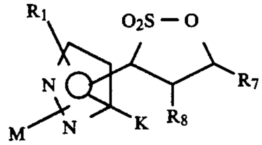

LXIc (b)

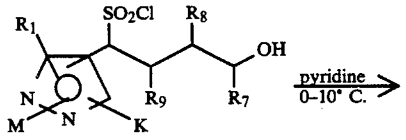

LXd

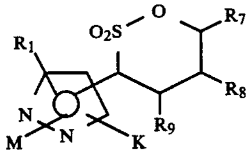

LXId (c)

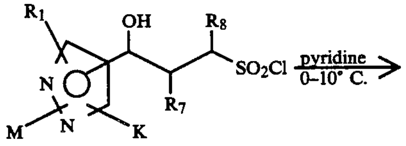

LXe

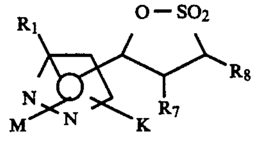

LXIe (d)

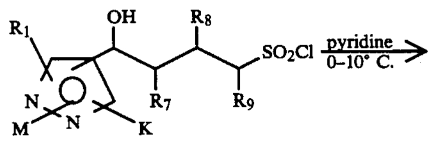

LXf

-continued

Equation 47

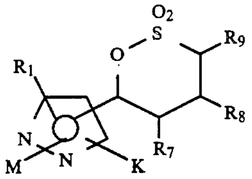

LXIf (e)

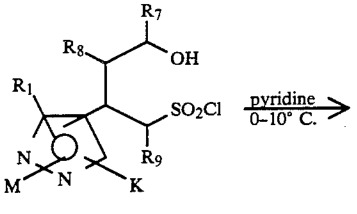

LXg

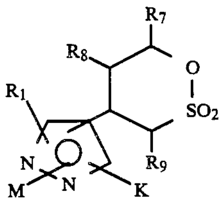

LXIg wherein

M, $R_1$, $R_7$, $R_8$ and $R_9$ are as previously defined, K is Br, H, or $SR_{12}$, and $R_{12}$ is $C_2$–$C_4$ alkyl or benzyl.

The synthesis of the requisite hydroxysulfonyl chlorides has been described previously. For example, γ-hydroxysulfonyl chlorides of Formula LXa can be obtained from the corresponding protected compounds of Formula LVa (Equation 44). In a similar fashion, the requisite hydroxysulfonyl chlorides LXb–LXg can be prepared from the appropriate protected alcohols by methods which would be obvious to one skilled in the art.

Sulfones of Formulas LXIIa–LXIIe can be conveniently prepared as shown in Equation 48 by oxidation of the appropriate 5- and 6-membered ring thioethers of Formulas LXIIIa–LXIIIe.

Equation 48

(a)

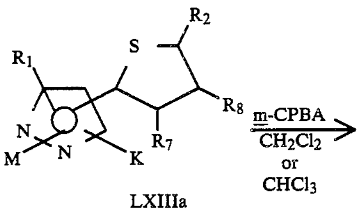

LXIIIa

-continued

Equation 48

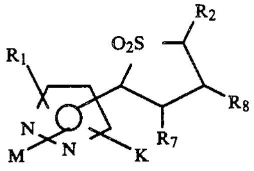

LXIIa (b)

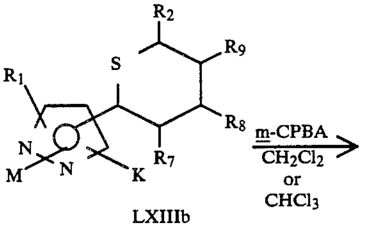

LXIIIb

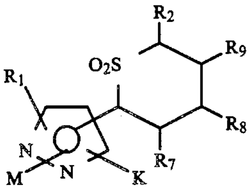

LXIIb (c)

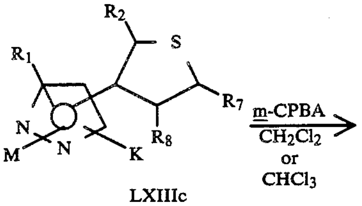

LXIIIc

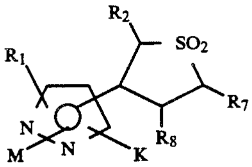

LXIIc (d)

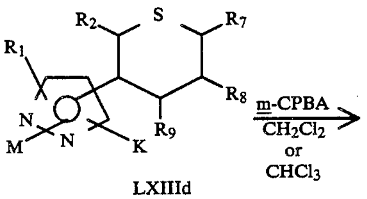

LXIIId

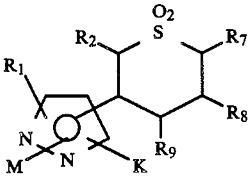

LXIId

-continued

Equation 48

(e)

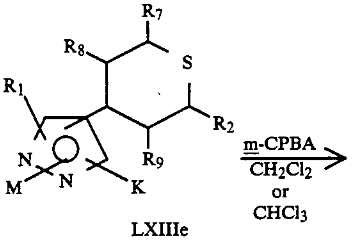

LXIIIe

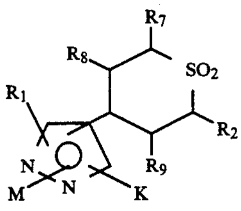

LXIIe wherein

M, $R_1$, $R_2$, $R_7$, $R_8$ and $R_9$ are as previously defined, and K is H, Br, or $SO_2NH$-t-Bu.

The oxidation shown in Equation 48 is most conveniently carried out by adding a solution of at least two molar equivalents of m-chloroperoxybenzoic acid (m-CPBA) in a suitable solvent such as methylene chloride or chloroform to a solution of the sulfide LXIII(a–e) in the same solvent at 0°–25° C. After the reaction mixture has been stirred at about 25° C. for 1–4 hours, excess oxidant is destroyed by the addition of saturated aqueous sodium bisulfite (ice-water cooling). The reaction mixture is then filtered to remove the by-product m-chlorobenzoic acid, and the filtrate is washed several times with portions of saturated aqueous sodium bicarbonate. The desired products of Formula LXII(a–e) are isolated by drying and evaporation of the organic layer, and are often sufficiently pure to be carried directly on to the next step.

The requisite sulfides of Formulas LXIIIa and LXIIIb can be prepared as shown in Equation 49, by conversion of the appropriate diols of Formulas LXIVa and LXIVb to the corresponding dibromides LXVa and LXVb, respectively, and subsequent treatment with sodium sulfide to effect cyclization.

Equation 49

(a)

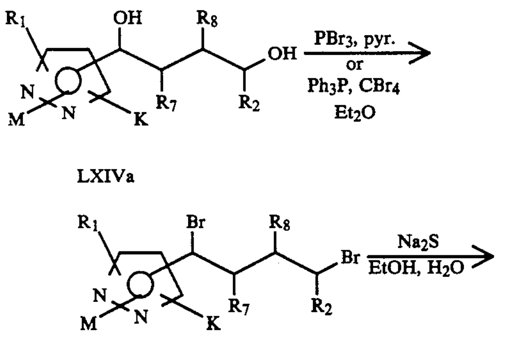

LXIVa

LXVa

-continued

Equation 49

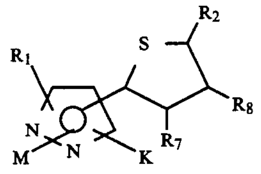

LXIIIa (b)

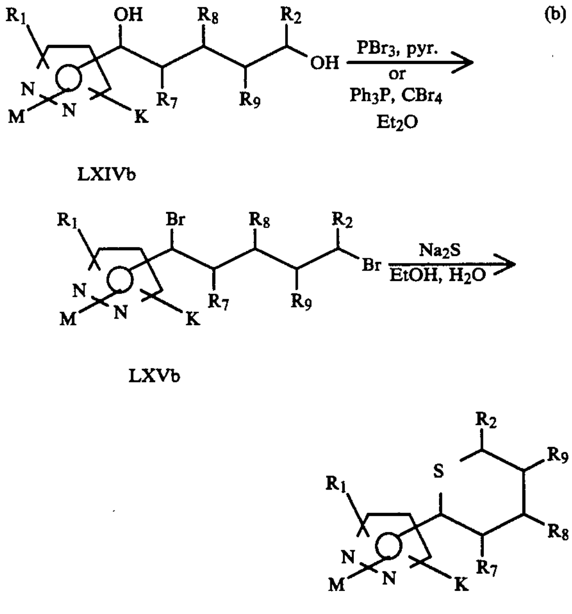

LXIVb

LXVb

LXIIIb wherein

M, $R_1$, $R_2$, $R_7$, $R_8$ and $R_9$ are as previously defined, and K is H, Br, or $SO_2NH$-t-Bu.

The first step of Equations 49(a) and 49(b) can be effected in a manner analogous to that described for Equation 31(d) except that two molar equivalents of the appropriate brominating agent are required. The second step shown above in Equations 49(a) and 49(b) can be conveniently carried out according to the method of Tarbell and Weaver, *J. Am. Chem. Soc.*, 63, 2940 (1941), or Naylor, *J. Chem. Soc.*, 1107 (1947).

In a similar manner, the requisite sulfides of Formulas LXIIIc–LXIIIe can be prepared via conversion of the appropriate diols to the corresponding dibromides, and subsequent cyclization by treatment with sodium sulfide.

Diols such as those of Formulas LXIVa and LXIVb can be prepared from the appropriately substituted intermediates, many of which have already been described. Methods needed to effect these transformations would be obvious to one skilled in the art.

The α,β-unsaturated sulfonamides, represented by Formula LXVIIa, can be prepared by a procedure identical to that described for the synthesis of α,β-unsaturated lactams of Formulas XLVa–XLVi as shown in Equations 36 and 37. For example, treatment of sulfonamides of Formula La with base, addition of diphenyl disulfide or phenylsulfenyl chloride, and subsequent oxidative elimination gives the unsaturated compounds of Formula LXVIIa as shown in Equation 50.

Equation 50

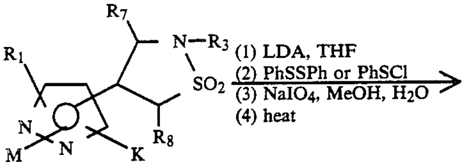

La

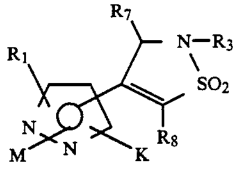

LXVIIa wherein

M, $R_1$, $R_3$, $R_7$ and $R_8$ are as previously defined, and K is H, Br, or $SR_{12}$, and $R_{12}$ is $C_2$-$C_4$ alkyl or benzyl.

The transformation depicted in Equation 50 is conveniently carried out in a manner analogous to that described in Equations 36 and 37. When $R_3$ is H in Equation 50, it is necessary to use one extra molar equivalent of lithium diisopropylamide (LDA) to form the α,N-dianions of sulfonamides La-Li. This procedure can be applied to the preparation of the remaining α,β-unsaturated analogues of sulfonamides Lb-Li.

The α,β-unsaturated sulfonates of Formulas LXVIIIa-LXVIIIg can be synthesized via the four-step sequence of reactions shown below in Equations 51(a-g), starting from the saturated compounds of Formulas LXIa-LXIg.

Equation 51

(a)

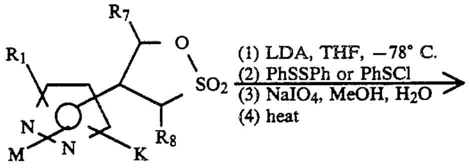

LXIa

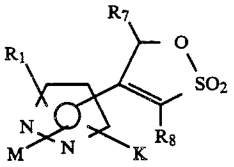

LXVIIIa (b)

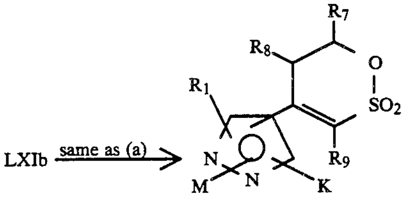

LXVIIIb

-continued

Equation 51

(c)

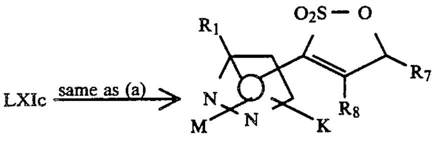

LXVIIIc (d)

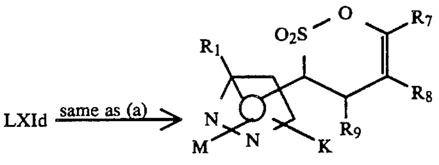

LXVIIId (e)

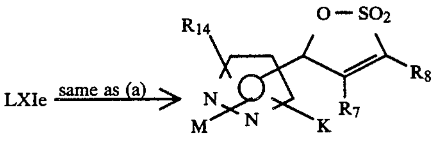

LXVIIIe (f)

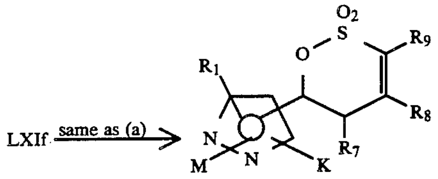

LXVIIIf (g)

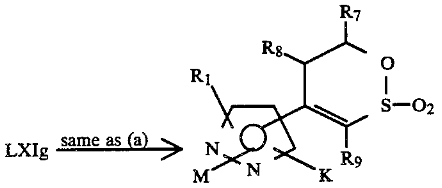

LXVIIIg wherein

M, $R_1$, $R_7$, $R_8$ and $R_9$ are as previously defined and K is H, Br, or $SR_{12}$, and $R_{12}$ is $C_2$-$C_4$ alkyl or benzyl.

The formation of anions alpha to the sulfonyl group of alkyl sulfonates such as those of Formulas LXIa-LXIg is a process with considerable precedent in the literature. For related examples, refer to Truce, Hollister, Lindy and Parr, *J. Org. Chem.*, 33, 43 (1968); Truce and Vrencur, *Can. J. Chem.*, 47, 860 (1969), *J. Org. Chem.*, 35, 1226 (1970); Julia and Arnould, *Bull. Soc. Chim. Fr.*, 743, 746 (1973); and Bird and Stirling, *J. Chem. Soc.* (*B*), 111 (1968). Reaction of these sulfonate anions with diphenyl disulfide or phenylsulfenyl chloride and subsequent oxidative elimination can be effected as described for Equations 36 and 37.

Compounds of Formulas LXXa-LXXd can be synthesized as shown in Equation 52 by the reaction of appropriate α,β-unsaturated carbonyl compounds LXXIa-LXXId with α-chloroketene acetals of Formulas LXXIIa or LXXIIb.

Equation 52

(a)

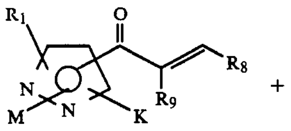

LXXIa

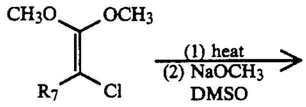

LXXIIa

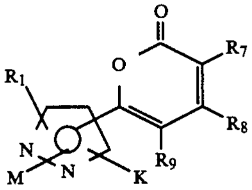

LXXa (b)

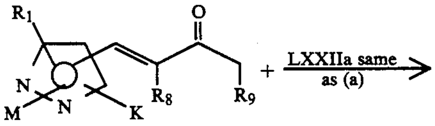

LXXIb

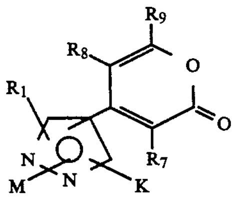

LXXb (c)

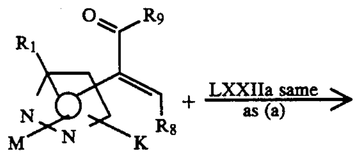

LXXIc

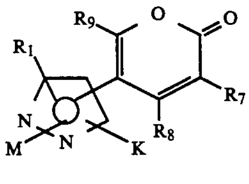

LXXc

-continued

Equation 52

(d)

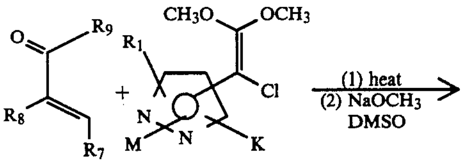

LXXId LXXIIb

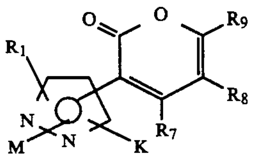

LXXd wherein

M, $R_1$, $R_7$, $R_8$ and $R_9$ are as previously defined, K is H, Br, or $SR_{12}$, and $R_{12}$ is $C_2$–$C_4$ alkyl or benzyl.

The transformations outlined in Equation 52 can be conveniently carried out by the procedure of A. Belanger and P. Brassard, *Chem. Comm.*, 863 (1972). Other syntheses of α-pyrones are known in the literature and have been reviewed by J. Fried in "Heterocyclic Compounds", ed. R. C. Elderfield, Wiley, New York, 1950, Vol. I, pp. 358-370, and L. F. Cavalieri, *Chem. Rev.*, 41, 525 (1947).

The requisite α,β-unsaturated carbonyl compounds of Formulas LXXIa-LXXId and the α-chloroketene acetals of Formula LXXIIb can be prepared by methods known to one skilled in the art.

The γ-pyrones of Formulas LXXIIIa and LXXIIIb can be prepared by one or more of several methods which have been reviewed by J. Fried in "Heterocyclic Compounds", ed. R. C. Elderfield, Wiley, New York, Vol. I, pp. 379-391. A more recent procedure involves the reaction of suitable potassium enolates of Formulas LXXIVa and LXXIVb with the appropriate acid chlorides of Formulas LXXVa and LXXVb, as shown in Equation 53.

Equation 53

(a)

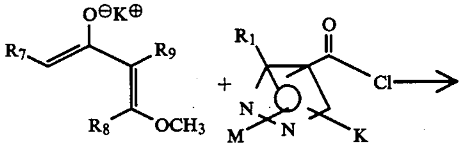

LXXIVa LXXVa

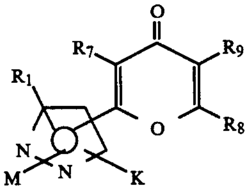

LXXIIIa

-continued

Equation 53

(b)

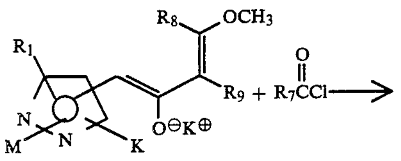

LXXIVb LXXVb

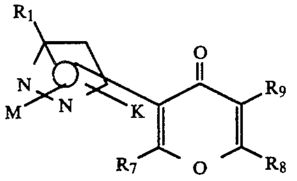

LXXIIIb wherein

M, $R_1$, $R_7$, $R_8$ and $R_9$ are as previously defined, K is H, Br, or $SR_{12}$, and $R_{12}$ is $C_2$-$C_4$ alkyl or benzyl.

The reactions shown above in Equations 53(a) and 53(b) can be carried out according to the procedures described by T. A. Morgan and B. Ganem, *Tetrahedron Lett.*, 21, 2773 (1980). For a closely-related method, refer to M. Koreeda and H. Akagi, *Tetrahedron Lett.*, 21, 1197 (1980).

The requisite potassium enolates of Formulas LXXIVa and LXXIVb can be most conveniently prepared by treatment of the appropriate unsaturated ketones of Formulas LXXVIa and LXXVIb with a suitable base such as potassium tert-butoxide as shown in Equation 54.

Equation 54

(a)

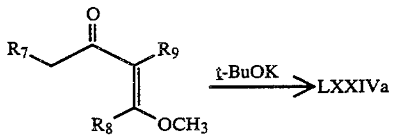

LXXVIa (b)

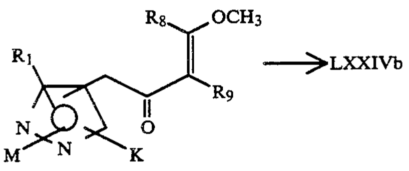

LXXVIb wherein

M, $R_1$, $R_7$, $R_8$ and $R_9$ are as previously defined, K is H, Br, $SR_{12}$, and $R_{12}$ is $C_2$-$C_4$ alkyl or benzyl.

The reaction shown in Equation 54 can best be carried out according to the method described in Morgan and Ganem, *tetrahedron Lett.*, 21, 2773 (footnote 6) (1980).

The requisite unsaturated ketones of Formulas LXXVIa and LXXVIb, as well as the acid chlorides of Formula LXXVa, can be synthesized by methods known to one skilled in the art.

α-Pyridones of Formulas LXXVIIa-LXXVIId can be prepared in a straightforward manner by treatment of the appropriate α-pyrones of Formulas LXXa-LXXd with suitable amines, $H_2NR_{11}$, as represented below in Equations 55(a-d).

Equation 55

(a)

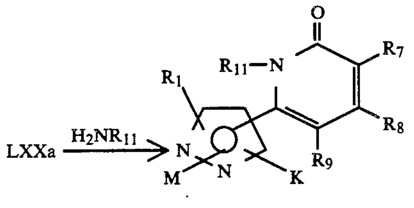

LXXVIIa (b)

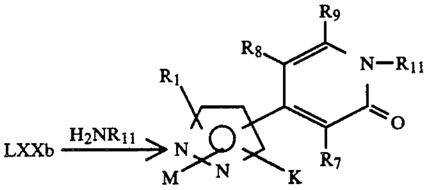

LXXVIIb (c)

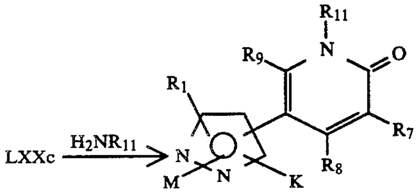

LXXVIIc (d)

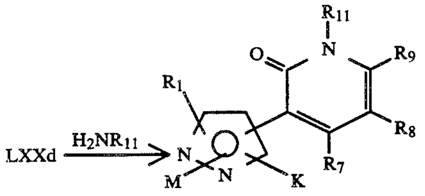

LXXVIId wherein

M, $R_1$, $R_7$, $R_8$, $R_9$ and $R_{11}$ are as previously defined, K is H, Br, or $SR_{12}$, and $R_{12}$ is $C_2$-$C_4$ alkyl or benzyl.

The conversion of α-pyrones to the corresponding pyridones as shown in Equation 55 is a well-precedented process in the literature. For detailed descriptions of the procedure, see the following references: J. A. Leben, *Ber.*, 29, 1673, (1896); von Pechmann and W. Welsh, *Ber.*, 17, 2391 (1884); and J. H. Boyer and W. Schoen, *Org. Syntheses*, Coll. Vol. IV, 532 (1963).

Compounds of Formula LXXVIIf can be conveniently prepared as shown in Equation 56 by the reaction of α-pyrones of Formula LXXX with the anions LXXIX of the appropriate aminopyrazole derivatives of Formula LXXVIII.

Equation 56

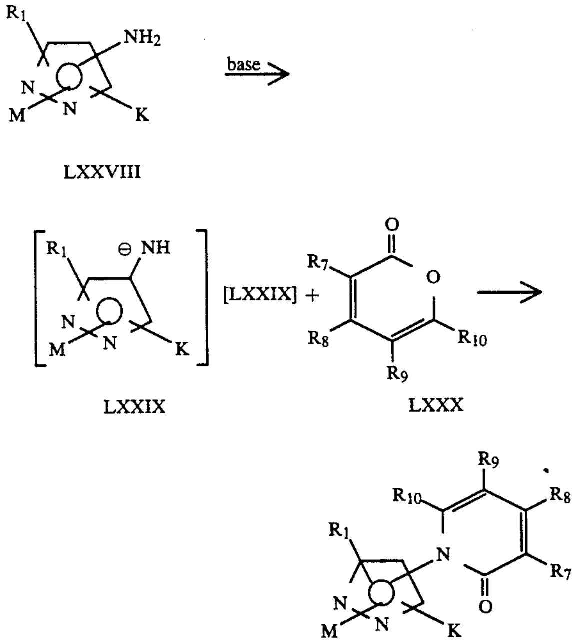

LXXVIII

LXXIX LXXX

LXXVIIf wherein

M, $R_1$, $R_7$, $R_8$, $R_9$ and $R_{10}$ are as previously defined, K is H, Br, or $SR_{12}$ and $R_{12}$ is $C_2$–$C_4$ alkyl or benzyl.

The first step of Equation 56, formation of the anions LXXIX of aminopyrazole derivatives LXXVIII by treatment with a suitable base such as ethoxide ion, can be carried out according to the methods described for aniline derivatives by DeFeo and Strickler, *J. Org. Chem.*, 28, 2915 (1963), Yang, Cannon and Rose. *Tetrahedron Lett.*, 1791 (1970), or Singh, *Tetrahedron Lett.*, 321 (1971). The second step of Equation 56 can be effected in a manner analogous to that described in Equation 55.

γ-Pyridones of Formulas LXXXIa and LXXXIb can be synthesized from the corresponding γ-pyrones of Formulas LXXIIIa and LXXIIIb by treatment with the appropriate amines, $H_2NR_{11}$. This transformation is depicted in Equation 57.

Equation 57

(a)

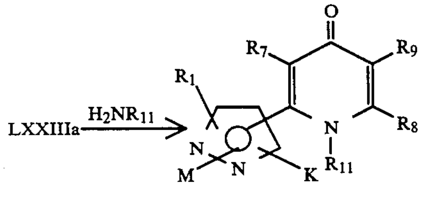

LXXXIa

-continued

Equation 57

(b)

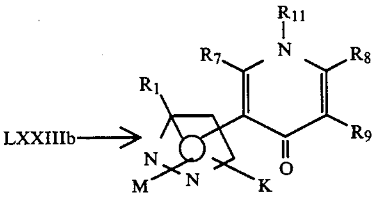

LXXXIb wherein

M, $R_1$, $R_7$, $R_8$, $R_9$ and $R_{11}$ are as previously defined, K is H, Br, or $SR_{12}$, and $R_{12}$ is $C_2$–$C_4$ alkyl or benzyl.

The reactions of Equations 57(a) and 57(b) can be conveniently carried out as described by C. F. Rassweiler and R. Adams, *J. Am. Chem. Soc.*, 46, 2758 (1924).

γ-Pyridones of Formula LXXXIc can be prepared in a manner analogous to that outlined above in Equation 56. Thus, addition to the anions of Formula LXXIX to γ-pyrones of Formula LXXXII, as shown in Equation 58, affords the desired products of Formula LXXXIc.

Equation 58

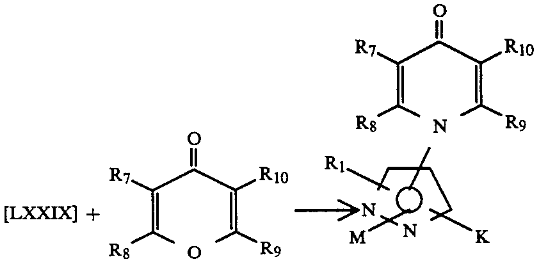

LXXXII LXXXIc wherein

M, $R_1$, $R_7$, $R_8$, $R_9$ and $R_{10}$ are as previously defined, K is H, Br, or $SR_{12}$ and $R_2$ is $C_2$–$C_4$ alkyl or benzyl.

Compounds of Formula LXXXIIIa, where $R_8$ is H, can be prepared as shown in Equation 59 by the three-step sequence of reactions involving: (a) conversion of suitably protected carboxylic acids of Formula LXXXVI to the acid chlorides LXXXV, (b) treatment with diazomethane to give diazoketones of Formula LXXXIV, and (c) acid-induced cyclization.

Equation 59

(a)

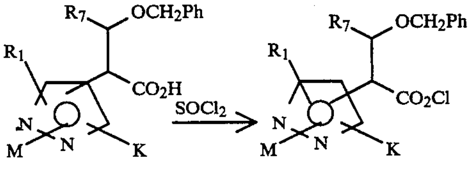

LXXXVI LXXXV

-continued

Equation 59

(b)

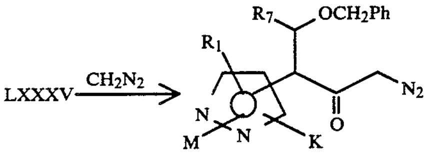

LXXXIV (c)

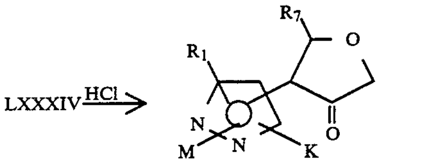

LXXXIIIa ($R_8$ = H)

wherein

M, $R_1$ and $R_7$ are as previously defined, K is H, Br, or $SR_{12}$, and $R_{12}$ is $C_2$-$C_4$ alkyl or benzyl.

The transformations outlined in Equations 59(a-c) can be achieved according to the procedure of V. Luhmann and W. Luttke, *Chem. Ber.*, 105, 1350 (1972).

Compounds of Formula LXXXIIIb can be prepared via an intramolecular epoxide opening reaction followed by oxidation of the resulting alcohol as depicted in Equation 60.

Equation 60

(a)

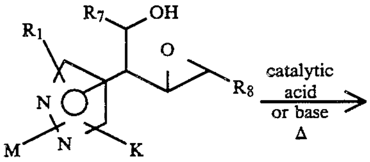

LXXXVIII

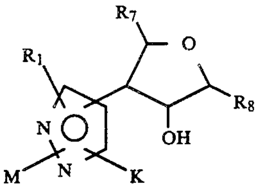

LXXXVII (b)

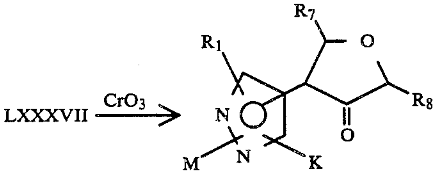

LXXXIIIb wherein

M, $R_1$, $R_7$ and $R_8$ are as previously defined, K is H, Br, or $SR_{12}$, and $R_{12}$ is $C_2$-$C_4$ alkyl or benzyl.

Equation 60(a)

The reaction of Equation 60(a) involves the intramolecular alcoholysis of epoxides of Formula LXXXVIII, and can be accomplished by treatment with either a catalytic amount of a suitable base such as potassium tert-butoxide, or with a catalytic amount of a suitable acid such as sulfuric acid. For relevant procedures, refer to Chitwood and Freure, *J. Am. Chem. Soc.*, 68, 680 (1946), Sexton and Britton, *ibid.*, 70 3606 (1948), or Winstein and Henderson, *ibid.*, 65, 2196 (1943).

Equation 60(b)

The oxidation of 3-hydroxytetrahydrofurans, such as those of Formula LXXXVII, to the corresponding furanones of Formula LXXXIIIb, can be accomplished with chromium trioxide as described by V. Luhmann and W. Luttke, *Chem. Ber.*, 105, 1350 (1972).

Furanones of Formula LXXXIIIc can be synthesized as depicted in Equation 61 via a three-step process involving: (a) O-alkylation of the appropriate alcohols of Formula XCI, (b) Dieckmann cyclization to give α-carboethoxy furanones LXXXIX, and (c) hydrolysis and decarboxylation of esters LXXXIX with sulfuric acid.

Equation 61

(a)

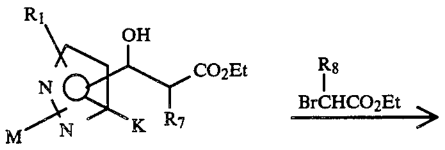

XCI

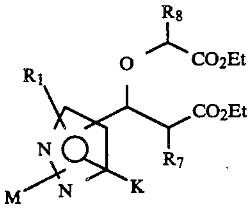

XC (b)

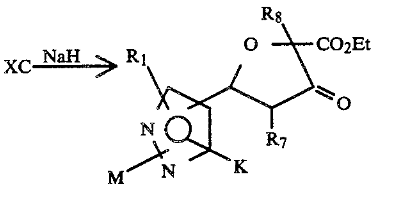

LXXXIX (c)

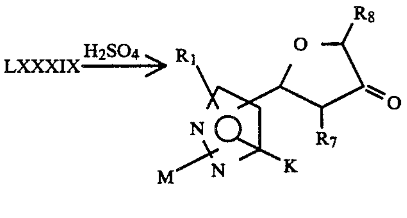

LXXXIIIc wherein

M, $R_1$, $R_7$ and $R_8$ are as previously defined, K is H, Br, or $SR_{12}$, and $R_{12}$ is $C_2$-$C_4$ alkyl or benzyl.

The transformation outlined above in Equations 61(a-c) can be effectively accomplished by the procedure of V. Luhmann and W. Luttke, *Chem. Ber.*, 105, 1350 (1972).

Furanones of Formula LXXXIIId can be prepared as shown in Equation 62 by addition of anions of Formula XCIII to the appropriate aldehydes XCIV, and subsequent acid-induced cyclization of the resultant α-hydroxyenones of Formula XCII.

Equation 62

(a)

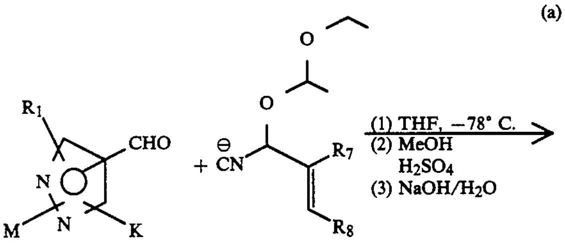

XCIV XCIII

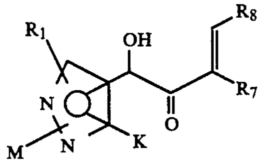

XCII (b)

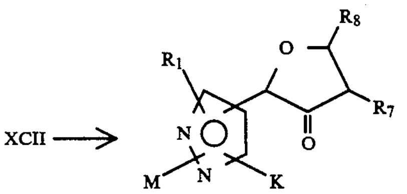

LXXXIIId wherein

M, $R_1$, $R_7$ and $R_8$ are as previously defined, K is H, Br, or $SR_{12}$, and $R_{12}$ is $C_2$–$C_4$ alkyl or benzyl.

Equation 62(a)

The addition of protected cyanohydrin anions of Formula XCIII, to aldehydes of Formula XCIV and subsequent hydrolysis to afford α-hydroxyenones of Formula XCII can be carried out according to the procedure of G. Stork and L. Maldonado, *J. Am. Chem. Soc.*, 93, 5286 (1971). Also, refer to Stork and Maldonado, *ibid.*, 96, 5272 (1974).

Equation 62(b)

The cyclization of Equation 62(b) can be carried out by heating a solution of the hydroxyenone of Formula XCII in a suitable solvent such as tetrahydrofuran in the presence of a catalytic amount of an appropriate acid such as hydrochloric or sulfuric acid. Alternatively, compounds of Formula XCII can be heated in a suitable solvent such as toluene at reflux temperature in the presence of a catalytic amount of p-toluenesulfonic acid.

Compounds of Formulas LXXXIIIe–LXXXIIIh, which are homologs of furanones LXXXIIIa–LXXXIIId, can be prepared by methods analogous to those described above in Equations 59, 60, 61 and 62. The minor modifications needed to implement these syntheses would be obvious to one skilled in the art. Equations 63(a)–63(d) depict the procedures for the preparation of compounds LXXXIIIe–LXXXIIIh.

Equation 63

(a)

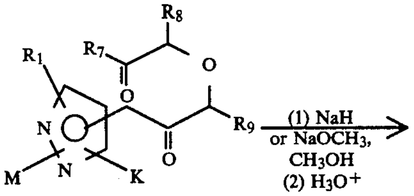

XCVI

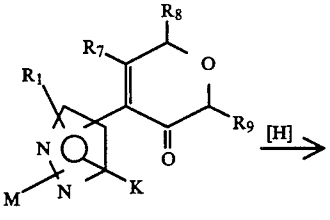

XCV

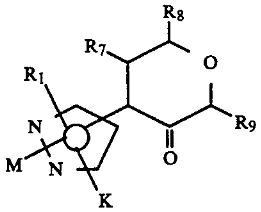

LXXXIIIe (b)

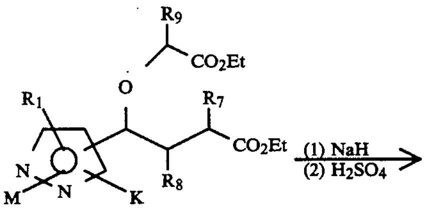

XCVII

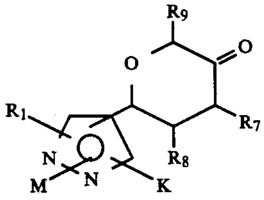

LXXXIIIf (c)

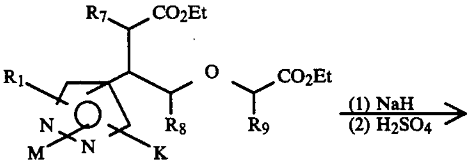

XCVIII

-continued

Equation 63

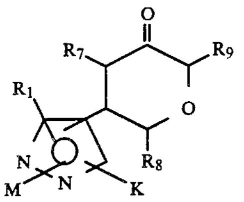

LXXXIIIq (d)

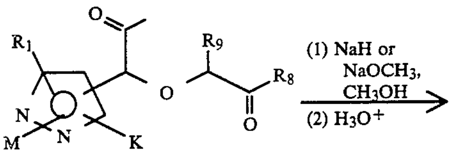

C

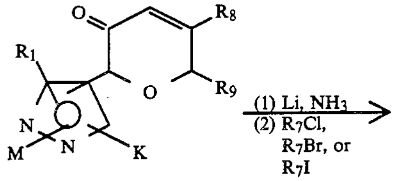

XCIX

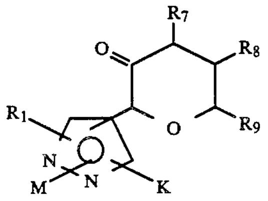

LXXXIIIh wherein

M, $R_1$, $R_7$, $R_8$ and $R_9$ are as previously defined, K is H, Br, or $SR_{12}$, and $R_{12}$ is $C_2$-$C_4$ alkyl or benzyl, and N is Cl, Br, or I.

Equation 63(a)

The first step of Equation 63(a) is an intramolecular aldol condensation and can be carried out in a manner analogous to that described for Equation 25(b). The second step of Equation 63(a) involves a selective 1,4-reduction of an $\alpha,\beta$-unsaturated ketone and can best be achieved by methods described in Equation 25(c).

Equations 63(b)-63(d)

For a description of the procedure for carrying out the reactions of Equations 63(b)-63(d), see the reference cited for Equation 61. The reductive alkylation process shown in the second step of Equation 63(d), whereby unsaturated ketones of Formula XCIX are converted to the desired products of Formula LXXXIIIh, can conveniently be effected according to the method of V. I. Mel'nikova and K. K. Pivnitskii, *J. Org. Chem. USSR* (*Engl. Trans.*), 6, 2635 (1970).

The pyrrolidones of Formulas CIa-CId can be synthesized as shown in Equation 64 via hydroboration/oxidation of the appropriate $\Delta^2$-pyrrolines of Formulas CIIa-CIId.

Equation 64

(a)

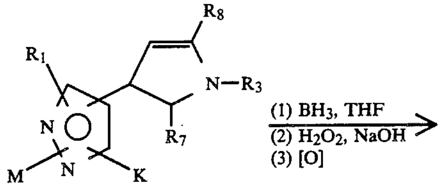

CIIa

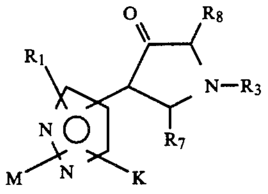

CIa (b)

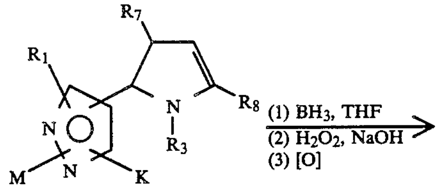

CIIb

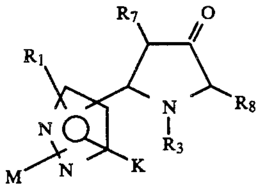

CIb (c)

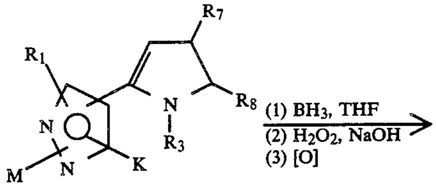

CIIc

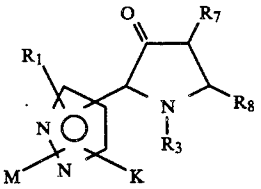

CIc (d)

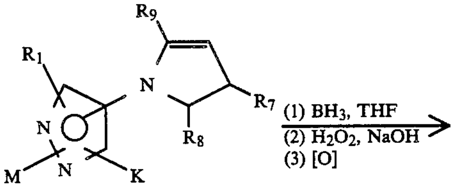

CIId

-continued

Equation 64

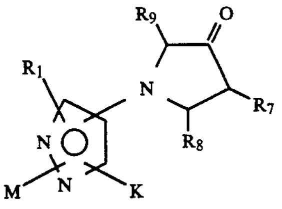

CId wherein

M, $R_1$, $R_3$, $R_7$, $R_8$ and $R_9$ are as previously defined, and K is H, Br, or $SO_2NH$-t-Bu.

The reactions of Equations 64(a)-(d) can conveniently be carried out according to the method of I. J. Borowitz and G. J. Williams, *J. Org. Chem.*, 32, 4157 (1967).

In a similar fashion, the compounds of Formulas CIe-CIi can be prepared from the appropriate enamines of Formulas CIIIa-CIIIe as represented in Equations 65(a-e).

Equation 65

(a)

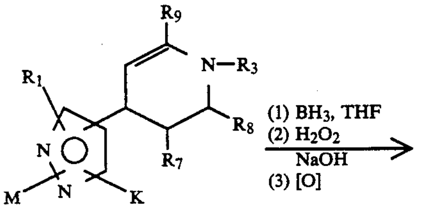

CIIIa

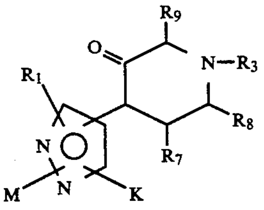

CIe (b)

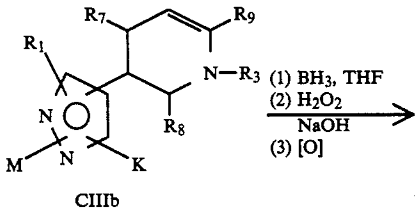

CIIIb

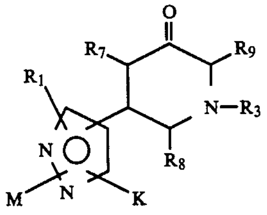

CIf

-continued

Equation 65

(c)

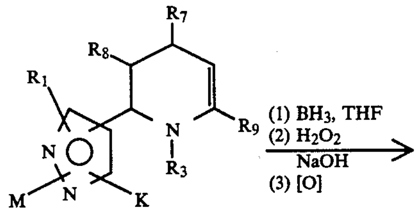

CIIIc

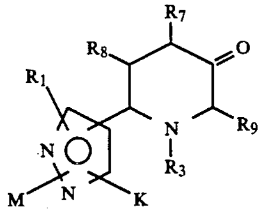

CIq (d)

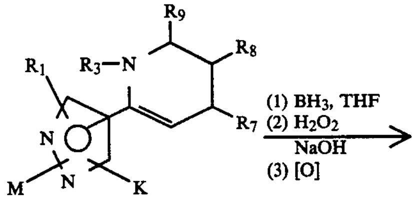

CIIId

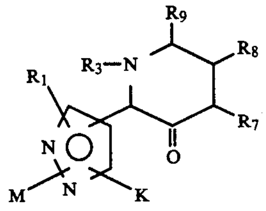

CIh (e)

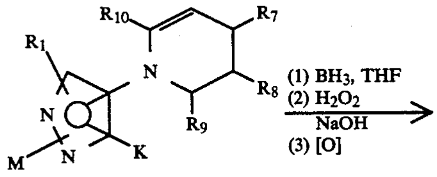

CIIIe

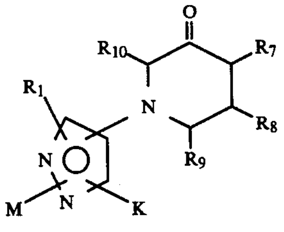

CIi wherein

M, $R_1$, $R_3$, $R_7$, $R_8$, $R_9$ and $R_{10}$ are as previously defined, and K is H, Br, or $SO_2NH$-t-Bu.

The requisite compounds of Formulas CIIa-CIId and CIIIa-CIIIe can be prepared by the method shown in Equation 66. For example, treatment of the appropriate compounds of Formulas CIVa or CIVb with suitable amines, $H_2NR_3$, affords the desired pyrrolines or tetrahydropyridines of Formulas CIIa and CIIIa, respectively.

Equation 66

(a)

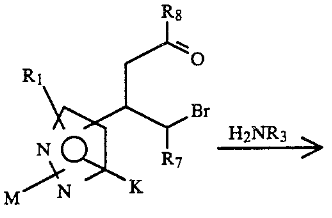

CIVa

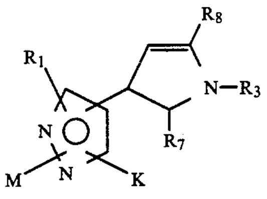

CIIa (b)

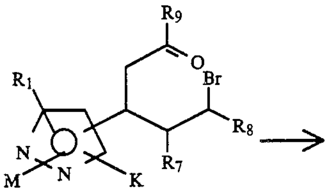

CIVb

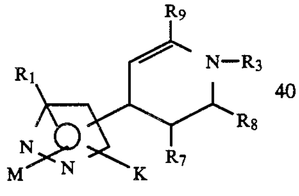

CIIIa wherein

M, $R_1$, $R_3$, $R_7$, $R_8$ and $R_9$ are as previously defined, and K is H, Br or $SO_2NH$-t-Bu.

The reactions of Equations 66(a) and 66(b) can be conveniently carried out according to procedures described in the following references: J. Cloke, *J. Am. Chem. Soc.*, 51, 1174 (1929); A. Wohl, Ber., 34, 1914 (1901); A. Kipp, *Ber.*, 18, 3284 (1895), and 25, 2190 (1892); and S. Gabriel, *Ber.*, 41, 2010 (1908).

The transformations depicted above in Equation 66 can be applied in a straightforward manner to the synthesis of the related compounds of Formulas CIIb–CIId and CIIIb–CIIIe.

The α,β-unsaturated compounds of Formulas CVa can be prepared by the same type of process described above in Equations 33 and 34 to synthesize unsaturated lactones of Formula XLIII. Thus, treatment of compounds CIe with a kinetic base such as lithium diisopropylamide (LDA) will generate the corresponding enolates of Formula CVIb. Trapping with diphenyl disulfide or phenylsulfenyl chloride, and subsequent oxidative elimination gives the desired compounds of Formula CVa, as shown in Equation 67.

Equation 67

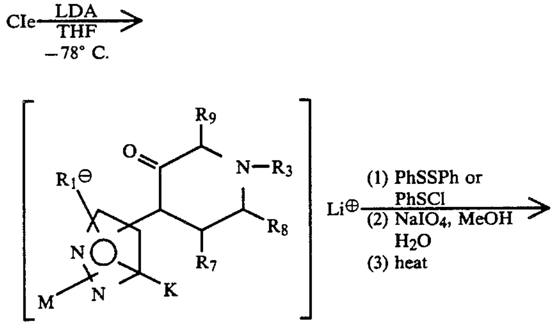

CVIb

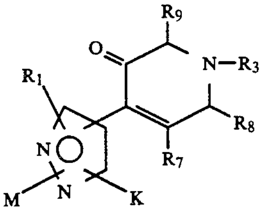

CVa wherein

M, $R_1$, $R_3$, $R_7$, $R_8$ and $R_9$ are as previously defined, and K is H, Br, or $SO_2NH$-t-Bu.

It should be noted in Equation 67 that for compounds of Formula CIe, where $R_3$ is H, one extra molar equivalent of base must be employed to generate the dianions. For a procedure describing the formation of enolates of 3-piperidones such as those of Formulas CIe–CIi, see McElvain, *J. Am. Chem. Soc.*, 55, 1233 (1933), and McElvain and Vozza, *ibid.*, 71, 896 (1949).

The procedure shown in Equations 67 can be quite easily applied to compounds of Formulas CIf–CIi. In this manner, the corresponding α,β-unsaturated derivatives can be synthesized and further transformed into the appropriate sulfonamides of Formula IVa or IVb, where Q is Q-128, Q-129, Q-131, and Q-130.

In an analogous fashion, compounds of Formulas LXXXIIIe–LXXXIIIh can be treated according to the procedures described in Equations 33 and 34 to give the corresponding α,β-unsaturated derivatives. Further elaborations of these compounds then affords the primary sulfonamides of Formula IVa or IVb, where Q is Q-123, Q-125, Q-124, and Q-126.

Compounds of Formulas CVIIa and CVIIb can be conveniently prepared as shown in Equations 68 (a and b) by a Dieckmann cyclization of the appropriate sulfides of Formulas CVIIIa and CVIIIb, followed by hydrolysis and decarboxylation.

Equation 68

(a)

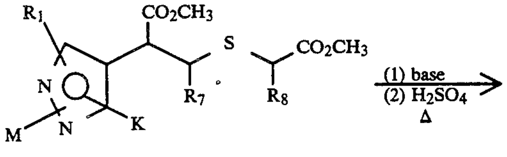

CVIIIa

-continued

Equation 68

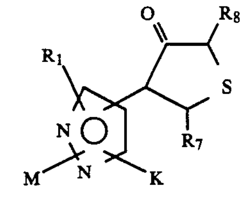

CVIIa (b)

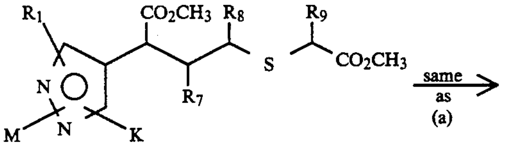

CVIIIb

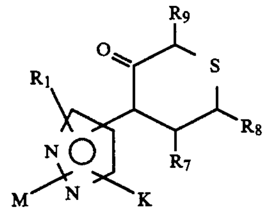

CVIIb wherein

M, $R_1$, $R_7$, $R_8$ and $R_9$ are as previously defined, and K is H, Br, or $SO_2NH$-t-Bu.

The reactions of Equations 68(a) and 68(b) can be carried out according to the procedure of Woodward and Eastman, *J. Am. Chem. Soc.* 68, 2229 (1946), and Woodward and Eastman, ibid., 66, 849 (1944). For a review of syntheses of these ring systems, see Wolf and Folkers, *Org. Reactions,* Vol. 6, 1951, pp. 443–468.

In a similar fashion, the 3-ketothiolanes of Formulas CVIIc–CVIIg can be prepared via Dieckmann cyclization of the appropriate sulfides in Formulas CVIIIc–CVIIIg as outlined below in Equations 69 (a–e).

Equation 69

(a)

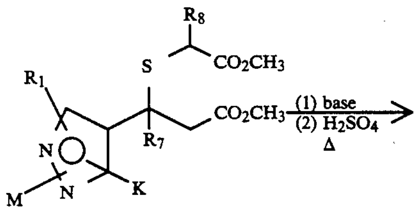

CVIIIc

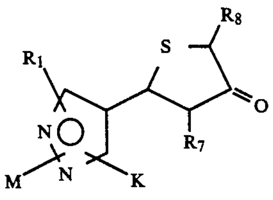

CVIIc

-continued

Equation 69

(b)

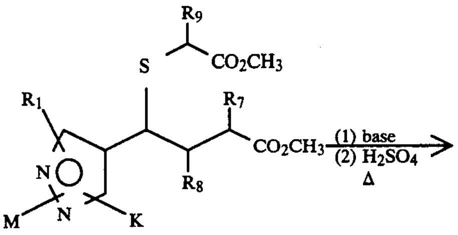

CVIIId

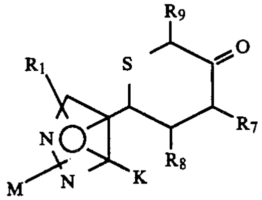

CVIId (c)

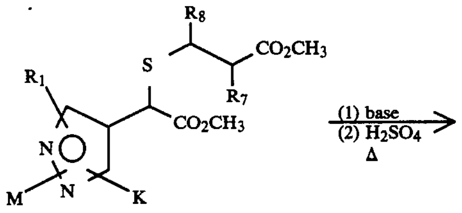

CVIIIe

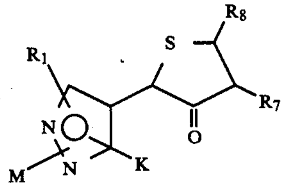

CVIIe (d)

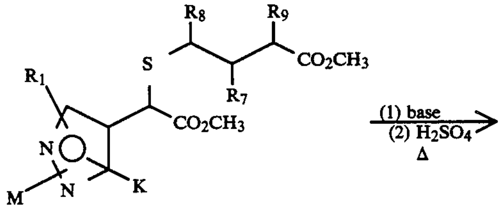

CVIIIf

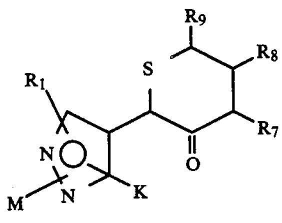

CVIIf

-continued

Equation 69

(e)

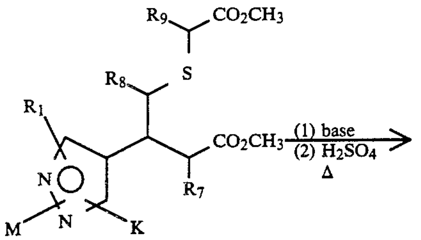

CVIIIg

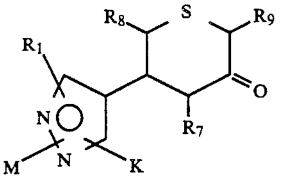

CVIIg wherein

M, $R_1$, $R_7$, $R_8$ and $R_9$ are as previously defined, and K is H, Br, or $SO_2NH$-t-Bu.

The requisite sulfides of Formulas CVIIIa-CVIIIg can be prepared by the reaction of appropriate alkyl bromides of Formula CIX with substituted mercaptans of Formula CX. Equation 70 shows this reaction for the example CVIIa.

Equation 70

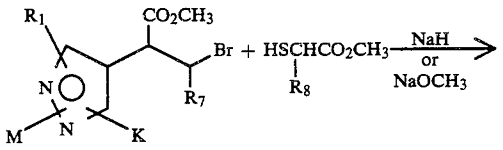

CIX CX

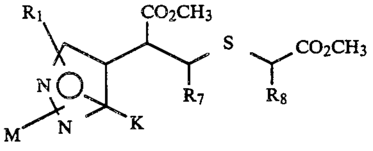

CVIIa wherein

M, $R_1$, $R_7$ and $R_8$ are as previously defined, and K is H, Br, or $SO_2NH$-t-Bu.

The alkylation of mercaptans such as those of Formula CX with alkyl halides is a well-known process with considerable precedent in the literature. For relevant references, see Shriner, Struck and Jorison, *J. Am. Chem. Soc.*, 52, 2066 (1930); Kirner and Richter, *ibid.*, 51, 3135 (1929); Kipnis and Ornfelt, *ibid.*, 71, 3571 (1949); and Fehnel and Carmack, *ibid.*, 71, 92 (1949).

By applying the procedures described above in Equation 70, one skilled in the art can prepare the requisite sulfides of Formulas CVIIIb-CVIIIg from the appropriate alkyl bromides and mercaptans.

In an analogous manner, the requisite ethers of Formulas XCVI, XCVII, XCVIII and XCIX can be prepared via treatment of the appropriate alkyl bromides of Formula CXI with the sodium salt of the appropriate alcohols of Formula CXII. This reaction is shown below in Equation 71 for the synthesis of compounds XCVI as a representative example.

Equation 71

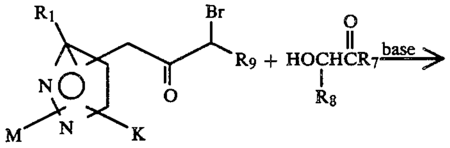

CXI CXII

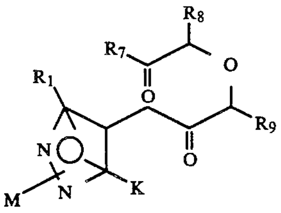

XCVI wherein

M, $R_1$, $R_7$, $R_8$ and $R_9$ are as previously defined, K is H, Br, or $SR_{12}$, and $R_2$ is $C_2$–$C_4$ alkyl or benzyl.

For a compilation of references dealing with the reaction of Equation 71, see R. B. Wagner and H. D. Zook, "Synthetic Organic Chemistry", John Wiley and Sons, Inc., New York, 1953, pp. 226–228.

Unsaturated sulfones of Formulas CXIIIa and CXIIIb can be prepared as shown in Equation 72 by a three-step sequence of reactions involving: (1) addition of the appropriate organometallic reagents, $R_8M_1$ or $R_7M_1$, to compounds of Formula CVIIa or CVIIb, (2) oxidation of the adducts of Formula CXVa or CXVb, and (3) dehydration of the sulfones CXVIa or CXVIb to the corresponding products of Formula CXIIIa or CXIIIb.

Equation 72

(a)

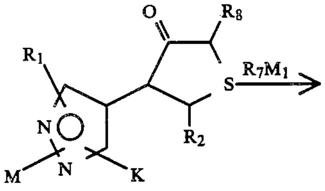

CVIIa

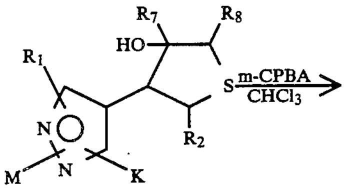

CXVa

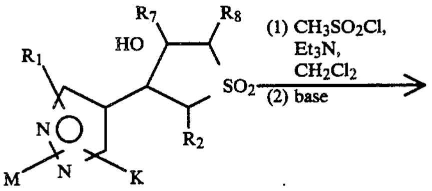

CXVIa

-continued
Equation 72

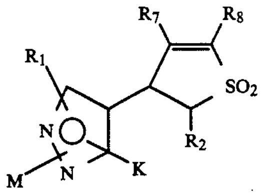

CXIIIa (b)

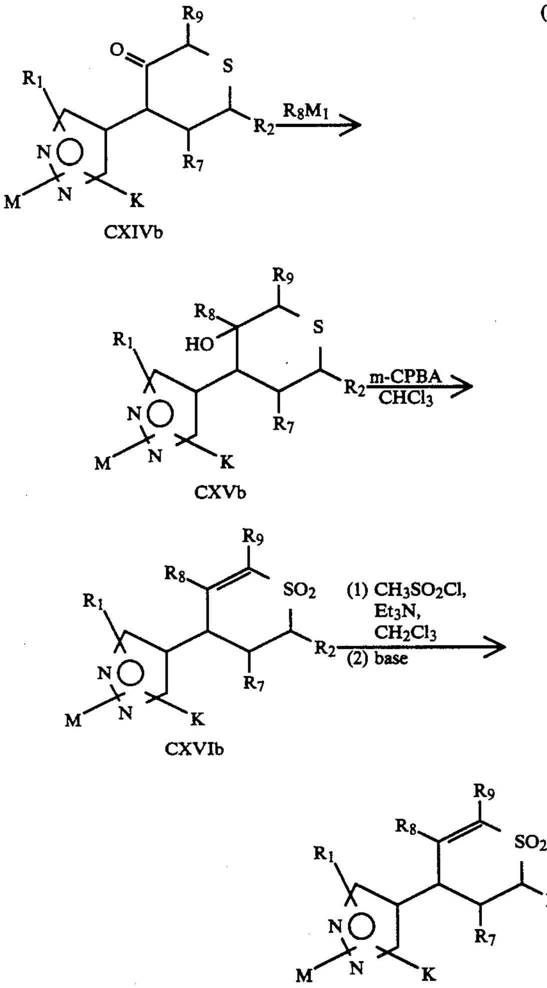

wherein

M, $R_1$, $R_2$, $R_7$, $R_8$ and $R_9$ are as previously defined, K is H, Br or $SO_2NH$-t-Bu, and $M_1$ is MgBr or Li.

The transformations shown above in Equations 72(a) and 72(b) can be effected according to the method of T. Takaya, et al., *Bull. Chem. Soc. Japan,* 41, 2086 (1968). An additional equivalent of the organometallic reagent must be used when K is $SO_2NH$-t-Bu.

In a similar fashion, compounds of Formulas CVIIc–CVIIg can be treated according to the procedures described above in Equations 72(a) and 72(b) to afford the corresponding unsaturated sulfones. Further elaboration of the unsaturated sulfones derived from the compounds of Formulas CVIIa–CVIIg by methods described previously yields the primary sulfonamides of Formula IVa or IVb, where Q is Q-49, Q-120, Q-84, Q-50, Q-118, Q-47, Q-122, and Q-119.

The unsaturated sulfones of Formulas CXIIIc and CXIIId can be prepared as shown in Equation 73 by: (1) addition of the dianions of N-t-butylpyrazole sulfonamides XX to the appropriately substituted compounds of Formulas CXVIIa and CXVIIb, and (2) oxidation and dehydration of the resultant adducts of Formulas CXVc and CXVd.

Equation 73

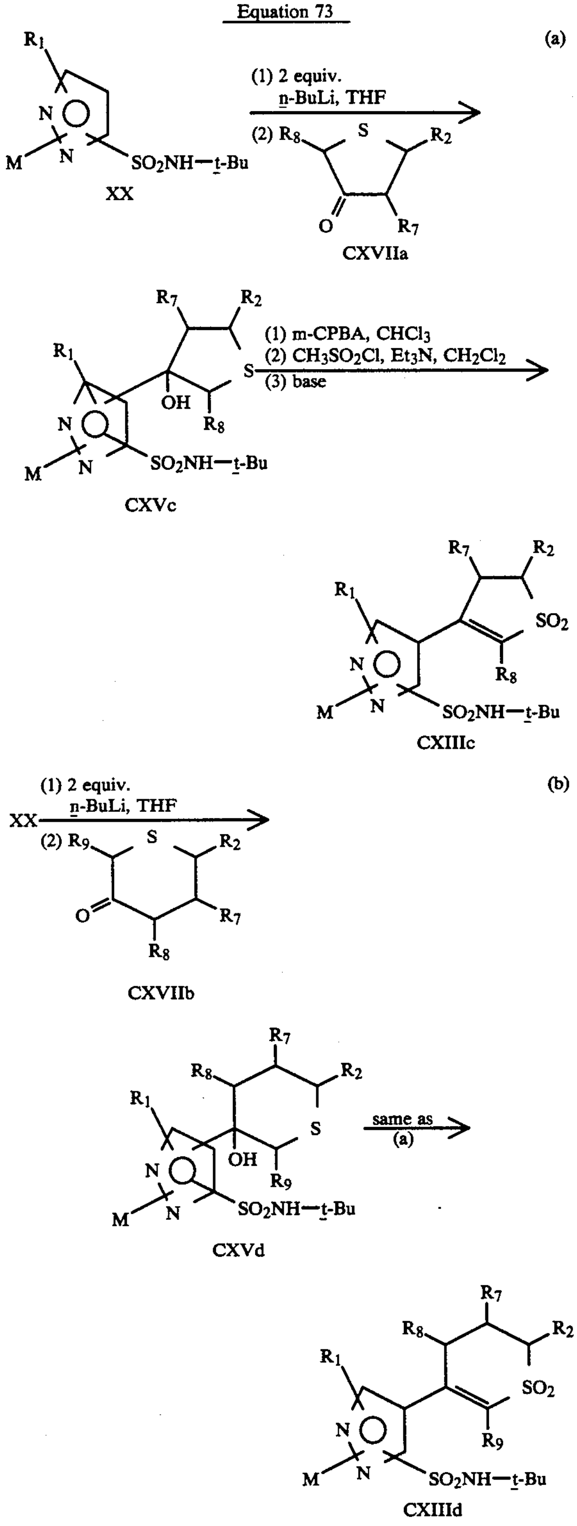

wherein

M, $R_1$, $R_2$, $R_7$, $R_8$ and $R_9$ are as previously defined.

The first step of the reactions of Equations 73(a) and 73(b) can be conveniently carried out according to the procedure of J. G. Lombardino, *J. Org. Chem.,* 36, 1843 (1971). The second step shown in Equations 73(a) and 73(b) is accomplished by the method described in Equation 72.

Dihydrothiopyran-3-ones of Formulas CXVIIIa-CXVIIId can be synthesized as depicted below in Equations 74 (a-d) in a Dieckmann-type cyclization of the appropriate sulfides of Formulas CXIX-a-CXIXd, and subsequent acid-induced hydrolysis and decarboxylation.

Equation 74

(a)

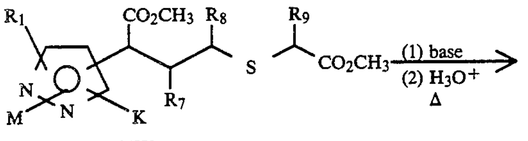

CXIXa

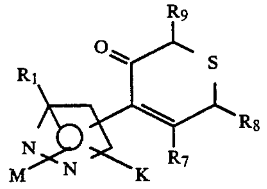

CXVIIIa (b)

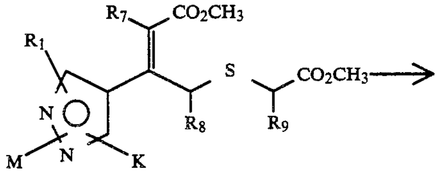

CXIXb

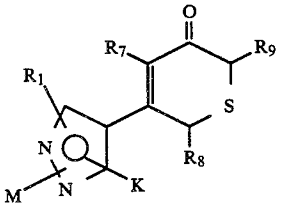

CXVIIIb (c)

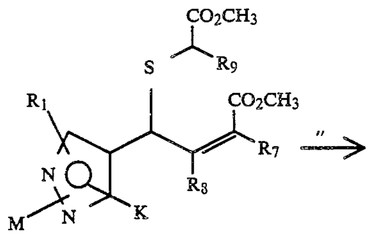

CXIXc

-continued

Equation 74

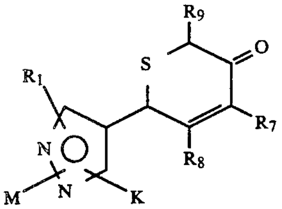

CXVIIIc (d)

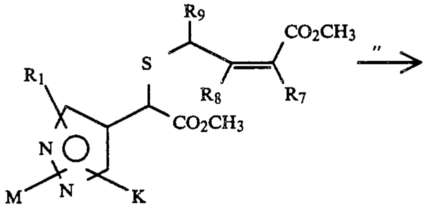

CXIXd

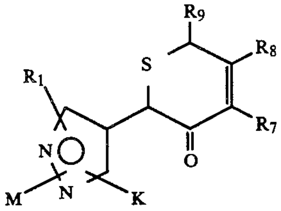

CXVIIId wherein

M, $R_1$, $R_7$, $R_8$ and $R_9$ are as previously defined, and K is H, Br, or $SO_2NH$-t-Bu.

The reaction of Equations 74(a-d) can be carried out according to the procedure of S. Rossi and G. Pagani, *Tetrahedron Lett.,* 2129 (1966).

The requisite sulfides of Formulas CXIXa-CXIXd can be prepared in a manner analogous to that described in Equation 70 for the preparation of compounds CVIIa.

Dihydropyrones of Formulas CXXa-CXXd can be conveniently prepared as shown in Equation 75 by reaction of the appropriate potassium enolates of Formulas CXXIa-CXXId with suitable acid chlorides of Formulas CXXIIa-CXXIId.

Equation 75

(a)

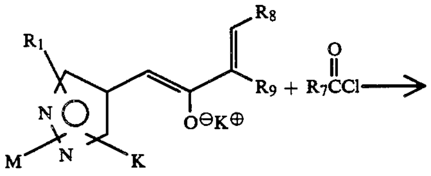

CXXIa CXXIIa

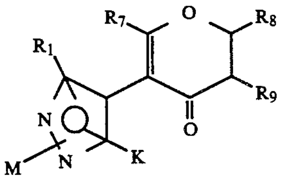

CXXa

-continued

Equation 75

(b)

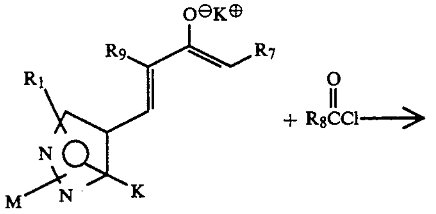

CXXIb CXXIIb

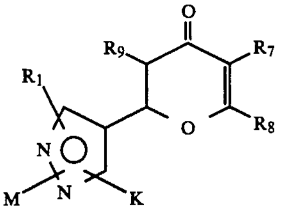

CXXb (c)

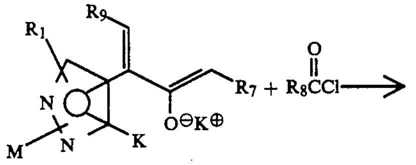

CXXIc CXXIIc

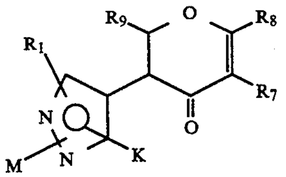

CXXc (d)

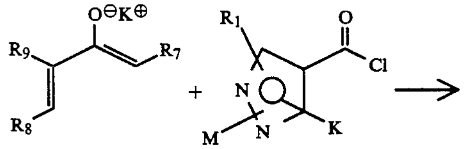

CXXId CXXIId

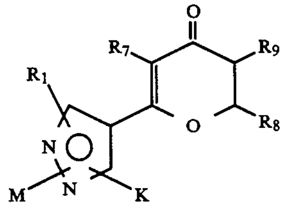

CXXd wherein

M, $R_1$, $R_7$, $R_8$ and $R_9$ are as previously defined, K is H, Br, or $SR_{12}$, and $R_{12}$ is $C_2$–$C_4$ alkyl or benzyl.

The reactions of Equation 75 can be carried out in a manner analogous to that described for Equation 53.

Reaction of dihydropyrones of Formulas CXXa-CXXd gives the corresponding tetrahydropyrones as shown in Equation 76 for the specific example of CXXa.

Equation 76

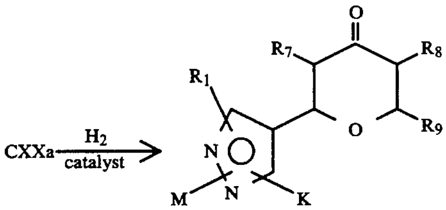

CXXIII wherein

M, $R_1$, $R_7$, $R_8$ and $R_9$ are as previously defined, K is H, Br, or $SR_{12}$, and $R_{12}$ is $C_2$–$C_4$ alkyl or benzyl.

The reduction shown in Equation 76 can be carried out in the presence of a suitable catalyst such as colloidal palladium (cf., Borsche, *Ber.*, 48, 682 (1915); 56, 2012, 2132 (1923); 59, 237 (1926)) or palladized strontium carbonate (see Cawley and Plant, *J. Chem. Soc.*, 1214 (1938); Attenburrow, et al., ibid., 571 (1945)).

In a similar fashion, compounds of Formulas CXXb-CXXd can be reduced to afford the corresponding tetrahydropyrones. Further elaboration of the compounds by methods described previously then yields the primary sulfonamides IVa or IVb, where Q is Q-88 or Q-89.

Compounds of Formulas CXXIVa-CXXIVe can be synthesized as shown in Equation 77 by condensation of 1,3-diketones of Formulas CXXVa-CXXVe with the appropriate imines of Formulas CXXIVa-CXXVId.

Equation 77

(a)

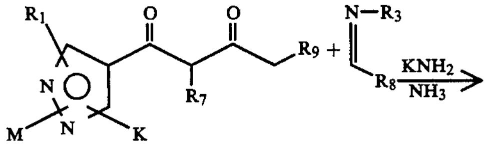

CXXVa CXXVIa

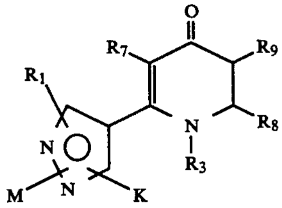

CXXIVa (b)

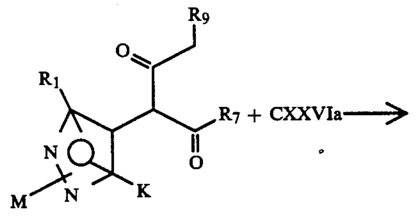

CXXVb

-continued

Equation 77

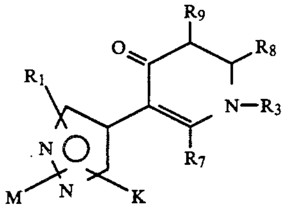

CXXIVb (c)

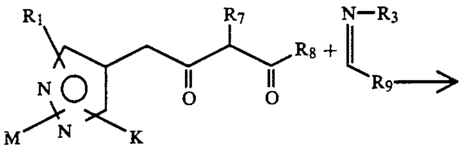

CXXVc CXXVIb

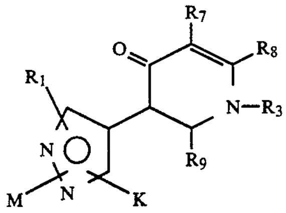

CXXIVc (d)

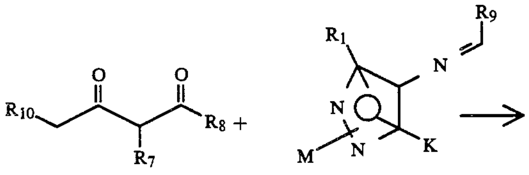

CXXVd CXXVIc

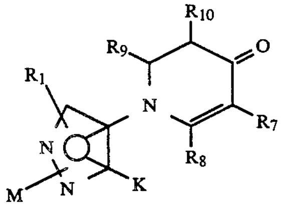

CXXIVd (e)

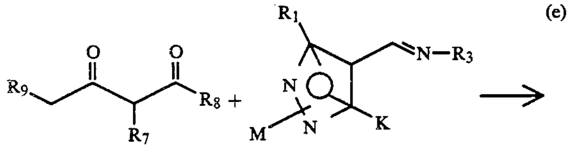

CXXVe CXXVId

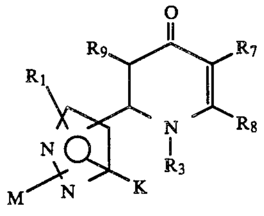

CXXIVe wherein

M, $R_1$, $R_3$, $R_7$, $R_8$, $R_9$ and $R_{10}$ are as previously defined, K is H, Br, or $SR_{12}$, and $R_{12}$ is $C_2$-$C_4$ alkyl or benzyl.

The reactions of Equation 77 are carried out by the procedure described by N. Sugiyama, M. Yamamoto and C. Kashima, *Bull. Chem. Soc. Japan*, 42, 1357 (1969).

Dihydropyridones, such as those of Formulas CXXIVa-CXXIVe, have also been prepared by reduction of the appropriate pyridones of Formulas LXXXIa and LXXXIb with lithium aluminum hydride (E. Winterfeldt, *Ber. deutsch Chem. Ges.*, 97, 2463 (1964)), lithium triethoxyaluminum hydride (Y., Tamura, et al., *Chem. and Ind.*, 168 (1972)), and catalytic hydrogenation (see J. Hebky and J. Kejha, CA, 50, 15532c).

Piperidones of Formulas CXXVIIa-CXXVIIc can be prepared in a straightforward manner via reduction of the appropriate dihydropyridones of Formulas CXXIVa-CXXIVe. Equation 78 depicts the reduction of compounds of Formula CXXIVa with lithium aluminum hydride to give piperidones of Formula CXXVIIa.

Equation 78

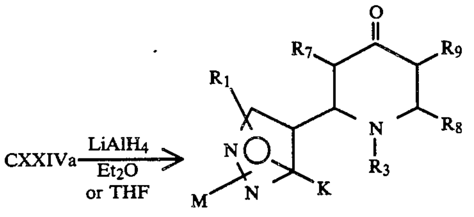

CXXVIIa wherein

M, $R_1$, $R_3$, $R_7$, $R_8$ and $R_9$ are as previously defined, K is H, Br, or $SR_{12}$, and $R_{12}$ is $C_2$-$C_4$ alkyl or benzyl.

The 1,4-reduction of enaminones such as those of Formula CXXIVa can be achieved with lithium aluminum hydride and a variety of other reagents. For a review of these methods, see J. V. Greenhill, *Chem. Soc. Rev.*, 6, 277 (1977).

The tetrahydrothiopyrones of Formulas CXXVIIIa and CXXVIIIb can be prepared as shown in Equation 79 by a Dieckmann-type cyclization of the appropriate sulfides of Formulas CXXIXa and CXXIXb, followed by acid- or base-induced ester cleavage and decarboxylation.

Equation 79

(a)

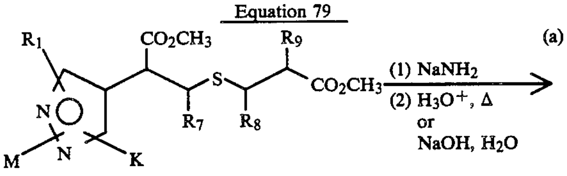

CXXIXa

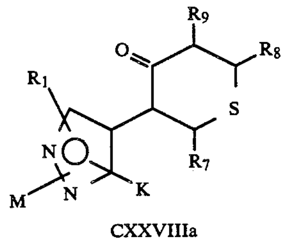

CXXVIIIa

-continued

Equation 79

(b)

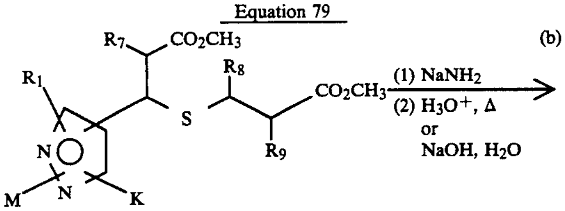

CXXIXb

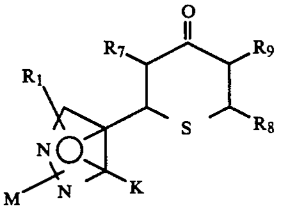

CXXVIIIb wherein

M, $R_1$, $R_7$, $R_8$ and $R_9$ are as previously defined, and K is H, Br, or $SO_2NH$-t-Bu.

The reactions of Equations 79(a) and 79(b) can be effectively accomplished by the procedure of G. M. Bennett and L. V. D. Scorah, *J. Chem. Soc.,* 194 (1927).

The requisite sulfides of Formulas CXXIXa and CXXIXb can be readily synthesized by either of the methods shown in Equation 80. Thus, treatment of the mercaptide salts of Formula CXXX with either (a) α,β-unsaturated esters of Formula CXXXI, or (b) alkyl halides of Formula CXXXII affords the desired products of Formula CXXIXa.

Equation 80

(a)

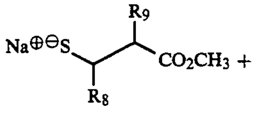

CXXX

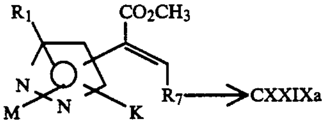

CXXXI (b)

CXXX +

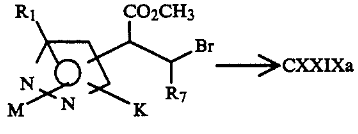

CXXXII wherein

M, $R_1$, $R_7$, $R_8$ and $R_9$ are as previously defined, and K is H, Br, or $SO_2NH$-t-Bu.

The reaction of Equation 80 can be carried out according to the procedures discussed by Bruson, *Org. Reactions,* 5 (1949), pp. 95–97 and 129–130.

The dihydrothiopyrones of Formulas CXXXIIIa-CXXXIIId can be prepared from the appropriate tetrahydropyrones of Formulas CXXVIIa-CXXVIIb by oxidation with N-chlorosuccinimide (NCS) as shown in Equations 81(a) and 81(b).

Equation 81

(a)

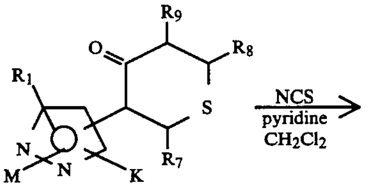

CXXVIIa

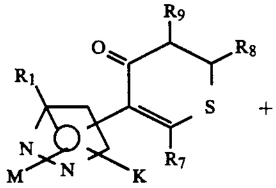

CXXXIIIa

+

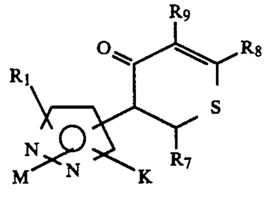

CXXXIIIb (b)

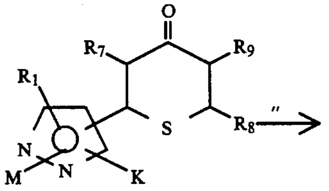

CXXVIIb

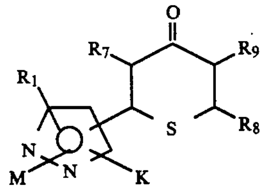

CXXXIIIc

+

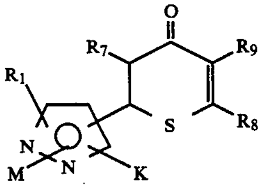

CXXXIIId wherein

M, $R_1$, $R_7$, $R_8$ and $R_9$ are as previously defined, and K is H, Br, or $SO_2NH$-t-Bu.

The reaction of Equation 81 can be carried out according to the procedure of C. H. Chen, G. A. Reynolds and J. A. Van Allan, *J. Org. Chem.,* 42 2777 (1977). It should be noted that the reaction shown in Equation 81, when applied to unsymmetrical tetrahydropyrones such as those of Formulas CXXVIIa and CXVIIb, give mixtures of isomers. These compounds can be separated by recrystallization from a suitable solvent such as diethyl ether, benzene, or ethyl acetate, or by column chromatography.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines", Vol. XVI of the series mentioned above which is herein incorporated by reference. The 2-amino-1,3,5-triazines of Formula III, where A is A-1 and Z is N, can be prepared according to methods described by E. M. Smolin and L. Rapaport in "s-Triazines and Derivatives," Vol. XIII.

Pyrimidines of Formula III, where A is A-1 and Y is an acetal or thioacetal substituent, can be prepared by methods taught in European Patent Application No. 84,224 (published July 27, 1983).

Pyrimidines of Formula III, where A is A-1 and Y is cyclopropyl or $OCF_2H$, can be synthesized according to the methods taught in South African Patent Application No. 837,434 and South African Publication No. 82,5045, respectively.

Compounds of Formula III, where A is A-2 or A-3, can be prepared by procedures disclosed in U.S. Pat. No. 4,339,267.

Compounds of Formula III, where A is A-4, can be prepared by methods taught in European Patent Application No. 46,677 (published Mar. 3, 1982).

Additional references dealing with the synthesis of bicyclic pyrimidines of Formula III, where A is A-2, A-3, or A-4 are Braker, Sheehan, Spitzmiller and Lott. *J. Am. Chem. Soc.*, 69, 3072 (1947); Mitler and Bhattacharya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964).

Compounds of Formula III, where A is A-5, can be prepared by methods taught in U.S. Pat. No. 4,421,550.

Compounds of Formula III, where A is A-6, can be prepared by methods taught in European Patent Application No. 94,260 (published Nov. 16, 1983).

A number of references are available which teach chemical transformations and preparations of pyrazole intermediates needed for this invention. For example:

A. H. Kost and I. I. Groundberg, *Advan. Heterocyclic Chem.*, 6, 347–429 (1966).

T. L. Jacobs, In "Heterocyclic Compounds", (R. C. Elderfield, Ed.), Vol. 5, pp 45–161, Wiley, New York, 1957.

R. Fusco, In "Heterocyclic Compounds," (A. Weisberger, Ed.), Vol. 22, pp. 3–174, Interscience Publishers, New York, 1967.

All of the above are herein incorporated by reference.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques. Detailed examples of such techniques are given in U.S. Pat. No. 4,127,405, the disclosure of which is herein incorporated by reference.

The compounds of this invention and their preparation are further illustrated by the following examples.

EXAMPLE 1

1-Methyl-4-(3-oxo-1-cyclohexenyl)-1H-pyrazole-5-sulfonamide

To a solution of 4.4 mL (6.8 mmol) of a 1.55M solution of n-butyllithium in hexanes in 5 mL of THF at −78° C. was added 1.0 g (3.1 mmol) of 4-bromo-N-(t-butyldimethylsilyl)-1-methyl-1H-pyrazole-5-sulfonamide in 5 mL of THF. After 15 minutes 0.58 mL (4.0 mmol) of 3-ethoxy-2-cyclohexen-1-one was added. The reaction mixture was allowed to warm to room temperature over a period of 3 h. After the addition of 10 mL of saturated aqueous $NH_4Cl$, the reaction mixture was extracted with 75 mL of ethyl acetate. The organic layer was shaken with 10% $H_2SO_4$ (2×10 mL). The layers were separated. The aqueous layer was neutralized with saturated aqueous $NaHCO_3$ and extracted with ethyl acetate. All of the organic layers were combined, dried ($Na_2SO_4$) and the solvent was removed with a rotary evaporator.

The residue was dissolved in 5 mL of THF and 5 mL of a 1N solution of tetra-n-butylammonium fluoride in THF was added. After 16 hours, 5 mL of water and 50 mL of ethyl acetate were added. The layers were separated. The aqueous layer was extracted with methylene chloride (3×30 mL). The combined organic layers were dried ($Na_2SO_4$) and the solvent was removed with a rotary evaporator. The residue was purified by medium pressure liquid chromatography (1:1 ethyl acetate:hexanes as eluant) to give 0.25 g of the title compound as a white solid m.p. 160°–165° C. (d).

EXAMPLE 2

N-((4,6-Dimethoxypyrimidin-2-yl)aminocarbonyl)-1-methyl-4-(3-oxo-1-cyclohexenyl)-1H-pyrazole-5-sulfonamide To a solution of 50.5 mg (0.198 mmol) of 1-methyl-4-(3-oxo-1-cyclohexenyl)-1H-pyrazole-5-sulfonamide and 54.5 g (0.198 mmol) of (4,6-dimethoxy-2-pyrimidinyl)-carbamic acid, phenyl ester in 1 mL of acetonitrile was added 0.03 mL (0.2 mmol) of DBU. After 45 minutes, 1 mL of water and 0.5 mL of 5% HCl were added. The white solid that precipitated out was filtered, washed with ether and dried, to give 50 mg of material m.p. 175°–182° C. (d).

By applying the procedures of Examples 1 and 2 and Equations 1 through 81, one skilled in the art can prepare the compounds shown in Tables 1 through 7.

General Formulas for Tables

General Formula 1 wherein J is J-1 to J-4 and $W_1$ is 0 unless indicated by *

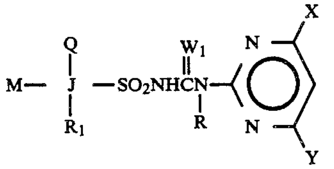

General Formula 2 wherein J is J-1 to J-4 and $W_1$ is 0 unless indicated by *

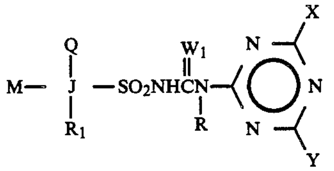

-continued
General Formulas for Tables
General Formula 3 wherein J is J-1 to J-4
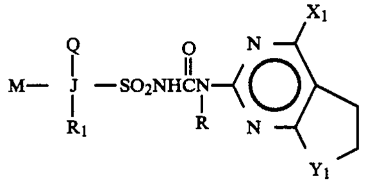
General Formula 4 wherein J is J-1 to J-4
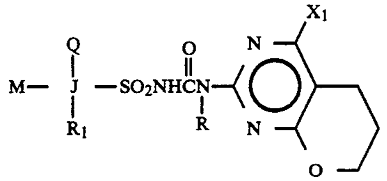
-continued
General Formulas for Tables
General Formula 5 wherein J is J-1 to J-4
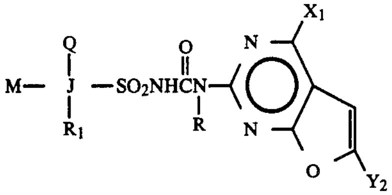
General Formula 6 wherein J is J-1 to J-4
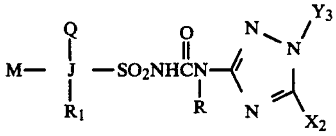
General Formula 7 wherein J is J-1 to J-4
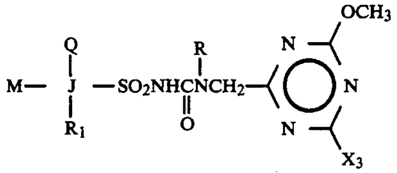

TABLE 1

General Formula 1

| J | M | Q | R | $R_1$ | X | Y | m.p. (°C.) |
|---|---|---|---|---|---|---|---|
| J-1 | $CH_3$ | Q-1 ($R_7$ = H, $R_8$ = H) | H | H | $CH_3$ | $CH_3$ | |
| J-1 | $CH_2CH_3$ | Q-1 ($R_7$ = H, $R_8$ = H) | H | H | $OCH_3$ | $CH_3$ | |
| J-1 | $CH_2CH_2CH_3$ | Q-1 ($R_7$ = H, $R_8$ = H) | H | H | $OCH_3$ | $OCH_3$ | |
| J-1 | $CH(CH_3)_2$ | Q-1 ($R_7$ = H, $R_8$ = H) | $CH_3$ | H | $OCH_3$ | $OCH_3$ | |
| J-1 | $CH_2(CH_2)_2CH_3$ | Q-1 ($R_7$ = H, $R_8$ = H) | $CH_3$ | H | $OCH_3$ | $CH_3$ | |
| J-1 | $C(CH_3)_3$ | Q-1 ($R_7$ = H, $R_8$ = H) | H | 5-$CH_3$ | $OCH_3$ | $OCH_3$ | |
| J-1 | H | Q-1 ($R_7$ = H, $R_8$ = H) | H | 5-$CH_2CH_3$ | $OCH_3$ | $OCH_3$ | |
| J-1 | $CH_2CH{=}CH_2$ | Q-1 ($R_7$ = H, $R_8$ = H) | H | 5-$CH(CH_3)_2$ | $OCH_3$ | $OCH_3$ | |
| J-1 | $CH_2CH{=}CHCH_3$ | Q-1 ($R_7$ = H, $R_8$ = H) | H | 5-$OCH_3$ | $OCH_3$ | $OCH_3$ | |
| J-1 | $C_6H_5$ | Q-1 ($R_7$ = H, $R_8$ = H) | H | 5-$OCH_2CH_3$ | $OCH_3$ | $OCH_3$ | |
| J-1 | $C_6H_4$—4Cl | Q-1 ($R_7$ = H, $R_8$ = H) | H | 5-$OCH(CH_3)_2$ | $OCH_3$ | $OCH_3$ | |
| J-1 | $C_6H_4$—3-$NO_2$ | Q-1 ($R_7$ = H, $R_8$ = H) | H | 5-$OCF_2H$ | $OCH_3$ | $OCH_3$ | |
| J-1 | $C_6H_4$—3-$CH_3$ | Q-1 ($R_7$ = H, $R_8$ = H) | H | 5-$OCH_2CH_2Br$ | $OCH_3$ | $OCH_3$ | |
| J-1 | $C_6H_4$—2-$OCH_3$ | Q-1 ($R_7$ = H, $R_8$ = H) | H | 5-$OCH(CH_3)(CH_2Cl)$ | $OCH_3$ | $OCH_3$ | |
| J-1 | $CO_2CH_3$ | Q-1 ($R_7$ = H, $R_8$ = H) | H | 5-$CH_2F$ | $OCH_3$ | $OCH_3$ | |
| J-1 | $CO_2CH_2CH_3$ | Q-1 ($R_7$ = H, $R_8$ = H) | H | 5-$CH_2CH_2Br$ | $OCH_3$ | $OCH_3$ | |
| J-1 | $SO_2CH_3$ | Q-1 ($R_7$ = H, $R_8$ = H) | H | 5-$CH(CH_3)(CH_2Cl)$ | $OCH_3$ | $OCH_3$ | |
| J-1 | $SO_2N(CH_3)_2$ | Q-1 ($R_7$ = H, $R_8$ = H) | H | 5-Cl | $OCH_3$ | $OCH_3$ | |
| J-2 | —$CH_2C{\equiv}CH$ | Q-1 ($R_7$ = H, $R_8$ = H) | H | 5-$SCH_2CH_3$ | $OCH_3$ | $OCH_3$ | |
| J-2 | —$CH(CH_3)_2$ | Q-1 ($R_7$ = H, $R_8$ = H) | H | 5-$SCH(CH_3)_2$ | $OCH_3$ | $OCH_3$ | |
| J-2 | —$C(CH_3)_3$ | Q-1 ($R_7$ = H, $R_8$ = H) | H | 5-$SCH_2F$ | $OCH_3$ | $OCH_3$ | |
| J-2 | —$C_6H_5$ | Q-1 ($R_7$ = H, $R_8$ = H) | H | 5-$SCH_2CH_2Br$ | $OCH_3$ | $OCH_3$ | |
| J-2 | —$C_6H_4$—3-Cl | Q-1 ($R_7$ = H, $R_8$ = H) | H | 5-$SCH(CH_3)(CH_2Cl)$ | $OCH_3$ | $OCH_3$ | |
| J-1 | —$CH_3$ | Q-1 ($R_7$ = H, $R_8$ = H) | H | 5-$SOCH_3$ | $OCH_3$ | $OCH_3$ | |
| J-1 | —$CH_3$ | Q-1 ($R_7$ = H, $R_8$ = H) | H | 5-$SO_2CH_3$ | $OCH_3$ | $OCH_3$ | |
| J-1 | —$CH_3$ | Q-1 ($R_7$ = H, $R_8$ = H) | H | 5-$SO_2N(CH_3)_2$ | $OCH_3$ | $OCH_3$ | |
| J-1 | —$CH_3$ | Q-1 ($R_7$ = H, $R_8$ = H) | H | 5-$CO_2CH_3$ | $OCH_3$ | $OCH_3$ | |
| J-2 | —$CH_3$ | Q-1 ($R_7$ = H, $R_8$ = H) | H | 5-$CO_2CH_2CH_3$ | $OCH_3$ | $OCH_3$ | |
| J-3 | —$CH_3$ | Q-1 ($R_7$ = H, $R_8$ = H) | H | 3-$CO_2CH_3$ | $OCH_3$ | $OCH_3$ | |
| J-4 | —$CH_3$ | Q-1 ($R_7$ = H, $R_8$ = H) | H | 3-$CO_2CH_3$ | $OCH_3$ | $OCH_3$ | |
| J-1 | —$CH_3$ | Q-1 ($R_7$ = H, $R_8$ = H) | H | 5-Cl | $OCH_3$ | $OCH_3$ | |
| J-2 | —$CH_3$ | Q-1 ($R_7$ = H, $R_8$ = H) | H | 5-Br | $OCH_3$ | $OCH_3$ | |
| J-2 | —$CH_3$ | Q-1 ($R_7$ = H, $R_8$ = H) | H | 5-F | $OCH_3$ | $OCH_3$ | |
| J-2 | —$CH_3$ | Q-1 ($R_7$ = H, $R_8$ = H) | H | 5-I | $OCH_3$ | $OCH_3$ | |
| J-3 | —$CH_3$ | Q-1 ($R_7$ = H, $R_8$ = H) | H | 3-$NO_2$ | $OCH_3$ | $OCH_3$ | |
| J-1 | —$CH_3$ | Q-1 ($R_7$ = H, $R_8$ = H) | H | 5-$CF_3$ | $OCH_3$ | $OCH_3$ | |
| J-1 | —$CH_3$ | Q-1 ($R_7$ = H, $R_8$ = H) | H | 5-$OCF_2H$ | $OCH_3$ | $OCH_3$ | |
| J-1* | —$CH_3$ | Q-1 ($R_7$ = H, $R_8$ = H) | H | H | $OCH_3$ | $OCH_3$ | |
| J-2 | —$CH_3$ | Q-1 ($R_7$ = H, $R_8$ = H) | H | H | $OCH_3$ | $CH(CH_3)_2$ | |
| J-3 | —$CH_3$ | Q-1 ($R_7$ = H, $R_8$ = H) | H | H | $OCH_3$ | $(CH_2)_3CH_3$ | |
| J-4 | —$CH_3$ | Q-1 ($R_7$ = H, $R_8$ = H) | H | H | $OCH_3$ | $OCH_2CH_3$ | |
| J-1 | —$CH_3$ | Q-1 ($R_7$ = H, $R_8$ = H) | H | H | $OCH_3$ | $OCH(CH_3)_2$ | |
| J-2* | —$CH_3$ | Q-1 ($R_7$ = H, $R_8$ = H) | H | H | $OCH_3$ | $OCH_3$ | |
| J-3 | —$CH_3$ | Q-1 ($R_7$ = H, $R_8$ = H) | H | H | $OCF_2H$ | $OCH_3$ | |
| J-4 | —$CH_3$ | Q-1 ($R_7$ = H, $R_8$ = H) | H | H | $OCH_2CH_2F$ | $OCH_3$ | |
| J-1 | —$CH_3$ | Q-1 ($R_7$ = H, $R_8$ = H) | H | H | $OCH_2CHF_2$ | $OCH_3$ | |
| J-2 | —$CH_3$ | Q-1 ($R_7$ = H, $R_8$ = H) | H | H | $OCH_2CF_3$ | $OCH_3$ | |
| J-3 | —$CH_3$ | Q-1 ($R_7$ = H, $R_8$ = H) | H | H | $OCH(CH_3)(CH_2Cl)$ | $OCH_3$ | |
| J-4 | —$CH_3$ | Q-1 ($R_7$ = H, $R_8$ = H) | H | H | $O(CH_2)_3CH_2Br$ | $OCH_3$ | |
| J-1 | —$CH_3$ | Q-1 ($R_7$ = H, $R_8$ = H) | H | H | $CH_2F$ | $OCH_3$ | |

TABLE 1-continued

General Formula 1

| J | M | Q | R | $R_1$ | X | Y | m.p. (°C.) |
|---|---|---|---|---|---|---|---|
| J-2 | $-CH_3$ | Q-1 ($R_7$ = H, $R_8$ = H) | H | H | $CH_2Cl$ | $OCH_3$ | |
| J-3 | $-CH_3$ | Q-1 ($R_7$ = H, $R_8$ = H) | H | H | $CH_2Br$ | $OCH_3$ | |
| J-4 | $-CH_3$ | Q-1 ($R_7$ = H, $R_8$ = H) | H | H | $CF_3$ | $OCH_3$ | |
| J-1 | $-CH_3$ | Q-1 ($R_7$ = H, $R_8$ = H) | H | H | $CH_2CH_2Br$ | $OCH_3$ | |
| J-2 | $-CH_3$ | Q-1 ($R_7$ = H, $R_8$ = H) | H | H | $CH(CH_3)(CH_2Cl)$ | $OCH_3$ | |
| J-3* | $-CH_3$ | Q-1 ($R_7$ = H, $R_8$ = H) | H | H | $OCH_3$ | $OCH_3$ | |
| J-4 | $-CH_3$ | Q-1 ($R_7$ = H, $R_8$ = H) | H | H | $SCH_3$ | $OCH_3$ | |
| J-1 | $-CH_3$ | Q-1 ($R_7$ = H, $R_8$ = H) | H | H | $SCH_2CH_3$ | $OCH_3$ | |
| J-2 | $-CH_3$ | Q-1 ($R_7$ = H, $R_8$ = H) | H | H | $SCH(CH_3)_2$ | $OCH_3$ | |
| J-3 | $-CH_3$ | Q-1 ($R_7$ = H, $R_8$ = H) | H | H | $S(CH_2)_3CH_3$ | $OCH_3$ | |
| J-4* | $-CH_3$ | Q-1 ($R_7$ = H, $R_8$ = H) | H | H | $OCH_3$ | $OCH_3$ | |
| J-1 | $-CH_3$ | Q-1 ($R_7$ = H, $R_8$ = H) | H | H | $SCH_2CH_2Br$ | $OCH_3$ | |
| J-2 | $-CH_3$ | Q-1 ($R_7$ = H, $R_8$ = H) | H | H | $SCH(CH_3)(CH_2Cl)$ | $OCH_3$ | |
| J-4 | $-CH_3$ | Q-1 ($R_7$ = H, $R_8$ = H) | H | H | $S(CH_2)_3CH_2F$ | $OCH_3$ | |
| J-1 | $-CH_3$ | Q-1 ($R_7$ = H, $R_8$ = H) | H | H | Cl | $OCH_3$ | |
| J-2 | $-CH_3$ | Q-1 ($R_7$ = H, $R_8$ = H) | H | H | Br | $OCH_3$ | |
| J-3 | $-CH_3$ | Q-1 ($R_7$ = H, $R_8$ = H) | H | H | F | $OCH_3$ | |
| J-4 | $-CH_3$ | Q-1 ($R_7$ = H, $R_8$ = H) | H | H | I | $OCH_3$ | |
| J-1 | $-CH_3$ | Q-1 ($R_7$ = H, $R_8$ = H) | H | H | $OCH_3$ | $CH_2OCH_3$ | |
| J-2 | $-CH_3$ | Q-1 ($R_7$ = H, $R_8$ = H) | H | H | $OCH_3$ | $CH_2CH_2OCH(CH_3)_2$ | |
| J-3 | $-CH_3$ | Q-1 ($R_7$ = H, $R_8$ = H) | H | H | $OCH_3$ | $CH(CH_3)(CH_2OCH_3)$ | |
| J-4 | $-CH_3$ | Q-1 ($R_7$ = H, $R_8$ = H) | H | H | $OCH_3$ | $CH_2OCH_2CH_3$ | |
| J-1 | $-CH_3$ | Q-1 ($R_7$ = H, $R_8$ = H) | H | H | $OCH_2O(CH_2)_3CH_3$ | $OCH_3$ | |
| J-2 | $-CH_3$ | Q-1 ($R_7$ = H, $R_8$ = H) | H | H | $OCH_2CH_2OCH(CH_3)_2$ | $OCH_3$ | |
| J-3 | $-CH_3$ | Q-1 ($R_7$ = H, $R_8$ = H) | H | H | $OCH(CH_3)(CH_2OCH_3)$ | $OCH_3$ | |
| J-4 | $-CH_3$ | Q-1 ($R_7$ = H, $R_8$ = H) | H | H | $OCH_2OCH_2CH_3$ | $OCH_3$ | |
| J-1 | $-CH_3$ | Q-1 ($R_7$ = H, $R_8$ = H) | H | H | $OCH_3$ | $NH_2$ | |
| J-2 | $-CH_3$ | Q-1 ($R_7$ = H, $R_8$ = H) | H | H | $OCH_3$ | $NHCH_3$ | |
| J-3 | $-CH_3$ | Q-1 ($R_7$ = H, $R_8$ = H) | H | H | $OCH_3$ | $NHCH_2CH_3$ | |
| J-4 | $-CH_3$ | Q-1 ($R_7$ = H, $R_8$ = H) | H | H | $OCH_3$ | $NHCH(CH_3)_2$ | |
| J-1 | $-CH_3$ | Q-1 ($R_7$ = H, $R_8$ = H) | H | H | $OCH_3$ | $N(CH_3)_2$ | |
| J-2 | $-CH_3$ | Q-1 ($R_7$ = H, $R_8$ = H) | H | H | $OCH_3$ | $N(CH_3)(CH_2CH_3)$ | |
| J-3 | $-CH_3$ | Q-1 ($R_7$ = H, $R_8$ = H) | H | H | $OCH_3$ | $N(CH_3)(CH(CH_3)_2)$ | |
| J-4 | $-CH_3$ | Q-1 ($R_7$ = H, $R_8$ = H) | H | H | $OCH_3$ | $OCH_2CH_2F$ | |
| J-1 | $-CH_3$ | Q-1 ($R_7$ = H, $R_8$ = H) | H | H | H | $OCH_3$ | |
| J-2 | $-CH_3$ | Q-1 ($R_7$ = H, $R_8$ = H) | H | H | $OCH_3$ | $OCH_2CH{=}CH_2$ | |
| J-3 | $-CH_3$ | Q-1 ($R_7$ = H, $R_8$ = H) | H | H | $OCH_3$ | $OCH_2C(CH_3){=}CH_2$ | |
| J-4 | $-CH_3$ | Q-1 ($R_7$ = H, $R_8$ = H) | H | H | $OCH_3$ | $OCH_2C{\equiv}CH$ | |
| J-1 | $-CH_3$ | Q-1 ($R_7$ = H, $R_8$ = H) | H | H | $OCH_3$ | $OCH_2C{\equiv}CCH_3$ | |
| J-2 | $-CH_3$ | Q-1 ($R_7$ = H, $R_8$ = H) | H | H | $OCH_3$ | $CH_2S(CH_2)_3CH_3$ | |
| J-3 | $-CH_3$ | Q-1 ($R_7$ = H, $R_8$ = H) | H | H | $OCH_3$ | $CH_2CH_2SCH(CH_3)_2$ | |
| J-4 | $-CH_3$ | Q-1 ($R_7$ = H, $R_8$ = H) | H | H | $OCH_3$ | $CH(CH_3)(CH_2SCH_3)$ | |
| J-1 | $-CH_3$ | Q-1 ($R_7$ = H, $R_8$ = H) | H | H | $OCH_3$ | $CH_2S(CH_2)_3CH_3$ | |
| J-2 | $-CH_3$ | Q-1 ($R_7$ = H, $R_8$ = H) | H | H | $OCH_3$ | cyclopropyl | |
| J-3 | $-CH_3$ | Q-1 ($R_7$ = H, $R_8$ = H) | H | H | $OCH_3$ | 2-methyl-cyclopropyl | |
| J-1 | $-CH_3$ | Q-1 ($R_7$ = H, $R_8$ = H) | H | H | $OCH_3$ | cyclopentyl | |
| J-2 | $-CH_3$ | Q-1 ($R_7$ = H, $R_8$ = H) | H | H | $OCH_3$ | $C{\equiv}CH$ | |
| J-3 | $-CH_3$ | Q-1 ($R_7$ = H, $R_8$ = H) | H | H | $OCH_3$ | $C{\equiv}CCH_3$ | |
| J-4 | $-CH_3$ | Q-1 ($R_7$ = H, $R_8$ = H) | H | H | $OCH_3$ | $-CHO$ | |

TABLE 1-continued

General Formula 1

| J | M | Q | R | $R_1$ | X | Y | m.p. (°C.) |
|---|---|---|---|---|---|---|---|
| J-1 | $-CH_3$ | Q-1 ($R_7$ = H, $R_8$ = H) | H | H | $OCH_3$ | $-COCH_3$ | |
| J-2 | $-CH_3$ | Q-1 ($R_7$ = H, $R_8$ = H) | H | H | $OCH_3$ | $-CH(OCH_3)_2$ | |
| J-3 | $-CH_3$ | Q-1 ($R_7$ = H, $R_8$ = H) | H | H | $OCH_3$ | $-CH(SCH_3)(OCH_2CH_3)$ | |
| J-4 | $-CH_3$ | Q-1 ($R_7$ = H, $R_8$ = H) | H | H | $OCH_3$ | $-C(CH_3)(SCH_3)_2$ | |
| J-1 | $-CH_3$ | Q-1 ($R_7$ = H, $R_8$ = H) | H | H | $OCH_3$ | $-CH(SCH_2CH_3)_2$ | |
| J-2 | $-CH_3$ | Q-1 ($R_7$ = H, $R_8$ = H) | H | H | $OCH_3$ | 1,3-dioxolan-2-yl | |
| J-3 | $-CH_3$ | Q-1 ($R_7$ = H, $R_8$ = H) | H | H | $OCH_3$ | 2-methyl-1,3-oxa-thiolan-2-yl | |
| J-4 | $-CH_3$ | Q-1 ($R_7$ = H, $R_8$ = H) | H | H | $OCH_3$ | 1,3-oxathian-2-yl | |
| J-1 | $-CH_3$ | Q-1 ($R_7$ = H, $R_8$ = H) | H | H | $OCH_3$ | 2-methyl-1,3-dithian-2-yl | |
| J-2 | $-CH_3$ | Q-1 ($R_7$ = H, $R_8$ = H) | H | H | $OCH_3$ | 4-methyl-1,3-dioxolan-2-yl | |
| J-3 | $-CH_3$ | Q-1 ($R_7$ = H, $R_8$ = H) | H | H | $OCH_3$ | 4-methyl-1,3-oxathiolan-2-yl | |
| J-4 | $-CH_3$ | Q-1 ($R_7$ = H, $R_8$ = H) | H | H | $OCH_3$ | 2,4-dimethyl-1,3-dithiolan-2-yl | |
| J-1 | $-CH_3$ | Q-1 ($R_7$ = H, $R_8$ = H) | H | H | $OCH_3$ | $N(OCH_3)(CH_3)_2$ | |
| J-2 | $-CH_3$ | Q-1 ($R_7$ = H, $R_8$ = H) | H | 5-$SO_2N(CH_3)_2$ | $OCH_3$ | $OCH_3$ | |
| J-3 | $-CH_3$ | Q-1 ($R_7$ = H, $R_8$ = H) | H | 3-$SO_2CH_3$ | $OCH_3$ | $OCH_3$ | |
| J-4 | $-CH_3$ | Q-1 ($R_7$ = H, $R_8$ = H) | H | $CO_2CH_2CH_3$ | $OCH_3$ | $OCH_3$ | |
| J-1 | $-CH_3$ | Q-1 ($R_7$ = H, $R_8$ = H) | H | 5-$CO_2CH_3$ | $OCH_3$ | $OCH_3$ | |
| J-2 | $-CH_3$ | Q-1 ($R_7$ = H, $R_8$ = H) | H | H | $OCH_3$ | $OCH_3$ | |
| J-3 | $-CH_3$ | Q-1 ($R_7$ = H, $R_8$ = H) | H | H | $CH_3$ | $CH_3$ | |
| J-4 | $-CH_3$ | Q-1 ($R_7$ = H, $R_8$ = H) | H | H | $CH_3$ | $OCH_3$ | |
| J-1 | $-CH_3$ | Q-1 ($R_7$ = H, $R_8$ = $CH_2CH_3$) | H | H | $OCH_3$ | $OCH_3$ | |
| J-2 | $-CH_3$ | Q-1 ($R_7$ = H, $R_8$ = $CH(CH_3)_2$) | H | H | $OCH_3$ | $OCH_3$ | |
| J-3 | $-CH_3$ | Q-1 ($R_7$ = H, $R_8$ = $(CH_2)_3CH_3$) | H | H | $OCH_3$ | $OCH_3$ | |
| J-1 | $-CH_3$ | Q-1 ($R_7$ = $CH_3$, $R_8$ = $CH_3$) | H | H | $OCH_3$ | $OCH_3$ | |
| J-2 | —H | Q-2 ($R_7$ = H, $R_8$ = H) | H | H | $OCH_3$ | $OCH_3$ | |
| J-3 | $-CH_3$ | Q-2 ($R_7$ = H, $R_8$ = H) | $CH_3$ | H | $OCH_3$ | $OCH_3$ | |
| J-4 | $-CH_3$ | Q-2 ($R_7$ = H, $R_8$ = $CH_3$) | H | 3-$OCH_3$ | $OCH_3$ | $OCH_3$ | |
| J-1 | $-CH_3$ | Q-3 ($R_7$ = H, $R_8$ = H) | H | H | $OCH_3$ | $OCH_3$ | |
| J-2 | $-CH_3$ | Q-3 ($R_7$ = $C_2H_5$, $R_8$ = H) | H | H | $OCF_2H$ | $CH_3$ | |
| J-3 | $-CH_3$ | Q-3 ($R_7$ = $CH_3$, $R_8$ = H) | H | 3-Cl | $OCH_3$ | $CH_3$ | |
| J-4 | $-CH_3$ | Q-4 ($R_7$ = H, $R_8$ = H, $R_3$ = $CH_3$) | H | H | $CH_3$ | $OCH_3$ | |
| J-1 | $-CH_3$ | Q-4 ($R_7$ = H, $R_8$ = H, $R_3$ = $C_2H_5$) | H | H | $CH_3$ | $OCH_3$ | |
| J-2 | $-CH_3$ | Q-4 ($R_7$ = H, $R_8$ = H, $R_3$ = i-$C_3H_7$) | H | 5-$CH_3$ | $OCH_3$ | $OCH_3$ | |
| J-3 | $-CH_3$ | Q-5 ($R_7$—H, $R_8$ = H, $R_3$ = H) | H | H | $OCH_3$ | $OCH_3$ | |
| J-4 | $-CH_3$ | Q-5 ($R_7$ = H, $R_8$ = H, $R_3$ = $CH_3$) | H | H | Cl | $OCH_3$ | |
| J-1 | $-CH_3$ | Q-5 ($R_7$ = H, $R_8$ = $CH_3$, $R_3$ = $CH_3$) | H | H | $CH_3$ | $OCH_3$ | |
| J-2 | $-CH_3$ | Q-6 ($R_7$ = $CH_3$, $R_8$ = H, $R_3$ = $CH_3$) | H | H | $CH_3$ | $OCH_3$ | |
| J-3 | $-CH_3$ | Q-6 ($R_7$—H, $R_8$ = H, $R_3$ = $C_2H_5$) | $CH_3$ | H | $CH_3$ | $OCH_3$ | |
| J-4 | $-CH_3$ | Q-6 ($R_7$ = $C_2H_5$, $R_8$ = H, $R_3$ = H) | H | H | $OCH_3$ | $OCH_3$ | |
| J-1 | $-CH_3$ | Q-7 ($R_7$ = H, $R_8$ = H, $R_9$ = H) | H | H | $OCH_3$ | $OCH_3$ | |
| J-2 | $-CH_3$ | Q-7 ($R_7$ = H, $R_8$ = $C_2H_5$, $R_9$ = H) | H | H | $OCH_3$ | $OCH_3$ | |
| J-3 | $-CH_3$ | Q-7 ($R_7$ = i-$C_3H_7$, $R_8$ = H, $R_9$ = $CH_3$) | H | 3-$OCH_3$ | $OCH_3$ | $OCH_3$ | |
| J-4 | $-CH_3$ | Q-8 ($R_7$ = H, $R_8$ = H, $R_2$ = H) | H | H | $OCH_3$ | $OCH_3$ | |
| J-1 | $-CH_3$ | Q-8 ($R_7$ = $CH_3$, $R_8$ = H, $R_2$ = $OCH_3$) | H | H | $OCH_3$ | $OCF_2H$ | |
| J-2 | $-CH_3$ | Q-8 ($R_7$ = H, $R_8$ = H, $R_2$ = $OCH(CH_3)CH_2CH_3$) | H | 5-Cl | $OCH_3$ | $OCH_3$ | |

TABLE 1-continued

General Formula 1

| J | M | Q | R | $R_1$ | X | Y | m.p. (°C.) |
|---|---|---|---|---|---|---|---|
| J-3 | $-CH_3$ | Q-9 ($R_7 = H, R_8 = H, R_2 = H$) | H | H | $OCH_3$ | $OCH_3$ | |
| J-4 | $-CH_3$ | Q-9 ($R_7 = CH_3, R_8 = H, R_2 = CH_3$) | $CH_3$ | H | $OCH_3$ | $OCH_3$ | |
| J-1 | $-CH_3$ | Q-9 ($R_7 = H, R_8 = H, R_2 = Cl$) | H | 5-$OCH_3$ | $OCH_3$ | $OCH_3$ | |
| J-2 | $-CH_3$ | Q-10 ($R_7 = H, R_8 = H$) | H | H | $OCH_3$ | $OCH_3$ | |
| J-3 | $-CH_3$ | Q-10 ($R_7 = CH_3, R_8 = H$) | H | H | $OCF_2H$ | $CH_3$ | |
| J-4 | $-CH_3$ | Q-10 ($R_7 = H, R_8 = CH_3$) | H | 3-Cl | $OCH_3$ | $CH_3$ | |
| J-1 | $-CH_3$ | Q-11 ($R_7 = H, R_8 = H$) | H | H | $CH_3$ | $OCH_3$ | |
| J-2 | $-CH_3$ | Q-11 ($R_7 = n\text{-}C_4H_9, R_8 = H$) | H | H | $CH_3$ | $OCH_3$ | |
| J-3 | $-CH_3$ | Q-11 ($R_7 = CH_3, R_8 = CH_3$) | H | 3-$CH_3$ | $OCH_3$ | $OCH_3$ | |
| J-4 | $-CH_3$ | Q-12 ($R_7 = H, R_8 = H$) | H | H | $OCH_3$ | $OCH_3$ | |
| J-1 | $-CH_3$ | Q-12 ($R_7 = CH_3, R_8 = H$) | H | H | Cl | $OCH_3$ | |
| J-2 | $-CH_3$ | Q-12 ($R_7 = H, R_8 = C_2H_5$) | H | H | $CH_3$ | $OCH_3$ | |
| J-3 | $-CH_3$ | Q-13 ($R_7 = H, R_8 = H, R_3 = H$) | H | H | $CH_3$ | $OCH_3$ | |
| J-4 | $-CH_3$ | Q-13 ($R_7 = H, R_8 = H, R_3 = CH_3$) | $CH_3$ | H | $CH_3$ | $OCH_3$ | |
| J-1 | $-CH_3$ | Q-13 ($R_7 = CH_3, R_8 = H, R_3 = CH_3$) | H | H | $OCH_3$ | $OCH_3$ | |
| J-2 | $-CH_3$ | Q-14 ($R_7 = H, R_8 = H, R_3 = CH_3$) | H | H | $OCH_3$ | $OCH_3$ | |
| J-3 | $-CH_3$ | Q-14 ($R_7 = CH_3, R_8 = H, R_3 = C_2H_5$) | H | H | $OCH_3$ | $OCH_3$ | |
| J-4 | $-CH_3$ | Q-14 ($R_7 = H, R_8 = CH_3, R_3 = CH_3$) | H | 3-$OCH_3$ | $OCH_3$ | $OCH_3$ | |
| J-1 | $-CH_3$ | Q-15 ($R_7 = H, R_8 = H, R_3 = H$) | H | H | $OCH_3$ | $OCH_3$ | |
| J-2 | $-CH_3$ | Q-15 ($R_7 = C_2H_5, R_8 = H, R_3 = CH_3$) | H | H | $OCH_3$ | $OCF_2H$ | |
| J-3 | $-CH_3$ | Q-15 ($R_7 = CH_3, R_8 = CH_3, R_3 = CH_3$) | H | 3-Cl | $OCH_3$ | $OCH_3$ | |
| J-4 | $-CH_3$ | Q-16 ($R_7 = H, R_8 = H, R_9 = H$) | H | H | $OCH_3$ | $OCH_3$ | |
| J-1 | $-CH_3$ | Q-16 ($R_7 = CH_3, R_8 = H, R_9 = H$) | $CH_3$ | H | $OCH_3$ | $OCH_3$ | |
| J-2 | $-CH_3$ | Q-16 ($R_7 = CH_3, R_8 = CH_3, R_9 = H$) | H | 5-$OCH_3$ | $OCH_3$ | $OCH_3$ | |
| J-3 | $-CH_3$ | Q-17 ($R_7 = H, R_8 = H, R_2 = H$) | H | H | $OCH_3$ | $OCH_3$ | |
| J-4 | $-CH_3$ | Q-17 ($R_7 = CH_3, R_8 = H, R_2 = CH_3$) | H | H | $OCF_2H$ | $CH_3$ | |
| J-1 | $-CH_3$ | Q-17 ($R_7 = H, R_8 = H, R_2 = C_2H_5$) | H | 5-Cl | $OCH_3$ | $CH_3$ | |
| J-2 | $-H$ | Q-18 ($R_7 = H, R_8 = H, R_2 = H$) | H | H | $CH_3$ | $OCH_3$ | |
| J-3 | $-CH_3$ | Q-18 ($R_7 = H, R_8 = OC_2H_5, R_2 = H$) | H | H | $CH_3$ | $OCH_3$ | |
| J-4 | $-CH_3$ | Q-18 ($R_7 = CH_3, R_8 = OCH(CH_3)_2, R_2 = CH_3$) | H | 3-$CH_3$ | $OCH_3$ | $OCH_3$ | |
| J-1 | $-CH_3$ | Q-19 ($R_7 = H, R_8 = H$) | H | H | $OCH_3$ | $OCH_3$ | |
| J-2 | $-CH_3$ | Q-19 ($R_7 = CH_3, R_8 = H$) | H | H | Cl | $OCH_3$ | |
| J-3 | $-CH_3$ | Q-19 ($R_7 = CH_3, R_8 = CH_3$) | H | H | $CH_3$ | $OCH_3$ | |
| J-4 | $-CH_3$ | Q-20 ($R_7 = H, R_8 = H$) | H | H | $CH_3$ | $OCH_3$ | |
| J-1 | $-CH_3$ | Q-20 ($R_7 = CH_3, R_8 = H$) | $CH_3$ | H | $CH_3$ | $OCH_3$ | |
| J-2 | $-CH_3$ | Q-20 ($R_7 = H, R_8 = CH_3$) | H | H | $OCH_3$ | $OCH_3$ | |
| J-3 | $-CH_3$ | Q-21 ($R_7 = H, R_8 = H$) | H | H | $OCH_3$ | $OCH_3$ | |
| J-4 | $-CH_3$ | Q-21 ($R_7 = CH_3, R_8 = H$) | H | H | $OCH_3$ | $OCH_3$ | |
| J-1 | $-CH_3$ | Q-21 ($R_7 = CH_3, R_8 = CH_3$) | H | 5-$OCH_3$ | $OCH_3$ | $OCH_3$ | |
| J-2 | $-CH_3$ | Q-22 ($R_7 = H, R_8 = H, R_3 = H$) | H | H | $OCH_3$ | $OCH_3$ | |
| J-3 | $-CH_3$ | Q-22 ($R_7 = H, R_8 = H, R_3 = CH_3$) | H | H | $OCH_3$ | $OCF_2H$ | |
| J-4 | $-CH_3$ | Q-22 ($R_7 = CH_3, R_8 = CH_3, R_3 = C_2H_5$) | H | 3-Cl | $OCH_3$ | $OCH_3$ | |
| J-1 | $-CH_3$ | Q-23 ($R_7 = H, R_8 = H, R_3 = H$) | H | H | $OCH_3$ | $OCH_3$ | |
| J-2 | $-CH_3$ | Q-23 ($R_7 = H, R_8 = H, R_3 = CH_3$) | $CH_3$ | H | $OCH_3$ | $OCH_3$ | |
| J-3 | $-CH_3$ | Q-23 ($R_7 = CH_3, R_8 = H, R_3 = n\text{-}C_4H_9$) | H | 3-$OCH_3$ | $OCH_3$ | $OCH_3$ | |
| J-4 | $-CH_3$ | Q-24 ($R_7 = H, R_8 = H, R_3 = CH_3$) | H | H | $OCH_3$ | $OCH_3$ | |
| J-1 | $-CH_3$ | Q-24 ($R_7 = CH_3, R_8 = CH_3, R_3 = C_2H_5$) | H | H | $OCF_2H$ | $CH_3$ | |
| J-2 | $-CH_3$ | Q-24 ($R_7 = CH_3, R_8 = CH_3, R_3 = i\text{-}C_3H_7$) | H | 5-Cl | $OCH_3$ | $CH_3$ | |
| J-3 | $-CH_3$ | Q-25 ($R_7 = H, R_8 = H, R_9 = H$) | H | H | $CH_3$ | $OCH_3$ | |
| J-4 | $-CH_3$ | Q-25 ($R_7 = CH_3, R_8 = H, R_9 = H$) | H | H | $CH_3$ | $OCH_3$ | |

TABLE 1-continued

General Formula 1

| J | M | Q | R | $R_1$ | X | Y | m.p. (°C.) |
|---|---|---|---|---|---|---|---|
| J-1 | $-CH_3$ | Q-25 ($R_7 = H, R_8 = H, R_9 = C_2H_5$) | H | 5-$CH_3$ | $OCH_3$ | $OCH_3$ | |
| J-2 | $-CH_3$ | Q-26 ($R_7 = H, R_8 = H$) | H | H | $OCH_3$ | $OCH_3$ | |
| J-3 | $-CH_3$ | Q-26 ($R_7 = CH_3, R_8 = H$) | H | H | Cl | $OCH_3$ | |
| J-4 | $-CH_3$ | Q-26 ($R_7 = CH_3, R_8 = CH_3$) | H | H | $CH_3$ | $OCH_3$ | |
| J-1 | $-CH_3$ | Q-27 ($R_7 = H, R_8 = H$) | H | H | $CH_3$ | $OCH_3$ | |
| J-2 | $-CH_3$ | Q-27 ($R_7 = CH_3, R_8 = H$) | $CH_3$ | H | $CH_3$ | $OCH_3$ | |
| J-3 | $-CH_3$ | Q-27 ($R_7 = H, R_8 = CH_3$) | H | H | $OCH_3$ | $OCH_3$ | |
| J-4 | $-CH_3$ | Q-28 ($R_7 = H, R_8 = H$) | H | H | $OCH_3$ | $OCH_3$ | |
| J-1 | $-CH_3$ | Q-28 ($R_7 = CH_3, R_8 = H$) | H | H | $OCH_3$ | $OCH_3$ | |
| J-2 | $-CH_3$ | Q-28 ($R_7 = CH_3, R_8 = CH_3$) | H | 5-$OCH_3$ | $OCH_3$ | $OCH_3$ | |
| J-3 | $-CH_3$ | Q-29 ($R_7 = H, R_8 = H$) | H | H | $OCH_3$ | $OCH_3$ | |
| J-4 | $-CH_3$ | Q-29 ($R_7 = CH_3, R_8 = H$) | H | H | $OCH_3$ | $OCF_2H$ | |
| J-1 | $-CH_3$ | Q-29 ($R_7 = H, R_8 = CH_3$) | H | 5-Cl | $OCH_3$ | $OCH_3$ | |
| J-2 | $-CH_3$ | Q-30 ($R_7 = H, R_8 = H$) | H | H | $OCH_3$ | $OCH_3$ | |
| J-3 | $-CH_3$ | Q-30 ($R_7 = CH_3, R_8 = CH_3$) | $CH_3$ | H | $OCH_3$ | $CH_3$ | |
| J-4 | $-CH_3$ | Q-30 ($R_7 = C_2H_5, R_8 = H$) | H | 3-$OCH_3$ | $OCH_3$ | $OCH_3$ | |
| J-1 | $-CH_3$ | Q-31 ($R_7 = H, R_8 = H$) | H | H | $OCH_3$ | $OCH_3$ | |
| J-2 | $-CH_3$ | Q-31 ($R_7 = \underline{i}-C_3H_7, R_8 = H$) | H | H | $OCF_2H$ | $CH_3$ | |
| J-3 | $-CH_3$ | Q-31 ($R_7 = H, R_8 = \underline{n}-C_4H_9$) | H | 3-Cl | $OCH_3$ | $CH_3$ | |
| J-4 | $-CH_3$ | Q-32 ($R_7 = H, R_8 = H, R_3 = H$) | H | H | $CH_3$ | $OCH_3$ | |
| J-1 | $-CH_3$ | Q-32 ($R_7 = CH_3, R_8 = H, R_3 = CH_3$) | H | H | $CH_3$ | $OCH_3$ | |
| J-2 | $-CH_3$ | Q-32 ($R_7 = H, R_8 = CH_3, R_3 = C_2H_5$) | H | 5-$CH_3$ | $OCH_3$ | $OCH_3$ | |
| J-3 | $-CH_3$ | Q-33 ($R_7 = H, R_8 = H, R_8 = CH_3$) | H | H | $OCH_3$ | $OCH_3$ | |
| J-4 | $-CH_3$ | Q-33 ($R_7 = CH_3, R_8 = CH_3, R_3 = \underline{i}-C_3H_7$) | H | H | Cl | $OCH_3$ | |
| J-1 | $-CH_3$ | Q-33 ($R_7 = C_2H_5, R_8 = H, R_3 = \underline{n}-C_4H_9$) | H | H | $CH_3$ | $OCH_3$ | |
| J-2 | $-CH_3$ | Q-34 ($R_7 = H, R_8 = H, R_3 = H$) | H | H | $CH_3$ | $OCH_3$ | |
| J-3 | $-CH_3$ | Q-34 ($R_7 = \underline{i}-C_3H_7, R_8 = H, R_3 = CH_3$) | $CH_3$ | H | $CH_3$ | $OCH_3$ | |
| J-4 | $-CH_3$ | Q-34 ($R_7 = H, R_8 = \underline{n}-C_4H_9, R_3 = CH_3$) | H | H | $OCH_3$ | $OCH_3$ | |
| J-1 | $-CH_3$ | Q-35 ($R_7 = H, R_8 = H, R_9 = H$) | H | H | $OCH_3$ | $OCH_3$ | |
| J-2 | $-CH_3$ | Q-35 ($R_7 = CH_3, R_8 = H, R_9 = H$) | H | H | $OCH_3$ | $OCH_3$ | |
| J-3 | $-CH_3$ | Q-35 ($R_7 = CH_3, R_8 = CH_3, R_9 = CH_3$) | H | 3-$OCH_3$ | $OCH_3$ | $OCH_3$ | |
| J-4 | $-CH_3$ | Q-36 ($R_7 = H, R_8 = H, R_2 = H$) | H | H | $OCH_3$ | $OCH_3$ | |
| J-1 | $-CH_3$ | Q-36 ($R_7 = CH_3, R_8 = H, R_2 = CH_3$) | H | H | $OCH_3$ | $OCF_2H$ | |
| J-2 | $-CH_3$ | Q-36 ($R_7 = H, R_8 = H, R_2 = C_2H_5$) | H | 5-Cl | $OCH_3$ | $OCH_3$ | |
| J-3 | $-CH_3$ | Q-37 ($R_7 = H, R_8 = H, R_2 = H$) | H | H | $OCH_3$ | $OCH_3$ | |
| J-4 | $-CH_3$ | Q-37 ($R_7 = H, R_8 = H, R_2 = \underline{i}-C_3H_7$) | $CH_3$ | H | $OCH_3$ | $OCH_3$ | |
| J-1 | $-CH_3$ | Q-37 ($R_7 = H, R_8 = H, R_2 = \underline{n}-C_4H_9$) | H | 5-$OCH_3$ | $OCH_3$ | $OCH_3$ | |
| J-2 | $-CH_3$ | Q-38 ($R_7 = H, R_8 = H, R_2 = OCF_2H$) | H | H | $OCH_3$ | $OCH_3$ | |
| J-3 | $-CH_3$ | Q-38 ($R_7 = CH_3, R_8 = H, R_2 = OCH_2CH_2F$) | H | H | $OCF_2H$ | $CH_3$ | |
| J-4 | $-CH_3$ | Q-38 ($R_7 = H, R_8 = H, R_2 = Cl$) | H | 3-Cl | $OCH_3$ | $CH_3$ | |
| J-1 | $-CH_3$ | Q-39 ($R_7 = H, R_8 = H, R_9 = H$) | H | H | $CH_3$ | $OCH_3$ | |
| J-2 | $-CH_3$ | Q-39 ($R_7 = C_2H_5, R_8 = H, R_9 = H$) | H | H | $CH_3$ | $OCH_3$ | |
| J-3 | $-CH_3$ | Q-39 ($R_7 = H, R_8 = H, R_9 = CH_3$) | H | 3-$CH_3$ | $OCH_3$ | $OCH_3$ | |
| J-4 | $-CH_3$ | Q-40 ($R_7 = H, R_8 = H$) | H | H | $OCH_3$ | $OCH_3$ | |
| J-1 | $-CH_3$ | Q-40 ($R_7 = CH_3, R_8 = H$) | H | H | Cl | $OCH_3$ | |
| J-2 | $-CH_3$ | Q-40 ($R_7 = H, R_8 = CH_3$) | H | H | $CH_3$ | $OCH_3$ | |
| J-3 | $-CH_3$ | Q-41 ($R_7 = H, R_8 = H$) | H | H | $CH_3$ | $OCH_3$ | |
| J-4 | $-CH_3$ | Q-41 ($R_7 = CH_3, R_8 = CH_3$) | $CH_3$ | H | $CH_3$ | $OCH_3$ | |
| J-1 | $-CH_3$ | Q-41 ($R_7 = H, R_8 = C_2H_5$) | H | H | $OCH_3$ | $OCH_3$ | |
| J-2 | $-CH_3$ | Q-42 ($R_7 = H, R_8 = H$) | H | H | $OCH_3$ | $OCH_3$ | |

TABLE 1-continued

General Formula 1

| J | M | Q | R | $R_1$ | X | Y | m.p. (°C.) |
|---|---|---|---|---|---|---|---|
| J-3 | $-CH_3$ | Q-42 ($R_7 = CH_3$, $R_8 = CH_3$) | H | H | $OCH_3$ | $OCH_3$ | |
| J-4 | $-CH_3$ | Q-42 ($R_7 = C_2H_5$, $R_8 = C_2H_5$) | H | 3-$OCH_3$ | $OCH_3$ | $OCH_3$ | |
| J-1 | $-CH_3$ | Q-43 ($R_7 = H$, $R_8 = H$, $R_3 = H$) | H | H | $OCH_3$ | $OCH_3$ | |
| J-2 | $-CH_3$ | Q-43 ($R_7 = H$, $R_8 = H$, $R_3 = CH_3$) | H | H | $OCH_3$ | $OCF_2H$ | |
| J-3 | $-CH_3$ | Q-43 ($R_7 = CH_3$, $R_8 = H$, $R_3 = CH_3$) | H | 3-Cl | $OCH_3$ | $OCH_3$ | |
| J-4 | $-CH_3$ | Q-44 ($R_7 = H$, $R_8 = H$, $R_3 = CH_3$) | H | H | $OCH_3$ | $OCH_3$ | |
| J-1 | $-CH_3$ | Q-44 ($R_7 = CH_3$, $R_8 = H$, $R_3 = C_2H_5$) | $CH_3$ | H | $OCH_3$ | $CH_3$ | |
| J-2 | $-CH_3$ | Q-44 ($R_7 = H$, $R_8 = CH_3$, $R_3 = CH_3$) | H | 5-$OCH_3$ | $OCH_3$ | $OCH_3$ | |
| J-3 | $-CH_3$ | Q-45 ($R_7 = H$, $R_8 = H$, $R_3 = H$) | H | H | $OCH_3$ | $OCH_3$ | |
| J-4 | $-CH_3$ | Q-45 ($R_7 = C_2H_5$, $R_8 = H$, $R_3 = CH_3$) | H | H | $OCF_2H$ | $CH_3$ | |
| J-1 | $-CH_3$ | Q-45 ($R_7 = CH_3$, $R_8 = CH_3$, $R_3 = CH_3$) | H | 5-Cl | $OCH_3$ | $CH_3$ | |
| J-2 | $-CH_3$ | Q-46 ($R_7 = H$, $R_8 = H$, $R_9 = H$) | H | H | $CH_3$ | $OCH_3$ | |
| J-3 | $-CH_3$ | Q-46 ($R_7 = CH_3$, $R_8 = H$, $R_9 = H$) | H | H | $CH_3$ | $OCH_3$ | |
| J-4 | $-CH_3$ | Q-46 ($R_7 = CH_3$, $R_8 = CH_3$, $R_9 = H$) | H | 3-$CH_3$ | $OCH_3$ | $OCH_3$ | |
| J-1 | $-CH_3$ | Q-47 ($R_7 = H$, $R_8 = H$, $R_2 = H$) | H | H | $OCH_3$ | $OCH_3$ | |
| J-2 | $-CH_3$ | Q-47 ($R_7 = H$, $R_8 = CH_3$, $R_2 = CH_3$) | H | H | Cl | $OCH_3$ | |
| J-3 | $-CH_3$ | Q-47 ($R_7 = H$, $R_8 = H$, $R_2 = C_2H_5$) | H | H | $CH_3$ | $OCH_3$ | |
| J-4 | $-CH_3$ | Q-48 ($R_7 = H$, $R_8 = H$, $R_2 = H$) | H | H | $CH_3$ | $OCH_3$ | |
| J-1 | $-CH_3$ | Q-48 ($R_7 = CH_3$, $R_8 = CH_3$, $R_2 = CH_3$) | $CH_3$ | H | $CH_3$ | $OCH_3$ | |
| J-2 | $-CH_3$ | Q-48 ($R_7 = H$, $R_8 = C_2H_5$, $R_2 = C_2H_5$) | H | H | $OCH_3$ | $OCH_3$ | |
| J-3 | $-CH_3$ | Q-49 ($R_7 = H$, $R_8 = H$, $R_2 = H$) | H | H | $OCH_3$ | $OCH_3$ | |
| J-4 | $-CH_3$ | Q-49 ($R_7 = CH_3$, $R_8 = CH_3$, $R_2 = H$) | H | H | $OCH_3$ | $OCH_3$ | |
| J-1 | $-CH_3$ | Q-49 ($R_7 = CH_3$, $R_8 = CH_3$, $R_2 = CH_3$) | H | 5-$OCH_3$ | $OCH_3$ | $OCH_3$ | |
| J-2 | $-CH_3$ | Q-50 ($R_7 = H$, $R_8 = H$, $R_2 = H$) | H | H | $OCH_3$ | $OCH_3$ | |
| J-3 | $-CH_3$ | Q-50 ($R_7 = CH_3$, $R_8 = CH_3$, $R_2 = H$) | H | H | $OCH_3$ | $OCF_2H$ | |
| J-4 | $-CH_3$ | Q-50 ($R_7 = CH_3$, $R_8 = CH_3$, $R_2 = CH_3$) | H | 3-Cl | $OCH_3$ | $OCH_3$ | |
| J-1 | $-CH_3$ | Q-51 ($R_7 = H$, $R_8 = H$, $R_9 = H$) | H | H | $OCH_3$ | $OCH_3$ | |
| J-2 | $-CH_3$ | Q-51 ($R_7 = H$, $R_8 = H$, $R_9 = CH_3$) | $CH_3$ | H | $OCH_3$ | $OCH_3$ | |
| J-3 | $-CH_3$ | Q-51 ($R_7 = H$, $R_8 = H$, $R_9 = \underline{s}\text{-}C_4H_9$) | H | 3-$OCH_3$ | $OCH_3$ | $OCH_3$ | |
| J-4 | $-CH_3$ | Q-52 ($R_7 = H$, $R_8 = H$, $R_9 = H$) | H | H | $OCH_3$ | $OCH_3$ | |
| J-1 | $-CH_3$ | Q-52 ($R_7 = CH_3$, $R_8 = H$, $R_9 = H$) | H | H | $OCF_2H$ | $CH_3$ | |
| J-2 | $-CH_3$ | Q-52 ($R_7 = H$, $R_8 = H$, $R_9 = CH_3$) | H | 5-Cl | $OCH_3$ | $CH_3$ | |
| J-3 | $-CH_3$ | Q-53 ($R_7 = H$, $R_8 = H$, $R_9 = H$) | H | H | $CH_3$ | $OCH_3$ | |
| J-4 | $-CH_3$ | Q-53 ($R_7 = CH_3$, $R_8 = CH_3$, $R_9 = CH_3$) | H | H | $CH_3$ | $OCH_3$ | |
| J-1 | $-CH_3$ | Q-53 ($R_7 = H$, $R_8 = H$, $R_9 = CH_3$) | H | 5-$CH_3$ | $OCH_3$ | $OCH_3$ | |
| J-2 | $-CH_3$ | Q-54 ($R_7 = H$, $R_8 = H$, $R_9 = H$) | H | H | $OCH_3$ | $OCH_3$ | |
| J-3 | $-CH_3$ | Q-54 ($R_7 = CH_3$, $R_8 = H$, $R_9 = H$) | H | H | Cl | $OCH_3$ | |
| J-4 | $-CH_3$ | Q-54 ($R_7 = H$, $R_8 = H$, $R_9 = \underline{i}\text{-}C_3H_7$) | H | H | $CH_3$ | $OCH_3$ | |
| J-1 | $-CH_3$ | Q-55 ($R_7 = H$, $R_8 = H$, $R_9 = H$, $R_3 = H$) | H | H | $CH_3$ | $OCH_3$ | |
| J-2 | $-CH_3$ | Q-55 ($R_7 = H$, $R_8 = H$, $R_9 = CH_3$, $R_3 = CH_3$) | $CH_3$ | H | $CH_3$ | $OCH_3$ | |
| J-3 | $-CH_3$ | Q-55 ($R_7 = H$, $R_8 = H$, $R_9 = \underline{s}\text{-}C_4H_9$, $R_3 = H$) | H | H | $OCH_3$ | $OCH_3$ | |
| J-4 | $-CH_3$ | Q-56 ($R_7 = H$, $R_8 = H$, $R_9 = H$, $R_3 = C_2H_5$) | H | H | $OCH_3$ | $OCH_3$ | |
| J-1 | $-CH_3$ | Q-56 ($R_7 = CH_3$, $R_8 = H$, $R_9 = H$, $R_3 = H$) | H | H | $OCH_3$ | $OCH_3$ | |
| J-2 | $-CH_3$ | Q-56 ($R_7 = H$, $R_8 = H$, $R_9 = CH_3$, $R_3 = CH_3$) | H | 5-$OCH_3$ | $OCH_3$ | $OCH_3$ | |
| J-3 | $-CH_3$ | Q-57 ($R_7 = H$, $R_8 = H$, $R_9 = H$, $R_3 = \underline{i}\text{-}C_3H_7$) | H | H | $OCH_3$ | $OCH_3$ | |
| J-4 | $-CH_3$ | Q-57 ($R_7 = CH_3$, $R_8 = CH_3$, $R_9 = CH_3$, $R_3 = H$) | H | H | $OCH_3$ | $OCF_2H$ | |
| J-1 | $-CH_3$ | Q-57 ($R_7 = H$, $R_8 = H$, $R_9 = CH_3$, $R_3 = CH_3$) | H | 5-Cl | $OCH_3$ | $OCH_3$ | |
| J-2 | $-CH_3$ | Q-58 ($R_7 = H$, $R_8 = H$, $R_9 = H$, $R_3 = H$) | H | H | $OCH_3$ | $OCH_3$ | |
| J-3 | $-CH_3$ | Q-58 ($R_7 = CH_3$, $R_8 = H$, $R_9 = H$, $R_3 = CH_3$) | $CH_3$ | H | $OCH_3$ | $CH_3$ | |
| J-4 | $-CH_3$ | Q-58 ($R_7 = H$, $R_8 = H$, $R_9 = \underline{i}\text{-}C_3H_7$, $R_3 = CH_3$) | H | 3-$OCH_3$ | $OCH_3$ | $OCH_3$ | |

TABLE 1-continued

General Formula 1

| J | M | Q | R | $R_1$ | X | Y | m.p. (°C.) |
|---|---|---|---|---|---|---|---|
| J-1 | $-CH_3$ | Q-59 ($R_7$ = H, $R_8$ = H, $R_9$ = H, $R_{10}$ = H) | H | H | $OCH_3$ | $OCH_3$ | |
| J-2 | $-CH_3$ | Q-59 ($R_7$ = $CH_3$, $R_8$ = H, $R_9$ = H, $R_{10}$ = $CH_3$) | H | H | $OCF_2H$ | $CH_3$ | |
| J-3 | $-CH_3$ | Q-59 ($R_7$ = H, $R_8$ = H, $R_9$ = H, $R_{10}$ = s-$C_4H_9$ | H | 3-Cl | $OCH_3$ | $CH_3$ | |
| J-4 | $-CH_3$ | Q-60 ($R_7$ = H, $R_8$ = H, $R_9$ = H, $R_2$ = H) | H | H | $CH_3$ | $OCH_3$ | |
| J-1 | $-CH_3$ | Q-60 ($R_7$ = $CH_3$, $R_8$ = H, $R_9$ = H, $R_2$ = $O(CH_2)_3CH_2Br$) | H | H | $CH_3$ | $OCH_3$ | |
| J-2 | $-CH_3$ | Q-60 ($R_7$ = H, $R_8$ = H, $R_9$ = H, $R_2$ = Br) | H | 5-$CH_3$ | $OCH_3$ | $OCH_3$ | |
| J-3 | $-CH_3$ | Q-61 ($R_7$ = H, $R_8$ = H, $R_9$ = H, $R_2$ = H) | H | H | $OCH_3$ | $OCH_3$ | |
| J-4 | $-CH_3$ | Q-61 ($R_7$ = $CH_3$, $R_8$ = H, $R_9$ = H, $R_2$ = $OCH_2F$) | H | H | Cl | $OCH_3$ | |
| J-1 | $-CH_3$ | Q-61 ($R_7$ = H, $R_8$ = $CH_3$, $R_9$ = H, $R_2$ = $O(CH_2)_3CH_3$) | H | H | $CH_3$ | $OCH_3$ | |
| J-2 | $-CH_3$ | Q-62 ($R_7$ = H, $R_8$ = H, $R_9$ = H, $R_2$ = H) | H | H | $CH_3$ | $OCH_3$ | |
| J-3 | $-CH_3$ | Q-62 ($R_7$ = $CH_3$, $R_8$ = H, $R_9$ = H, $R_2$ = $CH_3$) | $CH_3$ | H | $CH_3$ | $OCH_3$ | |
| J-4 | $-CH_3$ | Q-62 ($R_7$ = Cl, $R_8$ = H, $R_9$ = H, $R_2$ = H) | H | H | $OCH_3$ | $OCH_3$ | |
| J-1 | $-CH_3$ | Q-63 ($R_7$ = H, $R_8$ = H, $R_9$ = H) | H | H | $OCH_3$ | $OCH_3$ | |
| J-2 | $-CH_3$ | Q-63 ($R_7$ = $CH_3$, $R_8$ = H, $R_9$ = H) | H | H | $OCH_3$ | $OCH_3$ | |
| J-3 | $-CH_3$ | Q-63 ($R_7$ = H, $R_8$ = H, $R_9$ = $CH_3$) | H | 3-$OCH_3$ | $OCH_3$ | $OCH_3$ | |
| J-4 | $-CH_3$ | Q-64 ($R_7$ = H, $R_8$ = H, $R_9$ = H) | H | H | $OCH_3$ | $OCH_3$ | |
| J-1 | $-CH_3$ | Q-64 ($R_7$ = $C_2H_5$, $R_8$ = H) | H | H | $OCH_3$ | $OCF_2H$ | |
| J-2 | $-CH_3$ | Q-64 ($R_7$ = H, $R_8$ = H, $R_9$ = $C_2H_5$) | H | 5-Cl | $OCH_3$ | $OCH_3$ | |
| J-3 | $-CH_3$ | Q-65 ($R_7$ = H, $R_8$ = H, $R_9$ = H) | H | H | $OCH_3$ | $OCH_3$ | |
| J-4 | $-CH_3$ | Q-65 ($R_7$ = n-$C_4H_9$, $R_8$ = H, $R_9$ = H) | $CH_3$ | H | $OCH_3$ | $CH_3$ | |
| J-1 | $-CH_3$ | Q-65 ($R_7$ = H, $R_8$ = $CH_3$, $R_9$ = i-$C_3H_7$) | H | 5-$OCH_3$ | $OCH_3$ | $OCH_3$ | |
| J-2 | $-CH_3$ | Q-66 ($R_7$ = H, $R_8$ = H, $R_9$ = H) | H | H | $OCH_3$ | $OCH_3$ | |
| J-3 | $-CH_3$ | Q-66 ($R_7$ = i-$C_3H_7$, $R_8$ = H, $R_9$ = H) | H | H | $OCF_2H$ | $CH_3$ | |
| J-4 | $-CH_3$ | Q-66 ($R_7$ = H, $R_8$ = $C_2H_5$, $R_9$ = $CH_3$) | H | 3-Cl | $OCH_3$ | $CH_3$ | |
| J-1 | $-CH_3$ | Q-67 ($R_7$ = H, $R_8$ = H, $R_9$ = H, $R_3$ = H) | H | H | $CH_3$ | $OCH_3$ | |
| J-2 | $-CH_3$ | Q-67 ($R_7$ = $CH_3$, $R_8$ = H, $R_9$ = H, $R_3$ = $CH_3$) | H | H | $CH_3$ | $OCH_3$ | |
| J-3 | $-CH_3$ | Q-67 ($R_7$ = H, $R_8$ = H, $R_9$ = $CH_3$, $R_3$ = $C_2H_5$) | H | 5-$CH_3$ | $OCH_3$ | $OCH_3$ | |
| J-4 | $-CH_3$ | Q-68 ($R_7$ = H, $R_8$ = H, $R_9$ = H, $R_3$ = $CH_3$) | H | H | $OCH_3$ | $OCH_3$ | |
| J-1 | $-CH_3$ | Q-68 ($R_7$ = $C_2H_5$, $R_8$ = H, $R_9$ = H, $R_3$ = i-$C_3H_7$) | H | H | Cl | $OCH_3$ | |
| J-2 | $-CH_3$ | Q-68 ($R_7$ = H, $R_8$ = H, $R_9$ = $C_2H_5$, $R_3$ = n-$C_4H_9$) | H | H | $CH_3$ | $OCH_3$ | |
| J-3 | $-CH_3$ | Q-69 ($R_7$ = H, $R_8$ = H, $R_9$ = H, $R_3$ = $CH_3$) | H | H | $CH_3$ | $OCH_3$ | |
| J-4 | $-CH_3$ | Q-69 ($R_7$ = n-$C_4H_9$, $R_8$ = H, $R_9$ = H, $R_3$ = $C_2H_5$) | $CH_3$ | H | $CH_3$ | $OCH_3$ | |
| J-1 | $-CH_3$ | Q-69 ($R_7$ = H, $R_8$ = $CH_3$, $R_9$ = i-$C_3H_7$, $R_3$ = H) | H | H | $OCH_3$ | $OCH_3$ | |
| J-2 | $-CH_3$ | Q-70 ($R_7$ = H, $R_8$ = H, $R_9$ = H, $R_3$ = $CH_3$) | H | H | $OCH_3$ | $OCH_3$ | |
| J-3 | $-CH_3$ | Q-70 ($R_7$ = i-$C_3H_7$, $R_8$ = H, $R_9$ = H, $R_3$ = $CH_3$) | H | H | $OCH_3$ | $OCH_3$ | |
| J-4 | $-CH_3$ | Q-70 ($R_7$ = H, $R_8$ = $C_2H_5$, $R_9$ = $CH_3$, $R_3$ = H) | H | 3-$OCH_3$ | $OCH_3$ | $OCH_3$ | |
| J-1 | $-CH_3$ | Q-71 ($R_7$ = H, $R_8$ = H, $R_9$ = H, $R_{10}$ = H) | H | H | $OCH_3$ | $OCF_2H$ | |
| J-2 | $-CH_3$ | Q-71 ($R_7$ = $CH_3$, $R_8$ = H, $R_9$ = H, $R_{10}$ = H) | H | H | $OCH_3$ | $OCH_3$ | |
| J-3 | $-CH_3$ | Q-71 ($R_7$ = H, $R_8$ = H, $R_9$ = H, $R_{10}$ = $CH_3$) | H | 5-Cl | $OCH_3$ | $OCH_3$ | |
| J-4 | $-CH_3$ | Q-72 ($R_7$ = H, $R_8$ = H, $R_9$ = H, $R_2$ = H) | H | H | $OCH_3$ | $OCH_3$ | |
| J-1 | $-CH_3$ | Q-72 ($R_7$ = H, $R_8$ = H, $R_9$ = H, $R_2$ = $CH_3$) | $CH_3$ | H | $OCH_3$ | $CH_3$ | |
| J-2 | $-CH_3$ | Q-72 ($R_7$ = $CH_3$, $R_8$ = H, $R_9$ = H, $R_2$ = H) | H | 3-$OCH_3$ | $OCH_3$ | $OCH_3$ | |
| J-3 | $-CH_3$ | Q-73 ($R_7$ = H, $R_8$ = H, $R_9$ = H, $R_2$ = H) | H | H | $OCH_3$ | $OCH_3$ | |
| J-4 | $-CH_3$ | Q-73 ($R_7$ = H, $R_8$ = $CH_3$, $R_9$ = H, $R_2$ = $C_2H_5$) | H | H | $OCF_2H$ | $CH_3$ | |
| J-1 | $-CH_3$ | Q-73 ($R_7$ = $CH_3$, $R_8$ = H, $R_9$ = $CH_3$, $R_2$ = H) | H | 5-Cl | $OCH_3$ | $CH_3$ | |
| J-2 | $-CH_3$ | Q-74 ($R_7$ = H, $R_8$ = H, $R_9$ = H, $R_2$ = H) | H | H | $CH_3$ | $OCH_3$ | |
| J-3 | $-CH_3$ | Q-74 ($R_7$ = $CH_3$, $R_8$ = H, $R_9$ = H, $R_2$ = H) | H | H | $CH_3$ | $OCH_3$ | |
| J-4 | $-CH_3$ | Q-74 ($R_7$ = H, $R_8$ = H, $R_9$ = H, $R_2$ = $CH_3$) | H | 5-$CH_3$ | $OCH_3$ | $OCH_3$ | |
| J-1 | $-CH_3$ | Q-75 ($R_7$ = H, $R_8$ = H, $R_9$ = H) | H | H | $OCH_3$ | $OCH_3$ | |
| J-2 | $-CH_3$ | Q-75 ($R_7$ = H, $R_8$ = H, $R_9$ = $CH_3$) | H | H | Cl | $OCH_3$ | |

TABLE 1-continued

General Formula 1

| J | M | Q | R | $R_1$ | X | Y | m.p. (°C.) |
|---|---|---|---|---|---|---|---|
| J-3 | $-CH_3$ | Q-75 ($R_7 = CH_3$, $R_8 = H$, $R_9 = CH_3$) | H | H | $CH_3$ | $OCH_3$ | |
| J-4 | $-CH_3$ | Q-76 ($R_7 = H$, $R_8 = H$, $R_9 = H$) | H | H | $CH_3$ | $OCH_3$ | |
| J-1 | $-CH_3$ | Q-76 ($R_7 = H$, $R_8 = H$, $R_9 = CH_3$) | $CH_3$ | H | $CH_3$ | $OCH_3$ | |
| J-2 | $-CH_3$ | Q-76 ($R_7 = C_2H_5$, $R_8 = H$, $R_9 = C_2H_5$) | H | H | $OCH_3$ | $OCH_3$ | |
| J-3 | $-CH_3$ | Q-77 ($R_7 = H$, $R_8 = H$, $R_9 = H$) | H | H | $OCH_3$ | $OCH_3$ | |
| J-4 | $-CH_3$ | Q-77 ($R_7 = H$, $R_8 = H$, $R_9 = \underline{n}-C_3H_7$) | H | H | $OCH_3$ | $OCH_3$ | |
| J-1 | $-CH_3$ | Q-77 ($R_7 = H$, $R_8 = CH_3$, $R_9 = H$) | H | 5-$OCH_3$ | $OCH_3$ | $OCH_3$ | |
| J-2 | $-CH_3$ | Q-78 ($R_7 = H$, $R_8 = H$, $R_9 = H$) | H | H | $OCH_3$ | $OCH_3$ | |
| J-3 | $-CH_3$ | Q-78 ($R_7 = H$, $R_8 = H$, $R_9 = \underline{s}-C_4H_9$) | H | H | $OCH_3$ | $OCF_2H$ | |
| J-4 | $-CH_3$ | Q-78 ($R_7 = \underline{n}-C_3H_7$, $R_8 = H$, $R_9 = H$) | H | 3-Cl | $OCH_3$ | $OCH_3$ | |
| J-1 | $-CH_2CH_2CH_3$ | Q-79 ($R_7 = H$, $R_8 = H$, $R_9 = H$, $R_3 = H$) | H | H | $OCH_3$ | $OCH_3$ | |
| J-2 | $-CH_3$ | Q-79 ($R_7 = H$, $R_8 = H$, $R_9 = H$, $R_3 = CH_3$) | $CH_3$ | H | $OCH_3$ | $OCH_3$ | |
| J-3 | $-CH_3$ | Q-79 ($R_7 = CH_3$, $R_8 = H$, $R_9 = H$, $R_3 = C_2H_5$) | H | 3-$OCH_3$ | $OCH_3$ | $OCH_3$ | |
| J-4 | $-CH_3$ | Q-80 ($R_7 = H$, $R_8 = H$, $R_9 = H$, $R_3 = CH_3$) | H | H | $OCH_3$ | $OCH_3$ | |
| J-1 | $-CH_3$ | Q-80 ($R_7 = CH_3$, $R_8 = H$, $R_9 = H$, $R_3 = CH_3$) | H | H | $OCF_2H$ | $CH_3$ | |
| J-2 | $-CH_3$ | Q-80 ($R_7 = H$, $R_8 = H$, $R_9 = CH_3$, $R_3 = C_2H_5$) | H | 5-Cl | $OCH_3$ | $CH_3$ | |
| J-3 | $-CH_3$ | Q-81 ($R_7 = H$, $R_8 = H$, $R_9 = H$, $R_3 = CH_3$) | H | H | $CH_3$ | $OCH_3$ | |
| J-4 | $-CH_3$ | Q-81 ($R_7 = H$, $R_8 = CH_3$, $R_9 = H$, $R_3 = \underline{i}-C_3H_7$) | H | H | $CH_3$ | $OCH_3$ | |
| J-1 | $-CH_3$ | Q-81 ($R_7 = CH_3$, $R_8 = H$, $R_9 = CH_3$, $R_3 = CH_3$) | H | 5-$CH_3$ | $OCH_3$ | $OCH_3$ | |
| J-2 | $-CH_3$ | Q-82 ($R_7 = H$, $R_8 = H$, $R_9 = H$, $R_3 = CH_3$) | H | H | $OCH_3$ | $OCH_3$ | |
| J-3 | $-CH_3$ | Q-82 ($R_7 = CH_3$, $R_8 = H$, $R_9 = CH_3$, $R_3 = H$) | H | H | Cl | $OCH_3$ | |
| J-4 | $-CH_3$ | Q-82 ($R_7 = H$, $R_8 = H$, $R_9 = C_2H_5$, $R_3 = CH_3$) | H | H | $CH_3$ | $OCH_3$ | |
| J-1 | $-CH_3$ | Q-83 ($R_7 = H$, $R_8 = H$, $R_9 = H$, $R_{10} = H$) | H | H | $CH_3$ | $OCH_3$ | |
| J-2 | $-CH_3$ | Q-83 ($R_7 = CH_3$, $R_8 = H$, $R_9 = H$, $R_{10} = CH_3$) | $CH_3$ | H | $CH_3$ | $OCH_3$ | |
| J-3 | $-CH_3$ | Q-83 ($R_7 = CH_3$, $R_8 = CH_3$, $R_9 = H$, $R_{10} = H$) | H | H | $OCH_3$ | $OCH_3$ | |
| J-4 | $-CO_2CH_3$ | Q-84 ($R_7 = H$, $R_8 = H$, $R_9 = H$) | H | H | $OCH_3$ | $OCH_3$ | |
| J-1 | $-CH_3$ | Q-84 ($R_7 = H$, $R_8 = H$, $R_9 = CH_3$) | H | H | $OCH_3$ | $OCH_3$ | |
| J-2 | $-CH_3$ | Q-84 ($R_7 = H$, $R_8 = C_2H_5$, $R_9 = H$) | H | 5-$OCH_3$ | $OCH_3$ | $OCH_3$ | |
| J-3 | $-CH_3$ | Q-85 ($R_7 = H$, $R_8 = H$, $R_9 = H$) | H | H | $OCH_3$ | $OCH_3$ | |
| J-4 | $-CH_3$ | Q-85 ($R_7 = CH_3$, $R_8 = H$, $R_9 = H$) | H | H | $OCH_3$ | $OCF_2H$ | |
| J-1 | $-CH_3$ | Q-85 ($R_7 = H$, $R_8 = H$, $R_9 = C_2H_5$) | H | 5-Cl | $OCH_3$ | $OCH_3$ | |
| J-2 | $-CH_3$ | Q-86 ($R_7 = H$, $R_8 = H$, $R_9 = H$) | H | H | $OCH_3$ | $OCH_3$ | |
| J-3 | $-CH_3$ | Q-86 ($R_7 = CH_3$, $R_8 = H$, $R_9 = H$) | $CH_3$ | H | $OCH_3$ | $OCH_3$ | |
| J-4 | $-CH_3$ | Q-86 ($R_7 = H$, $R_8 = H$, $R_9 = C_2H_5$) | H | 3-$OCH_3$ | $OCH_3$ | $OCH_3$ | |
| J-1 | $-CH_3$ | Q-87 ($R_7 = H$, $R_8 = H$, $R_9 = H$) | H | H | $OCH_3$ | $OCH_3$ | |
| J-2 | $-CH_3$ | Q-87 ($R_7 = H$, $R_8 = H$, $R_9 = CH_3$) | H | H | $OCF_2H$ | $CH_3$ | |
| J-3 | $-CH_3$ | Q-87 ($R_7 = CH_3$, $R_8 = H$, $R_9 = H$) | H | 3-Cl | $OCH_3$ | $CH_3$ | |
| J-4 | $-CH_3$ | Q-88 ($R_7 = H$, $R_8 = H$, $R_9 = H$) | H | H | $CH_3$ | $OCH_3$ | |
| J-1 | $-C(CH_3)_3$ | Q-88 ($R_7 = CH_3$, $R_8 = H$, $R_9 = H$) | H | H | $CH_3$ | $OCH_3$ | |
| J-2 | $-CH_3$ | Q-88 ($R_7 = H$, $R_8 = H$, $R_9 = CH_3$) | H | 5-$CH_3$ | $OCH_3$ | $OCH_3$ | |
| J-3 | $-CH_3$ | Q-89 ($R_7 = H$, $R_8 = H$, $R_9 = H$) | H | H | $OCH_3$ | $OCH_3$ | |
| J-4 | $-CH_3$ | Q-89 ($R_7 = CH_3$, $R_8 = H$, $R_9 = C_2H_5$) | H | H | Cl | $OCH_3$ | |
| J-1 | $-CH_3$ | Q-89 ($R_7 = H$, $R_8 = CH_3$, $R_9 = H$) | H | H | $CH_3$ | $OCH_3$ | |
| J-2 | $-CH_3$ | Q-90 ($R_7 = H$, $R_8 = H$, $R_9 = H$, $R_3 = CH_3$) | H | H | $CH_3$ | $OCH_3$ | |
| J-3 | $-CH_3$ | Q-90 ($R_7 = CH_3$, $R_8 = H$, $R_9 = H$, $R_3 = C_2H_5$) | $CH_3$ | H | $CH_3$ | $OCH_3$ | |
| J-4 | $-CH_3$ | Q-90 ($R_7 = H$, $R_8 = H$, $R_9 = CH_3$, $R_3 = CH_3$) | H | H | $OCH_3$ | $OCH_3$ | |
| J-1 | $-CH_3$ | Q-91 ($R_7 = H$, $R_8 = H$, $R_9 = H$, $R_3 = CH_3$) | H | H | $OCH_3$ | $OCH_3$ | |
| J-2 | $-CH_3$ | Q-91 ($R_7 = CH_3$, $R_8 = H$, $R_9 = H$, $R_3 = H$) | H | H | $OCH_3$ | $OCH_3$ | |
| J-3 | $-CH_3$ | Q-91 ($R_7 = H$, $R_8 = H$, $R_9 = CH_3$, $R_3 = CH_3$) | H | 3-$OCH_3$ | $OCH_3$ | $OCH_3$ | |
| J-4 | $-CH_3$ | Q-92 ($R_7 = H$, $R_8 = H$, $R_9 = H$, $R_{10} = H$) | H | H | $OCH_3$ | $OCH_3$ | |

TABLE 1-continued

General Formula 1

| J | M | Q | R | $R_1$ | X | Y | m.p. (°C.) |
|---|---|---|---|---|---|---|---|
| J-1 | $-CH_3$ | Q-92 ($R_7$ = H, $R_8$ = H, $R_9$ = H, $R_{10}$ = $CH_3$) | H | H | $OCH_3$ | $OCF_2H$ | |
| J-2 | $-CH_3$ | Q-92 ($R_7$ = H, $R_8$ = $CH_3$, $R_9$ = H, $R_{10}$ = H) | H | 5-Cl | $OCH_3$ | $OCH_3$ | |
| J-3 | $-CH_3$ | Q-93 ($R_7$ = H, $R_8$ = H, $R_9$ = H) | H | H | $OCH_3$ | $OCH_3$ | |
| J-4 | $-CH_3$ | Q-93 ($R_7$ = H, $R_8$ = H, $R_9$ = $CH_3$) | $CH_3$ | H | $OCH_3$ | $OCH_3$ | |
| J-1 | $-CH_3$ | Q-93 ($R_7$ = $CH_3$, $R_8$ = H, $R_9$ = H) | H | 5-$OCH_3$ | $OCH_3$ | $OCH_3$ | |
| J-2 | $SO_2N(CH_3)_2$ | Q-94 ($R_7$ = H, $R_8$ = H, $R_9$ = H) | H | H | $OCH_3$ | $OCH_3$ | |
| J-3 | $-CH_3$ | Q-94 ($R_7$ = $CH_3$, $R_8$ = H, $R_9$ = H) | H | H | $OCF_2H$ | $CH_3$ | |
| J-4 | $-CH_3$ | Q-94 ($R_7$ = H, $R_8$ = H, $R_9$ = n-$C_4H_9$) | H | 3-Cl | $OCH_3$ | $CH_3$ | |
| J-1 | $-CH_3$ | Q-95 ($R_7$ = H, $R_8$ = H, $R_9$ = H) | H | H | $CH_3$ | $OCH_3$ | |
| J-2 | $-CH_3$ | Q-95 ($R_7$ = H, $R_8$ = H, $R_9$ = $CH_3$) | H | H | $CH_3$ | $OCH_3$ | |
| J-3 | $-CH_3$ | Q-95 ($R_7$ = H, $R_8$ = H, $R_9$ = s-$C_4H_9$) | H | 3-$CH_3$ | $OCH_3$ | $OCH_3$ | |
| J-4 | $-CH_3$ | Q-96 ($R_7$ = H, $R_8$ = H, $R_9$ = H) | H | H | $OCH_3$ | $OCH_3$ | |
| J-1 | $-CH_3$ | Q-96 ($R_7$ = $CH_3$, $R_8$ = H, $R_9$ = H) | H | H | Cl | $OCH_3$ | |
| J-2 | $-CH_3$ | Q-96 ($R_7$ = H, $R_8$ = H, $R_9$ = $CH_3$) | H | H | $CH_3$ | $OCH_3$ | |
| J-3 | $-CH_3$ | Q-97 ($R_7$ = H, $R_8$ = H, $R_9$ = H) | H | H | $CH_3$ | $OCH_3$ | |
| J-4 | $-CH_3$ | Q-97 ($R_7$ = $CH_3$, $R_8$ = $CH_3$, $R_9$ = $CH_3$) | $CH_3$ | H | $CH_3$ | $OCH_3$ | |
| J-1 | $-CH_3$ | Q-97 ($R_7$ = H, $R_8$ = H, $R_9$ = $CH_3$) | H | H | $OCH_3$ | $OCH_3$ | |
| J-2 | $-CH_3$ | Q-98 ($R_7$ = H, $R_8$ = H, $R_9$ = H) | H | H | $OCH_3$ | $OCH_3$ | |
| J-3 | $-CH_3$ | Q-98 ($R_7$ = $CH_3$, $R_8$ = H, $R_9$ = H) | H | H | $OCH_3$ | $OCH_3$ | |
| J-4 | $-CH_3$ | Q-98 ($R_7$ = H, $R_8$ = H, $R_9$ = i-$C_3H_7$) | H | 3-$OCH_3$ | $OCH_3$ | $OCH_3$ | |
| J-1 | $-CH_3$ | Q-99 ($R_7$ = H, $R_8$ = H, $R_9$ = H, $R_3$ = H) | H | H | $OCH_3$ | $OCH_3$ | |
| J-2 | $-CH_3$ | Q-99 ($R_7$ = H, $R_8$ = H, $R_9$ = $CH_3$, $R_3$ = $CH_3$) | H | H | $OCH_3$ | $OCF_2H$ | |
| J-3 | $-CH_3$ | Q-99 ($R_7$ = H, $R_8$ = H, $R_9$ = s-$C_4H_9$, $R_3$ = H) | H | 3-Cl | $OCH_3$ | $OCH_3$ | |
| J-4 | $-CH_3$ | Q-100 ($R_7$ = H, $R_8$ = H, $R_9$ = H, $R_3$ = $C_2H_5$) | H | H | $OCH_3$ | $OCH_3$ | |
| J-1 | $-CH_3$ | Q-100 ($R_7$ = $CH_3$, $R_8$ = H, $R_9$ = H, $R_3$ = H) | $CH_3$ | H | $OCH_3$ | $CH_3$ | |
| J-2 | $-CH_3$ | Q-100 ($R_7$ = H, $R_8$ = H, $R_9$ = $CH_3$, $R_3$ = $CH_3$) | H | 5-$OCH_3$ | $OCH_3$ | $OCH_3$ | |
| J-3 | $-CH_3$ | Q-101 ($R_7$ = H, $R_8$ = H, $R_9$ = H, $R_3$ = i-$C_3H_7$) | H | H | $OCH_3$ | $OCH_3$ | |
| J-4 | $-CH_3$ | Q-101 ($R_7$ = $CH_3$, $R_8$ = $CH_3$, $R_9$ = $CH_3$, $R_3$ = H) | H | H | $OCF_2H$ | $CH_3$ | |
| J-1 | $-CH_3$ | Q-101 ($R_7$ = H, $R_8$ = H, $R_9$ = $CH_3$, $R_3$ = $CH_3$) | H | 5-Cl | $OCH_3$ | $CH_3$ | |
| J-2 | $-CH_3$ | Q-102 ($R_7$ = H, $R_8$ = H, $R_9$ = H, $R_3$ = H) | H | H | $CH_3$ | $OCH_3$ | |
| J-3 | $-CH_3$ | Q-102 ($R_7$ = $CH_3$, $R_8$ = H, $R_9$ = H, $R_3$ = $CH_3$) | H | H | $CH_3$ | $OCH_3$ | |
| J-4 | $-CH_3$ | Q-102 ($R_7$ = H, $R_8$ = H, $R_9$ = i-$C_3H_7$, $R_3$ = $CH_3$) | H | 3-$CH_3$ | $OCH_3$ | $OCH_3$ | |
| J-1 | $-CH_3$ | Q-103 ($R_7$ = H, $R_8$ = H, $R_9$ = H, $R_{10}$ = H) | H | H | $OCH_3$ | $OCH_3$ | |
| J-2 | $-CH_3$ | Q-103 ($R_7$ = $CH_3$, $R_8$ = H, $R_9$ = H, $R_{10}$ = $CH_3$) | H | H | Cl | $OCH_3$ | |
| J-3 | $-CH_3$ | Q-103 ($R_7$ = H, $R_8$ = H, $R_9$ = H, $R_{10}$ = s-$C_4H_9$) | H | H | $CH_3$ | $OCH_3$ | |
| J-4 | $-CH_3$ | Q-104 ($R_7$ = H, $R_8$ = H, $R_9$ = H, $R_2$ = H) | H | H | $CH_3$ | $OCH_3$ | |
| J-1 | $-CH_3$ | Q-104 ($R_7$ = $CH_3$, $R_8$ = H, $R_9$ = H, $R_2$ = $OC_2H_5$) | $CH_3$ | H | $CH_3$ | $OCH_3$ | |
| J-2 | $-CH_3$ | Q-104 ($R_7$ = H, $R_8$ = H, $R_9$ = H, $R_2$ = Br) | H | H | $OCH_3$ | $OCH_3$ | |
| J-3 | $-C_6H_5$ | Q-105 ($R_7$ = H, $R_8$ = H, $R_9$ = H, $R_2$ = H) | H | H | $OCH_3$ | $OCH_3$ | |
| J-4 | $-CH_3$ | Q-105 ($R_7$ = $CH_3$, $R_8$ = H, $R_9$ = H, $R_2$ = $CH_3$) | H | H | $OCH_3$ | $OCH_3$ | |
| J-1 | $-CH_3$ | Q-105 ($R_7$ = H, $R_8$ = $CH_3$, $R_9$ = H, $R_2$ = $C_2H_5$) | H | 5-$OCH_3$ | $OCH_3$ | $OCH_3$ | |
| J-4 | $-CH_3$ | Q-105 ($R_7$ = H, $R_8$ = H, $R_9$ = H, $R_2$ = H) | H | H | $OCH_3$ | $OCH_3$ | 175-182 d |
| J-2 | $-CH_3$ | Q-106 ($R_7$ = H, $R_8$ = H, $R_9$ = H, $R_2$ = H) | H | H | $CH_3$ | $OCH_3$ | |
| J-3 | $-CH_3$ | Q-106 ($R_7$ = $CH_3$, $R_8$ = H, $R_9$ = H, $R_2$ = $CH_3$) | H | H | $OCH_3$ | $OCF_2H$ | |
| J-1 | $-CH_3$ | Q-107 ($R_7$ = H, $R_8$ = H, $R_9$ = H, $R_2$ = H) | H | H | $OCH_3$ | $OCH_3$ | |
| J-2 | $-CH_3$ | Q-107 ($R_7$ = $CH_3$, $R_8$ = H, $R_9$ = H, $R_2$ = H) | $CH_3$ | H | $OCH_3$ | $OCH_3$ | |
| J-3 | $-CH_3$ | Q-107 ($R_7$ = H, $R_8$ = H, $R_9$ = H, $R_2$ = $CH_3$) | H | 3-$OCH_3$ | $OCH_3$ | $OCH_3$ | |
| J-4 | $-CH_3$ | Q-108 ($R_7$ = H, $R_8$ = H, $R_9$ = H, $R_2$ = H) | H | H | $OCH_3$ | $OCH_3$ | |
| J-1 | $-CH_3$ | Q-108 ($R_7$ = $CH_3$, $R_8$ = H, $R_9$ = H, $R_2$ = Cl) | H | H | $OCF_2H$ | $CH_3$ | |
| J-2 | $-CH_3$ | Q-108 ($R_7$ = H, $R_8$ = H, $R_9$ = H, $R_2$ = $CH_3$) | H | 5-Cl | $OCH_3$ | $CH_3$ | |

TABLE 1-continued

General Formula 1

| J | M | Q | R | $R_1$ | X | Y | m.p. (°C.) |
|---|---|---|---|---|---|---|---|
| J-3 | —$CH_3$ | Q-109 ($R_7$ = H, $R_8$ = H, $R_9$ = H) | H | H | $CH_3$ | $OCH_3$ | |
| J-4 | —$CH_3$ | Q-109 ($R_7$ = $CH_3$, $R_8$ = H, $R_9$ = H) | H | H | $CH_3$ | $OCH_3$ | |
| J-1 | —$CH_3$ | Q-109 ($R_7$ = H, $R_8$ = H, $R_9$ = $CH_3$) | H | 5-$CH_3$ | $OCH_3$ | $OCH_3$ | |
| J-2 | —$CH_3$ | Q-110 ($R_7$ = H, $R_8$ = H, $R_9$ = H) | H | H | $OCH_3$ | $OCH_3$ | |
| J-3 | —$CH_3$ | Q-110 ($R_7$ = $CH_3$, $R_8$ = H, $R_9$ = H) | H | H | Cl | $OCH_3$ | |
| J-4 | —$CH_3$ | Q-110 ($R_7$ = H, $R_8$ = $CH_3$, $R_9$ = H) | H | H | $CH_3$ | $OCH_3$ | |
| J-1 | —$CH_3$ | Q-111 ($R_7$ = H, $R_8$ = H, $R_9$ = H) | H | H | $CH_3$ | $OCH_3$ | |
| J-2 | —$CH_3$ | Q-111 ($R_7$ = $CH_3$, $R_8$ = H, $R_9$ = H) | $CH_3$ | H | $CH_3$ | $OCH_3$ | |
| J-3 | —$CH_3$ | Q-111 ($R_7$ = H, $R_8$ = H, $R_9$ = $CH_3$) | H | H | $OCH_3$ | $OCH_3$ | |
| J-4 | $C_6H_5$ | Q-112 ($R_7$ = H, $R_8$ = H, $R_9$ = H) | H | H | $OCH_3$ | $OCH_3$ | |
| J-1 | —$CH_3$ | Q-112 ($R_7$ = $CH_3$, $R_8$ = H, $R_9$ = H) | H | H | $OCH_3$ | $OCH_3$ | |
| J-2 | —$CH_3$ | Q-112 ($R_7$ = H, $R_8$ = $CH_3$, $R_9$ = $CH_3$) | H | 5-$OCH_3$ | $OCH_3$ | $OCH_3$ | |
| J-3 | —$CH_3$ | Q-113 ($R_7$ = H, $R_8$ = H, $R_9$ = H, $R_3$ = $CH_3$) | H | H | $OCH_3$ | $OCH_3$ | |
| J-4 | —$CH_3$ | Q-113 ($R_7$ = $C_2H_5$, $R_8$ = H, $R_9$ = H, $R_3$ = i-$C_3H_7$) | H | H | $OCH_3$ | $OCF_2H$ | |
| J-1 | —$CH_3$ | Q-113 ($R_7$ = H, $R_8$ = H, $R_9$ = $C_2H_5$, $R_3$ = n-$C_4H_9$) | H | 5-Cl | $OCH_3$ | $OCH_3$ | |
| J-2 | —$CH_3$ | Q-114 ($R_7$ = H, $R_8$ = H, $R_9$ = H, $R_3$ = $CH_3$) | H | H | $OCH_3$ | $OCH_3$ | |
| J-3 | —$CH_3$ | Q-114 ($R_7$ = n-$C_4H_9$, $R_8$ = H, $R_9$ = H, $R_3$ = $C_2H_5$) | $CH_3$ | H | $OCH_3$ | $CH_3$ | |
| J-4 | —$CH_3$ | Q-114 ($R_7$ = H, $R_8$ = $CH_3$, $R_8$ = i-$C_3H_7$, $R_3$ = H) | H | 3-$OCH_3$ | $OCH_3$ | $OCH_3$ | |
| J-1 | —$CH_3$ | Q-115 ($R_7$ = H, $R_8$ = H, $R_9$ = H, $R_3$ = $CH_3$) | H | H | $OCH_3$ | $OCH_3$ | |
| J-2 | —$CH_3$ | Q-115 ($R_7$ = i-$C_3H_7$, $R_8$ = H, $R_9$ = H, $R_3$ = $CH_3$) | H | H | $OCF_2H$ | $CH_3$ | |
| J-3 | —$CH_3$ | Q-115 ($R_7$ = H, $R_8$ = $C_2H_5$, $R_9$ = $CH_3$, $R_3$ = H) | H | 3-Cl | $OCH_3$ | $CH_3$ | |
| J-4 | $C(CH_3)_3$ | Q-116 ($R_7$ = H, $R_8$ = H, $R_9$ = H, $R_{10}$ = H) | H | H | $CH_3$ | $OCH_3$ | |
| J-1 | —$CH_3$ | Q-116 ($R_7$ = $CH_3$, $R_8$ = H, $R_9$ = H, $R_{10}$ = H) | H | H | $CH_3$ | $OCH_3$ | |
| J-2 | —$CH_3$ | Q-116 ($R_7$ = H, $R_8$ = H, $R_9$ = H, $R_{10}$ = $CH_3$) | H | 5-$CH_3$ | $OCH_3$ | $OCH_3$ | |
| J-3 | —$CH_3$ | Q-117 ($R_7$ = H, $R_8$ = H, $R_9$ = H, $R_2$ = H) | H | H | $OCH_3$ | $OCH_3$ | |
| J-4 | —$CH_3$ | Q-117 ($R_7$ = H, $R_8$ = H, $R_9$ = H, $R_2$ = $CH_3$) | H | H | Cl | $OCH_3$ | |
| J-1 | —$CH_3$ | Q-117 ($R_7$ = $CH_3$, $R_8$ = H, $R_9$ = H, $R_2$ = H) | H | H | $CH_3$ | $OCH_3$ | |
| J-2 | —$CH_3$ | Q-118 ($R_7$ = H, $R_8$ = H, $R_9$ = H, $R_{10}$ = H) | H | H | $CH_3$ | $OCH_3$ | |
| J-3 | —$CH_3$ | Q-118 ($R_7$ = $CH_3$, $R_8$ = H, $R_9$ = H, $R_{10}$ = H) | $CH_3$ | H | $CH_3$ | $OCH_3$ | |
| J-4 | —$CH_3$ | Q-118 ($R_7$ = H, $R_8$ = H, $R_9$ = H, $R_{10}$ = $CH_3$) | H | H | $OCH_3$ | $OCH_3$ | |
| J-1 | —$CH_3$ | Q-119 ($R_7$ = H, $R_8$ = H, $R_9$ = H, $R_2$ = H) | H | H | $OCH_3$ | $OCH_3$ | |
| J-2 | —$CH_3$ | Q-119 ($R_7$ = H, $R_8$ = H, $R_9$ = H, $R_2$ = $CH_3$) | H | H | $OCH_3$ | $OCH_3$ | |
| J-3 | —$CH_3$ | Q-119 ($R_7$ = H, $R_8$ = $CH_3$, $R_9$ = H, $R_2$ = $C_2H_5$) | H | 3-$OCH_3$ | $OCH_3$ | $OCH_3$ | |
| J-4 | —$CH_3$ | Q-120 ($R_7$ = H, $R_8$ = H, $R_9$ = H, $R_2$ = H) | H | H | $OCH_3$ | $OCH_3$ | |
| J-1 | —$CH_3$ | Q-120 ($R_7$ = H, $R_8$ = H, $R_9$ = H, $R_2$ = $CH_3$) | H | H | $OCH_3$ | $OCF_2H$ | |
| J-2 | —$CH_3$ | Q-120 ($R_7$ = H, $R_8$ = H, $R_9$ = $CH_3$, $R_2$ = $CH_3$) | H | 5-Cl | $OCH_3$ | $OCH_3$ | |
| J-3 | —$CH_3$ | Q-121 ($R_7$ = H, $R_8$ = H, $R_9$ = H, $R_2$ = H) | H | H | $OCH_3$ | $OCH_3$ | |
| J-4 | —$CH_3$ | Q-121 ($R_7$ = H, $R_8$ = H, $R_9$ = H, $R_2$ = $C_2H_5$) | $CH_3$ | H | $OCH_3$ | $CH_3$ | |
| J-1 | —$CH_3$ | Q-121 ($R_7$ = $CH_3$, $R_8$ = $CH_3$, $R_9$ = H, $R_2$ = H) | H | 5-$OCH_3$ | $OCH_3$ | $OCH_3$ | |
| J-2 | —$SO_2N(CH_3)_2$ | Q-122 ($R_7$ = H, $R_8$ = H, $R_9$ = H, $R_2$ = H) | H | H | $OCH_3$ | $OCH_3$ | |
| J-3 | —$CH_3$ | Q-122 ($R_7$ = H, $R_8$ = H, $R_9$ = H, $R_2$ = $CH_3$) | H | H | $OCF_2H$ | $CH_3$ | |
| J-4 | —$CH_3$ | Q-122 ($R_7$ = $CH_3$, $R_8$ = H, $R_9$ = H, $R_2$ = H) | H | 3-Cl | $OCH_3$ | $CH_3$ | |
| J-1 | —$CH_3$ | Q-123 ($R_7$ = H, $R_8$ = H, $R_9$ = H) | H | H | $CH_3$ | $OCH_3$ | |
| J-2 | —$CH_3$ | Q-123 ($R_7$ = H, $R_8$ = H, $R_9$ = $CH_3$) | H | H | $CH_3$ | $OCH_3$ | |
| J-3 | —$CH_3$ | Q-123 ($R_7$ = $CH_3$, $R_8$ = H, $R_9$ = $CH_3$) | H | 3-$CH_3$ | $OCH_3$ | $OCH_3$ | |
| J-4 | —$CH_3$ | Q-124 ($R_7$ = H, $R_8$ = H, $R_9$ = H) | H | H | $OCH_3$ | $OCH_3$ | |
| J-1 | —$CH_3$ | Q-124 ($R_7$ = H, $R_8$ = H, $R_9$ = $CH_3$) | H | H | Cl | $OCH_3$ | |
| J-2 | —$CH_3$ | Q-124 ($R_7$ = $C_2H_5$, $R_8$ = H, $R_9$ = $C_2H_5$) | H | H | $CH_3$ | $OCH_3$ | |
| J-3 | —$C(CH_3)_3$ | Q-125 ($R_7$ = H, $R_8$ = H, $R_9$ = H) | H | H | $CH_3$ | $OCH_3$ | |
| J-4 | —$CH_3$ | Q-125 ($R_7$ = H, $R_8$ = H, $R_9$ = n-$C_4H_9$) | $CH_3$ | H | $CH_3$ | $OCH_3$ | |

TABLE 1-continued

General Formula 1

| J | M | Q | R | $R_1$ | X | Y | m.p. (°C.) |
|---|---|---|---|---|---|---|---|
| J-1 | $-CH_3$ | Q-125 ($R_7$ = H, $R_8$ = $CH_3$, $R_9$ = H) | H | H | $OCH_3$ | $OCH_3$ | |
| J-2 | $-CH_3$ | Q-126 ($R_7$ = H, $R_8$ = H, $R_9$ = H) | H | H | $OCH_3$ | $OCH_3$ | |
| J-3 | $-CH_3$ | Q-126 ($R_7$ = H, $R_8$ = H, $R_9$ = s-$C_3H_7$) | H | H | $OCH_3$ | $OCH_3$ | |
| J-4 | $-CH_3$ | Q-126 ($R_7$ = n-$C_3H_7$, $R_8$ = H, $R_9$ = H) | H | 3-$OCH_3$ | $OCH_3$ | $OCH_3$ | |
| J-1 | $-CH_3$ | Q-127 ($R_7$ = H, $R_8$ = H, $R_9$ = H, $R_3$ = H) | H | H | $OCH_3$ | $OCH_3$ | |
| J-2 | $-CH_3$ | Q-127 ($R_7$ = H, $R_8$ = H, $R_9$ = H, $R_3$ = $CH_3$) | H | H | $OCH_3$ | $OCF_2H$ | |
| J-3 | $-CH_3$ | Q-127 ($R_7$ = $CH_3$, $R_8$ = H, $R_9$ = H, $R_3$ = $C_2H_5$) | H | 3-Cl | $OCH_3$ | $OCH_3$ | |
| J-4 | $-CH_3$ | Q-128 ($R_7$ = H, $R_8$ = H, $R_9$ = H, $R_3$ = $CH_3$) | H | H | $OCH_3$ | $OCH_3$ | |
| J-1 | $-CH_3$ | Q-128 ($R_7$ = $CH_3$, $R_8$ = H, $R_9$ = H, $R_3$ = $CH_3$) | $CH_3$ | H | $OCH_3$ | $OCH_3$ | |
| J-2 | $-CH_3$ | Q-128 ($R_7$ = H, $R_8$ = H, $R_9$ = $CH_3$, $R_3$ = $C_2H_5$) | H | 5-$OCH_3$ | $OCH_3$ | $OCH_3$ | |
| J-3 | $-CH_3$ | Q-129 ($R_7$ = H, $R_8$ = H, $R_9$ = H, $R_3$ = $CH_3$) | H | H | $OCH_3$ | $OCH_3$ | |
| J-4 | $-CH_3$ | Q-129 ($R_7$ = H, $R_8$ = $CH_3$, $R_9$ = H, $R_3$ = i-$C_3H_7$) | H | H | $OCF_2H$ | $CH_3$ | |
| J-1 | $-CH_3$ | Q-129 ($R_7$ = $CH_3$, $R_8$ = H, $R_9$ = $CH_3$, $R_3$ = $CH_3$) | H | 5-Cl | $OCH_3$ | $CH_3$ | |
| J-2 | $-CH_3$ | Q-130 ($R_7$ = H, $R_8$ = H, $R_9$ = H, $R_3$ = $CH_3$) | H | H | $CH_3$ | $OCH_3$ | |
| J-3 | $-CH_3$ | Q-130 ($R_7$ = $CH_3$, $R_8$ = H, $R_9$ = $CH_3$, $R_3$ = H) | H | H | $CH_3$ | $OCH_3$ | |
| J-4 | $-CH_3$ | Q-130 ($R_7$ = H, $R_8$ = H, $R_9$ = $C_2H_5$, $R_3$ = $CH_3$) | H | 3-$CH_3$ | $OCH_3$ | $OCH_3$ | |
| J-1 | $-CH_3$ | Q-131 ($R_7$ = H, $R_8$ = H, $R_9$ = H, $R_{10}$ = H) | H | H | $OCH_3$ | $OCH_3$ | |
| J-2 | $-CH_3$ | Q-131 ($R_7$ = $CH_3$, $R_8$ = H, $R_9$ = H, $R_{10}$ = $CH_3$) | H | H | Cl | $OCH_3$ | |
| J-3 | $-CH_3$ | Q-131 ($R_7$ = $CH_3$, $R_8$ = $CH_3$, $R_9$ = H, $R_{10}$ = H) | H | H | $CH_3$ | $OCH_3$ | |
| J-4 | $-CH_3$ | Q-132 ($R_7$ = H, $R_8$ = H, $R_9$ = H) | H | H | $CH_3$ | $OCH_3$ | |
| J-1 | $-CH_3$ | Q-132 ($R_7$ = H, $R_8$ = H, $R_9$ = $CH_3$) | $CH_3$ | H | $CH_3$ | $OCH_3$ | |
| J-2 | $-CH_3$ | Q-132 ($R_7$ = H, $R_8$ = $C_2H_5$, $R_9$ = H) | H | H | $OCH_3$ | $OCH_3$ | |
| J-3 | $-CH_3$ | Q-133 ($R_7$ = H, $R_8$ = H, $R_9$ = H) | H | H | $OCH_3$ | $OCH_3$ | |
| J-4 | $-CH_3$ | Q-133 ($R_7$ = $CH_3$, $R_8$ = H, R = H) | H | H | $OCH_3$ | $OCH_3$ | |
| J-1 | $-CH_3$ | Q-133 ($R_7$ = H, $R_8$ = H, $R_9$ = $C_2H_5$) | H | 5-$OCH_3$ | $OCH_3$ | $OCH_3$ | |
| J-2 | $-CH_3$ | Q-134 ($R_7$ = H, $R_8$ = H, $R_9$ = H) | H | H | $OCH_3$ | $OCH_3$ | |
| J-3 | $-CH_3$ | Q-134 ($R_7$ = $CH_3$, $R_8$ = H, $R_9$ = H) | H | H | $OCH_3$ | $OCF_2H$ | |
| J-4 | $-CH_3$ | Q-134 ($R_7$ = H, $R_8$ = H, $R_9$ = $C_2H_5$) | H | 3-Cl | $OCH_3$ | $OCH_3$ | |
| J-1 | $-CH_3$ | Q-135 ($R_7$ = H, $R_8$ = H, R = H) | H | H | $OCH_3$ | $OCH_3$ | |
| J-2 | $-CH_3$ | Q-135 ($R_7$ = H, $R_8$ = H, R = $CH_3$) | $CH_3$ | H | $OCH_3$ | $OCH_3$ | |
| J-3 | $-CH_3$ | Q-135 ($R_7$ = $CH_3$, $R_8$ = H, $R_9$ = H) | H | 3-$OCH_3$ | $OCH_3$ | $OCH_3$ | |
| J-4 | $-CH_2CH_2CH_3$ | Q-136 ($R_7$ = H, $R_8$ = H, $R_9$ = H) | H | H | $OCH_3$ | $OCH_3$ | |
| J-1 | $-CH_3$ | Q-136 ($R_7$ = H, $R_8$ = H, $R_9$ = $CH_3$) | H | H | $OCF_2H$ | $CH_3$ | |
| J-2 | $-CH_3$ | Q-136 ($R_7$ = H, $R_8$ = $CH_3$, $R_9$ = $C_2H_5$) | H | 5-Cl | $OCH_3$ | $CH_3$ | |
| J-3 | $-CH_3$ | Q-137 ($R_7$ = H, $R_8$ = H, $R_9$ = H) | H | H | $CH_3$ | $OCH_3$ | |
| J-4 | $-CH_3$ | Q-137 ($R_7$ = $CH_3$, $R_8$ = H, $R_9$ = H) | H | H | $CH_3$ | $OCH_3$ | |
| J-1 | $-CH_3$ | Q-137 ($R_7$ = H, $R_8$ = H, $R_9$ = $CH_3$) | H | 5-$CH_3$ | $OCH_3$ | $OCH_3$ | |
| J-2 | $-CH_3$ | Q-138 ($R_7$ = H, $R_8$ = H, $R_9$ = H) | H | H | $OCH_3$ | $OCH_3$ | |
| J-3 | $-CH_3$ | Q-138 ($R_7$ = $CH_3$, $R_8$ = H, $R_9$ = H) | H | H | Cl | $OCH_3$ | |
| J-4 | $-CH_3$ | Q-138 ($R_7$ = H, $R_8$ = H, $R_9$ = $CH_3$) | H | H | $CH_3$ | $OCH_3$ | |
| J-1 | $-CH_3$ | Q-139 ($R_7$ = H, $R_8$ = H, $R_9$ = H) | H | H | $CH_3$ | $OCH_3$ | |
| J-2 | $-CH_3$ | Q-139 ($R_7$ = $CH_3$, $R_8$ = H, $R_9$ = H) | $CH_3$ | H | $CH_3$ | $OCH_3$ | |
| J-3 | $-CH_3$ | Q-139 ($R_7$ = $CH_3$, $R_8$ = $CH_3$, $R_9$ = H) | H | H | $OCH_3$ | $OCH_3$ | |
| J-4 | $-CH_3$ | Q-140 ($R_7$ = H, $R_8$ = H, $R_9$ = H, $R_3$ = $CH_3$) | H | H | $OCH_3$ | $OCH_3$ | |
| J-1 | $-CH_3$ | Q-140 ($R_7$ = H, $R_8$ = H, $R_9$ = $CH_3$, $R_3$ = H) | H | H | $OCH_3$ | $OCH_3$ | |
| J-2 | $-CH_3$ | Q-140 ($R_7$ = H, $R_8$ = $CH_3$, $R_9$ = H, $R_3$ = $C_2H_5$) | H | 5-$OCH_3$ | $OCH_3$ | $OCH_3$ | |
| J-3 | $-CH_3$ | Q-141 ($R_7$ = H, $R_8$ = H, $R_9$ = H, $R_3$ = $CH_3$) | H | H | $OCH_3$ | $OCH_3$ | |
| J-4 | $-CH_3$ | Q-141 ($R_7$ = H, $R_8$ = H, $R_9$ = H, $R_3$ = H) | H | H | $OCH_3$ | $OCF_2H$ | |
| J-1 | $-CH_3$ | Q-141 ($R_7$ = H, $R_8$ = H, $R_9$ = $CH_3$, $R_3$ = $CH_3$) | H | 5-Cl | $OCH_3$ | $OCH_3$ | |
| J-2 | $-CO_2CH_2CH_3$ | Q-142 ($R_7$ = H, $R_8$ = H, $R_9$ = H, $R_{10}$ = H) | H | H | $OCH_3$ | $OCH_3$ | |

TABLE 1-continued

General Formula 1

| J | M | Q | R | $R_1$ | X | Y | m.p. (°C.) |
|---|---|---|---|---|---|---|---|
| J-3 | $-CH_3$ | Q-142 ($R_7 = CH_3, R_8 = H, R_9 = H, R_{10} = H$) | $CH_3$ | H | $OCH_3$ | $CH_3$ | |
| J-4 | $-CH_3$ | Q-142 ($R_7 = H, R_8 = H, R_9 = H, R_{10} = CH_3$) | H | 3-$OCH_3$ | $OCH_3$ | $OCH_3$ | |
| J-1 | $-CH_3$ | Q-143 ($R_7 = H, R_8 = H, R_9 = H, R_3 = CH_3$) | H | H | $OCH_3$ | $OCH_3$ | |
| J-2 | $-CH_3$ | Q-143 ($R_7 = H, R_8 = H, R_9 = H, R_3 = H$) | H | H | $OCF_2H$ | $CH_3$ | |
| J-3 | $-CH_3$ | Q-143 ($R_7 = CH_3, R_8 = H, R_9 = CH_3, R_3 = CH_3$) | H | 3-Cl | $OCH_3$ | $CH_3$ | |
| J-4 | $-CH_3$ | Q-144 ($R_7 = H, R_8 = H, R_9 = H, R_3 = CH_3$) | H | H | $CH_3$ | $OCH_3$ | |
| J-1 | $-CH_3$ | Q-144 ($R_7 = CH_3, R_8 = H, R_9 = H, R_3 = CH_3$) | H | H | $CH_3$ | $OCH_3$ | |
| J-2 | $-CH_3$ | Q-144 ($R_7 = H, R_8 = C_2H_5, R_9 = H, R_3 = CH_3$) | H | 5-$CH_3$ | $OCH_3$ | $OCH_3$ | |
| J-3 | $-CH_3$ | Q-145 ($R_7 = H, R_8 = H, R_9 = H$) | H | H | $OCH_3$ | $OCH_3$ | |
| J-4 | $-CH_3$ | Q-145 ($R_7 = H, R_8 = H, R_9 = CH_3$) | H | H | Cl | $OCH_3$ | |
| J-1 | $-CH_3$ | Q-145 ($R_7 = CH_3, R_8 = H, R_9 = H$) | H | H | $CH_3$ | $OCH_3$ | |
| J-2 | $-CH_3$ | Q-146 ($R_7 = H, R_8 = H, R_9 = H$) | H | H | $CH_3$ | $OCH_3$ | |
| J-3 | $-CH_3$ | Q-146 ($R_7 = CH_3, R_8 = H, R_9 = H$) | $CH_3$ | H | $CH_3$ | $OCH_3$ | |
| J-4 | $-CH_3$ | Q-146 ($R_7 = H, R_8 = H, R_9 = \underline{n}-C_4H_9$) | H | H | $OCH_3$ | $OCH_3$ | |
| J-1 | $-CH_3$ | Q-147 ($R_7 = H, R_8 = H, R_9 = H$) | H | H | $OCH_3$ | $OCH_3$ | |
| J-2 | $-CH_3$ | Q-147 ($R_7 = CH_3, R_8 = H, R_9 = H$) | H | H | $OCH_3$ | $OCH_3$ | |
| J-3 | $-CH_3$ | Q-147 ($R_7 = H, R_8 = H, R_9 = \underline{n}-C_4H_9$) | H | 3-$OCH_3$ | $OCH_3$ | $OCH_3$ | |
| J-4 | $-C(CH_3)_3$ | Q-148 ($R_7 = H, R_8 = H, R_9 = H$) | H | H | $OCH_3$ | $OCH_3$ | |
| J-1 | $-CH_3$ | Q-148 ($R_7 = H, R_8 = H, R_9 = CH_3$) | H | H | $OCH_3$ | $OCF_2H$ | |
| J-2 | $-CH_3$ | Q-148 ($R_7 = CH_3, R_8 = H, R_9 = H$) | H | 5-Cl | $OCH_3$ | $OCH_3$ | |
| J-3 | $-CH_3$ | Q-149 ($R_7 = H, R_8 = H, R_9 = H$) | H | H | $OCH_3$ | $OCH_3$ | |
| J-4 | $-CH_3$ | Q-149 ($R_7 = H, R_8 = H, R_9 = CH_3$) | $CH_3$ | H | $OCH_3$ | $OCH_3$ | |
| J-1 | $-CH_3$ | Q-149 ($R_7 = CH_3, R_8 = H, R_9 = H$) | H | 5-$OCH_3$ | $OCH_3$ | $OCH_3$ | |
| J-2 | $-CH_3$ | Q-150 ($R_7 = H, R_8 = H, R_9 = H$) | H | H | $OCH_3$ | $OCH_3$ | |
| J-3 | $-CH_3$ | Q-150 ($R_7 = CH_3, R_8 H, R_9 = H$) | H | H | $OCF_2H$ | $CH_3$ | |
| J-4 | $-CH_3$ | Q-150 ($R_7 = H, R_8 = CH_3, R_9 = CH_3$) | H | 3-Cl | $OCH_3$ | $CH_3$ | |
| J-1 | $-CH_3$ | Q-151 ($R_7 = H, R_8 = H, R_9 = H$) | H | H | $CH_3$ | $OCH_3$ | |
| J-2 | $-CH_3$ | Q-151 ($R_7 = CH_3, R_8 = H, R_9 = H$) | H | H | $CH_3$ | $OCH_3$ | |
| J-3 | $-CH_3$ | Q-151 ($R_7 = CH_3, R_8 = CH_3, R_9 = H$) | H | 3-$CH_3$ | $OCH_3$ | $OCH_3$ | |
| J-4 | $-CH_3$ | Q-152 ($R_7 = H, R_8 = H, R_9 = H$) | H | H | $OCH_3$ | $OCH_3$ | |
| J-1 | $-CH_3$ | Q-152 ($R_7 = C_2H_5, R_8 = H, R_9 = H$) | H | H | Cl | $OCH_3$ | |
| J-2 | $-CH_3$ | Q-152 ($R_7 = CH_3, R_8 = CH_3, R_9 = H$) | H | H | $CH_3$ | $OCH_3$ | |
| J-3 | $-CH_3$ | Q-153 ($R_7 = H, R_8 = H, R_9 = H, R_{11} = CH_3$) | H | H | $CH_3$ | $OCH_3$ | |
| J-4 | $-CH_3$ | Q-153 ($R_7 = H, R_8 = H, R_9 = H, R_{11} = H$) | $CH_3$ | H | $CH_3$ | $OCH_3$ | |
| J-1 | $-CH_3$ | Q-153 ($R_7 = CH_3, R_8 = H, R_9 = H, R_{11} = CH_3$) | H | H | $OCH_3$ | $OCH_3$ | |
| J-2 | $-CH_3$ | Q-154 ($R_7 = H, R_8 = H, R_9 = H, R_{11} = CH_3$) | H | H | $OCH_3$ | $OCH_3$ | |
| J-3 | $-CH_3$ | Q-154 ($R_7 = CH_3, R_8 = H, R_9 = H$) | H | H | $OCH_3$ | $OCH_3$ | |
| J-4 | $-CH_3$ | Q-154 ($R_7 = H, R_8 = CH_3, R_9 = CH_3$) | H | 3-$OCH_3$ | $OCH_3$ | $OCH_3$ | |
| J-1 | $-CH_2CH_3$ | Q-155 ($R_7 = H, R_8 = H, R_9 = H$) | H | H | $OCH_3$ | $OCH_3$ | |
| J-2 | $-CH_3$ | Q-155 ($R_7 = CH_3, R_8 = H, R_9 = H$) | H | H | $OCH_3$ | $OCF_2H$ | |
| J-3 | $-CH_3$ | Q-155 ($R_7 = CH_3, R_8 = CH_3, R_9 = H$) | H | 3-Cl | $OCH_3$ | $OCH_3$ | |
| J-4 | $-CH_3$ | Q-156 ($R_7 = H, R_8 = H, R_9 = H$) | H | H | $OCH_3$ | $OCH_3$ | |
| J-1 | $-CH_3$ | Q-156 ($R_7 = C_2H_5, R_8 = H, R_9 = H$) | $CH_3$ | H | $OCH_3$ | $OCH_3$ | |
| J-2 | $-CH_3$ | Q-156 ($R_7 = CH_3, R_8 = CH_3, R_9 = H$) | H | 5-$OCH_3$ | $OCH_3$ | $OCH_3$ | |
| J-3 | $-CH_3$ | Q-157 ($R_7 = H, R_8 = H, R_9 = H, R_{10} = H$) | H | H | $OCH_3$ | $OCH_3$ | |
| J-4 | $-CH_3$ | Q-157 ($R_7 = CH_3, R_8 = H, R_9 = H, R_{10} = H$) | H | H | $OCF_2H$ | $CH_3$ | |
| J-1 | $-CH_3$ | Q-157 ($R_7 = H, R_8 = H, R_9 = H, R_{10} = CH_3$) | H | 5-Cl | $OCH_3$ | $CH_3$ | |
| J-2 | $-CH_3$ | Q-158 ($R_7 = H, R_8 = H, R_9 = H$) | H | H | $CH_3$ | $OCH_3$ | |
| J-3 | $-CH_3$ | Q-158 ($R_7 = H, R_8 = H, R_9 = CH_3$) | H | H | $CH_3$ | $OCH_3$ | |
| J-4 | $-CH_3$ | Q-158 ($R_7 = CH_3, R_8 = H, R_9 = H$) | H | 3-$CH_3$ | $OCH_3$ | $OCH_3$ | |

TABLE 1-continued

General Formula 1

| J | M | Q | R | $R_1$ | X | Y | m.p. (°C.) |
|---|---|---|---|---|---|---|---|
| J-1 | $—C_6H_5$ | Q-159 ($R_7$ = H, $R_8$ = H, $R_9$ = H) | H | H | $OCH_3$ | $OCH_3$ | |
| J-2 | $—CH_3$ | Q-159 ($R_7$ = $CH_3$, $R_8$ = H, $R_9$ = H) | H | H | Cl | $OCH_3$ | |
| J-3 | $—CH_3$ | Q-159 ($R_7$ = H, $R_8$ = H, $R_9$ = $CH_3$) | H | H | $CH_3$ | $OCH_3$ | |
| J-4 | $—CH_3$ | Q-160 ($R_7$ = H, $R_8$ = H, $R_9$ = H, $R_{11}$ = $CH_3$) | H | H | $CH_3$ | $OCH_3$ | |
| J-1 | $—CH_3$ | Q-160 ($R_7$ = H, $R_8$ = H, $R_9$ = $CH_3$, $R_{11}$ = H) | $CH_3$ | H | $CH_3$ | $OCH_3$ | |
| J-2 | $—CH_3$ | Q-160 ($R_7$ = $CH_3$, $R_8$ = H, $R_9$ = H, $R_{11}$ = i-$C_3H_7$) | H | H | $OCH_3$ | $OCH_3$ | |
| J-3 | $—CH_3$ | Q-161 ($R_7$ = H, $R_8$ = H, $R_9$ = H, $R_{11}$ = $CH_3$) | H | H | $OCH_3$ | $OCH_3$ | |
| J-4 | $—CH_3$ | Q-161 ($R_7$ = $CH_3$, $R_8$ = H, $R_9$ = H, $R_{11}$ = H) | H | H | $OCH_3$ | $OCH_3$ | |
| J-1 | $—CH_3$ | Q-161 ($R_7$ = H, $R_8$ = H, $R_9$ = $CH_3$, $R_{11}$ = $CH_3$) | H | 5-$OCH_3$ | $OCH_3$ | $OCH_3$ | |
| J-2 | $—CH_3$ | Q-162 ($R_7$ = H, $R_8$ = H, $R_9$ = H, $R_{10}$ = H) | H | H | $OCH_3$ | $OCH_3$ | |
| J-3 | $—CH_3$ | Q-162 ($R_7$ = $CH_3$, $R_8$ = H, $R_9$ = H, $R_{10}$ = H) | H | H | $OCH_3$ | $OCF_2H$ | |
| J-4 | $—CH_3$ | Q-162 ($R_7$ = H, $R_8$ = H, $R_9$ = H, $R_{10}$ = $CH_3$) | H | 3-Cl | $OCH_3$ | $OCH_3$ | |
| J-1 | $—CH_3$ | Q-163 ($R_7$ = H, $R_8$ = H, $R_9$ = H, $R_{10}$ = H) | H | $CH_3$ | $OCH_3$ | $OCH_3$ | |
| J-2 | $—CH_3$ | Q-163 ($R_7$ = H, $R_8$ = H, $R_9$ = H, $R_{10}$ = H) | H | $CH_3$ | $OCH_3$ | $OCH_3$ | |
| J-3 | $—CH_3$ | Q-163 ($R_7$ = H, $R_8$ = H, $R_9$ = H, $R_{10}$ = H) | H | $CH_3$ | $OCH_3$ | $OCH_3$ | |
| J-4 | $—CH_3$ | Q-163 ($R_7$ = H, $R_8$ = H, $R_9$ = H, $R_{10}$ = H) | H | $CH_3$ | $OCH_3$ | $OCH_3$ | |
| J-1 | $CH_3$ | Q-164 ($R_7$ = H) | H | $CH_3$ | $OCH_3$ | $OCH_3$ | |
| J-2 | $CH_3$ | Q-164 ($R_7$ = H) | H | $CH_3$ | $OCH_3$ | $OCH_3$ | |
| J-3 | $CH_3$ | Q-164 ($R_7$ = H) | H | $CH_3$ | $OCH_3$ | $OCH_3$ | |
| J-4 | $CH_3$ | Q-164 ($R_7$ = H) | H | $CH_3$ | $OCH_3$ | $OCH_3$ | |
| J-1 | $CH_3$ | Q-165 ($R_3$ = $CH_3$, $R_7$ = H) | H | $CH_3$ | $OCH_3$ | $OCH_3$ | |
| J-2 | $CH_3$ | Q-165 ($R_3$ = $CH_3$, $R_7$ = H) | H | $CH_3$ | $OCH_3$ | $OCH_3$ | |
| J-3 | $CH_3$ | Q-165 ($R_3$ = $CH_3$, $R_7$ = H) | H | $CH_3$ | $OCH_3$ | $OCH_3$ | |
| J-4 | $CH_3$ | Q-165 ($R_3$ = $CH_3$, $R_7$ = H) | H | $CH_3$ | $OCH_3$ | $OCH_3$ | |
| J-1 | $CH_3$ | Q-166 ($R_3$ = $CH_3$, $R_7$ = H) | H | $CH_3$ | $OCH_3$ | $OCH_3$ | |
| J-2 | $CH_3$ | Q-166 ($R_3$ = $CH_3$, $R_7$ = H) | H | $CH_3$ | $OCH_3$ | $OCH_3$ | |
| J-3 | $CH_3$ | Q-166 ($R_3$ = $CH_3$, $R_7$ = H) | H | $CH_3$ | $OCH_3$ | $OCH_3$ | |
| J-4 | $CH_3$ | Q-166 ($R_3$ = $CH_3$, $R_7$ = H) | H | $CH_3$ | $OCH_3$ | $OCH_3$ | |

TABLE 2

General Formula 2

| J | M | Q | R | $R_1$ | X | Y | m.p. (°C.) |
|---|---|---|---|---|---|---|---|
| J-1 | $CH_3$ | Q-1 ($R_7$ = H, $R_8$ = H) | H | H | $CH_3$ | $CH_3$ | |
| J-1 | $CH_2CH_3$ | Q-1 ($R_7$ = H, $R_8$ = H) | H | H | $OCH_3$ | $CH_3$ | |
| J-1 | $CH_2CH_2CH_3$ | Q-1 ($R_7$ = H, $R_8$ = H) | H | H | $OCH_3$ | $OCH_3$ | |
| J-1 | $CH(CH_3)_2$ | Q-1 ($R_7$ = H, $R_8$ = H) | $CH_3$ | H | $OCH_3$ | $OCH_3$ | |
| J-1 | $CH_2(CH_2)_2CH_3$ | Q-1 ($R_7$ = H, $R_8$ = H) | $CH_3$ | H | $OCH_3$ | $CH_3$ | |
| J-1 | $C(CH_3)_3$ | Q-1 ($R_7$ = H, $R_8$ = H) | H | 5-$CH_3$ | $OCH_3$ | $OCH_3$ | |
| J-1 | H | Q-1 ($R_7$ = H, $R_8$ = H) | H | 5-$CH_2CH_3$ | $OCH_3$ | $OCH_3$ | |
| J-1 | $CH_2CH{=}CH_2$ | Q-1 ($R_7$ = H, $R_8$ = H) | H | 5-$CH(CH_3)_2$ | $OCH_3$ | $OCH_3$ | |
| J-1 | $CH_2CH{=}CHCH_3$ | Q-1 ($R_7$ = H, $R_8$ = H) | H | 5-$OCH_3$ | $OCH_3$ | $OCH_3$ | |
| J-1 | $C_6H_5$ | Q-1 ($R_7$ = H, $R_8$ = H) | H | 5-$OCH_2CH_3$ | $OCH_3$ | $OCH_3$ | |
| J-1 | $C_6H_4$—4-Cl | Q-1 ($R_7$ = H, $R_8$ = H) | H | 5-$OCH(CH_3)_2$ | $OCH_3$ | $OCH_3$ | |
| J-1 | $C_6H_4$—3-$NO_2$ | Q-1 ($R_7$ = H, $R_8$ = H) | H | 5-$OCF_2H$ | $OCH_3$ | $OCH_3$ | |
| J-1 | $C_6H_4$—3-$CH_3$ | Q-1 ($R_7$ = H, $R_8$ = H) | H | 5-$OCH_2CH_2Br$ | $OCH_3$ | $OCH_3$ | |
| J-1 | $C_6H_4$—2-$OCH_3$ | Q-1 ($R_7$ = H, $R_8$ = H) | H | 5-$OCH(CH_3)(CH_2Cl)$ | $OCH_3$ | $OCH_3$ | |
| J-1 | $CO_2CH_3$ | Q-1 ($R_7$ = H, $R_8$ = H) | H | 5-$CH_2F$ | $OCH_3$ | $OCH_3$ | |
| J-1 | $CO_2CH_2CH_3$ | Q-1 ($R_7$ = H, $R_8$ = H) | H | 5-$CH_2CH_2Br$ | $OCH_3$ | $OCH_3$ | |
| J-1 | $SO_2CH_3$ | Q-1 ($R_7$ = H, $R_8$ = H) | H | 5-$CH(CH_3)(CH_2Cl)$ | $OCH_3$ | $OCH_3$ | |
| J-1 | $SO_2N(CH_3)_2$ | Q-1 ($R_7$ = H, $R_8$ = H) | H | 5-Cl | $OCH_3$ | $OCH_3$ | |
| J-1 | $CH_2C{\equiv}CH$ | Q-1 ($R_7$ = H, $R_8$ = H) | H | 5-$SCH_2CH_3$ | $OCH_3$ | $OCH_3$ | |
| J-1 | $CH(CH_3)_2$ | Q-1 ($R_7$ = H, $R_8$ = H) | H | 5-$SCH(CH_3)_2$ | $OCH_3$ | $OCH_3$ | |
| J-1 | $C(CH_3)_3$ | Q-1 ($R_7$ = H, $R_8$ = H) | H | 5-$SCH_2F$ | $OCH_3$ | $OCH_3$ | |
| J-1 | $C_6H_5$ | Q-1 ($R_7$ = H, $R_8$ = H) | H | 5-$SCH_2CH_2Br$ | $OCH_3$ | $OCH_3$ | |
| J-1 | $C_6H_4$—3-Cl | Q-1 ($R_7$ = H, $R_8$ = H) | H | 5-$SCH(CH_3)(CH_2Cl)$ | $OCH_3$ | $OCH_3$ | |
| J-1 | $CH_3$ | Q-1 ($R_7$ = H, $R_8$ = H) | H | 5-$SOCH_3$ | $OCH_3$ | $OCH_3$ | |
| J-1 | $CH_3$ | Q-1 ($R_7$ = H, $R_8$ = H) | H | 5-$SO_2CH_3$ | $OCH_3$ | $OCH_3$ | |
| J-1 | $CH_3$ | Q-1 ($R_7$ = H, $R_8$ = H) | H | 5-$SO_2N(CH_3)_2$ | $OCH_3$ | $OCH_3$ | |
| J-1 | $CH_3$ | Q-1 ($R_7$ = H, $R_8$ = H) | H | 5-$CO_2CH_3$ | $OCH_3$ | $OCH_3$ | |
| J-2 | $CH_3$ | Q-1 ($R_7$ = H, $R_8$ = H) | H | 5-$CO_2CH_2CH_3$ | $OCH_3$ | $OCH_3$ | |
| J-3 | $CH_3$ | Q-1 ($R_7$ = H, $R_8$ = H) | H | 3-$CO_2CH_3$ | $OCH_3$ | $OCH_3$ | |
| J-4 | $CH_3$ | Q-1 ($R_7$ = H, $R_8$ = H) | H | 3-$CO_2CH_3$ | $OCH_3$ | $OCH_3$ | |
| J-1 | $CH_3$ | Q-1 ($R_7$ = H, $R_8$ = H) | H | 5-Cl | $OCH_3$ | $OCH_3$ | |
| J-1 | $CH_3$ | Q-1 ($R_7$ = H, $R_8$ = H) | H | 5-Br | $OCH_3$ | $OCH_3$ | |
| J-2 | $CH_3$ | Q-1 ($R_7$ = H, $R_8$ = H) | H | 5-F | $OCH_3$ | $OCH_3$ | |
| J-3 | $CH_3$ | Q-1 ($R_7$ = H, $R_8$ = H) | H | 3-I | $OCH_3$ | $OCH_3$ | |
| J-4 | $CH_3$ | Q-1 ($R_7$ = H, $R_8$ = H) | H | 3-$CH_3$ | $OCH_3$ | $OCH_3$ | |
| J-1 | $CH_3$ | Q-1 ($R_7$ = H, $R_8$ = H) | H | 5-$CF_3$ | $OCH_3$ | $OCH_3$ | |
| J-2 | $CH_3$ | Q-1 ($R_7$ = H, $R_8$ = H) | H | 5-$OCF_2H$ | $OCH_3$ | $OCH_3$ | |
| J-3 | $CH_3$ | Q-1 ($R_7$ = H, $R_8$ = H) | H | H | $OCH_3$ | $CH_2CH_3$ | |
| J-4 | $CH_3$ | Q-1 ($R_7$ = H, $R_8$ = H) | H | H | $OCH_3$ | $CH(CH_3)_2$ | |
| J-1* | $CH_3$ | Q-1 ($R_7$ = H, $R_8$ = H) | H | H | $OCH_3$ | $OCH_3$ | |
| J-2 | $CH_3$ | Q-1 ($R_7$ = H, $R_8$ = H) | H | H | $OCH_3$ | $OCH_2CH_3$ | |
| J-3 | $CH_3$ | Q-1 ($R_7$ = H, $R_8$ = H) | H | H | $OCH_3$ | $OCH(CH_3)_2$ | |
| J-4* | $CH_3$ | Q-1 ($R_7$ = H, $R_8$ = H) | H | H | $OCH_3$ | $OCH_3$ | |
| J-1 | $CH_3$ | Q-1 ($R_7$ = H, $R_8$ = H) | H | H | $OCH_2CH_2F$ | $OCH_3$ | |
| J-2 | $CH_3$ | Q-1 ($R_7$ = H, $R_8$ = H) | H | H | $OCH_2CHF_2$ | $OCH_3$ | |
| J-3 | $CH_3$ | Q-1 ($R_7$ = H, $R_8$ = H) | H | H | $OCH_2CF_3$ | $OCH_3$ | |
| J-4 | $CH_3$ | Q-1 ($R_7$ = H, $R_8$ = H) | H | H | $OCH(CH_3)(CH_2Cl)$ | $OCH_3$ | |
| J-1 | $CH_3$ | Q-1 ($R_7$ = H, $R_8$ = H) | H | H | $O(CH_2)_3CH_2Br$ | $OCH_3$ | |
| J-2 | $CH_3$ | Q-1 ($R_7$ = H, $R_8$ = H) | H | H | $CH_2F$ | $OCH_3$ | |
| J-3 | $CH_3$ | Q-1 ($R_7$ = H, $R_8$ = H) | H | H | $CH_2Cl$ | $OCH_3$ | |

TABLE 2-continued

General Formula 2

| J | M | Q | R | $R_1$ | X | Y | m.p. (°C.) |
|---|---|---|---|---|---|---|---|
| J-4 | $CH_3$ | Q-1 ($R_7$ = H, $R_8$ = H) | H | H | $CH_2Br$ | $OCH_3$ | |
| J-1 | $CH_3$ | Q-1 ($R_7$ = H, $R_8$ = H) | H | H | $CF_3$ | $OCH_3$ | |
| J-2* | $CH_3$ | Q-1 ($R_7$ = H, $R_8$ = H) | H | H | $OCH_3$ | $OCH_3$ | |
| J-3 | $CH_3$ | Q-1 ($R_7$ = H, $R_8$ = H) | H | H | $CH(CH_3)(CH_2Cl)$ | $OCH_3$ | |
| J-4 | $CH_3$ | Q-1 ($R_7$ = H, $R_8$ = H) | H | H | $(CH_2)_3CH_2I$ | $OCH_3$ | |
| J-1 | $CH_3$ | Q-1 ($R_7$ = H, $R_8$ = H) | H | H | $SCH_3$ | $OCH_3$ | |
| J-2 | $CH_3$ | Q-1 ($R_7$ = H, $R_8$ = H) | H | H | $SCH_2CH_3$ | $OCH_3$ | |
| J-3 | $CH_3$ | Q-1 ($R_7$ = H, $R_8$ = H) | H | H | $SCH(CH_3)_2$ | $OCH_3$ | |
| J-4 | $CH_3$ | Q-1 ($R_7$ = H, $R_8$ = H) | H | H | $S(CH_2)_3CH_3$ | $OCH_3$ | |
| J-1 | $CH_3$ | Q-1 ($R_7$ = H, $R_8$ = H) | H | H | $SCHF_2$ | $OCH_3$ | |
| J-2 | $CH_3$ | Q-1 ($R_7$ = H, $R_8$ = H) | H | H | $SCH_2CH_2Br$ | $OCH_3$ | |
| J-3* | $CH_3$ | Q-1 ($R_7$ = H, $R_8$ = H) | H | H | $OCH_3$ | $OCH_3$ | |
| J-1 | $CH_3$ | Q-1 ($R_7$ = H, $R_8$ = H) | H | H | $S(CH_2)_3CH_2F$ | $OCH_3$ | |
| J-2 | $CH_3$ | Q-1 ($R_7$ = H, $R_8$ = H) | H | H | $OCH_3$ | $CH_2OCH_3$ | |
| J-3 | $CH_3$ | Q-1 ($R_7$ = H, $R_8$ = H) | H | H | $OCH_3$ | $CH_2CH_2OCH(CH_3)_2$ | |
| J-4 | $CH_3$ | Q-1 ($R_7$ = H, $R_8$ = H) | H | H | $OCH_3$ | $CH(CH_3)(CH_2OCH_3)$ | |
| J-1 | $CH_3$ | Q-1 ($R_7$ = H, $R_8$ = H) | H | H | $OCH_3$ | $CH_2OCH_2CH_3$ | |
| J-2 | $CH_3$ | Q-1 ($R_7$ = H, $R_8$ = H) | H | H | $OCH_2O(CH_2)_3CH_3$ | $OCH_3$ | |
| J-3 | $CH_3$ | Q-1 ($R_7$ = H, $R_8$ = H) | H | H | $OCH_2CH_2OCH(CH_3)_2$ | $OCH_3$ | |
| J-4 | $CH_3$ | Q-1 ($R_7$ = H, $R_8$ = H) | H | H | $OCH(CH_3)(CH_2OCH_3)$ | $OCH_3$ | |
| J-2 | $CH_3$ | Q-1 ($R_7$ = H, $R_8$ = H) | H | H | $OCH_3$ | $NH_2$ | |
| J-3 | $CH_3$ | Q-1 ($R_7$ = H, $R_8$ = H) | H | H | $OCH_3$ | $NHCH_3$ | |
| J-4 | $CH_3$ | Q-1 ($R_7$ = H, $R_8$ = H) | H | H | $OCH_3$ | $NHCH_2CH_3$ | |
| J-1 | $CH_3$ | Q-1 ($R_7$ = H, $R_8$ = H) | H | H | $OCH_3$ | $NHCH(CH_3)_2$ | |
| J-2 | $CH_3$ | Q-1 ($R_7$ = H, $R_8$ = H) | H | H | $OCH_3$ | $N(CH_3)_2$ | |
| J-3 | $CH_3$ | Q-1 ($R_7$ = H, $R_8$ = H) | H | H | $OCH_3$ | $N(CH_3)(CH_2CH_3)$ | |
| J-4 | $CH_3$ | Q-1 ($R_7$ = H, $R_8$ = H) | H | H | $OCH_3$ | $N(CH_3)(CH(CH_3)_2)$ | |
| J-1 | $CH_3$ | Q-1 ($R_7$ = H, $R_8$ = H) | H | H | $OCH_3$ | $SCH_3$ | |
| J-2 | $CH_3$ | Q-1 ($R_7$ = H, $R_8$ = H) | H | H | H | $OCH_3$ | |
| J-3 | $CH_3$ | Q-1 ($R_7$ = H, $R_8$ = H) | H | H | $OCH_3$ | $OCH_2CH{=}CH_2$ | |
| J-4 | $CH_3$ | Q-1 ($R_7$ = H, $R_8$ = H) | H | H | $OCH_3$ | $OCH_2C(CH_3){=}CH_2$ | |
| J-1 | $CH_3$ | Q-1 ($R_7$ = H, $R_8$ = H) | H | H | $OCH_3$ | $OCH_2C{\equiv}CH$ | |
| J-2 | $CH_3$ | Q-1 ($R_7$ = H, $R_8$ = H) | H | H | $OCH_3$ | $OCH_2C{\equiv}CCH_3$ | |
| J-3 | $CH_3$ | Q-1 ($R_7$ = H, $R_8$ = H) | H | H | $OCH_3$ | $CH_2S(CH_2)_3CH_3$ | |
| J-4 | $CH_3$ | Q-1 ($R_7$ = H, $R_8$ = H) | H | H | $OCH_3$ | $CH_2CH_2SCH(CH_3)_2$ | |
| J-1 | $CH_3$ | Q-1 ($R_7$ = H, $R_8$ = H) | H | H | $OCH_3$ | $CH(CH_3)(CH_2SCH_3)$ | |
| J-2 | $CH_3$ | Q-1 ($R_7$ = H, $R_8$ = H) | H | H | $OCH_3$ | $CH_2SCH_3$ | |
| J-3 | $CH_3$ | Q-1 ($R_7$ = H, $R_8$ = H) | H | H | $OCH_3$ | cyclopropyl | |
| J-4 | $CH_3$ | Q-1 ($R_7$ = H, $R_8$ = H) | H | H | $OCH_3$ | 2-methylcyclopropyl | |
| J-1 | $CH_3$ | Q-1 ($R_7$ = H, $R_8$ = H) | H | H | $OCH_3$ | cyclopentyl | |
| J-2 | $CH_3$ | Q-1 ($R_7$ = H, $R_8$ = H) | H | H | $OCH_3$ | $C{\equiv}CH$ | |
| J-3 | $CH_3$ | Q-1 ($R_7$ = H, $R_8$ = H) | H | H | $OCH_3$ | $C{\equiv}CCH_3$ | |
| J-4 | $CH_3$ | Q-1 ($R_7$ = H, $R_8$ = H) | H | H | $OCH_3$ | $-CHO$ | |
| J-1 | $CH_3$ | Q-1 ($R_7$ = H, $R_8$ = H) | H | H | $OCH_3$ | $-COCH_3$ | |
| J-2 | $CH_3$ | Q-1 ($R_7$ = H, $R_8$ = H) | H | H | $OCH_3$ | $-CH(OCH_3)_2$ | |
| J-3 | $CH_3$ | Q-1 ($R_7$ = H, $R_8$ = H) | H | H | $OCH_3$ | $-CH(SCH_3)(OCH_2CH_3)$ | |
| J-4 | $CH_3$ | Q-1 ($R_7$ = H, $R_8$ = H) | H | H | $OCH_3$ | $-C(CH_3)(SCH_3)_2$ | |
| J-1 | $CH_3$ | Q-1 ($R_7$ = H, $R_8$ = H) | H | H | $OCH_3$ | $-CH(SCH_2CH_3)_2$ | |
| J-2 | $CH_3$ | Q-1 ($R_7$ = H, $R_8$ = H) | H | H | $OCH_3$ | 1,3-dioxolan-2-yl | |
| J-3 | $CH_3$ | Q-1 ($R_7$ = H, $R_8$ = H) | H | H | $OCH_3$ | 2-methyl-1,3-oxa- | |

TABLE 2-continued

General Formula 2

| J | M | Q | R | $R_1$ | X | Y | m.p. (°C.) |
|---|---|---|---|---|---|---|---|
| | | | | | | thiolan-2-yl | |
| J-4 | $CH_3$ | Q-1 ($R_7$ = H, $R_8$ = H) | H | H | $OCH_3$ | 1,3-oxathian-2-yl | |
| J-1 | $CH_3$ | Q-1 ($R_7$ = H, $R_8$ = H) | H | H | $OCH_3$ | 2-methyl-1,3-dithian-2-yl | |
| J-2 | $CH_3$ | Q-1 ($R_7$ = H, $R_8$ = H) | H | H | $OCH_3$ | 4-methyl-1,3-dioxolan-2-yl | |
| J-3 | $CH_3$ | Q-1 ($R_7$ = H, $R_8$ = H) | H | H | $OCH_3$ | 4-methyl-1,3-oxathiolan-2-yl | |
| J-4 | $CH_3$ | Q-1 ($R_7$ = H, $R_8$ = H) | H | H | $OCH_3$ | 2,4-dimethyl-1,3-dithiolan-2-yl | |
| J-1 | $CH_3$ | Q-1 ($R_7$ = H, $R_8$ = H) | H | H | $OCH_3$ | $N(OCH_3)(CH_3)_2$ | |
| J-2 | $CH_3$ | Q-1 ($R_7$ = H, $R_8$ = H) | H | 5-$SO_2N(CH_3)_2$ | $OCH_3$ | $OCH_3$ | |
| J-3 | $CH_3$ | Q-1 ($R_7$ = H, $R_8$ = H) | H | 3-$SO_2CH_3$ | $OCH_3$ | $OCH_3$ | |
| J-4 | $CH_3$ | Q-1 ($R_7$ = H, $R_8$ = H) | H | 3-$SO_2CH(CH_3)_2$ | $OCH_3$ | $OCH_3$ | |
| J-1 | $CH_3$ | Q-1 ($R_7$ = H, $R_8$ = H) | H | 5-$CO_2CH_3$ | $OCH_3$ | $OCH_3$ | |
| J-2 | $CH_3$ | Q-1 ($R_7$ = H, $R_8$ = $CH_3$) | H | H | $OCH_3$ | $OCH_3$ | |
| J-3 | $CH_3$ | Q-1 ($R_7$ = H, $R_8$ = $CH_3$) | H | H | $CH_3$ | $CH_3$ | |
| J-4 | $CH_3$ | Q-1 ($R_7$ = H, $R_8$ = $CH_3$) | H | H | $CH_3$ | $OCH_3$ | |
| J-1 | $CH_3$ | Q-1 ($R_7$ = H, $R_8$ = $CH_2CH_3$) | H | H | $OCH_3$ | $OCH_3$ | |
| J-2 | $CH_3$ | Q-1 ($R_7$ = H, $R_8$ = $CH(CH_3)_2$) | H | H | $OCH_3$ | $OCH_3$ | |
| J-3 | $CH_3$ | Q-1 ($R_7$ = H, $R_8$ = $(CH_2)_3CH_3$) | H | H | $OCH_3$ | $OCH_3$ | |
| J-4 | $CH_3$ | Q-1 ($R_7$ = $CH_3$, $R_8$ = $CH_3$) | H | H | $OCH_3$ | $OCH_3$ | |
| J-1 | $CH_3$ | Q-2 ($R_7$ = H, $R_8$ = H) | H | H | $OCH_3$ | $OCH_3$ | |
| J-2 | $CH_3$ | Q-2 ($R_7$ = H, $R_8$ = H) | $CH_3$ | H | $OCH_3$ | $OCH_3$ | |
| J-3 | $CH_3$ | Q-2 ($R_7$ = H, $R_8$ = $CH_3$) | H | 3-$OCH_3$ | $OCH_3$ | $OCH_3$ | |
| J-4 | $CH_3$ | Q-3 ($R_7$ = H, $R_8$ = H) | H | H | $OCH_3$ | $OCH_3$ | |
| J-1 | $CH_3$ | Q-3 ($R_7$ = $CH_3$, $R_8$ = H) | H | 5-Cl | $OCH_3$ | $CH_3$ | |
| J-2 | $CH_3$ | Q-4 ($R_7$ = H, $R_8$ = H, $R_3$ = $CH_3$) | H | H | $CH_3$ | $OCH_3$ | |
| J-3 | $CH_3$ | Q-4 ($R_7$ = H, $R_8$ = H, $R_3$ = $C_2H_5$) | H | H | $CH_3$ | $OCH_3$ | |
| J-4 | $CH_3$ | Q-4 ($R_7$ = H, $R_8$ = H, $R_3$ = i-$C_3H_7$) | H | 3-$CH_3$ | $OCH_3$ | $OCH_3$ | |
| J-1 | $CH_3$ | Q-5 ($R_7$—H, $R_8$ = H, $R_3$ = H) | H | H | $OCH_3$ | $OCH_3$ | |
| J-2 | $CH_3$ | Q-5 ($R_7$ = H, $R_8$ = H, $R_3$ = $CH_3$) | H | H | $CH_3$ | $OCH_3$ | |
| J-3 | $CH_3$ | Q-5 ($R_7$ = H, $R_8$ = $CH_3$, $R_3$ = $CH_3$) | H | H | $CH_3$ | $OCH_3$ | |
| J-4 | $CH_3$ | Q-6 ($R_7$ = $CH_3$, $R_8$ = H, $R_3$ = $CH_3$) | H | H | $CH_3$ | $OCH_3$ | |
| J-1 | $CH_3$ | Q-6 ($R_7$—H, $R_8$ = H, $R_3$ = $C_2H_5$) | $CH_3$ | H | $CH_3$ | $OCH_3$ | |
| J-2 | $CH_3$ | Q-6 ($R_7$ = $C_2H_5$, $R_8$ = H, $R_3$ = H) | H | H | $OCH_3$ | $OCH_3$ | |
| J-3 | $CH_3$ | Q-7 ($R_7$ = H, $R_8$ = H, $R_9$ = H) | H | H | $OCH_3$ | $OCH_3$ | |
| J-4 | $CH_3$ | Q-7 ($R_7$ = H, $R_8$ = $C_2H_5$, $R_9$ = H) | H | H | $OCH_3$ | $OCH_3$ | |
| J-1 | $CH_3$ | Q-7 ($R_7$ = i-$C_3H_7$, $R_8$ = H, $R_9$ = $CH_3$) | H | 5-$OCH_3$ | $OCH_3$ | $OCH_3$ | |
| J-2 | $CH_3$ | Q-8 ($R_7$ = H, $R_8$ = H, $R_2$ = H) | H | H | $OCH_3$ | $OCH_3$ | |
| J-3 | $CH_3$ | Q-8 ($R_7$ = H, $R_8$ = H, $R_2$ = $OCH(CH_3)CH_2CH_3$) | H | 3-Cl | $OCH_3$ | $OCH_3$ | |
| J-4 | $CH_3$ | Q-9 ($R_7$ = H, $R_8$ = H, $R_2$ = H) | H | H | $OCH_3$ | $OCH_3$ | |
| J-1 | $CH_3$ | Q-9 ($R_7$ = $CH_3$, $R_8$ = H, $R_2$ = $CH_3$) | $CH_3$ | H | $OCH_3$ | $OCH_3$ | |
| J-2 | $CH_3$ | Q-9 ($R_7$ = H, $R_8$ = H, $R_2$ = Cl) | H | 5-$OCH_3$ | $OCH_3$ | $OCH_3$ | |
| J-3 | $CH_3$ | Q-10 ($R_7$ = H, $R_8$ = H) | H | H | $OCH_3$ | $OCH_3$ | |
| J-4 | $CH_3$ | Q-10 ($R_7$ = H, $R_8$ = $CH_3$) | H | 3-Cl | $OCH_3$ | $CH_3$ | |
| J-1 | $CH_3$ | Q-11 ($R_7$ = H, $R_8$ = H) | H | H | $CH_3$ | $OCH_3$ | |
| J-2 | $CH_3$ | Q-11 ($R_7$ = n-$C_4H_9$, $R_8$ = H) | H | H | $CH_3$ | $OCH_3$ | |
| J-3 | $CH_3$ | Q-11 ($R_7$ = $CH_3$, $R_8$ = $CH_3$) | H | 3-$CH_3$ | $OCH_3$ | $OCH_3$ | |
| J-4 | $CH_3$ | Q-12 ($R_7$ = H, $R_8$ = H) | H | H | $OCH_3$ | $OCH_3$ | |

TABLE 2-continued

General Formula 2

| J | M | Q | R | $R_1$ | X | Y | m.p. (°C.) |
|---|---|---|---|---|---|---|---|
| J-1 | $CH_3$ | Q-12 ($R_7 = CH_3$, $R_8 = H$) | H | H | $CH_3$ | $OCH_3$ | |
| J-2 | $CH_3$ | Q-12 ($R_7 = H$, $R_8 = C_2H_5$) | H | H | $CH_3$ | $OCH_3$ | |
| J-3 | $CH_3$ | Q-13 ($R_7 = H$, $R_8 = H$, $R_3 = H$) | H | H | $CH_3$ | $OCH_3$ | |
| J-4 | $CH_3$ | Q-13 ($R_7 = H$, $R_8 = H$, $R_3 = CH_3$) | $CH_3$ | H | $CH_3$ | $OCH_3$ | |
| J-1 | $CH_3$ | Q-13 ($R_7 = CH_3$, $R_8 = H$, $R_3 = CH_3$) | H | H | $OCH_3$ | $OCH_3$ | |
| J-1 | $CH_3$ | Q-14 ($R_7 = H$, $R_8 = H$, $R_3 = CH_3$) | H | H | $OCH_3$ | $OCH_3$ | |
| J-2 | $CH_3$ | Q-14 ($R_7 = CH_3$, $R_8 = H$, $R_3 = C_2H_5$) | H | H | $OCH_3$ | $OCH_3$ | |
| J-3 | $CH_3$ | Q-14 ($R_7 = H$, $R_8 = CH_3$, $R_3 = CH_3$) | H | 3-$OCH_3$ | $OCH_3$ | $OCH_3$ | |
| J-4 | $CH_3$ | Q-15 ($R_7 = H$, $R_8 = H$, $R_3 = H$) | H | H | $OCH_3$ | $OCH_3$ | |
| J-1 | $CH_3$ | Q-15 ($R_7 = CH_3$, $R_8 = CH_3$, $R_3 = CH_3$) | H | 5-Cl | $OCH_3$ | $OCH_3$ | |
| J-2 | $CH_3$ | Q-16 ($R_7 = H$, $R_8 = H$, $R_9 = H$) | H | H | $OCH_3$ | $OCH_3$ | |
| J-3 | $CH_3$ | Q-16 ($R_7 = CH_3$, $R_8 = H$, $R_9 = H$) | $CH_3$ | H | $OCH_3$ | $OCH_3$ | |
| J-4 | $CH_3$ | Q-16 ($R_7 = CH_3$, $R_8 = CH_3$, $R_9 = H$) | H | 3-$OCH_3$ | $OCH_3$ | $OCH_3$ | |
| J-1 | $CH_3$ | Q-17 ($R_7 = H$, $R_8 = H$, $R_2 = H$) | H | H | $OCH_3$ | $OCH_3$ | |
| J-2 | $CH_3$ | Q-17 ($R_7 = H$, $R_8 = H$, $R_2 = C_2H_5$) | H | 5-Cl | $OCH_3$ | $CH_3$ | |
| J-3 | $CH_3$ | Q-18 ($R_7 = H$, $R_8 = H$, $R_2 = H$) | H | H | $CH_3$ | $OCH_3$ | |
| J-4 | $CH_3$ | Q-18 ($R_7 = H$, $R_8 = OC_2H_5$, $R_2 = H$) | H | H | $CH_3$ | $OCH_3$ | |
| J-1 | $CH_3$ | Q-18 ($R_7 = CH_3$, $R_8 = OCH(CH_3)_2$, $R_2 = CH_3$) | H | 5-$CH_3$ | $OCH_3$ | $OCH_3$ | |
| J-2 | $CH_3$ | Q-19 ($R_7 = H$, $R_8 = H$) | H | H | $OCH_3$ | $OCH_3$ | |
| J-3 | $CH_3$ | Q-19 ($R_7 = CH_3$, $R_8 = H$) | H | H | $CH_3$ | $OCH_3$ | |
| J-4 | $CH_3$ | Q-19 ($R_7 = CH_3$, $R_8 = CH_3$) | H | H | $CH_3$ | $OCH_3$ | |
| J-1 | $CH_3$ | Q-20 ($R_7 = H$, $R_8 = H$) | H | H | $CH_3$ | $OCH_3$ | |
| J-2 | $CH_3$ | Q-20 ($R_7 = CH_3$, $R_8 = H$) | $CH_3$ | H | $CH_3$ | $OCH_3$ | |
| J-3 | $CH_3$ | Q-20 ($R_7 = H$, $R_8 = CH_3$) | H | H | $OCH_3$ | $OCH_3$ | |
| J-4 | $CH_3$ | Q-21 ($R_7 = H$, $R_8 = H$) | H | H | $OCH_3$ | $OCH_3$ | |
| J-1 | $CH_3$ | Q-21 ($R_7 = CH_3$, $R_8 = H$) | H | H | $OCH_3$ | $OCH_3$ | |
| J-2 | $CH_3$ | Q-21 ($R_7 = CH_3$, $R_8 = CH_3$) | H | 5-$OCH_3$ | $OCH_3$ | $OCH_3$ | |
| J-3 | $CH_3$ | Q-22 ($R_7 = H$, $R_8 = H$, $R_3 = H$) | H | H | $OCH_3$ | $OCH_3$ | |
| J-4 | $CH_3$ | Q-22 ($R_7 = CH_3$, $R_8 = CH_3$, $R_3 = C_2H_5$) | H | 3-Cl | $OCH_3$ | $OCH_3$ | |
| J-1 | $CH_3$ | Q-23 ($R_7 = H$, $R_8 = H$, $R_3 = H$) | H | H | $OCH_3$ | $OCH_3$ | |
| J-2 | $CH_3$ | Q-23 ($R_7 = H$, $R_8 = H$, $R_3 = CH_3$) | $CH_3$ | H | $OCH_3$ | $OCH_3$ | |
| J-3 | $CH_3$ | Q-23 ($R_7 = CH$, $R_8 = H$, $R_3 = \underline{n}\text{-}C_4H_9$) | H | 3-$OCH_3$ | $OCH_3$ | $OCH_3$ | |
| J-4 | $CH_3$ | Q-24 ($R_7 = H$, $R_8 = H$, $R_3 = CH_3$) | H | H | $OCH_3$ | $OCH_3$ | |
| J-1 | $CH_3$ | Q-24 ($R_7 = CH_3$, $R_8 = CH_3$, $R_3 = \underline{i}\text{-}C_3H_7$) | H | 5-Cl | $OCH_3$ | $CH_3$ | |
| J-2 | $CH_3$ | Q-25 ($R_7 = H$, $R_8 = H$, $R_9 = H$) | H | H | $CH_3$ | $OCH_3$ | |
| J-3 | $CH_3$ | Q-25 ($R_7 = CH_3$, $R_8 = H$, $R_9 = H$) | H | H | $CH_3$ | $OCH_3$ | |
| J-4 | $CH_3$ | Q-25 ($R_7 = H$, $R_8 = H$, $R_9 = C_2H_5$) | H | 3-$CH_3$ | $OCH_3$ | $OCH_3$ | |
| J-1 | $CH_3$ | Q-26 ($R_7 = H$, $R_8 = H$) | H | H | $OCH_3$ | $OCH_3$ | |
| J-2 | $CH_3$ | Q-26 ($R_7 = CH_3$, $R_8 = H$) | H | H | $CH_3$ | $OCH_3$ | |
| J-3 | $CH_3$ | Q-26 ($R_7 = CH_3$, $R_8 = CH_3$) | H | H | $CH_3$ | $OCH_3$ | |
| J-4 | $CH_3$ | Q-27 ($R_7 = H$, $R_8 = H$) | H | H | $CH_3$ | $OCH_3$ | |
| J-1 | $CH_3$ | Q-27 ($R_7 = CH_3$, $R_8 = H$) | $CH_3$ | H | $CH_3$ | $OCH_3$ | |
| J-2 | $CH_3$ | Q-27 ($R_7 = H$, $R_8 = CH_3$) | H | H | $OCH_3$ | $OCH_3$ | |
| J-3 | $CH_3$ | Q-28 ($R_7 = H$, $R_8 = H$) | H | H | $OCH_3$ | $OCH_3$ | |
| J-4 | $CH_3$ | Q-28 ($R_7 = CH_3$, $R_8 = H$) | H | H | $OCH_3$ | $OCH_3$ | |
| J-1 | $CH_3$ | Q-28 ($R_7 = CH_3$, $R_8 = CH_3$) | H | 5-$OCH_3$ | $OCH_3$ | $OCH_3$ | |
| J-2 | $CH_3$ | Q-29 ($R_7 = H$, $R_8 = H$) | H | H | $OCH_3$ | $OCH_3$ | |
| J-3 | $CH_3$ | Q-29 ($R_7 = H$, $R_8 = CH_3$) | H | 3-Cl | $OCH_3$ | $OCH_3$ | |
| J-4 | $CH_3$ | Q-30 ($R_7 = H$, $R_8 = H$) | H | H | $OCH_3$ | $OCH_3$ | |
| J-1 | $CH_3$ | Q-30 ($R_7 = CH_3$, $R_8 = CH_3$) | $CH_3$ | H | $OCH_3$ | $CH_3$ | |

TABLE 2-continued

| | | General Formula 2 | | | | | |
|---|---|---|---|---|---|---|---|
| J | M | Q | R | $R_1$ | X | Y | m.p. (°C.) |
| J-2 | $CH_3$ | Q-30 ($R_7 = C_2H_5, R_8 = H$) | H | 5-$OCH_3$ | $OCH_3$ | $OCH_3$ | |
| J-3 | $CH_3$ | Q-31 ($R_7 = H, R_8 = H$) | H | H | $OCH_3$ | $OCH_3$ | |
| J-4 | $CH_3$ | Q-31 ($R_7 = H, R_8 =$ n-$C_4H_9$) | H | 3-Cl | $OCH_3$ | $CH_3$ | |
| J-1 | $CH_3$ | Q-32 ($R_7 = H, R_8 = H, R_3 = H$) | H | H | $CH_3$ | $OCH_3$ | |
| J-2 | $CH_3$ | Q-32 ($R_7 = CH_3, R_8 = H, R_3 = CH_3$) | H | H | $CH_3$ | $OCH_3$ | |
| J-3 | $CH_3$ | Q-32 ($R_7 = H, R_8 = CH_3, R_3 = C_2H_5$) | H | 3-$CH_3$ | $OCH_3$ | $OCH_3$ | |
| J-4 | $CH_3$ | Q-33 ($R_7 = H, R_8 = H, R_8 = CH_3$) | H | H | $OCH_3$ | $OCH_3$ | |
| J-1 | $CH_3$ | Q-33 ($R_7 = CH_3, R_8 = CH_3, R_3 =$ i-$C_3H_7$) | H | H | $CH_3$ | $OCH_3$ | |
| J-2 | $CH_3$ | Q-33 ($R_7 = C_2H_5, R_8 = H, R_3 =$ n-$C_4H_9$) | H | H | $CH_3$ | $OCH_3$ | |
| J-3 | $CH_3$ | Q-34 ($R_7 = H, R_8 = H, R_3 = H$) | H | H | $CH_3$ | $OCH_3$ | |
| J-4 | $CH_3$ | Q-34 ($R_7 =$ i-$C_3H_7$, $R_8 = H, R_3 = CH_3$) | $CH_3$ | H | $CH_3$ | $OCH_3$ | |
| J-1 | $CH_3$ | Q-34 ($R_7 = H, R_8 =$ n-$C_4H_9$, $R_3 = CH_3$) | H | H | $OCH_3$ | $OCH_3$ | |
| J-2 | $CH_3$ | Q-35 ($R_7 = H, R_8 = H, R_9 = H$) | H | H | $OCH_3$ | $OCH_3$ | |
| J-1 | $CH_3$ | Q-35 ($R_7 = CH_3, R_8 = H, R_9 = H$) | H | H | $OCH_3$ | $OCH_3$ | |
| J-2 | $CH_3$ | Q-35 ($R_7 = CH_3, R_8 = CH_3, R_9 = CH_3$) | H | 5-$OCH_3$ | $OCH_3$ | $OCH_3$ | |
| J-3 | $CH_3$ | Q-36 ($R_7 = H, R_8 = H, R_2 = H$) | H | H | $OCH_3$ | $OCH_3$ | |
| J-4 | $CH_3$ | Q-36 ($R_7 = H, R_8 = H, R_2 = C_2H_5$) | H | 3-Cl | $OCH_3$ | $OCH_3$ | |
| J-1 | $CH_3$ | Q-37 ($R_7 = H, R_8 = H, R_2 = H$) | H | H | $OCH_3$ | $OCH_3$ | |
| J-2 | $CH_3$ | Q-37 ($R_7 = H, R_8 = H, R_2 =$ i-$C_3H_7$) | $CH_3$ | H | $OCH_3$ | $OCH_3$ | |
| J-3 | $CH_3$ | Q-37 ($R_7 = H, R_8 = H, R_2 =$ n-$C_4H_9$) | H | 3-$OCH_3$ | $OCH_3$ | $OCH_3$ | |
| J-4 | $CH_3$ | Q-38 ($R_7 = H, R_8 = H, R_2 = OCF_2H$) | H | H | $OCH_3$ | $OCH_3$ | |
| J-1 | $CH_3$ | Q-38 ($R_7 = H, R_8 = H, R_2 = Cl$) | H | 5-Cl | $OCH_3$ | $CH_3$ | |
| J-2 | $CH_2CH_2$ | Q-39 ($R_7 = H, R_8 = H, R_9 = H$) | H | H | $CH_3$ | $OCH_3$ | |
| J-3 | $CH_3$ | Q-39 ($R_7 = C_2H_5, R_8 = H, R_9 = H$) | H | H | $CH_3$ | $OCH_3$ | |
| J-4 | $CH_3$ | Q-39 ($R_7 = H, R_8 = H, R_9 = CH_3$) | H | 3-$CH_3$ | $OCH_3$ | $OCH_3$ | |
| J-1 | $CH_3$ | Q-40 ($R_7 = H, R_8 = H$) | H | H | $OCH_3$ | $OCH_3$ | |
| J-2 | $CH_3$ | Q-40 ($R_7 = CH_3, R_8 = H$) | H | H | $CH_3$ | $OCH_3$ | |
| J-3 | $CH_3$ | Q-40 ($R_7 = H, R_8 = CH_3$) | H | H | $CH_3$ | $OCH_3$ | |
| J-4 | $CH_3$ | Q-41 ($R_7 = H, R_8 = H$) | H | H | $CH_3$ | $OCH_3$ | |
| J-1 | $CH_3$ | Q-41 ($R_7 = CH_3, R_8 = CH_3$) | $CH_3$ | H | $CH_3$ | $OCH_3$ | |
| J-2 | $CH_3$ | Q-41 ($R_7 = H, R_8 = C_2H_5$) | H | H | $OCH_3$ | $OCH_3$ | |
| J-3 | $CH_2CH_2CH_3$ | Q-42 ($R_7 = H, R_8 = H$) | H | H | $OCH_3$ | $OCH_3$ | |
| J-4 | $CH_3$ | Q-42 ($R_7 = CH_3, R_8 = CH_3$) | H | H | $OCH_3$ | $OCH_3$ | |
| J-1 | $CH_3$ | Q-42 ($R_7 = C_2H_5, R_8 = C_2H_5$) | H | 5-$OCH_3$ | $OCH_3$ | $OCH_3$ | |
| J-2 | $CH_3$ | Q-43 ($R_7 = H, R_8 = H, R_3 = H$) | H | H | $OCH_3$ | $OCH_3$ | |
| J-3 | $CH_3$ | Q-43 ($R_7 = CH_3, R_8 = H, R_3 = CH_3$) | H | 3-Cl | $OCH_3$ | $OCH_3$ | |
| J-4 | $CH_3$ | Q-44 ($R_7 = H, R_8 = H, R_3 = CH_3$) | H | H | $OCH_3$ | $OCH_3$ | |
| J-1 | $CH_3$ | Q-44 ($R_7 = CH_3, R_8 = H, R_3 = C_2H_5$) | $CH_3$ | H | $OCH_3$ | $CH_3$ | |
| J-2 | $CH_3$ | Q-44 ($R_7 = H, R_8 = CH_3, R_3 = CH_3$) | H | 5-$OCH_3$ | $OCH_3$ | $OCH_3$ | |
| J-3 | $CH_3$ | Q-45 ($R_7 = H, R_8 = H, R_3 = H$) | H | H | $OCH_3$ | $OCH_3$ | |
| J-4 | $CH_3$ | Q-45 ($R_7 = CH_3, R_8 = CH_3, R_3 = CH_3$) | H | 3-Cl | $OCH_3$ | $CH_3$ | |
| J-1 | $CH_3$ | Q-46 ($R_7 = H, R_8 = H, R_9 = H$) | H | H | $CH_3$ | $OCH_3$ | |
| J-2 | $CH_3$ | Q-46 ($R_7 = CH_3, R_8 = H, R_9 = H$) | H | H | $CH_3$ | $OCH_3$ | |
| J-3 | $CH_3$ | Q-46 ($R_7 = CH_3, R_8 = CH_3, R_9 = H$) | H | 3-$CH_3$ | $OCH_3$ | $OCH_3$ | |
| J-4 | $CH_3$ | Q-47 ($R_7 = H, R_8 = H, R_2 = H$) | H | H | $OCH_3$ | $OCH_3$ | |
| J-1 | $CH_3$ | Q-47 ($R_7 = H, R_8 = CH_3, R_2 = CH_3$) | H | H | $CH_3$ | $OCH_3$ | |
| J-2 | $CH_3$ | Q-47 ($R_7 = H, R_8 = H, R_2 = C_2H_5$) | H | H | $CH_3$ | $OCH_3$ | |
| J-3 | $CH_3$ | Q-48 ($R_7 = H, R_8 = H, R_2 = H$) | H | H | $CH_3$ | $OCH_3$ | |
| J-4 | $CH_3$ | Q-48 ($R_7 = CH_3, R_8 = CH_3, R_2 = CH_3$) | $CH_3$ | H | $CH_3$ | $OCH_3$ | |
| J-1 | $CH_3$ | Q-48 ($R_7 = H, R_8 = C_2H_5, R_2 = C_2H_5$) | H | H | $OCH_3$ | $OCH_3$ | |

TABLE 2-continued

General Formula 2

| J | M | Q | R | $R_1$ | X | Y | m.p. (°C.) |
|---|---|---|---|---|---|---|---|
| J-2 | $CH(CH_3)_2$ | Q-49 ($R_7$ = H, $R_8$ = H, $R_2$ = H) | H | H | $OCH_3$ | $OCH_3$ | |
| J-3 | $CH_3$ | Q-49 ($R_7$ = $CH_3$, $R_8$ = $CH_3$, $R_2$ = H) | H | H | $OCH_3$ | $OCH_3$ | |
| J-4 | $CH_3$ | Q-49 ($R_7$ = $CH_3$, $R_8$ = $CH_3$, $R_2$ = $CH_3$) | H | 3-$OCH_3$ | $OCH_3$ | $OCH_3$ | |
| J-1 | $CH_3$ | Q-50 ($R_7$ = H, $R_8$ = H, $R_2$ = H) | H | H | $OCH_3$ | $OCH_3$ | |
| J-2 | $CH_3$ | Q-50 ($R_7$ = $CH_3$, $R_8$ = $CH_3$, $R_2$ = $CH_3$) | H | 5-Cl | $OCH_3$ | $OCH_3$ | |
| J-3 | $CH_3$ | Q-51 ($R_7$ = H, $R_8$ = H, $R_9$ = H) | H | H | $OCH_3$ | $OCH_3$ | |
| J-4 | $CH_3$ | Q-51 ($R_7$ = H, $R_8$ = H, $R_9$ = $CH_3$) | $CH_3$ | H | $OCH_3$ | $OCH_3$ | |
| J-1 | $CH_3$ | Q-51 ($R_7$ = H, $R_8$ = H, $R_9$ = s-$C_4H_9$) | H | 5-$OCH_3$ | $OCH_3$ | $OCH_3$ | |
| J-2 | $CH_3$ | Q-52 ($R_7$ = H, $R_8$ = H, $R_9$ = H) | H | H | $OCH_3$ | $OCH_3$ | |
| J-3 | $CH_3$ | Q-52 ($R_7$ = H, $R_8$ = H, $R_9$ = $CH_3$) | H | 3-Cl | $OCH_3$ | $CH_3$ | |
| J-4 | $C_6H_5$ | Q-53 ($R_7$ = H, $R_8$ = H, $R_9$ = H) | H | H | $CH_3$ | $OCH_3$ | |
| J-1 | $CH_3$ | Q-53 ($R_7$ = $CH_3$, $R_8$ = $CH_3$, $R_9$ = $CH_3$) | H | H | $CH_3$ | $OCH_3$ | |
| J-2 | $CH_3$ | Q-53 ($R_7$ = H, $R_8$ = H, $R_9$ = $CH_3$) | H | 5-$CH_3$ | $OCH_3$ | $OCH_3$ | |
| J-3 | $CH_3$ | Q-54 ($R_7$ = H, $R_8$ = H, $R_9$ = H) | H | H | $OCH_3$ | $OCH_3$ | |
| J-4 | $CH_3$ | Q-54 ($R_7$ = $CH_3$, $R_8$ = H, $R_9$ = H) | H | H | $CH_3$ | $OCH_3$ | |
| J-1 | $CH_3$ | Q-54 ($R_7$ = H, $R_8$ = H, $R_9$ = i-$C_3H_7$) | H | H | $CH_3$ | $OCH_3$ | |
| J-2 | $CH_3$ | Q-55 ($R_7$ = H, $R_8$ = H, $R_9$ = H, $R_3$ = H) | H | H | $CH_3$ | $OCH_3$ | |
| J-3 | $CH_3$ | Q-55 ($R_7$ = H, $R_8$ = $CH_3$, $R_3$ = $CH_3$) | $CH_3$ | H | $CH_3$ | $OCH_3$ | |
| J-4 | $CH_3$ | Q-55 ($R_7$ = H, $R_8$ = H, $R_9$ = s-$C_4H_9$, $R_3$ = H) | H | H | $OCH_3$ | $OCH_3$ | |
| J-1 | $CH_3$ | Q-56 ($R_7$ = H, $R_8$ = H, $R_9$ = H, $R_3$ = $C_2H_5$) | H | H | $OCH_3$ | $OCH_3$ | |
| J-2 | $CH_3$ | Q-56 ($R_7$ = $CH_3$, $R_8$ = H, $R_9$ = H, $R_3$ = H) | H | H | $OCH_3$ | $OCH_3$ | |
| J-1 | $CH_3$ | Q-56 ($R_7$ = H, $R_8$ = H, $R_9$ = $CH_3$, $R_3$ = $CH_3$) | H | 5-$OCH_3$ | $OCH_3$ | $OCH_3$ | |
| J-2 | $CH_3$ | Q-57 ($R_7$ = H, $R_8$ = H, $R_9$ = H, $R_3$ = i-$C_3H_7$ | H | H | $OCH_3$ | $OCH_3$ | |
| J-3 | $CH_3$ | Q-57 ($R_7$ = H, $R_8$ = H, $R_9$ = $CH_3$, $R_3$ = $CH_3$) | H | 3-Cl | $OCH_3$ | $OCH_3$ | |
| J-4 | $CH_3$ | Q-58 ($R_7$ = H, $R_8$ = H, $R_9$ = H, $R_3$ = H) | H | H | $OCH_3$ | $OCH_3$ | |
| J-1 | $CH_3$ | Q-58 ($R_7$ = $CH_3$, $R_8$ = H, $R_9$ = H, $R_3$ = $CH_3$) | $CH_3$ | H | $OCH_3$ | $CH_3$ | |
| J-2 | $CH_3$ | Q-58 ($R_7$ = H, $R_8$ = H, $R_9$ = i-$C_3H_7$, $R_3$ = $CH_3$) | H | 5-$OCH_3$ | $OCH_3$ | $OCH_3$ | |
| J-3 | $CH_3$ | Q-59 ($R_7$ = H, $R_8$ = H, $R_9$ = H, $R_{10}$ = H) | H | H | $OCH_3$ | $OCH_3$ | |
| J-4 | $CH_3$ | Q-59 ($R_7$ = H, $R_8$ = H, $R_9$ = H, $R_{10}$ = s-$C_4H_9$) | H | 3-Cl | $OCH_3$ | $CH_3$ | |
| J-1 | $CO_2CH_3$ | Q-60 ($R_7$ = H, $R_8$ = H, $R_9$ = H, $R_2$ = H) | H | H | $CH_3$ | $OCH_3$ | |
| J-2 | $CH_3$ | Q-60 ($R_7$ = $CH_3$, $R_8$ = H, $R_9$ = H, $R_2$ = $O(CH_2)_3CH_2Br$) | H | H | $CH_3$ | $OCH_3$ | |
| J-3 | $CH_3$ | Q-60 ($R_7$ = H, $R_8$ = H, $R_9$ = H, $R_2$ = Br) | H | 3-$CH_3$ | $OCH_3$ | $OCH_3$ | |
| J-4 | $CH_3$ | Q-61 ($R_7$ = H, $R_8$ = H, $R_9$ = H, $R_2$ = H) | H | H | $OCH_3$ | $OCH_3$ | |
| J-1 | $CH_3$ | Q-61 ($R_7$ = $CH_3$, $R_8$ = H, $R_9$ = H, $R_2$ = $OCH_2F$) | H | H | $CH_3$ | $OCH_3$ | |
| J-2 | $CH_3$ | Q-61 ($R_7$ = H, $R_8$ = $CH_3$, $R_9$ = H, $R_2$ = $O(CH_2)_3CH_3$) | H | H | $CH_3$ | $OCH_3$ | |
| J-3 | $CH_2CH_3$ | Q-62 ($R_7$ = H, $R_8$ = H, $R_9$ = H, $R_2$ = H) | H | H | $CH_3$ | $OCH_3$ | |
| J-4 | $CH_3$ | Q-62 ($R_7$ = $CH_3$, $R_8$ = H, $R_9$ = H, $R_2$ = $CH_3$) | $CH_3$ | H | $CH_3$ | $OCH_3$ | |
| J-1 | $CH_3$ | Q-62 ($R_7$ = Cl, $R_8$ = H, $R_9$ = H, $R_2$ = H) | H | H | $OCH_3$ | $OCH_3$ | |
| J-2 | $CH_3$ | Q-63 ($R_7$ = H, $R_8$ = H, $R_9$ = H) | H | H | $OCH_3$ | $OCH_3$ | |
| J-3 | $CH_3$ | Q-63 ($R_7$ = $CH_3$, $R_8$ = H, $R_9$ = H) | H | H | $OCH_3$ | $OCH_3$ | |
| J-4 | $CH_3$ | Q-63 ($R_7$ = H, $R_8$ = H, $R_9$ = $CH_3$) | H | 3-$OCH_3$ | $OCH_3$ | $OCH_3$ | |
| J-1 | $CH_3$ | Q-64 ($R_7$ = H, $R_8$ = H, $R_9$ = H) | H | H | $OCH_3$ | $OCH_3$ | |
| J-2 | $CH_3$ | Q-64 ($R_7$ = H, $R_8$ = H, $R_9$ = $C_2H_5$) | H | 5-Cl | $OCH_3$ | $OCH_3$ | |
| J-3 | $CH_3$ | Q-65 ($R_7$ = H, $R_8$ = H, $R_9$ = H) | H | H | $OCH_3$ | $OCH_3$ | |
| J-4 | $CH_3$ | Q-65 ($R_7$ = n-$C_4H_9$, $R_8$ = H, $R_9$ = H) | $CH_3$ | H | $OCH_3$ | $CH_3$ | |
| J-1 | $CH_3$ | Q-65 ($R_7$ = H, $R_8$ = $CH_3$, $R_9$ = i-$C_3H_7$) | H | 5-$OCH_3$ | $OCH_3$ | $OCH_3$ | |
| J-2 | $CH_3$ | Q-66 ($R_7$ = H, $R_8$ = H, $R_9$ = H) | H | H | $OCH_3$ | $OCH_3$ | |
| J-3 | $CH_3$ | Q-66 ($R_7$ = H, $R_8$ = $C_2H_5$, $R_9$ = $CH_3$) | H | 3-Cl | $OCH_3$ | $CH_3$ | |
| J-4 | $CH_3$ | Q-67 ($R_7$ = H, $R_8$ = H, $R_9$ = H, $R_3$ = H) | H | H | $CH_3$ | $OCH_3$ | |
| J-1 | $CH_3$ | Q-67 ($R_7$ = $CH_3$, $R_8$ = H, $R_9$ = H, $R_3$ = $CH_3$) | H | H | $CH_3$ | $OCH_3$ | |

TABLE 2-continued

| J | M | Q | R | $R_1$ | X | Y | m.p. (°C.) |
|---|---|---|---|---|---|---|---|
| | | General Formula 2 | | | | | |
| J-2 | $CH_3$ | Q-67 ($R_7 = H, R_8 = H, R_9 = CH_3, R_3 = C_2H_5$) | H | 5-$CH_3$ | $OCH_3$ | $OCH_3$ | |
| J-3 | $CH_3$ | Q-68 ($R_7 = H, R_8 = H, R_9 = H, R_3 = CH_3$) | H | H | $OCH_3$ | $OCH_3$ | |
| J-4 | $CH_3$ | Q-68 ($R_7 = C_2H_5, R_8 = H, R_9 = H, R_3 = \underline{i}\text{-}C_3H_7$) | H | H | $CH_3$ | $OCH_3$ | |
| J-1 | $CH_3$ | Q-68 ($R_7 = H, R_8 = H, R_9 = C_2H_5, R_3 = \underline{n}\text{-}C_4H_9$) | H | H | $CH_3$ | $OCH_3$ | |
| J-2 | $CH_3$ | Q-69 ($R_7 = H, R_8 = H, R_9 = H, R_3 = CH_3$) | H | H | $CH_3$ | $OCH_3$ | |
| J-3 | $CH_3$ | Q-69 ($R_7 = \underline{n}\text{-}C_4H_9, R_8 = H, R_9 = H, R_3 = C_2H_5$) | $CH_3$ | H | $CH_3$ | $OCH_3$ | |
| J-4 | $CH_3$ | Q-69 ($R_7 = H, R_8 = CH_3, R_9 = \underline{i}\text{-}C_3H_7, R_3 = H$) | H | H | $OCH_3$ | $OCH_3$ | |
| J-1 | $CH_3$ | Q-70 ($R_7 = H, R_8 = H, R_9 = H, R_3 = CH_3$) | H | H | $OCH_3$ | $OCH_3$ | |
| J-2 | $CH_3$ | Q-70 ($R_7 = \underline{i}\text{-}C_3H_7, R_8 = H, R_9 = H, R_3 = CH_3$) | H | H | $OCH_3$ | $OCH_3$ | |
| J-3 | $CH_3$ | Q-70 ($R_7 = H, R_8 = C_2H_5, R_9 = CH_3, R_3 = H$) | H | 3-$OCH_3$ | $OCH_3$ | $OCH_3$ | |
| J-4 | $CH_3$ | Q-71 ($R_7 = CH_3, R_8 = H, R_9 = H, R_{10} = H$) | H | H | $OCH_3$ | $OCH_3$ | |
| J-1 | $CH_3$ | Q-71 ($R_7 = H, R_8 = H, R_9 = H, R_{10} = CH_3$) | H | 5-Cl | $OCH_3$ | $OCH_3$ | |
| J-2 | $CH_2CH_2CH_3$ | Q-72 ($R_7 = H, R_8 = H, R_9 = H, R_2 = H$) | H | H | $OCH_3$ | $OCH_3$ | |
| J-3 | $CH_3$ | Q-72 ($R_7 = H, R_8 = H, R_9 = H, R_2 = CH_3$) | $CH_3$ | H | $OCH_3$ | $CH_3$ | |
| J-4 | $CH_3$ | Q-72 ($R_7 = CH_3, R_8 = H, R_9 = H, R_2 = H$) | H | 3-$OCH_3$ | $OCH_3$ | $OCH_3$ | |
| J-1 | $CH_3$ | Q-73 ($R_7 = H, R_8 = H, R_9 = H, R_2 = H$) | H | H | $OCH_3$ | $OCH_3$ | |
| J-2 | $CH_3$ | Q-73 ($R_7 = CH_3, R_8 = H, R_9 = CH_3, R_2 = H$) | H | 5-Cl | $OCH_3$ | $CH_3$ | |
| J-3 | $C_6H_5$ | Q-74 ($R_7 = H, R_8 H, R_9 = H, R_2 = H$) | H | H | $CH_3$ | $OCH_3$ | |
| J-4 | $CH_3$ | Q-74 ($R_7 = CH_3, R_8 = H, R_9 = H, R_2 = H$) | H | H | $CH_3$ | $OCH_3$ | |
| J-1 | $CH_3$ | Q-74 ($R_7 = H, R_8 = H, R_9 = H, R_2 = CH_3$) | H | 5-$CH_3$ | $OCH_3$ | $OCH_3$ | |
| J-2 | $CH_3$ | Q-75 ($R_7 = H, R_8 = H, R_9 = H$) | H | H | $OCH_3$ | $OCH_3$ | |
| J-3 | $CH_3$ | Q-75 ($R_7 = H, R_8 = H, R_9 = CH_3$) | H | H | $CH_3$ | $OCH_3$ | |
| J-4 | $CH_3$ | Q-75 ($R_7 = CH_3, R_8 = H, R_9 = CH_3$) | H | H | $CH_3$ | $OCH_3$ | |
| J-1 | $CH_3$ | Q-76 ($R_7 = H, R_8 = H, R_9 = H$) | H | H | $CH_3$ | $OCH_3$ | |
| J-2 | $CH_3$ | Q-76 ($R_7 = H, R_8 = H, R_9 = CH_3$) | $CH_3$ | H | $CH_3$ | $OCH_3$ | |
| J-3 | $CH_3$ | Q-76 ($R_7 = C_2H_5, R_8 = H, R_9 = C_2H_5$) | H | H | $OCH_3$ | $OCH_3$ | |
| J-4 | $CH_3$ | Q-77 ($R_7 = H, R_8 = H, R_9 = H$) | H | H | $OCH_3$ | $OCH_3$ | |
| J-1 | $CH_3$ | Q-77 ($R_7 = H, R_8 = H, R_9 = \underline{n}\text{-}C_3H_7$) | H | H | $OCH_3$ | $OCH_3$ | |
| J-2 | $CH_3$ | Q-77 ($R_7 = H, R_8 = CH_3, R_9 = H$) | H | 5-$OCH_3$ | $OCH_3$ | $OCH_3$ | |
| J-1 | $CH_3$ | Q-78 ($R_7 = H, R_8 = H, R_9 = H$) | H | H | $OCH_3$ | $OCH_3$ | |
| J-2 | $CH_3$ | Q-78 ($R_7 = \underline{n}\text{-}C_3H_7, R_8 = H, R_9 = H$) | H | 5-Cl | $OCH_3$ | $OCH_3$ | |
| J-3 | $CH_3$ | Q-79 ($R_7 = H, R_8 = H, R_9 = H, R_3 = H$) | H | H | $OCH_3$ | $OCH_3$ | |
| J-4 | $CH_3$ | Q-79 ($R_7 = H, R_8 = H, R_9 = H, R_3 = CH_3$) | $CH_3$ | H | $OCH_3$ | $OCH_3$ | |
| J-1 | $CH_3$ | Q-79 ($R_7 = CH_3, R_8 = H, R_9 = H, R_3 = C_2H_5$) | H | 5-$OCH_3$ | $OCH_3$ | $OCH_3$ | |
| J-2 | $CH_3$ | Q-80 ($R_7 = H, R_8 = H, R_9 = H, R_3 = CH_3$) | H | H | $OCH_3$ | $OCH_3$ | |
| J-3 | $CH_3$ | Q-80 ($R_7 = H, R_8 = H, R_9 = CH_3, R_3 = C_2H_5$) | H | 3-Cl | $OCH_3$ | $CH_3$ | |
| J-4 | $CH_3$ | Q-81 ($R_7 = H, R_8 = H, R_9 = H, R_3 = CH_3$) | H | H | $CH_3$ | $OCH_3$ | |
| J-1 | $CH_3$ | Q-81 ($R_7 = H, R_8 = CH_3, R_9 = H, R_3 = \underline{i}\text{-}C_3H_7$) | H | H | $CH_3$ | $OCH_3$ | |
| J-2 | $CH_3$ | Q-81 ($R_7 = CH_3, R_8 = H, R_9 = CH_3, R_3 = CH_3$) | H | 5-$CH_3$ | $OCH_3$ | $OCH_3$ | |
| J-3 | $CH_3$ | Q-82 ($R_7 = H, R_8 = H, R_9 = H, R_3 = CH_3$) | H | H | $OCH_3$ | $OCH_3$ | |
| J-4 | $CH_3$ | Q-82 ($R_7 = CH_3, R_8 = H, R_9 = CH_3, R_3 = H$) | H | H | $CH_3$ | $OCH_3$ | |
| J-1 | $CH_3$ | Q-82 ($R_7 = H, R_8 = H, R_9 = C_2H_5, R_3 = CH_3$) | H | H | $CH_3$ | $OCH_3$ | |
| J-2 | $CH(CH_3)_2$ | Q-83 ($R_7 = H, R_8 = H, R_9 = H, R_{10} = H$) | H | H | $CH_3$ | $OCH_3$ | |
| J-3 | $CH_3$ | Q-83 ($R_7 = CH_3, R_8 = H, R_9 = H, R_{10} = CH_3$) | $CH_3$ | H | $CH_3$ | $OCH_3$ | |
| J-4 | $CH_3$ | Q-83 ($R_7 = CH_3, R_8 = CH_3, R_9 = H, R_{10} = H$) | H | H | $OCH_3$ | $OCH_3$ | |
| J-1 | $CH_3$ | Q-84 ($R_7 = H, R_8 = H, R_9 = H$) | H | H | $OCH_3$ | $OCH_3$ | |
| J-2 | $CH_3$ | Q-84 ($R_7 = H, R_8 = H, R_9 = CH_3$) | H | H | $OCH_3$ | $OCH_3$ | |
| J-3 | $CH_3$ | Q-84 ($R_7 = H, R_8 = C_2H_5, R_9 = H$) | H | 3-$OCH_3$ | $OCH_3$ | $OCH_3$ | |
| J-4 | $C(CH_3)_3$ | Q-85 ($R_7 = H, R_8 = H, R_9 = H$) | H | H | $OCH_3$ | $OCH_3$ | |
| J-1 | $CH_3$ | Q-85 ($R_7 = H, R_8 = H, R_9 = C_2H_5$) | H | 5-Cl | $OCH_3$ | $OCH_3$ | |

TABLE 2-continued

General Formula 2

| J | M | Q | R | $R_1$ | X | Y | m.p. (°C.) |
|---|---|---|---|---|---|---|---|
| J-2 | $CH_3$ | Q-86 ($R_7$ = H, $R_8$ = H, $R_9$ = H) | H | H | $OCH_3$ | $OCH_3$ | |
| J-3 | $CH_3$ | Q-86 ($R_7$ = $CH_3$, $R_8$ = H, $R_9$ = H) | $CH_3$ | H | $OCH_3$ | $OCH_3$ | |
| J-4 | $CH_3$ | Q-86 ($R_7$ = H, $R_8$ = H, $R_9$ = $C_2H_5$) | H | 3-$OCH_3$ | $OCH_3$ | $OCH_3$ | |
| J-1 | $CH_3$ | Q-87 ($R_7$ = H, $R_8$ = H, $R_9$ = H) | H | H | $OCH_3$ | $OCH_3$ | |
| J-2 | $CH_3$ | Q-87 ($R_7$ = $CH_3$, $R_8$ = H, $R_9$ = H) | H | 5-Cl | $OCH_3$ | $CH_3$ | |
| J-3 | $CH_3$ | Q-88 ($R_7$ = H, $R_8$ = H, $R_9$ = H) | H | H | $CH_3$ | $OCH_3$ | |
| J-4 | $CH_3$ | Q-88 ($R_7$ = $CH_3$, $R_8$ = H, $R_9$ = H) | H | H | $CH_3$ | $OCH_3$ | |
| J-1 | $CH_3$ | Q-88 ($R_7$ = H, $R_8$ = H, $R_9$ = $CH_3$) | H | 5-$CH_3$ | $OCH_3$ | $OCH_3$ | |
| J-2 | $CH_3$ | Q-89 ($R_7$ = H, $R_8$ = H, $R_9$ = H) | H | H | $OCH_3$ | $OCH_3$ | |
| J-3 | $CH_3$ | Q-89 ($R_7$ = $CH_3$, $R_8$ = H, $R_9$ = $C_2H_5$) | H | H | $CH_3$ | $OCH_3$ | |
| J-4 | $CH_3$ | Q-89 ($R_7$ = H, $R_8$ = $CH_3$, $R_9$ = H) | H | H | $CH_3$ | $OCH_3$ | |
| J-1 | $CH_3$ | Q-90 ($R_7$ = H, $R_8$ = H, $R_9$ = H, $R_3$ = $CH_3$) | H | H | $CH_3$ | $OCH_3$ | |
| J-2 | $CH_3$ | Q-90 ($R_7$ = $CH_3$, $R_8$ = H, $R_9$ = H, $R_3$ = $C_2H_5$) | $CH_3$ | H | $CH_3$ | $OCH_3$ | |
| J-3 | $CH_3$ | Q-90 ($R_7$ = H, $R_8$ = H, $R_9$ = $CH_3$, $R_3$ = $CH_3$) | H | H | $OCH_3$ | $OCH_3$ | |
| J-4 | $CH_3$ | Q-91 ($R_7$ = H, $R_8$ = H, $R_9$ = H, $R_3$ = $CH_3$ | H | H | $OCH_3$ | $OCH_3$ | |
| J-1 | $CH_3$ | Q-91 ($R_7$ = $CH_3$, $R_8$ = H, $R_9$ = H, $R_3$ = H) | H | H | $OCH_3$ | $OCH_3$ | |
| J-2 | $CH_3$ | Q-91 ($R_7$ = H, $R_8$ = H, $R_9$ = $CH_3$, $R_3$ = $CH_3$) | H | 5-$OCH_3$ | $OCH_3$ | $OCH_3$ | |
| J-3 | $CO_2CH_3$ | Q-92 ($R_7$ = H, $R_8$ = H, $R_9$ = H, $R_{10}$ = H) | H | H | $OCH_3$ | $OCH_3$ | |
| J-4 | $CH_3$ | Q-92 ($R_7$ = H, $R_8$ = $CH_3$, $R_9$ = H, $R_{10}$ = H) | H | 3-Cl | $OCH_3$ | $OCH_3$ | |
| J-1 | $CH_3$ | Q-93 ($R_7$ = H, $R_8$ = H, $R_9$ = H) | H | H | $OCH_3$ | $OCH_3$ | |
| J-2 | $CH_3$ | Q-93 ($R_7$ = H, $R_8$ = H, $R_9$ = $CH_3$) | $CH_3$ | H | $OCH_3$ | $OCH_3$ | |
| J-3 | $CH_3$ | Q-93 ($R_7$ = $CH_3$, $R_8$ = H, $R_9$ = H) | H | 3-$OCH_3$ | $OCH_3$ | $OCH_3$ | |
| J-4 | $CH_3$ | Q-94 ($R_7$ = H, $R_8$ = H, $R_9$ = H) | H | H | $OCH_3$ | $OCH_3$ | |
| J-1 | $CH_3$ | Q-94 ($R_7$ = H, $R_8$ = H, $R_9$ = n-$C_4H_9$) | H | 5-Cl | $OCH_3$ | $CH_3$ | |
| J-2 | $CH_3$ | Q-95 ($R_7$ = H, $R_8$ = H, $R_9$ = H) | H | H | $CH_3$ | $OCH_3$ | |
| J-3 | $CH_3$ | Q-95 ($R_7$ = H, $R_8$ = H, $R_9$ = $CH_3$) | H | H | $CH_3$ | $OCH_3$ | |
| J-4 | $CH_3$ | Q-95 ($R_7$ = H, $R_8$ = H, $R_9$ = s-$C_4H_9$) | H | 3-$CH_3$ | $OCH_3$ | $OCH_3$ | |
| J-1 | $CH_2CH_3$ | Q-96 ($R_7$ = H, $R_8$ = H, $R_9$ = H) | H | H | $OCH_3$ | $OCH_3$ | |
| J-2 | $CH_3$ | Q-96 ($R_7$ = $CH_3$, $R_8$ = H, $R_9$ = H) | H | H | $CH_3$ | $OCH_3$ | |
| J-3 | $CH_3$ | Q-96 ($R_7$ = H, $R_8$ = H, $R_9$ = $CH_3$) | H | H | $CH_3$ | $OCH_3$ | |
| J-4 | $CH_3$ | Q-97 ($R_7$ = H, $R_8$ = H, $R_9$ = H) | H | H | $CH_3$ | $OCH_3$ | |
| J-1 | $CH_3$ | Q-97 ($R_7$ = $CH_3$, $R_8$ = $CH_3$, $R_9$ = $CH_3$) | $CH_3$ | H | $CH_3$ | $OCH_3$ | |
| J-2 | $CH_3$ | Q-97 ($R_7$ = H, $R_8$ = H, $R_9$ = $CH_3$) | H | H | $OCH_3$ | $OCH_3$ | |
| J-3 | $CH_3$ | Q-98 ($R_7$ = H, $R_8$ = H, $R_9$ = H) | H | H | $OCH_3$ | $OCH_3$ | |
| J-4 | $CH_3$ | Q-98 ($R_7$ = H, $R_8$ = H, $R_9$ = H) | H | H | $OCH_3$ | $OCH_3$ | |
| J-1 | $CH_3$ | Q-98 ($R_7$ = H, $R_8$ = H, $R_9$ = i-$C_3H_7$) | H | 5-$OCH_3$ | $OCH_3$ | $OCH_3$ | |
| J-2 | $CH_3$ | Q-99 ($R_7$ = H, $R_8$ = H, $R_9$ = H, $R_3$ = H) | H | H | $OCH_3$ | $OCH_3$ | |
| J-1 | $CH_3$ | Q-99 ($R_7$ = H, $R_8$ = H, $R_9$ = s-$C_4H_9$, $R_3$ = H) | H | 5-Cl | $OCH_3$ | $OCH_3$ | |
| J-2 | $CH_3$ | Q-100 ($R_7$ = H, $R_8$ = H, $R_9$ = H, $R_3$ = $C_2H_5$) | H | H | $OCH_3$ | $OCH_3$ | |
| J-3 | $CH_3$ | Q-100 ($R_7$ = $CH_3$, $R_8$ = H, $R_9$ = H, $R_3$ = H) | $CH_3$ | H | $OCH_3$ | $CH_3$ | |
| J-4 | $CH_3$ | Q-100 ($R_7$ = H, $R_8$ = H, $R_9$ = $CH_3$, $R_3$ = $CH_3$) | H | 3-$OCH_3$ | $OCH_3$ | $OCH_3$ | |
| J-1 | $CH_3$ | Q-101 ($R_7$ = H, $R_8$ = H, $R_9$ = H, $R_3$ = i-$C_3H_7$) | H | H | $OCH_3$ | $OCH_3$ | |
| J-2 | $CH_3$ | Q-101 ($R_7$ = H, $R_8$ = H, $R_9$ = $CH_3$, $R_3$ = $CH_3$) | H | 5-Cl | $OCH_3$ | $CH_3$ | |
| J-3 | $CH_3$ | Q-102 ($R_7$ = H, $R_8$ = H, $R_9$ = H, $R_3$ = H) | H | H | $CH_3$ | $OCH_3$ | |
| J-4 | $CH_3$ | Q-102 ($R_7$ = $CH_3$, $R_8$ = H, $R_9$ = H, $R_3$ = $CH_3$) | H | H | $CH_3$ | $OCH_3$ | |
| J-1 | $CH_3$ | Q-102 ($R_7$ = H, $R_8$ = H, $R_9$ = i-$C_3H_7$, $R_3$ = $CH_3$) | H | 5-$CH_3$ | $OCH_3$ | $OCH_3$ | |
| J-2 | $CH_2CH_2CH_3$ | Q-103 ($R_7$ = H, $R_8$ = H, $R_9$ = H, $R_{10}$ = H) | H | H | $OCH_3$ | $OCH_3$ | |
| J-3 | $CH_3$ | Q-103 ($R_7$ = $CH_3$, $R_8$ = H, $R_9$ = H, $R_{10}$ = $CH_3$) | H | H | $CH_3$ | $OCH_3$ | |
| J-4 | $CH_3$ | Q-103 ($R_7$ = H, $R_8$ = H, $R_9$ = H, $R_{10}$ = s-$C_4H_9$) | H | H | $CH_3$ | $OCH_3$ | |
| J-1 | $CH_3$ | Q-104 ($R_7$ = H, $R_8$ = H, $R_9$ = H, $R_2$ = H) | H | H | $CH_3$ | $OCH_3$ | |

TABLE 2-continued

General Formula 2

| J | M | Q | R | $R_1$ | X | Y | m.p. (°C.) |
|---|---|---|---|---|---|---|---|
| J-2 | $CH_3$ | Q-104 ($R_7 = CH_3$, $R_8 = H$, $R_9 = H$, $R_2 = OC_2H_5$) | $CH_3$ | H | $CH_3$ | $OCH_3$ | |
| J-3 | $CH_3$ | Q-104 ($R_7 = H$, $R_8 = H$, $R_9 = H$, $R_2 = Br$) | H | H | $OCH_3$ | $OCH_3$ | |
| J-4 | $CH_3$ | Q-105 ($R_7 = H$, $R_8 = H$, $R_9 = H$, $R_2 = H$) | H | H | $OCH_3$ | $OCH_3$ | 155-165 |
| J-1 | $CH_3$ | Q-105 ($R_7 = CH_3$, $R_8 = H$, $R_9 = H$, $R_2 = CH_3$) | H | H | $OCH_3$ | $OCH_3$ | |
| J-2 | $CH_3$ | Q-105 ($R_7 = H$, $R_8 = CH_3$, $R_9 = H$, $R_2 = C_2H_5$) | H | 5-$OCH_3$ | $OCH_3$ | $OCH_3$ | |
| J-3 | $CH(CH_3)_2$ | Q-106 ($R_7 = H$, $R_8 = H$, $R_9 = H$, $R_2 = H$) | H | H | $OCH_3$ | $OCH_3$ | |
| J-4 | $CH_3$ | Q-106 ($R_7 = Cl$, $R_8 = H$, $R_9 = H$, $R_2 = H$) | H | 3-Cl | $OCH_3$ | $OCH_3$ | |
| J-1 | $CH_3$ | Q-107 ($R_7 = H$, $R_8 = H$, $R_9 = H$, $R_2 = H$) | H | H | $OCH_3$ | $OCH_3$ | |
| J-2 | $CH_3$ | Q-107 ($R_7 = CH_3$, $R_8 = H$, $R_9 = H$, $R_2 = H$) | $CH_3$ | H | $OCH_3$ | $OCH_3$ | |
| J-3 | $CH_3$ | Q-107 ($R_7 = H$, $R_8 = H$, $R_9 = H$, $R_2 = CH_3$) | H | 3-$OCH_3$ | $OCH_3$ | $OCH_3$ | |
| J-4 | $CH_3$ | Q-108 ($R_7 = H$, $R_8 = H$, $R_9 = H$, $R_2 = H$) | H | H | $OCH_3$ | $OCH_3$ | |
| J-1 | $CH_3$ | Q-108 ($R_7 = H$, $R_8 = H$, $R_9 = H$, $R_2 = CH_3$) | H | 5-Cl | $OCH_3$ | $CH_3$ | |
| J-2 | $CH_3$ | Q-109 ($R_7 = H$, $R_8 = H$, $R_9 = H$) | H | H | $CH_3$ | $OCH_3$ | |
| J-3 | $CH_3$ | Q-109 ($R_7 = CH_3$, $R_8 = H$, $R_9 = H$) | H | H | $CH_3$ | $OCH_3$ | |
| J-4 | $CH_3$ | Q-109 ($R_7 = H$, $R_8 = H$, $R_9 = CH_3$) | H | 3-$CH_3$ | $OCH_3$ | $OCH_3$ | |
| J-1 | $CH_3$ | Q-110 ($R_7 = H$, $R_8 = H$, $R_9 = H$) | H | H | $OCH_3$ | $OCH_3$ | |
| J-2 | $CH_3$ | Q-110 ($R_7 = CH_3$, $R_8 = H$, $R_9 = H$) | H | H | $CH_3$ | $OCH_3$ | |
| J-3 | $CH_3$ | Q-110 ($R_7 = H$, $R_8 = CH_3$, $R_9 = H$) | H | H | $CH_3$ | $OCH_3$ | |
| J-4 | $CH_3$ | Q-111 ($R_7 = H$, $R_8 = H$, $R_9 = H$) | H | H | $CH_3$ | $OCH_3$ | |
| J-1 | $CH_3$ | Q-111 ($R_7 = CH_3$, $R_8 = H$, $R_9 = H$) | $CH_3$ | H | $CH_3$ | $OCH_3$ | |
| J-2 | $CH_3$ | Q-111 ($R_7 = H$, $R_8 = H$, $R_9 = CH_3$) | H | H | $OCH_3$ | $OCH_3$ | |
| J-3 | $C(CH_3)_3$ | Q-112 ($R_7 = H$, $R_8 = H$, $R_9 = H$) | H | H | $OCH_3$ | $OCH_3$ | |
| J-4 | $CH_3$ | Q-112 ($R_7 = CH_3$, $R_8 = H$, $R_9 = H$) | H | H | $OCH_3$ | $OCH_3$ | |
| J-1 | $CH_3$ | Q-112 ($R_7 = H$, $R_8 = CH_3$, $R_9 = CH_3$) | H | 5-$OCH_3$ | $OCH_3$ | $OCH_3$ | |
| J-2 | $CH_3$ | Q-113 ($R_7 = H$, $R_8 = H$, $R_9 = H$, $R_3 = CH_3$) | H | H | $OCH_3$ | $OCH_3$ | |
| J-3 | $CH_3$ | Q-113 ($R_7 = H$, $R_8 = H$, $R_9 = C_2H_5$, $R_3$ = n-$C_4H_9$) | H | 3-Cl | $OCH_3$ | $OCH_3$ | |
| J-4 | $CH_3$ | Q-114 ($R_7 = H$, $R_8 = H$, $R_9 = H$, $R_3 = CH_3$) | H | H | $OCH_3$ | $OCH_3$ | |
| J-1 | $CH_3$ | Q-114 ($R_7$ = n-$C_4H_9$, $R_8 = H$, $R_9 = H$, $R_3 = C_2H_5$) | $CH_3$ | H | $OCH_3$ | $CH_3$ | |
| J-2 | $CH_3$ | Q-114 ($R_7 = H$, $R_8 = CH_3$, $R_8$ = i-$C_3H_7$, $R_3 = H$) | H | 5-$OCH_3$ | $OCH_3$ | $OCH_3$ | |
| J-3 | $CH_3$ | Q-115 ($R_7 = H$, $R_8 = H$, $R_9 = H$, $R_3 = CH_3$) | H | H | $OCH_3$ | $OCH_3$ | |
| J-4 | $CH_3$ | Q-115 ($R_7 = H$, $R_8 = C_2H_5$, $R_9 = CH_3$, $R_3 = H$) | H | 3-Cl | $OCH_3$ | $CH_3$ | |
| J-1 | $C_6H_5$ | Q-116 ($R_7 = H$, $R_8 = H$, $R_9 = H$, $R_{10} = H$) | H | H | $CH_3$ | $OCH_3$ | |
| J-2 | $CH_3$ | Q-116 ($R_7 = CH_3$, $R_8 = H$, $R_9 = H$, $R_{10} = H$) | H | H | $CH_3$ | $OCH_3$ | |
| J-3 | $CH_3$ | Q-116 ($R_7 = H$, $R_8 = H$, $R_9 = H$, $R_{10} = CH_3$) | H | 3-$CH_3$ | $OCH_3$ | $OCH_3$ | |
| J-4 | $CH_3$ | Q-117 ($R_7 = H$, $R_8 = H$, $R_9 = H$, $R_2 = H$) | H | H | $OCH_3$ | $OCH_3$ | |
| J-1 | $CH_3$ | Q-117 ($R_7 = H$, $R_8 = H$, $R_9 = H$, $R_2 = CH_3$) | H | H | $CH_3$ | $OCH_3$ | |
| J-2 | $CH_3$ | Q-117 ($R_7 = CH_3$, $R_8 = H$, $R_9 = H$, $R_2 = H$) | H | H | $CH_3$ | $OCH_3$ | |
| J-3 | $CH_3$ | Q-118 ($R_7 = H$, $R_8 = H$, $R_9 = H$, $R_{10} = H$) | H | H | $CH_3$ | $OCH_3$ | |
| J-4 | $CH_3$ | Q-118 ($R_7 = CH_3$, $R_8 = H$, $R_9 = H$, R = H) | $CH_3$ | H | $CH_3$ | $OCH_3$ | |
| J-1 | $CH_3$ | Q-118 ($R_7 = H$, $R_8 = H$, $R_9 = H$, $R_{10} = CH_3$) | H | H | $OCH_3$ | $OCH_3$ | |
| J-2 | $CO_2CH_3$ | Q-119 ($R_7 = H$, $R_8 = H$, $R_9 = H$, $R_2 = H$) | H | H | $OCH_3$ | $OCH_3$ | |
| J-3 | $CH_3$ | Q-119 ($R_7 = H$, $R_8 = H$, $R_9 = H$, $R_2 = CH_3$) | H | H | $OCH_3$ | $OCH_3$ | |
| J-4 | $CH_3$ | Q-119 ($R_7 = H$, $R_8 = CH_3$, $R_9 = H$, $R_2 = C_2H_5$) | H | 3-$OCH_3$ | $OCH_3$ | $OCH_3$ | |
| J-1 | $CH_3$ | Q-120 ($R_7 = H$, $R_8 = H$, $R_9 = H$, $R_2 = H$) | H | H | $OCH_3$ | $OCH_3$ | |
| J-1 | $CH_3$ | Q-120 ($R_7 = H$, $R_8 = H$, $R_9 = CH_3$, $R_2 = CH_3$) | H | 5-Cl | $OCH_3$ | $OCH_3$ | |
| J-2 | $CH_3$ | Q-121 ($R_7 = H$, $R_8 = H$, $R_9 = H$, $R_2 = H$) | H | H | $OCH_3$ | $OCH_3$ | |
| J-3 | $CH_3$ | Q-121 ($R_7 = H$, $R_8 = H$, $R_9 = H$, $R_2 = C_2H_5$) | $CH_3$ | H | $OCH_3$ | $CH_3$ | |
| J-4 | $CH_3$ | Q-121 ($R_7 = CH_3$, $R_8 = CH_3$, $R_9 = H$, $R_2 = H$) | H | 3-$OCH_3$ | $OCH_3$ | $OCH_3$ | |
| J-1 | $CH_3$ | Q-122 ($R_7 = H$, $R_8 = H$, $R_9 = H$, $R_2 = H$) | H | H | $OCH_3$ | $OCH_3$ | |
| J-2 | $CH_3$ | Q-122 ($R_7 = CH_3$, $R_8 = H$, $R_9 = H$, $R_2 = H$) | H | 5-Cl | $OCH_3$ | $CH_3$ | |

TABLE 2-continued

General Formula 2

| J | M | Q | R | $R_1$ | X | Y | m.p. (°C.) |
|---|---|---|---|---|---|---|---|
| J-3 | $CH_3$ | Q-123 ($R_7$ = H, $R_8$ = H, $R_9$ = H) | H | H | $CH_3$ | $OCH_3$ | |
| J-4 | $CH_3$ | Q-123 ($R_7$ = H, $R_8$ = H, $R_9$ = $CH_3$) | H | H | $CH_3$ | $OCH_3$ | |
| J-1 | $CH_3$ | Q-123 ($R_7$ = $CH_3$, $R_8$ = H, $R_9$ = $CH_3$) | H | 5-$CH_3$ | $OCH_3$ | $OCH_3$ | |
| J-2 | $CH_2CH_3$ | Q-124 ($R_7$ = H, $R_8$ = H, $R_9$ = H) | H | H | $OCH_3$ | $OCH_3$ | |
| J-3 | $CH_3$ | Q-124 ($R_7$ = H, $R_8$ = H, $R_9$ = $CH_3$) | H | H | $CH_3$ | $OCH_3$ | |
| J-4 | $CH_3$ | Q-124 ($R_7$ = $C_2H_5$, $R_8$ = H, $R_9$ = $C_2H_5$) | H | H | $CH_3$ | $OCH_3$ | |
| J-1 | $CH_3$ | Q-125 ($R_7$ = H, $R_8$ = H, $R_9$ = H) | H | H | $CH_3$ | $OCH_3$ | |
| J-2 | $CH_3$ | Q-125 ($R_7$ = H, $R_8$ = H, $R_9$ = n-$C_4H_9$) | $CH_3$ | H | $CH_3$ | $OCH_3$ | |
| J-3 | $CH_3$ | Q-125 ($R_7$ = H, $R_8$ = $CH_3$, $R_9$ = H) | H | H | $OCH_3$ | $OCH_3$ | |
| J-4 | $CH_2CH_2CH_3$ | Q-126 ($R_7$ = H, $R_8$ = H, $R_9$ = H) | H | H | $OCH_3$ | $OCH_3$ | |
| J-1 | $CH_3$ | Q-126 ($R_7$ = H, $R_8$ = H, $R_9$ = s-$C_3H_7$) | H | H | $OCH_3$ | $OCH_3$ | |
| J-2 | $CH_3$ | Q-126 ($R_7$ = n-$C_3H_7$, $R_8$ = H, $R_9$ = H) | H | 5-$OCH_3$ | $OCH_3$ | $OCH_3$ | |
| J-3 | $CH_3$ | Q-127 ($R_7$ = H, $R_8$ = H, $R_9$ = H, $R_3$ = H) | H | H | $OCH_3$ | $OCH_3$ | |
| J-4 | $CH_3$ | Q-127 ($R_7$ = $CH_3$, $R_8$ = H, $R_9$ = H, $R_3$ = $C_2H_5$) | H | 3-Cl | $OCH_3$ | $OCH_3$ | |
| J-1 | $CH_3$ | Q-128 ($R_7$ = H, $R_8$ = H, $R_9$ = H, $R_3$ = $CH_3$) | H | H | $OCH_3$ | $OCH_3$ | |
| J-2 | $CH_3$ | Q-128 ($R_7$ = $CH_3$, $R_8$ = H, $R_9$ = H, $R_3$ = $CH_3$) | $CH_3$ | H | $OCH_3$ | $OCH_3$ | |
| J-3 | $CH_3$ | Q-128 ($R_7$ = H, $R_8$ = H, $R_9$ = $CH_3$, $R_3$ = $C_2H_5$) | H | 3-$OCH_3$ | $OCH_3$ | $OCH_3$ | |
| J-4 | $CH_3$ | Q-129 ($R_7$ = H, $R_8$ = H, $R_9$ = H, $R_3$ = $CH_3$) | H | H | $OCH_3$ | $OCH_3$ | |
| J-1 | $CH_3$ | Q-129 ($R_7$ = $CH_3$, $R_8$ = H, $R_9$ = $CH_3$, $R_3$ = $CH_3$) | H | 5-Cl | $OCH_3$ | $CH_3$ | |
| J-2 | $CH_3$ | Q-130 ($R_7$ = H, $R_8$ = H, $R_9$ = H, $R_3$ = $CH_3$) | H | H | $CH_3$ | $OCH_3$ | |
| J-3 | $CH_3$ | Q-130 ($R_7$ = $CH_3$, $R_8$ = H, $R_9$ = $CH_3$, $R_3$ = H) | H | H | $CH_3$ | $OCH_3$ | |
| J-4 | $CH_3$ | Q-130 ($R_7$ = H, $R_8$ = H, $R_9$ = $C_2H_5$, $R_3$ = $CH_3$) | H | 3-$CH_3$ | $OCH_3$ | $OCH_3$ | |
| J-1 | $CH_3$ | Q-131 ($R_7$ = H, $R_8$ = H, $R_9$ = H, $R_{10}$ = H) | H | H | $OCH_3$ | $OCH_3$ | |
| J-1 | $CH_3$ | Q-131 ($R_7$ = $CH_3$, $R_8$ = H, $R_9$ = H, $R_{10}$ = $CH_3$) | H | H | $CH_3$ | $OCH_3$ | |
| J-2 | $CH_3$ | Q-131 ($R_7$ = $CH_3$, $R_8$ = $CH_3$, $R_9$ = H, $R_{10}$ = H) | H | H | $CH_3$ | $OCH_3$ | |
| J-3 | $CH_3$ | Q-132 ($R_7$ = H, $R_8$ = H, $R_9$ = H) | H | H | $CH_3$ | $OCH_3$ | |
| J-4 | $CH_3$ | Q-132 ($R_7$ = H, $R_8$ = H, $R_9$ = $CH_3$) | $CH_3$ | H | $CH_3$ | $OCH_3$ | |
| J-1 | $CH_3$ | Q-132 ($R_7$ = H, $R_8$ = $C_2H_5$, $R_9$ = H) | H | H | $OCH_3$ | $OCH_3$ | |
| J-2 | $CH_3$ | Q-133 ($R_7$ = H, $R_8$ = H, $R_9$ = H) | H | H | $OCH_3$ | $OCH_3$ | |
| J-3 | $CH_3$ | Q-133 ($R_7$ = $CH_3$, $R_8$ = H, $R_9$ = H) | H | H | $OCH_3$ | $OCH_3$ | |
| J-4 | $CH_3$ | Q-133 ($R_7$ = H, $R_8$ = H, $R_9$ = $C_2H_5$) | H | 3-$OCH_3$ | $OCH_3$ | $OCH_3$ | |
| J-1 | $CH(CH_3)_2$ | Q-134 ($R_7$ = H, $R_8$ = H, $R_9$ = H) | H | H | $OCH_3$ | $OCH_3$ | |
| J-2 | $CH_3$ | Q-134 ($R_7$ = H, $R_8$ = H, $R_9$ = $C_2H_5$) | H | 5-Cl | $OCH_3$ | $OCH_3$ | |
| J-3 | $CH_3$ | Q-135 ($R_7$ = H, $R_8$ = H, $R_9$ = H) | H | H | $OCH_3$ | $OCH_3$ | |
| J-4 | $CH_3$ | Q-135 ($R_7$ = H, $R_8$ = H, $R_9$ = $CH_3$) | $CH_3$ | H | $OCH_3$ | $OCH_3$ | |
| J-1 | $CH_3$ | Q-135 ($R_7$ = $CH_3$, $R_8$ = H, $R_9$ = H) | H | 5-$OCH_3$ | $OCH_3$ | $OCH_3$ | |
| J-2 | $CH_3$ | Q-135 ($R_7$ = H, $R_8$ = H, $R_9$ = H) | H | H | $OCH_3$ | $OCH_3$ | |
| J-3 | $CH_3$ | Q-136 ($R_7$ = H, $R_8$ = $CH_3$, $R_9$ = $C_2H_5$) | H | 3-Cl | $OCH_3$ | $CH_3$ | |
| J-4 | $CH_3$ | Q-137 ($R_7$ = H, $R_8$ = H, $R_9$ = H) | H | H | $CH_3$ | $OCH_3$ | |
| J-1 | $CH_3$ | Q-137 ($R_7$ = $CH_3$, $R_8$ = H, $R_9$ = H) | H | H | $CH_3$ | $OCH_3$ | |
| J-2 | $CH_3$ | Q-137 ($R_7$ = H, $R_8$ = H, $R_9$ = $CH_3$) | H | 5-$CH_3$ | $OCH_3$ | $OCH_3$ | |
| J-3 | $C(CH_3)_3$ | Q-138 ($R_7$ = H, $R_8$ = H, $R_9$ = H) | H | H | $OCH_3$ | $OCH_3$ | |
| J-4 | $CH_3$ | Q-138 ($R_7$ = $CH_3$, $R_8$ = H, $R_9$ = H) | H | H | $CH_3$ | $OCH_3$ | |
| J-1 | $CH_3$ | Q-138 ($R_7$ = H, $R_8$ = H, $R_9$ = $CH_3$) | H | H | $CH_3$ | $OCH_3$ | |
| J-2 | $CH_3$ | Q-139 ($R_7$ = H, $R_8$ = H, $R_9$ = H) | H | H | $CH_3$ | $OCH_3$ | |
| J-3 | $CH_3$ | Q-139 ($R_7$ = $CH_3$, $R_8$ = H, $R_9$ = H) | $CH_3$ | H | $CH_3$ | $OCH_3$ | |
| J-4 | $CH_3$ | Q-139 ($R_7$ = $CH_3$, $R_8$ = $CH_3$, $R_9$ = H) | H | H | $OCH_3$ | $OCH_3$ | |
| J-1 | $CH_3$ | Q-140 ($R_7$ = H, $R_8$ = H, $R_9$ = H, $R_3$ = $CH_3$) | H | H | $OCH_3$ | $OCH_3$ | |
| J-2 | $CH_3$ | Q-140 ($R_7$ = H, $R_8$ = H, $R_9$ = $CH_3$, $R_3$ = H) | H | H | $OCH_3$ | $OCH_3$ | |
| J-3 | $CH_3$ | Q-140 ($R_7$ = H, $R_8$ = $CH_3$, $R_9$ = H, $R_3$ = $C_2H_5$) | H | 3-$OCH_3$ | $OCH_3$ | $OCH_3$ | |

TABLE 2-continued

General Formula 2

| J | M | Q | R | $R_1$ | X | Y | m.p. (°C.) |
|---|---|---|---|---|---|---|---|
| J-4 | $CH_3$ | Q-141 ($R_7$ = H, $R_8$ = H, $R_9$ = H, $R_3$ = $CH_3$) | H | H | $OCH_3$ | $OCH_3$ | |
| J-1 | $CH_3$ | Q-141 ($R_7$ = H, $R_8$ = H, $R_9$ = $CH_3$, $R_3$ = $CH_3$) | H | 5-Cl | $OCH_3$ | $OCH_3$ | |
| J-1 | $CH_3$ | Q-142 ($R_7$ = H, $R_8$ = H, $R_9$ = H, $R_{10}$ = H) | H | H | $OCH_3$ | $OCH_3$ | |
| J-2 | $CH_3$ | Q-142 ($R_7$ = $CH_3$, $R_8$ = H, $R_9$ = H, $R_{10}$ = H) | $CH_3$ | H | $OCH_3$ | $CH_3$ | |
| J-3 | $CH_3$ | Q-142 ($R_7$ = H, $R_8$ = H, $R_9$ = H, $R_{10}$ = $CH_3$) | H | 3-$OCH_3$ | $OCH_3$ | $OCH_3$ | |
| J-4 | $CH_3$ | Q-143 ($R_7$ = H, $R_8$ = H, $R_9$ = H, $R_3$ = $CH_3$) | H | H | $OCH_3$ | $OCH_3$ | |
| J-1 | $CH_3$ | Q-143 ($R_7$ = $CH_3$, $R_8$ = H, $R_9$ = $CH_3$, $R_3$ = $CH_3$) | H | 5-Cl | $OCH_3$ | $CH_3$ | |
| J-2 | $CH_3$ | Q-144 ($R_7$ = H, $R_8$ = H, $R_9$ = H, $R_3$ = $CH_3$) | H | H | $CH_3$ | $OCH_3$ | |
| J-3 | $CH_3$ | Q-144 ($R_7$ = $CH_3$, $R_8$ = H, $R_9$ = H, $R_3$ = $CH_3$) | H | H | $CH_3$ | $OCH_3$ | |
| J-4 | $CH_3$ | Q-144 ($R_7$ = H, $R_8$ = $C_2H_5$, $R_9$ = H, $R_3$ = $CH_3$) | H | 3-$CH_3$ | $OCH_3$ | $OCH_3$ | |
| J-1 | $C_6H_5$ | Q-145 ($R_7$ = H, $R_8$ = H, $R_9$ = H) | H | H | $OCH_3$ | $OCH_3$ | |
| J-2 | $CH_3$ | Q-145 ($R_7$ = H, $R_8$ = H, $R_9$ = $CH_3$) | H | H | $CH_3$ | $OCH_3$ | |
| J-3 | $CH_3$ | Q-145 ($R_7$ = $CH_3$, $R_8$ = H, $R_9$ = H) | H | H | $CH_3$ | $OCH_3$ | |
| J-4 | $CH_3$ | Q-146 ($R_7$ = H, $R_8$ = H, $R_9$ = H) | H | H | $CH_3$ | $OCH_3$ | |
| J-1 | $CH_3$ | Q-146 ($R_7$ = $CH_3$, $R_8$ = H, $R_9$ = H) | $CH_3$ | H | $CH_3$ | $OCH_3$ | |
| J-2 | $CH_3$ | Q-146 ($R_7$ = H, $R_8$ = H, $R_9$ = n-$C_4H_9$) | H | H | $OCH_3$ | $OCH_3$ | |
| J-3 | $CH_3$ | Q-147 ($R_7$ = H, $R_8$ = H, $R_9$ = H) | H | H | $OCH_3$ | $OCH_3$ | |
| J-4 | $CH_3$ | Q-147 ($R_7$ = $CH_3$, $R_8$ = H, $R_9$ = H) | H | H | $OCH_3$ | $OCH_3$ | |
| J-1 | $CH_3$ | Q-147 ($R_7$ = H, $R_8$ = H, $R_9$ = n-$C_4H_9$) | H | 5-$OCH_3$ | $OCH_3$ | $OCH_3$ | |
| J-2 | $CO_2CH_3$ | Q-148 ($R_7$ = H, $R_8$ = H, $R_9$ = H) | H | H | $OCH_3$ | $OCH_3$ | |
| J-3 | $CH_3$ | Q-148 ($R_7$ = $CH_3$, $R_8$ = H, $R_9$ = H) | H | 3-Cl | $OCH_3$ | $OCH_3$ | |
| J-4 | $CH_3$ | Q-149 ($R_7$ = H, $R_8$ = H, $R_9$ = H) | H | H | $OCH_3$ | $OCH_3$ | |
| J-1 | $CH_3$ | Q-149 ($R_7$ = H, $R_8$ = H, $R_9$ = $CH_3$) | $CH_3$ | H | $OCH_3$ | $OCH_3$ | |
| J-2 | $CH_3$ | Q-149 ($R_7$ = $CH_3$, $R_8$ = H, $R_9$ = H) | H | 5-$OCH_3$ | $OCH_3$ | $OCH_3$ | |
| J-3 | $CH_3$ | Q-150 ($R_7$ = H, $R_8$ = H, $R_9$ = H) | H | H | $OCH_3$ | $OCH_3$ | |
| J-1 | $CH_3$ | Q-150 ($R_7$ = H, $R_8$ = $CH_3$, $R_9$ = $CH_3$) | H | 3-Cl | $OCH_3$ | $CH_3$ | |
| J-2 | $CH_3$ | Q-151 ($R_7$ = H, $R_8$ = H, $R_9$ = H) | H | H | $CH_3$ | $OCH_3$ | |
| J-3 | $CH_3$ | Q-151 ($R_7$ = $CH_3$, $R_8$ = H, $R_9$ = H) | H | H | $CH_3$ | $OCH_3$ | |
| J-4 | $CH_3$ | Q-151 ($R_7$ = $CH_3$, $R_8$ = $CH_3$, $R_9$ = H) | H | 3-$CH_3$ | $OCH_3$ | $OCH_3$ | |
| J-1 | $CH_3$ | Q-152 ($R_7$ = H, $R_8$ = H, $R_9$ = H) | H | H | $OCH_3$ | $OCH_3$ | |
| J-2 | $CH_3$ | Q-152 ($R_7$ = $C_2H_5$, $R_8$ = H, $R_9$ = H) | H | H | $CH_3$ | $OCH_3$ | |
| J-1 | $CH_3$ | Q-152 ($R_7$ = $CH_3$, $R_8$ = $CH_3$, $R_9$ = H) | H | H | $CH_3$ | $OCH_3$ | |
| J-2 | $CH_3$ | Q-153 ($R_7$ = H, $R_8$ = H, $R_9$ = H, $R_{11}$ = $CH_3$) | H | H | $CH_3$ | $OCH_3$ | |
| J-3 | $CH_3$ | Q-153 ($R_7$ = H, $R_8$ = H, $R_9$ = H, $R_{11}$ = H) | $CH_3$ | H | $CH_3$ | $OCH_3$ | |
| J-4 | $CH_3$ | Q-153 ($R_7$ = $CH_3$, $R_8$ = H, $R_9$ = H, $R_{11}$ = $CH_3$) | H | H | $OCH_3$ | $OCH_3$ | |
| J-1 | $CH_3$ | Q-154 ($R_7$ = H, $R_8$ = H, $R_9$ = H, $R_{11}$ = $CH_3$) | H | H | $OCH_3$ | $OCH_3$ | |
| J-2 | $CH_3$ | Q-154 ($R_7$ = $CH_3$, $R_8$ = H, $R_9$ = H) | H | H | $OCH_3$ | $OCH_3$ | |
| J-3 | $CH_3$ | Q-154 ($R_7$ = H, $R_8$ = $CH_3$, $R_9$ = $CH_3$) | H | 3-$OCH_3$ | $OCH_3$ | $OCH_3$ | |
| J-4 | $C_6H_5$ | Q-155 ($R_7$ = H, $R_8$ = H, $R_9$ = H) | H | H | $OCH_3$ | $OCH_3$ | |
| J-1 | $CH_3$ | Q-155 ($R_7$ = $CH_3$, $R_8$ = $CH_3$, $R_9$ = H) | H | 5-Cl | $OCH_3$ | $OCH_3$ | |
| J-2 | $CH_3$ | Q-156 ($R_7$ = H, $R_8$ = H, $R_9$ = H) | H | H | $OCH_3$ | $OCH_3$ | |
| J-3 | $CH_3$ | Q-156 ($R_7$ = $C_2H_5$, $R_8$ = H, $R_9$ = H) | $CH_3$ | H | $OCH_3$ | $OCH_3$ | |
| J-4 | $CH_3$ | Q-156 ($R_7$ = $CH_3$, $R_8$ = $CH_3$, $R_9$ = H) | H | 3-$OCH_3$ | $OCH_3$ | $OCH_3$ | |
| J-1 | $CH_3$ | Q-157 ($R_7$ = H, $R_8$ = H, $R_9$ = H, $R_{10}$ = H) | H | H | $OCH_3$ | $OCH_3$ | |
| J-2 | $CH_3$ | Q-157 ($R_7$ = H, $R_8$ = H, $R_9$ = H, $R_{10}$ = $CH_3$) | H | 5-Cl | $OCH_3$ | $CH_3$ | |
| J-3 | $CH_3$ | Q-158 ($R_7$ = H, $R_8$ = H, $R_9$ = H) | H | H | $CH_3$ | $OCH_3$ | |
| J-4 | $CH_3$ | Q-158 ($R_7$ = H, $R_8$ = H, $R_9$ = $CH_3$) | H | H | $CH_3$ | $OCH_3$ | |
| J-1 | $CH_3$ | Q-158 ($R_7$ = $CH_3$, $R_8$ = H, $R_9$ = H) | H | 5-$CH_3$ | $OCH_3$ | $OCH_3$ | |
| J-2 | $C(CH_3)_3$ | Q-159 ($R_7$ = H, $R_8$ = H, $R_9$ = H) | H | H | $OCH_3$ | $OCH_3$ | |
| J-3 | $CH_3$ | Q-159 ($R_7$ = $CH_3$, $R_8$ = H, $R_9$ = H) | H | H | $CH_3$ | $OCH_3$ | |

TABLE 2-continued

General Formula 2

| J | M | Q | R | $R_1$ | X | Y | m.p. (°C.) |
|---|---|---|---|---|---|---|---|
| J-4 | $CH_3$ | Q-159 ($R_7$ = H, $R_8$ = H, $R_9$ = $CH_3$) | H | H | $CH_3$ | $OCH_3$ | |
| J-1 | $CH_3$ | Q-160 ($R_7$ = H, $R_8$ = H, $R_9$ = H, $R_{11}$ = $CH_3$) | H | H | $CH_3$ | $OCH_3$ | |
| J-2 | $CH_3$ | Q-160 ($R_7$ = H, $R_8$ = H, $R_9$ = $CH_3$, $R_{11}$ = H) | $CH_3$ | H | $CH_3$ | $OCH_3$ | |
| J-3 | $CH_3$ | Q-160 ($R_7$ = $CH_3$, $R_8$ = H, $R_9$ = H, $R_{11}$ = i-$C_3H_7$ | H | H | $OCH_3$ | $OCH_3$ | |
| J-4 | $CH_3$ | Q-161 ($R_7$ = H, $R_8$ = H, $R_9$ = H, $R_{11}$ = $CH_3$) | H | H | $OCH_3$ | $OCH_3$ | |
| J-1 | $CH_3$ | Q-161 ($R_7$ = $CH_3$, $R_8$ = H, $R_9$ = H, $R_{11}$ = H) | H | H | $OCH_3$ | $OCH_3$ | |
| J-2 | $CH_3$ | Q-161 ($R_7$ = H, $R_8$ = H, $R_9$ = $CH_3$, $R_{11}$ = $CH_3$) | H | 5-$OCH_3$ | $OCH_3$ | $OCH_3$ | |
| J-3 | $CH_3$ | Q-162 ($R_7$ = H, $R_8$ = H, $R_9$ = H, $R_{10}$ = H) | H | H | $OCH_3$ | $OCH_3$ | |
| J-4 | $CH_3$ | Q-162 ($R_7$ = H, $R_8$ = H, $R_9$ = H, $R_{10}$ = $CH_3$) | H | 3-Cl | $OCH_3$ | $OCH_3$ | |
| J-1 | —$CH_3$ | Q-163 ($R_7$ = H, $R_8$ = H, $R_9$ = H, $R_{10}$ = H) | H | $CH_3$ | $OCH_3$ | $OCH_3$ | |
| J-2 | —$CH_3$ | Q-163 ($R_7$ = H, $R_8$ = H, $R_9$ = H, $R_{10}$ = H) | H | $CH_3$ | $OCH_3$ | $OCH_3$ | |
| J-3 | —$CH_3$ | Q-163 ($R_7$ = H, $R_8$ = H, $R_9$ = H, $R_{10}$ = H) | H | $CH_3$ | $OCH_3$ | $OCH_3$ | |
| J-4 | —$CH_3$ | Q-163 ($R_7$ = H, $R_8$ = H, $R_9$ = H, $R_{10}$ = H) | H | $CH_3$ | $OCH_3$ | $OCH_3$ | |
| J-1 | $CH_3$ | Q-164 ($R_7$ = H) | H | $CH_3$ | $OCH_3$ | $OCH_3$ | |
| J-2 | $CH_3$ | Q-164 ($R_7$ = H) | H | $CH_3$ | $OCH_3$ | $OCH_3$ | |
| J-3 | $CH_3$ | Q-164 ($R_7$ = H) | H | $CH_3$ | $OCH_3$ | $OCH_3$ | |
| J-4 | $CH_3$ | Q-164 ($R_7$ = H) | H | $CH_3$ | $OCH_3$ | $OCH_3$ | |
| J-1 | $CH_3$ | Q-165 ($R_3$ = $CH_3$, $R_7$ = H) | H | $CH_3$ | $OCH_3$ | $OCH_3$ | |
| J-2 | $CH_3$ | Q-165 ($R_3$ = $CH_3$, $R_7$ = H) | H | $CH_3$ | $OCH_3$ | $OCH_3$ | |
| J-3 | $CH_3$ | Q-165 ($R_3$ = $CH_3$, $R_7$ = H) | H | $CH_3$ | $OCH_3$ | $OCH_3$ | |
| J-4 | $CH_3$ | Q-165 ($R_3$ = $CH_3$, $R_7$ = H) | H | $CH_3$ | $OCH_3$ | $OCH_3$ | |
| J-1 | $CH_3$ | Q-166 ($R_3$ = $CH_3$, $R_7$ = H) | H | $CH_3$ | $OCH_3$ | $OCH_3$ | |
| J-2 | $CH_3$ | Q-166 ($R_3$ = $CH_3$, $R_7$ = H) | H | $CH_3$ | $OCH_3$ | $OCH_3$ | |
| J-3 | $CH_3$ | Q-166 ($R_3$ = $CH_3$, $R_7$ = H) | H | $CH_3$ | $OCH_3$ | $OCH_3$ | |
| J-4 | $CH_3$ | Q-166 ($R_3$ = $CH_3$, $R_7$ = H) | H | $CH_3$ | $OCH_3$ | $OCH_3$ | |

TABLE 3

| | | General Formula 3 | | | | |
|---|---|---|---|---|---|---|
| J | M | Q | R | $R_1$ | $X_1$ | $Y_1$ |
| J-1 | $CH_3$ | Q-1 ($R_7$ = H, $R_8$ = H) | H | H | $CH_3$ | $CH_2$ |
| J-2 | $CH_2CH_3$ | Q-1 ($R_7$ = H, $R_8$ = H) | H | H | $CH_3$ | $CH_2$ |
| J-3 | $CH_2CH_2CH_3$ | Q-1 ($R_7$ = H, $R_8$ = H) | $CH_3$ | H | $OCH_3$ | $CH_2$ |
| J-4 | $CH(CH_3)_2$ | Q-1 ($R_7$ = H, $R_8$ = H) | $CH_3$ | H | $OC_2H_5$ | $CH_2$ |
| J-1 | $C(CH_3)_3$ | Q-1 ($R_7$ = H, $R_8$ = H) | $CH_3$ | H | $OCF_2H$ | $CH_2$ |
| J-2 | H | Q-1 ($R_7$ = H, $R_8$ = H) | $CH_3$ | H | $CH_3$ | O |
| J-3 | $CH_2CH{=}CH_2$ | Q-1 ($R_7$ = H, $R_8$ = H) | $CH_3$ | H | $OCH_3$ | O |
| J-4 | $CH_2CH{=}CHCH_3$ | Q-1 ($R_7$ = H, $R_8$ = H) | $CH_3$ | H | $OC_2H_5$ | O |
| J-1 | $C_6H_5$ | Q-1 ($R_7$ = H, $R_8$ = H) | $CH_3$ | H | $OCF_2H$ | O |
| J-2 | $C_6H_4$—4Cl | Q-1 ($R_7$ = H, $R_8$ = H) | H | H | $CH_3$ | $CH_2$ |
| J-3 | $C_6H_4$—3-$NO_2$ | Q-1 ($R_7$ = H, $R_8$ = H) | H | 3-$OCH_3$ | $CH_3$ | $CH_2$ |
| J-4 | $C_6H_4$—3Cl | Q-1 ($R_7$ = H, $R_8$ = H) | H | 3-$OCH_2CH_3$ | $CH_3$ | $CH_2$ |
| J-1 | $C_6H_4$—2-$OCH_3$ | Q-1 ($R_7$ = H, $R_8$ = H) | H | 5-$OCH(CH_3)_2$ | $CH_3$ | $CH_2$ |
| J-2 | $CO_2CH_3$ | Q-1 ($R_7$ = H, $R_8$ = H) | H | 5-$CH_3$ | $CH_3$ | $CH_2$ |
| J-3 | $CO_2CH_2CH_3$ | Q-1 ($R_7$ = H, $R_8$ = H) | H | 3-$CH_2CH_3$ | $CH_3$ | $CH_2$ |
| J-4 | $SO_2CH_3$ | Q-1 ($R_7$ = H, $R_8$ = H) | H | 3-$CH(CH_3)_2$ | $CH_3$ | $CH_2$ |
| J-1 | $SO_2N(CH_3)_2$ | Q-1 ($R_7$ = H, $R_8$ = H) | H | 5-$CH_2F$ | $CH_3$ | $CH_2$ |
| J-2 | $CH_2C{\equiv}CH$ | Q-1 ($R_7$ = H, $R_8$ = H) | H | 5-$OCH_2CH_2Br$ | $CH_3$ | $CH_2$ |
| J-3 | $CH(CH_3)_2$ | Q-1 ($R_7$ = H, $R_8$ = H) | H | 3-$OCH(CH_3)(CH_2Cl)$ | $CH_3$ | $CH_2$ |
| J-4 | $C(CH_3)_3$ | Q-1 ($R_7$ = H, $R_8$ = H) | H | 3-$CH_2F$ | $CH_3$ | $CH_2$ |
| J-1 | $C_6H_5$ | Q-1 ($R_7$ = H, $R_8$ = H) | H | 5-$CH_2CH_2Br$ | $CH_3$ | $CH_2$ |
| J-2 | $C_6H_4$—3-Cl | Q-1 ($R_7$ = H, $R_8$ = H) | H | 5-$CH(CH_3)(CH_2Cl)$ | $CH_3$ | $CH_2$ |
| J-3 | $CH_2CH_2CH_2CH_3$ | Q-1 ($R_7$ = H, $R_8$ = H) | H | 3-$SCH_3$ | $CH_3$ | $CH_2$ |
| J-4 | $CH_3$ | Q-1 ($R_7$ = H, $R_8$ = H) | H | 3-$SCH_2CH_3$ | $CH_3$ | $CH_2$ |
| J-1 | $CH_3$ | Q-1 ($R_7$ = H, $R_8$ = H) | H | 5-$SCH(CH_3)_2$ | $CH_3$ | $CH_2$ |
| J-2 | $CH_3$ | Q-1 ($R_7$ = H, $R_8$ = H) | H | 5-$SCH_2F$ | $CH_3$ | $CH_2$ |
| J-3 | $CH_3$ | Q-1 ($R_7$ = H, $R_8$ = H) | H | 3-$SCH_2CH_2Br$ | $CH_3$ | $CH_2$ |
| J-4 | $CH_3$ | Q-1 ($R_7$ = H, $R_8$ = H) | H | 3-$SCH(CH_3)(CH_2Cl)$ | $CH_3$ | $CH_2$ |
| J-1 | $CH_3$ | Q-1 ($R_7$ = H, $R_8$ = H) | H | 5-$SOCH_3$ | $CH_3$ | $CH_2$ |
| J-2 | $CH_3$ | Q-1 ($R_7$ = H, $R_8$ = H) | H | 5-$SOCH_3$ | $CH_3$ | $CH_2$ |
| J-1 | $CH_3$ | Q-1 ($R_7$ = H, $R_8$ = H) | H | 5-$SO_2N(CH_3)_2$ | $CH_3$ | $CH_2$ |
| J-2 | $CH_3$ | Q-1 ($R_7$ = H, $R_8$ = H) | H | 5-$CO_2CH_3$ | $CH_3$ | $CH_2$ |
| J-3 | $CH_3$ | Q-1 ($R_7$ = H, $R_8$ = H) | H | 3-$CO_2CH_2$ | $CH_3$ | $CH_2$ |
| J-4 | $CH_3$ | Q-1 ($R_7$ = H, $R_8$ = H) | H | 3-$CO_2CH_3$ | $CH_3$ | $CH_2$ |
| J-1 | $CH_3$ | Q-1 ($R_7$ = H, $R_8$ = H) | H | 5-$CO_2CH_3$ | $CH_3$ | $CH_2$ |
| J-2 | $CH_3$ | Q-1 ($R_7$ = H, $R_8$ = H) | H | 5-Cl | $CH_3$ | $CH_2$ |
| J-3 | $CH_3$ | Q-1 ($R_7$ = H, $R_8$ = H) | H | 3-Br | $CH_3$ | $CH_2$ |
| J-4 | $CH_3$ | Q-1 ($R_7$ = H, $R_8$ = H) | H | 3-F | $CH_3$ | $CH_2$ |
| J-1 | $CH_3$ | Q-1 ($R_7$ = H, $R_8$ = H) | H | 5-I | $CH_3$ | $CH_2$ |
| J-2 | $CH_3$ | Q-1 ($R_7$ = H, $R_8$ = H) | H | 5-$CH_3$ | $CH_3$ | $CH_2$ |
| J-3 | $CH_2CH_3$ | Q-1 ($R_7$ = H, $R_8$ = H) | H | 3-$CF_3$ | $CH_3$ | $CH_2$ |
| J-4 | $CH_3$ | Q-1 ($R_7$ = H, $R_8$ = H) | H | 3-$OCF_2H$ | $CH_3$ | $CH_2$ |
| J-1 | $CH_3$ | Q-1 ($R_7$ = H, $R_8$ = H) | H | 5-$CH_3$ | $CH_3$ | O |
| J-2 | $CH_3$ | Q-1 ($R_7$ = H, $R_8$ = H) | H | 5-$CH_2CH_3$ | $CH_3$ | O |
| J-3 | $CH_3$ | Q-1 ($R_7$ = H, $R_8$ = H) | H | 3-$CH(CH_3)_2$ | $CH_3$ | O |
| J-4 | $CH_3$ | Q-1 ($R_7$ = H, $R_8$ = H) | H | 3-$OCH_3$ | $CH_3$ | O |
| J-1 | $CH_3$ | Q-1 ($R_7$ = H, $R_8$ = H) | H | 5-$OC_2H_5$ | $CH_3$ | O |
| J-2 | $CH_3$ | Q-1 ($R_7$ = H, $R_8$ = H) | H | 5-$OCH(CH_3)_2$ | $CH_3$ | O |
| J-3 | $CH_3$ | Q-1 ($R_7$ = H, $R_8$ = H) | H | 3-$OCH_2F$ | $CH_3$ | O |
| J-4 | $CH_3$ | Q-1 ($R_7$ = H, $R_8$ = H) | H | 3-$OCH_2CH_2Br$ | $CH_3$ | O |
| J-1 | $CH_3$ | Q-1 ($R_7$ = H, $R_8$ = H) | H | 5-$OCH(CH_3)(CH_2Cl)$ | $CH_3$ | O |
| J-2 | $CH_3$ | Q-1 ($R_7$ = H, $R_8$ = H) | H | 5-$CH_2F$ | $CH_3$ | O |
| J-3 | $CH_2CH_2CH_3$ | Q-1 ($R_7$ = H, $R_8$ = H) | H | 3-$CH_2CH_2Br$ | $CH_3$ | O |
| J-4 | $CH_3$ | Q-1 ($R_7$ = H, $R_8$ = H) | H | 3-$CH(CH_3)(CH_2Cl)$ | CH | O |
| J-1 | $CH_3$ | Q-1 ($R_7$ = H, $R_8$ = H) | H | 5-$SCH_3$ | $CH_3$ | O |
| J-2 | $CH_3$ | Q-1 ($R_7$ = H, $R_8$ = H) | H | 5-$SCH_2CH_3$ | $CH_3$ | O |
| J-3 | $CH_3$ | Q-1 ($R_7$ = H, $R_8$ = H) | H | 3-$SCH(CH_3)_2$ | $CH_3$ | O |
| J-4 | $CH_3$ | Q-1 ($R_7$ = H, $R_8$ = H) | H | 3-$SCH_2F$ | $CH_3$ | O |
| J-1 | $CH_3$ | Q-1 ($R_7$ = H, $R_8$ = H) | H | 5-$SCH_2CH_2Br$ | $CH_3$ | O |
| J-2 | $CH_3$ | Q-1 ($R_7$ = H, $R_8$ = H) | H | 5-$SCH(CH_3)(CH_2Cl)$ | $CH_3$ | O |
| J-3 | $CH_3$ | Q-1 ($R_7$ = H, $R_8$ = H) | H | 3-$SOCH_3$ | $CH_3$ | O |
| J-4 | $CH_3$ | Q-1 ($R_7$ = H, $R_8$ = H) | H | 3-$SO_2CH_3$ | $CH_3$ | O |
| J-1 | $CH_3$ | Q-1 ($R_7$ = H, $R_8$ = H) | H | 5-$OCH_2CH_2Br$ | $CH_3$ | O |
| J-2 | $CH_3$ | Q-1 ($R_7$ = H, $R_8$ = H) | H | 5-$CO_2CH_3$ | $CH_3$ | O |
| J-3 | $CH_3$ | Q-1 ($R_7$ = H, $R_8$ = H) | H | 3-$SO_2N(CH_3)_2$ | $CH_3$ | O |
| J-4 | $CH_3$ | Q-1 ($R_7$ = H, $R_8$ = H) | H | 3-$CO_2CH_3$ | $CH_3$ | O |
| J-1 | $CH_3$ | Q-1 ($R_7$ = H, $R_8$ = H) | H | 5-$CO_2CH_3$ | $CH_3$ | O |
| J-2 | $CH_3$ | Q-1 ($R_7$ = H, $R_8$ = H) | H | 5-Cl | $CH_3$ | O |
| J-3 | $CH_3$ | Q-1 ($R_7$ = H, $R_8$ = H) | H | 3-Br | $CH_3$ | O |
| J-4 | $CH(CH_3)_2$ | Q-1 ($R_7$ = H, $R_8$ = H) | H | 3-F | $CH_3$ | O |
| J-1 | $CH_3$ | Q-1 ($R_7$ = H, $R_8$ = H) | H | 5-I | $CH_3$ | O |
| J-2 | $CH_3$ | Q-1 ($R_7$ = H, $R_8$ = H) | H | 5-$CH_3$ | $CH_3$ | O |
| J-3 | $CH_3$ | Q-1 ($R_7$ = H, $R_8$ = H) | H | 3-$CF_3$ | $CH_3$ | O |
| J-4 | $CH_3$ | Q-1 ($R_7$ = H, $R_8$ = H) | H | 3-$OCF_2H$ | $CH_3$ | O |
| J-1 | $CH_3$ | Q-1 ($R_7$ = H, $R_8$ = H) | H | 5-$SO_2N(CH_3)_2$ | $OCH_3$ | O |
| J-2 | $CH_3$ | Q-1 ($R_7$ = H, $R_8$ = H) | H | 5-$SOCH_3$ | $OCH_3$ | O |
| J-3 | $CH_3$ | Q-1 ($R_7$ = H, $R_8$ = H) | H | 3-$CO_2CH_3$ | $OCH_3$ | O |
| J-4 | $CH_3$ | Q-1 ($R_7$ = H, $R_8$ = H) | H | 3-$CO_2CH_3$ | $OCH_3$ | O |
| J-1 | $CH_3$ | Q-1 ($R_7$ = H, $R_8$ = H) | H | H | $CH_3$ | O |
| J-2 | $CH_3$ | Q-1 ($R_7$ = H, $R_8$ = H) | H | H | $OCH_3$ | O |

TABLE 3-continued

General Formula 3

| J | M | Q | R | $R_1$ | $X_1$ | $Y_1$ |
|---|---|---|---|---|---|---|
| J-3 | $CH_3$ | Q-1 ($R_7$ = H, $R_8$ = H) | H | H | $OC_2H_5$ | O |
| J-4 | $CH_3$ | Q-1 ($R_7$ = H, $R_8$ = H) | H | H | $OCF_2H$ | O |
| J-1 | $CH_3$ | Q-1 ($R_7$ = H, $R_8$ = H) | H | H | $OCH_3$ | $CH_2$ |
| J-2 | $CH_3$ | Q-1 ($R_7$ = H, $R_8$ = H) | H | H | $OC_2H_5$ | $CH_2$ |
| J-3 | $C(CH_3)_3$ | Q-1 ($R_7$ = H, $R_8$ = H) | H | H | $OCF_2H$ | $CH_2$ |
| J-4 | $CH_3$ | Q-1 ($R_7$ = H, $R_8$ = $CH_3$) | H | H | $CH_3$ | O |
| J-1 | $CH_3$ | Q-1 ($R_7$ = H, $R_8$ = $CH_3$) | H | H | $CH_3$ | $CH_2$ |
| J-2 | $CH_3$ | Q-1 ($R_7$ = H, $R_8$ = $CH_2CH)_3$ | H | H | $CH_3$ | $CH_2$ |
| J-3 | $CH_3$ | Q-1 ($R_7$ = H, $R_8$ = $CH(CH_3)_2$) | H | H | $OCH_3$ | $CH_2$ |
| J-4 | $CH_3$ | Q-1 ($R_7$ = H, $R_8$ = n-$C_4H_9$) | H | H | $OCH_3$ | O |
| J-1 | $CH_3$ | Q-1 ($R_7$ = H, $R_8$ = $CH_3$) | H | H | $OCH_3$ | O |
| J-3 | $C_6H_5$ | Q-37 ($R_7$ = H, $R_8$ = H, $R_2$ = H) | H | H | $CH_3$ | $CH_2$ |
| J-4 | $CH_3$ | Q-37 ($R_7$ = H, $R_8$ = H, $R_2$ = i-$C_3H_7$) | H | H | $CH_3$ | O |
| J-1 | $CH_3$ | Q-37 ($R_7$ = H, $R_8$ = H, $R_2$ = n-$C_4H_9$) | H | 5-$OCH_3$ | $OCH_3$ | $CH_2$ |
| J-2 | $CH_3$ | Q-98 ($R_7$ = H, $R_8$ = H, $R_9$ = H) | H | H | $CH_3$ | $CH_2$ |
| J-3 | $CH_3$ | Q-98 ($R_7$ = $CH_3$, $R_8$ = H, $R_9$ = H) | H | H | $CH_3$ | O |
| J-4 | $CH_3$ | Q-98 ($R_7$ = H, $R_8$ = H, $R_9$ = i-$C_3H_7$) | H | 3-$OCH_3$ | $OCH_3$ | $CH_2$ |
| J-1 | $CH_3$ | Q-98 ($R_7$ = H, $R_8$ = H, $R_9$ = H) | H | H | $CH_3$ | O |
| J-3 | $CH_3$ | Q-105 ($R_7$ = H, $R_8$ = H, $R_9$ = H, $R_2$ = H) | H | H | $CH_3$ | $CH_2$ |
| J-4 | $CH_3$ | Q-105 ($R_7$ = $CH_3$, $R_8$ = H, $R_9$ = H, $R_2$ = $CH_3$) | H | H | $CH_3$ | O |
| J-1 | $CH_3$ | Q-105 ($R_7$ = H, $R_8$ = $CH_3$, $R_9$ = H, $R_2$ = $C_2H_5$) | H | 5-$OCH_3$ | $OCH_3$ | $CH_2$ |
| J-2 | $CH_3$ | Q-105 ($R_7$ = H, $R_8$ = $CH_3$, $R_9$ = H, $R_2$ = H) | H | $CH_3$ | $CH_3$ | O |
| J-2 | $CH_3$ | Q-138 ($R_7$ = H, $R_8$ = H, $R_9$ = H) | H | H | $CH_3$ | $CH_2$ |
| J-3 | $CH_3$ | Q-138 ($R_7$ = $CH_3$, $R_8$ = H, $R_9$ = H) | H | H | $CH_3$ | O |
| J-4 | $CH_3$ | Q-138 ($R_7$ = H, $R_8$ = H, $R_9$ = $CH_3$) | H | H | $OCH_3$ | $CH_2$ |
| J-1 | $CH_3$ | Q-138 ($R_7$ = H, $R_8$ = H, $R_9$ = H) | H | $CH_3$ | $CH_3$ | O |
| J-1 | $CH_3$ | Q-143 ($R_7$ = H, $R_8$ = H, $R_9$ = H, $R_3$ = $CH_3$) | H | H | $CH_3$ | $CH_2$ |
| J-2 | $CH_3$ | Q-143 ($R_7$ = H, $R_8$ = H, $R_9$ = H, $R_3$ = H) | H | H | $CH_3$ | O |
| J-3 | $CH_3$ | Q-143 ($R_7$ = $CH_3$, $R_8$ = H, $R_3$= $CH_3$) | H | 3-Cl | $OCH_3$ | $CH_2$ |
| J-3 | $CH_3$ | Q-143 ($R_7$ = H, $R_8$ = H, $R_9$ = H, $R_3$ = $CH_3$) | H | $CH_3$ | $OCH_3$ | O |

TABLE 4

General Formula 4

| J | M | Q | R | $R_1$ | $X_1$ |
|---|---|---|---|---|---|
| J-1 | $CH_3$ | Q-1 ($R_7$ = H, $R_8$ = H) | H | H | $CH_3$ |
| J-2 | $CH_2CH_3$ | Q-1 ($R_7$ = H, $R_8$ = H) | $CH_3$ | H | $OCH_3$ |
| J-3 | $CH_2CH_2CH_3$ | Q-1 ($R_7$ = H, $R_8$ = H) | $CH_3$ | H | $OC_2H_5$ |
| J-4 | $CH(CH_3)_2$ | Q-1 ($R_7$ = H, $R_8$ = H) | $CH_3$ | H | $OCF_2H$ |
| J-1 | $C(CH_3)_3$ | Q-1 ($R_7$ = H, $R_8$ = H) | H | 5-$CH_3$ | $CH_3$ |
| J-2 | H | Q-1 ($R_7$ = H, $R_8$ = H) | H | 5-$CH_2CH_3$ | $CH_3$ |
| J-3 | $CH_2CH{=}CH_2$ | Q-1 ($R_7$ = H, $R_8$ = H) | H | 3-$CH(CH_3)_2$ | $CH_3$ |
| J-4 | $CH_2CH{=}CHCH_3$ | Q-1 ($R_7$ = H, $R_8$ = H) | H | 3-$OCH_3$ | $CH_3$ |
| J-1 | $C_6H_5$ | Q-1 ($R_7$ = H, $R_8$ = H) | H | 5-$OCH_2CH_3$ | $CH_3$ |
| J-2 | $C_6H_5$—4-Cl | Q-1 ($R_7$ = H, $R_8$ = H) | H | 5-$OCH_2(CH_3)_2$ | $CH_3$ |
| J-3 | $C_6H_4$—3-$NO_2$ | Q-1 ($R_7$ = H, $R_8$ = H) | H | 3-$OCH_2F$ | $CH_3$ |
| J-4 | $C_6H_4$3-$CH_3$ | Q-1 ($R_7$ = H, $R_8$ = H) | H | 3-$OCH_2CH_2Br$ | $CH_3$ |
| J-1 | $C_6H_4$—2-$OCH_3$ | Q-1 ($R_7$ = H, $R_8$ = H) | H | 5-$OCH(CH_3)(CH_2Cl)$ | $CH_3$ |
| J-2 | $CO_2CH_3$ | Q-1 ($R_7$ = H, $R_8$ = H) | H | 5-$CH_2F$ | $CH_3$ |
| J-3 | $CO_3CH_2CH_3$ | Q-1 ($R_7$ = H, $R_8$ = H) | H | 3-$CH_2CH_2Br$ | $CH_3$ |
| J-4 | $SO_2CH_3$ | Q-1 ($R_7$ = H, $R_8$ = H) | H | 3-$CH(CH_3)(CH_2Cl)$ | $CH_3$ |
| J-1 | $SO_2N(CH_3)_2$ | Q-1 ($R_7$ = H, $R_8$ = H) | H | 5-Cl | $CH_3$ |
| J-2 | $CH_2CH_2CH_2CH_3$ | Q-1 ($R_7$ = H, $R_8$ = H) | H | 5-$SCH_2CH_3$ | $CH_3$ |
| J-3 | $CH_2C{\equiv}CH$ | Q-1 ($R_7$ = H, $R_8$ = H) | H | 3-$SCH(CH_3)_2$ | $CH_3$ |
| J-4 | $CH(CH_3)_2$ | Q-1 ($R_7$ = H, $R_8$ = H) | H | 3-$SCH_2F$ | $CH_3$ |
| J-1 | $CH(CH_3)_2$ | Q-1 ($R_7$ = H, $R_8$ = H) | H | 5-$SCH_2CH_2Br$ | $CH_3$ |
| J-2 | $C_6H_5$ | Q-1 ($R_7$ = H, $R_8$ = H) | H | 5-$SCH(CH_3)(CH_2Cl)$ | $CH_3$ |
| J-3 | $C_6H_4$—3-Cl | Q-1 ($R_7$ = H, $R_8$ = H) | H | 3-$SOCH_3$ | $CH_3$ |
| J-4 | $CH_3$ | Q-1 ($R_7$ = H, $R_8$ = H) | H | 3-$SO_2CH_3$ | $CH_3$ |
| J-1 | $CH_3$ | Q-1 ($R_7$ = H, $R_8$ = H) | H | 5-$SO_2N(CH_3)_2$ | $CH_3$ |
| J-2 | $CH_3$ | Q-1 ($R_7$ = H, $R_8$ = H) | H | 5-$CO_2CH_3$ | $CH_3$ |
| J-3 | $CH_3$ | Q-1 ($R_7$ = H, $R_8$ = H) | H | 3-$CO_2CH_2CH_3$ | $CH_3$ |
| J-4 | $CH_3$ | Q-1 ($R_7$ = H, $R_8$ = H) | H | 3-$CO_2CH_3$ | $CH_3$ |
| J-1 | $CH_3$ | Q-1 ($R_7$ = H, $R_8$ = H) | H | 5-$CO_2CH_3$ | $CH_3$ |
| J-1 | $CH_3$ | Q-1 ($R_7$ = H, $R_8$ = H) | H | 5-Cl | $CH_3$ |
| J-2 | $CH_3$ | Q-1 ($R_7$ = H, $R_8$ = H) | H | 5-Br | $CH_3$ |
| J-3 | $CH_3$ | Q-1 ($R_7$ = H, $R_8$ = H) | H | 3-F | $CH_3$ |
| J-4 | $CH_3$ | Q-1 ($R_7$ = H, $R_8$ = H) | H | 3-I | $CH_3$ |
| J-1 | $CH_3$ | Q-1 ($R_7$ = H, $R_8$ = H) | H | 5-$CH_3$ | $CH_3$ |
| J-2 | $CH_3$ | Q-1 ($R_7$ = H, $R_8$ = H) | H | 5-$CF_3$ | $CH_3$ |
| J-3 | $CH_3$ | Q-1 ($R_7$ = H, $R_8$ = H) | H | 3-$OCF_2H$ | $CH_3$ |
| J-4 | $CH_2CH_3$ | Q-1 ($R_7$ = H, $R_8$ = H) | H | 3-$SO_2N(CH_3)_2$ | $CH_3$ |
| J-1 | $CH_3$ | Q-1 ($R_7$ = H, $R_8$ = H) | H | 5-$SOCH_3$ | $CH_3$ |
| J-2 | $CH_3$ | Q-1 ($R_7$ = H, $R_8$ = H) | H | 5-$SO_2CH(CH_3)_2$ | $CH_3$ |
| J-3 | $CH_3$ | Q-1 ($R_7$ = H, $R_8$ = H) | H | 3-$CO_2CH_3$ | $CH_3$ |
| J-4 | $CH_3$ | Q-1 ($R_7$ = H, $R_8$ = H) | H | H | $OCH_3$ |
| J-1 | $CH_3$ | Q-1 ($R_7$ = H, $R_8$ = H) | H | H | $OC_2H_5$ |
| J-2 | $CH_3$ | Q-1 ($R_7$ = H, $R_8$ = H) | H | H | $OCF_2H$ |

TABLE 4-continued

General Formula 4

| J | M | Q | R | $R_1$ | $X_1$ |
|---|---|---|---|---|---|
| J-3 | $CH_3$ | Q-1 ($R_7$ = H, $R_8$ = $CH_3$) | H | H | $CH_3$ |
| J-4 | $CH_3$ | Q-1 ($R_7$ = H, $R_8$ = $CH_2CH_3$) | H | H | $CH_3$ |
| J-1 | $CH_3$ | Q-1 ($R_7$ = H, $R_8$ = $CH(CH_3)_2$) | H | H | $OCH_3$ |
| J-2 | $CH_3$ | Q-1 ($R_7$ = H, $R_8$ = n-$C_4H_9$) | H | H | $OCH_3$ |
| J-3 | $CH_3$ | Q-1 ($R_7$ = H, $R_8$ = $CH_3$) | H | H | $OCH_3$ |
| J-1 | $CH_3$ | Q-37 ($R_7$ = H, $R_8$ = H, $R_2$ = H) | H | H | $CH_3$ |
| J-2 | $CH_3$ | Q-37 ($R_7$ = H, $R_8$ = H, $R_2$ = i-$C_3H_7$) | H | H | $CH_3$ |
| J-3 | $CH_3$ | Q-37 ($R_7$ = H, $R_8$ = H, $R_2$ = n-$C_4H_9$) | H | 3-$OCH_3$ | $OCH_3$ |
| J-4 | $CH_3$ | Q-37 ($R_7$ = H, $R_8$ = H, $R_2$ = H) | H | $CH_3$ | $OCH_3$ |
| J-3 | $CH_3$ | Q-98 ($R_7$ = H, $R_8$ = H, $R_9$ = H) | H | H | $CH_3$ |
| J-4 | $CH_3$ | Q-98 ($R_7$ = $CH_3$, $R_8$ = H, $R_9$ = H) | H | H | $CH_3$ |
| J-1 | $CH_3$ | Q-98 ($R_7$ = H, $R_8$ = H, $R_9$ = i-$C_3H_7$) | H | 5-$OCH_3$ | $OCH_3$ |
| J-2 | $CH_3$ | Q-98 ($R_7$ = H, $R_8$ = H, $R_9$ = H) | H | $CH_3$ | $OCH_3$ |
| J-4 | $CH_3$ | Q-105 ($R_7$ = H, $R_8$ = H, $R_9$ = H, $R_2$ = H) | H | H | $CH_3$ |
| J-1 | $CH_3$ | Q-105 ($R_7$ = $CH_3$, $R_8$ = H, $R_9$ = H, $R_2$ = $CH_3$) | H | H | $CH_3$ |
| J-2 | $CH_3$ | Q-105 ($R_7$ = H, $R_8$ = $CH_3$, $R_9$ = H, $R_2$ = $C_2H_5$) | H | 5-$OCH_3$ | $OCH_3$ |
| J-3 | $CH_3$ | Q-105 ($R_7$ = H, $R_8$ = $CH_3$, $R_9$ = H, $R_2$ = H) | H | $CH_3$ | $OCH_3$ |
| J-3 | $CH_3$ | Q-138 ($R_7$ = H, $R_8$ = H; $R_9$ = H) | H | H | $CH_3$ |
| J-4 | $CH_3$ | Q-138 ($R_7$ = $CH_3$, $R_8$ = H, $R_9$ = H) | H | H | $CH_3$ |
| J-1 | $CH_3$ | Q-138 ($R_7$ = H, $R_8$ = H, $R_9$ = $CH_3$) | H | H | $OCH_3$ |
| J-2 | $CH_3$ | Q-138 ($R_7$ = H, $R_8$ = H, $R_9$ = H) | H | $CH_3$ | $OCH_3$ |
| J-2 | $CH_3$ | Q-143 ($R_7$ = H, $R_8$ = H, $R_9$ = H, $R_3$ = $CH_3$) | H | H | $CH_3$ |
| J-3 | $CH_3$ | Q-143 ($R_7$ = H, $R_8$ = H, $R_9$ = H, $R_3$ = H) | H | H | $CH_3$ |
| J-4 | $CH_3$ | Q-143 ($R_7$ = $CH_3$, $R_8$ = H, $R_9$ = $CH_3$, $R_3$ = $CH_3$) | H | 3-Cl | $OCH_3$ |
| J-1 | $CH_3$ | Q-143 ($R_7$ = H, $R_8$ = H, $R_9$ = H, $R_3$ = H) | H | $CH_3$ | $OCH_3$ |

TABLE 5

General Formula 5

| J | M | Q | R | $R_1$ | $X_1$ | $Y_2$ |
|---|---|---|---|---|---|---|
| J-1 | $CH_3$ | Q-1 ($R_7$ = H, $R_8$ = H) | H | H | $CH_3$ | $CH_3$ |
| J-2 | $CH_2CH_3$ | Q-1 ($R_7$ = H, $R_8$ = H) | H | H | $CH_3$ | H |
| J-3 | $CH_2CH_2CH_3$ | Q-1 ($R_7$ = H, $R_8$ = H) | H | H | $OCH_3$ | $CH_3$ |
| J-4 | $CH(CH_3)_2$ | Q-1 ($R_7$ = H, $R_8$ = H) | H | H | $OC_2H_5$ | $CH_3$ |
| J-1 | $CH_2CH_2CH_2CH_3$ | Q-1 ($R_7$ = H, $R_8$ = H) | H | H | $OCF_2H$ | $CH_3$ |
| J-2 | $C(CH_3)_3$ | Q-1 ($R_7$ = H, $R_8$ = H) | H | H | $OCH_3$ | H |
| J-3 | $CH_2CH{=}CH_2$ | Q-1 ($R_7$ = H, $R_8$ = H) | H | H | $OC_2H_5$ | H |
| J-4 | $CH_2CH{=}CHCH_3$ | Q-1 ($R_7$ = H, $R_8$ = H) | H | H | $OCF_2H$ | H |
| J-1 | $C_6H_5$ | Q-1 ($R_7$ = H, $R_8$ = H) | CH | H | $CH_3$ | $CH_3$ |
| J-2 | $C_6H_4$—4-Cl | Q-1 ($R_7$ = H, $R_8$ = H) | $CH_3$ | H | $OCH_3$ | $CH_3$ |
| J-3 | $C_6H_4$—3-$NO_2$ | Q-1 ($R_7$ = H, $R_8$ = H) | $CH_3$ | H | $CH_3$ | H |
| J-4 | $C_6H_4$—3-$CH_3$ | Q-1 ($R_7$ = H, $R_8$ = H) | H | 3-$OCH_3$ | $OCH_3$ | H |
| J-1 | $C_6H_4$—2-$OCH_3$ | Q-1 ($R_7$ = H, $R_8$ = H) | H | 5-$OCH_2CH_3$ | $OCH_3$ | H |
| J-2 | $CO_2CH_3$ | Q-1 ($R_7$ = H, $R_8$ = H) | H | 5-$OCH(CH_3)_2$ | $OCH_3$ | H |
| J-3 | $CO_2CH_2CH_3$ | Q-1 ($R_7$ = H, $R_8$ = H) | H | 3-$CH_3$ | $OCH_3$ | H |
| J-4 | $SO_2CH_3$ | Q-1 ($R_7$ = H, $R_8$ = H) | H | 3-$CH_2CH_3$ | $OCH_3$ | H |
| J-1 | $SO_2N(CH_3)_2$ | Q-1 ($R_7$ = H, $R_8$ = H) | H | 5-$CH(CH_3)_2$ | $OCH_3$ | H |
| J-2 | H | Q-1 ($R_7$ = H, $R_8$ = H) | H | 5-$OCF_2H$ | $OCH_3$ | H |
| J-3 | $CH_2C{\equiv}CH$ | Q-1 ($R_7$ = H, $R_8$ = H) | H | 3-$OCH_2CH_2Br$ | $OCH_3$ | H |
| J-4 | $CH_3$ | Q-1 ($R_7$ = H, $R_8$ = H) | H | 3-$OCH(CH_3)(CH_2Cl)$ | $OCH_3$ | H |
| J-1 | $CH_3$ | Q-1 ($R_7$ = H, $R_8$ = H) | H | 5-$CH_2F$ | $OCH_3$ | H |
| J-2 | $CH_3$ | Q-1 ($R_7$ = H, $R_8$ = H) | H | 5-$CH_2CH_2Br$ | $OCH_3$ | H |
| J-3 | $CH_3$ | Q-1 ($R_7$ = H, $R_8$ = H) | H | 3-$CH(CH_3)(CH_2Cl)$ | $OCH_3$ | H |
| J-4 | $CH_3$ | Q-1 ($R_7$ = H, $R_8$ = H) | H | 3-$SCH_3$ | $OCH_3$ | H |
| J-1 | $CH_3$ | Q-1 ($R_7$ = H, $R_8$ = H) | H | 5-$SCH_2CH_3$ | $OCH_3$ | H |
| J-2 | $CH_3$ | Q-1 ($R_7$ = H, $R_8$ = H) | H | 5-$SCH(CH_3)_2$ | $OCH_3$ | H |
| J-3 | $CH_3$ | Q-1 ($R_7$ = H, $R_8$ = H) | H | 3-$SCH_2F$ | $OCH_3$ | H |
| J-4 | $CH_3$ | Q-1 ($R_7$ = H, $R_8$ = H) | H | 3-$SCH_2CH_2Br$ | $OCH_3$ | H |
| J-1 | $CH_3$ | Q-1 ($R_7$ = H, $R_8$ = H) | H | 5-$SCH(CH_3)(CH_2Cl)$ | $OCH_3$ | H |
| J-2 | $CH_3$ | Q-1 ($R_7$ = H, $R_8$ = H) | H | 5-$SOCH_3$ | $OCH_3$ | H |
| J-3 | $CH_3$ | Q-1 ($R_7$ = H, $R_8$ = H) | H | 3-$SO_2CH_3$ | $OCH_3$ | H |
| J-1 | $CH_3$ | Q-1 ($R_7$ = H, $R_8$ = H) | H | 5-$SO_2N(CH_3)_2$ | $OCH_3$ | H |
| J-2 | $CH_3$ | Q-1 ($R_7$ = H, $R_8$ = H) | H | 5-$CO_2CH_3$ | $OCH_3$ | H |
| J-3 | $CH_3$ | Q-1 ($R_7$ = H, $R_8$ = H) | H | 3-$CO_2CH_2CH_3$ | $OCH_3$ | H |
| J-4 | $CH_3$ | Q-1 ($R_7$ = H, $R_8$ = H) | H | 3-$CO_2CH_3$ | $OCH_3$ | H |
| J-1 | $CH_3$ | Q-1 ($R_7$ = H, $R_8$ = H) | H | 5-$CO_2CH_3$ | $OCH_3$ | H |
| J-2 | $CH_3$ | Q-1 ($R_7$ = H, $R_8$ = H) | H | 5-Cl | $OCH_3$ | H |
| J-3 | $CH_3$ | Q-1 ($R_7$ = H, $R_8$ = H) | H | 3-Br | $OCH_3$ | H |
| J-4 | $CH_3$ | Q-1 ($R_7$ = H, $R_8$ = H) | H | 3-F | $OCH_3$ | H |
| J-1 | $CH_3$ | Q-1 ($R_7$ = H, $R_8$ = H) | H | 5-I | $OCH_3$ | H |
| J-2 | $CH_3$ | Q-1 ($R_7$ = H, $R_8$ = H) | H | 5-$CH_3$ | $OCH_3$ | H |
| J-3 | $CH_3$ | Q-1 ($R_7$ = H, $R_8$ = H) | H | 3-$CF_3$ | $OCH_3$ | H |
| J-4 | $CH_3$ | Q-1 ($R_7$ = H, $R_8$ = H) | H | 3-$OCF_2H$ | $OCH_3$ | H |
| J-1 | $CH_3$ | Q-1 ($R_7$ = H, $R_8$ = H) | H | 5-$SO_2N(CH_3)_2$ | $OCH_3$ | H |
| J-2 | $CH_3$ | Q-1 ($R_7$ = H, $R_8$ = H) | H | 5-$SOCH_3$ | $OCH_3$ | H |
| J-3 | $CH_3$ | Q-1 ($R_7$ = H, $R_8$ = H) | H | 3-$SO_2CH(CH_3)_2$ | $OCH_3$ | H |
| J-4 | $CH_3$ | Q-1 ($R_7$ = H, $R_8$ = H) | H | 3-$CO_2CH_3$ | $OCH_3$ | H |
| J-1 | $CH_3$ | Q-1 ($R_7$ = H, $R_8$ = $CH_3$) | H | H | $OCH_3$ | H |

TABLE 5-continued

General Formula 5

| J | M | Q | R | $R_1$ | $X_1$ | $Y_2$ |
|---|---|---|---|---|---|---|
| J-2 | $CH_3$ | Q-1 ($R_7$ = H, $R_8$ = $CH_3$) | H | H | $OCH_3$ | $CH_3$ |
| J-3 | $CH_3$ | Q-1 ($R_7$ = H, $R_8$ = $CH_2CH_3$) | H | H | $CH_3$ | H |
| J-4 | $CH_3$ | Q-1 ($R_7$ = H, $R_8$ = $CH(CH_3)_2$) | H | H | $CH_3$ | $CH_3$ |
| J-1 | $CH_3$ | Q-1 ($R_7$ = H, $R_8$ = n-$C_4H_9$) | H | H | $OCF_2H$ | H |
| J-2 | $CH_3$ | Q-1 ($R_7$ = $CH_3$, $R_8$ = $CH_3$) | H | H | $OCH_3$ | H |
| J-4 | $CH_3$ | Q-37 ($R_7$ = H, $R_8$ = H, $R_2$ = H) | H | H | $OCH_3$ | H |
| J-1 | $CH_3$ | Q-37 ($R_7$ = H, $R_8$ = H, $R_2$ = i-$C_3H_7$) | H | H | $OCH_3$ | $CH_3$ |
| J-2 | $CH_3$ | Q-37 ($R_7$ = H, $R_8$ = H, $R_2$ = n-$C_4H_9$) | H | 5-$OCH_3$ | $OCF_2H$ | H |
| J-2 | $CH_3$ | Q-37 ($R_7$ = H, $R_8$ = H, $R_2$ = H) | H | $CH_3$ | $OCH_3$ | H |
| J-3 | $CO_2CH_3$ | Q-98 ($R_7$ = H, $R_8$ = H, $R_2$ = H) | H | H | $OCH_3$ | H |
| J-4 | $CH_3$ | Q-98 ($R_7$ = $CH_3$, $R_8$ = H, $R_9$ = H) | H | H | $OCH_3$ | H |
| J-1 | $CH_3$ | Q-98 ($R_7$ = H, $R_8$ = H, $R_9$ = i-$C_3H_7$) | H | 5-$OCH_3$ | OCHhd 3 | H |
| J-2 | $CH_3$ | Q-98 ($R_7$ = H, $R_8$ = H, $R_9$ = H) | H | $CH_3$ | $OCH_3$ | H |
| J-4 | $CH_3$ | Q-105 ($R_7$ = H, $R_8$ = H, $R_9$ = H, $R_2$ = H) | H | H | $OCH_3$ | H |
| J-1 | $CH_3$ | Q-105 ($R_7$ = $CH_3$, $R_8$ = H, $R_9$ = H, $R_2$ = $CH_3$) | H | H | $OCH_3$ | H |
| J-2 | $CH_3$ | Q-105 ($R_7$ = H, $R_8$ = $CH_3$, $R_9$ H, $R_2$ = $C_2H_5$) | H | 5-$OCH_3$ | $OCH_3$ | H |
| J-3 | $CH_3$ | Q-105 ($R_7$ = H, $R_8$ = $CH_3$, $R_9$ = H, $R_2$ = H) | H | $CH_3$ | $OCH_3$ | H |
| J-3 | $CH_3$ | Q-138 ($R_7$ = H, $R_8$ = H, $R_9$ = H) | H | H | $OCH_3$ | H |
| J-4 | $CH_3$ | Q-138 ($R_7$ = $CH_3$, $R_8$ = H, $R_9$ = H) | H | H | $OCH_3$ | H |
| J-1 | $CH_3$ | Q-138 ($R_7$ = H, $R_8$ = H, $R_9$ = $CH_3$) | H | H | $OCH_3$ | H |
| J-2 | $CH_3$ | Q-138 ($R_7$ = H, $R_8$ = H, $R_9$ = H) | H | $CH_3$ | $OCH_3$ | H |
| J-2 | $CH_3$ | Q-143 ($R_7$ = H, $R_8$ = H, $R_9$ = H, $R_3$ = $CH_3$) | H | H | $OCH_3$ | H |
| J-3 | $CH_3$ | Q-143 ($R_7$ = H, $R_8$ = H, $R_9$ = H, $R_3$ = H) | H | H | $OCH_3$ | $CH_3$ |
| J-4 | $CH_3$ | Q-143 ($R_7$ = $CH_3$, $R_8$ = H, $R_9$ = $CH_3$, $R_3$ = $CH_3$) | H | 3-Cl | $CH_3$ | H |
| J-1 | $CH_3$ | Q-143 ($R_7$ = H, $R_8$ = H, $R_9$ = H, $R_3$ = $CH_3$) | H | $CH_3$ | $OCH_3$ | H |

TABLE 6

General Formula 6

| J | M | Q | R | $R_1$ | $X_2$ | $Y_3$ |
|---|---|---|---|---|---|---|
| J-1 | $CH_3$ | Q-1 ($R_7$ = H, $R_8$ = H) | H | H | $CH_3$ | $CH_3$ |
| J-2 | $CH_2CH_3$ | Q-1 ($R_7$ = H, $R_8$ = H) | H | H | $OCH_3$ | $CH_3$ |
| J-3 | $CH_2CH_2CH_3$ | Q-1 ($R_7$ = H, $R_8$ = H) | H | H | $SCH_3$ | $CH_3$ |
| J-4 | $CH(CH_3)_2$ | Q-1 ($R_7$ = H, $R_8$ = H) | H | H | $CH_3$ | $CH_2CH_3$ |
| J-1 | $CH_2CH_2CH_2CH_3$ | Q-1 ($R_7$ = H, $R_8$ = H) | H | H | $OCH_3$ | $CH_2CH_3$ |
| J-2 | $C(CH_3)_3$ | Q-1 ($R_7$ = H, $R_8$ = H) | H | H | $SCH_3$ | $CH_2CH_3$ |
| J-3 | H | Q-1 ($R_7$ = H, $R_8$ = H) | H | H | $CH_3$ | $CH_2CF_3$ |
| J-4 | $CH_2CH{=}CH_2$ | Q-1 ($R_7$ = H, $R_8$ = H) | H | H | $OCH_3$ | $CH_2CF_3$ |
| J-1 | $CH_2CH{=}CHCH_3$ | Q-1 ($R_7$ = H, $R_8$ = H) | H | H | $SCH_3$ | $CH_2CF_3$ |
| J-2 | $C_6H_5$ | Q-1 ($R_7$ = H, $R_8$ = H) | $CH_3$ | 5-$OCH_3$ | $CH_3$ | $CH_3$ |
| J-3 | $C_6H_4$—4-Cl | Q-1 ($R_7$ = H, $R_8$ = H) | $CH_3$ | 3-$OCH_2CH_3$ | $OCH_3$ | $CH_3$ |
| J-4 | $C_6H_4$—3-$NO_2$ | Q-1 ($R_7$ = H, $R_8$ = H) | $CH_3$ | 3-$OCH(CH_3)_2$ | $SCH_3$ | $CH_3$ |
| J-1 | $C_6H_4$—3-$CH_3$ | Q-1 ($R_7$ = H, $R_8$ = H) | H | 5-$OCH_3$ | $OCH_3$ | $CH_3$ |
| J-2 | $C_6H_4$—2-$OCH_3$ | Q-1 ($R_7$ = H, $R_8$ = H) | H | 5-$OCH_2CH_3$ | $OCH_3$ | $CH_3$ |
| J-3 | $CO_2CH_3$ | Q-1 ($R_7$ = H, $R_8$ = H) | H | 3-$CH(CH_3)_2$ | $OCH_3$ | $CH_3$ |
| J-4 | $CO_2CH_2CH_3$ | Q-1 ($R_7$ = H, $R_8$ = H) | H | 3-$CF_2H$ | $OCH_3$ | $CH_3$ |
| J-1 | $SO_2CH_3$ | Q-1 ($R_7$ = H, $R_8$ = H) | H | 5-$CH_2CH_2Br$ | $OCH_3$ | $CH_3$ |
| J-2 | $SO_2N(CH_3)_2$ | Q-1 ($R_7$ = H, $R_8$ = H) | H | 5-$CH(CH_3)(CH_2Cl)$ | $OCH_3$ | $CH_3$ |
| J-3 | $CH_2C{\equiv}CH$ | Q-1 ($R_7$ = H, $R_8$ = H) | H | 3-$CH_2F$ | $OCH_3$ | $CH_3$ |
| J-4 | $CH_3$ | Q-1 ($R_7$ = H, $R_8$ = H) | H | 3-$CH_2CH_2Br$ | $OCH_3$ | $CH_3$ |
| J-1 | $CH_3$ | Q-1 ($R_7$ = H, $R_8$ = H) | H | 5-$CH(CH_3)(CH_2Cl)$ | $OCH_3$ | $CH_3$ |
| J-2 | $CH_3$ | Q-1 ($R_7$ = H, $R_8$ = H) | H | 5-$SCH_3$ | $OCH_3$ | $CH_3$ |
| J-3 | $CH_3$ | Q-1 ($R_7$ = H, $R_8$ = H) | H | 3-$SCH_2CH_3$ | $OCH_3$ | $CH_3$ |
| J-4 | $CH_3$ | Q-1 ($R_7$ = H, $R_8$ = H) | H | 3-$SCH(CH_3)_2$ | $OCH_3$ | $CH_3$ |
| J-1 | $CH_3$ | Q-1 ($R_7$ = H, $R_8$ = H) | H | 5-$SCH_2F$ | $OCH_3$ | $CH_3$ |
| J-2 | $CH_3$ | Q-1 ($R_7$ = H, $R_8$ = H) | H | 5-$SCH_2CH_2Br$ | $OCH_3$ | $CH_3$ |
| J-3 | $CH_3$ | Q-1 ($R_7$ = H, $R_8$ = H) | H | 3-$SCH(CH_3)(CH_2Cl)$ | $OCH_3$ | $CH_3$ |
| J-4 | $CH_3$ | Q-1 ($R_7$ = H, $R_8$ = H) | H | 3-$SOCH_3$ | $OCH_3$ | $CH_3$ |
| J-1 | $CH_3$ | Q-1 ($R_7$ = H, $R_8$ = H) | H | 5-$SO_2CH_3$ | $OCH_3$ | $CH_3$ |
| J-2 | $CH_3$ | Q-1 ($R_7$ = H, $R_8$ = H) | H | 5-$SO_2N(CH_3)_2$ | $OCH_3$ | $CH_3$ |
| J-3 | $CH_3$ | Q-1 ($R_7$ = H, $R_8$ = H) | H | 3-$CO_2CH_3$ | $OCH_3$ | $CH_3$ |
| J-1 | $CH_3$ | Q-1 ($R_7$ = H, $R_8$ = H) | H | 5-$CO_2CH_2CH_3$ | $OCH_3$ | $CH_3$ |
| J-2 | $CH_3$ | Q-1 ($R_7$ = H, $R_8$ = H) | H | 5-$CO_2CH_3$ | $OCH_3$ | $CH_3$ |
| J-3 | $CH_3$ | Q-1 ($R_7$ = H, $R_8$ = H) | H | 3-$CO_2CH_3$ | $OCH_3$ | $CH_3$ |
| J-4 | $CH_3$ | Q-1 ($R_7$ = H, $R_8$ = H) | H | 5-Cl | $OCH_3$ | $CH_3$ |
| J-1 | $CH_3$ | Q-1 ($R_7$ = H, $R_8$ = H) | H | 5-Br | $OCH_3$ | $CH_3$ |
| J-2 | $CH_3$ | Q-1 ($R_7$ = H, $R_8$ = H) | H | 5-F | $OCH_3$ | $CH_3$ |
| J-3 | $CH_3$ | Q-1 ($R_7$ = H, $R_8$ = H) | H | 3-I | $OCH_3$ | $CH_3$ |
| J-4 | $CH_3$ | Q-1 ($R_7$ = H, $R_8$ = H) | H | 3-$CH_3$ | $OCH_3$ | $CH_3$ |
| J-1 | $CH_3$ | Q-1 ($R_7$ = H, $R_8$ = H) | H | 5-$CF_3$ | $OCH_3$ | $CH_3$ |
| J-2 | $CH_3$ | Q-1 ($R_7$ = H, $R_8$ = H) | H | 5-$OCF_2H$ | $OCH_3$ | $CH_3$ |
| J-3 | $CH_3$ | Q-1 ($R_7$ = H, $R_8$ = H) | H | 3-$SO_2N(CH_3)_2$ | $OCH_3$ | $CH_3$ |
| J-4 | $CH_3$ | Q-1 ($R_7$ = H, $R_8$ = H) | H | 3-$SOCH_3$ | $OCH_3$ | $CH_3$ |
| J-1 | $CH_3$ | Q-1 ($R_7$ = H, $R_8$ = H) | H | 5-$SO_2CH(CH_3)_2$ | $OCH_3$ | $CH_3$ |
| J-2 | $CH_3$ | Q-1 ($R_7$ = H, $R_8$ = H) | H | 5-$CO_2CH_3$ | $OCH_3$ | $CH_3$ |
| J-3 | $CH_3$ | Q-1 ($R_7$ = H, $R_8$ = $CH_3$) | H | H | $OCH_3$ | $CH_3$ |
| J-4 | $CH_3$ | Q-1 ($R_7$ = H, $R_8$ = $CH_3$) | H | H | $CH_3$ | $CH_2CF_3$ |
| J-1 | $CH_3$ | Q-1 ($R_7$ = H, $R_8$ = $CH_2CH_3$) | H | H | $CH_3$ | $CH_3$ |

TABLE 6-continued

General Formula 6

| J | M | Q | R | $R_1$ | $X_2$ | $Y_3$ |
|---|---|---|---|---|---|---|
| J-2 | $CH_3$ | Q-1 ($R_7$ = H, $R_8$ = $CH(CH_3)_2$) | H | H | $OCH_3$ | $CH_3$ |
| J-3 | $CH_3$ | Q-1 ($R_7$ = H, $R_8$ = n-$C_4H_9$) | H | H | $SCH_3$ | $CH_3$ |
| J-4 | $CH_3$ | Q-1 ($R_7$ = $CH_3$, $R_8$ = $CH_3$) | H | H | $OCH_3$ | $CH_3$ |
| J-2 | $CH_3$ | Q-37 ($R_7$ = H, $R_8$ = H, $R_2$ = H) | H | H | $OCH_3$ | $CH_3$ |
| J-3 | $CH_3$ | Q-37 ($R_7$ = H, $R_8$ = H, $R_2$ = i-$C_3H_7$) | H | H | $OCH_3$ | $CH_3$ |
| J-4 | $CH_3$ | Q-37 ($R_7$ = H, $R_8$ = H, $R_2$ = n-$C_4H_9$) | H | 3-$OCH_3$ | $CH_3$ | $CH_2CF_3$ |
| J-1 | $CH_3$ | Q-37 ($R_7$ = H, $R_8$ = H, $R_2$ = H) | H | $CH_3$ | $CH_3$ | $CH_3$ |
| J-1 | $CH_3$ | Q-98 ($R_7$ = H, $R_8$ = H, $R_9$ = H) | H | H | $OCH_3$ | $CH_3$ |
| J-2 | $CH_3$ | Q-98 ($R_7$ = $CH_3$, $R_8$ = H, $R_9$ = H) | H | H | $OCH_3$ | $CH_3$ |
| J-3 | $CH_3$ | Q-98 ($R_7$ = H, $R_8$ = H, $R_9$ = i-$C_3H_7$) | H | 3-$OCH_3$ | $CH_3$ | $CH_2CF_3$ |
| J-3 | $CH_3$ | Q-98 ($R_7$ = H, $R_8$ = H, $R_9$ = H) | H | $CH_3$ | $OCH_3$ | $CH_3$ |
| J-2 | $CH_2CH_3$ | Q-105 ($R_7$ = H, $R_8$ = H, $R_9$ = H, $R_2$ = H) | H | H | $OCH_3$ | $CH_3$ |
| J-3 | $CH_3$ | Q-105 ($R_7$ = $CH_3$, $R_8$ = H, $R_9$ = H, $R_2$ = $CH_3$) | H | H | $OCH_3$ | $CH_3$ |
| J-4 | $CH_3$ | Q-105 ($R_7$ = H, $R_8$ = $CH_3$, $R_9$ = H, $R_2$ = $C_2H_5$) | H | 3-$OCH_3$ | $CH_3$ | $CH_2CF_3$ |
| J-1 | $CH_3$ | Q-105 ($R_7$ = H, $R_8$ = H, $R_9$ = H, $R_2$= H) | H | $CH_3$ | $OCH_3$ | $CH_3$ |
| J-1 | $CH_3$ | Q-138 ($R_7$ = H, $R_8$ = H, $R_9$ = H) | H | H | $OCH_3$ | $CH_3$ |
| J-2 | $CH_3$ | Q-138 ($R_7$ = $CH_3$, $R_8$ = H, $R_9$ =H) | H | H | $OCH_3$ | $CH_3$ |
| J-3 | $CH_3$ | Q-138 ($R_7$ = H, $R_8$ = H, $R_9$ = $CH_3$) | H | H | $OCH_3$ | $CH_3$ |
| J-3 | $CH_3$ | Q-138 ($R_7$ = H, $R_8$ = H, $R_9$ = H) | H | $CH_3$ | $OCH_3$ | $CH_3$ |
| J-4 | $CH_3$ | Q-143 ($R_7$ = H, $R_8$ = H, $R_9$ = H, $R_3$ = $CH_3$) | H | H | $OCH_3$ | $CH_3$ |
| J-1 | $CH_3$ | Q-143 ($R_7$ = H, $R_8$ = H, $R_9$ = H, $R_3$ = H) | H | H | $OCH_3$ | $CH_3$ |
| J-2 | $CH_3$ | Q-143 ($R_7$ = $CH_3$, $R_8$ = H, $R_9$ = $CH_3$, $R_3$ = $CH_3$) | H | 5-Cl | $CH_3$ | $CH_3$ |
| J-3 | $CH_3$ | Q-143 ($R_7$ = H, $R_8$ = H, $R_9$ = H, $R_3$ = $CH_3$) | H | $CH_3$ | $OCH_3$ | $CH_3$ |

TABLE 7

General Formula 7

| J | M | Q | R | $R_1$ | $X_3$ |
|---|---|---|---|---|---|
| J-1 | $CH_3$ | Q-1 ($R_7$ =H, $R_8$ = H) | H | H | $CH_3$ |
| J-2 | $CH_2CH_3$ | Q-1 ($R_7$ = H, $R_8$ = H) | H | H | $OCH_3$ |
| J-3 | $CH_2CH_2CH_3$ | Q-1 ($R_7$ = H, $R_8$ = H) | $CH_3$ | H | $OCH_3$ |
| J-4 | $CH(CH_3)_2$ | Q-1 ($R_7$ = H, $R_8$ = $CH_3$) | H | H | $CH_3$ |
| J-1 | $CH_2CH_2CH_2CH_3$ | Q-1 ($R_7$ = H, $R_8$ = H) | H | 5-$CH_3$ | $OCH_3$ |
| J-2 | $C(CH_3)_3$ | Q-1 ($R_7$ = H, $R_8$ = H) | H | 5-$SO_2N(CH_3)_2$ | $OCH_3$ |
| J-3 | $CH_3$ | Q-1 ($R_7$ = H, $R_8$ = H) | H | 3-$SOCH_3$ | $OCH_3$ |
| J-4 | $CH_3$ | Q-1 ($R_7$ = H, $R_8$ = H) | H | 3-$SO_2CH(CH_3)_2$ | $OCH_3$ |
| J-1 | $CH_3$ | Q-1 ($R_7$ = H, $R_8$ = H) | H | 5-$CO_2CH_3$ | $OCH_3$ |
| J-2 | $CH_3$ | Q-2 ($R_7$ = H, $R_8$ = H) | H | 5-$CH_2CH_3$ | $OCH_3$ |
| J-3 | $CH_3$ | Q-2 ($R_7$ = H, $R_8$ = H) | H | 3-$CH(CH_3)_2$ | $OCH_3$ |
| J-4 | H | Q-2 ($R_7$ = H, $R_8$ = H) | H | H | $OCH_3$ |
| J-1 | $CH_3$ | Q-3 ($R_7$ = H, $R_8$ = H) | H | 5-$OCH_3$ | $OCH_3$ |
| J-2 | $CH_3$ | Q-3 ($R_7$ = $C_2H_5$, $R_8$ = H) | H | 5-$OCH_2CH_3$ | $OCH_3$ |
| J-3 | $CH_2CH{=}CH_2$ | Q-3 ($R_7$ = $C_2H_5$, $R_8$ = H) | H | H | $OCH_3$ |
| J-4 | $CH_3$ | Q-4 ($R_3$ = $CH_3$, $R_7$ = H, $R_8$ = H) | H | 3-$OCH(CH_3)_2$ | $OCH_3$ |
| J-1 | $CH_2CH{=}CHCH_3$ | Q-4 ($R_3$ = $CH_3$, $R_7$ = H, $R_8$ = H) | H | H | $OCH_3$ |
| J-2 | $CH_3$ | Q-5 ($R_3$ = H, $R_7$ = H, $R_8$ = H) | H | 5-$OCF_2H$ | $OCH_3$ |
| J-3 | $C_6H_5$ | Q-5 ($R_3$ = H, $R_7$ = H, $R_8$ = H) | H | H | $OCH_3$ |
| J-4 | $CH_3$ | Q-7 ($R_7$ = H, $R_8$ = H, $R_9$ = H) | H | 3-$OCH_2CH_2Br$ | $OCH_3$ |
| J-1 | $C_6H_4$—4-Cl | Q-7 ($R_7$ = H, $R_8$ = H, $R_9$ = H) | H | H | $OCH_3$ |
| J-2 | $CH_3$ | Q-8 ($R_2$ = H, $R_7$ = H, $R_8$ = H) | H | 5-$OCH(CH_3)(CH_2Cl)$ | $OCH_3$ |
| J-3 | $C_6H_4$—3-$NO_2$ | Q-8 ($R_2$ = H, $R_7$ = H, $R_8$ = H) | H | H | $OCH_3$ |
| J-4 | $CH_3$ | Q-9 ($R_2$ = H, $R_7$ = H, $R_8$ = H) | H | 3-$CH_2F$ | $OCH_3$ |
| J-1 | $C_6H_4$—3-$CH_3$ | Q-9 ($R_2$ = H, $R_7$ = H, $R_8$ = H) | H | H | $OCH_3$ |
| J-2 | $CH_3$ | Q-11 ($R_7$ = H, $R_8$ = H) | H | 5-$CH_2CH_2Br$ | $OCH_3$ |
| J-3 | $C_6H_4$—2-$OCH_3$ | Q-11 ($R_7$ = H, $R_8$ = H) | H | H | $OCH_3$ |
| J-4 | $CH_3$ | Q-13 ($R_3$ = $CH_3$, $R_7$ = H, $R_8$ = H) | H | 3-$CH(CH_3)(CH_2Cl)$ | $OCH_3$ |
| J-1 | $CO_2CH_3$ | Q-13 ($R_3$ = $CH_3$, $R_7$ = H, $R_8$ = H) | H | H | $OCH_3$ |
| J-2 | $CH_3$ | Q-14 ($R_3$ = $CH_3$, $R_7$ = H, $R_8$ = H) | H | 5-$SCH_3$ | $OCH_3$ |
| J-3 | $CO_2CH_2CH_3$ | Q-14 ($R_3$ = $CH_3$, $R_7$ = H, $R_8$ = H) | H | H | $OCH_3$ |
| J-1 | $CH_3$ | Q-16 ($R_7$ = H, $R_8$ = H, $R_9$ = H) | H | 5-$SCH_2CH_3$ | $OCH_3$ |
| J-2 | $SO_2CH_3$ | Q-16 ($R_7$ = H, $R_8$ = H, $R_9$ = H) | H | H | $OCH_3$ |
| J-3 | $CH_3$ | Q-17 ($R_2$ = H, $R_7$ = H, $R_8$ = H) | H | 3-$SCH(CH_3)_2$ | $OCH_3$ |
| J-4 | $SO_2N(CH_3)_2$ | Q-17 ($R_2$ = H, $R_7$ = H, $R_8$ = H) | H | H | $OCH_3$ |
| J-1 | $CH_3$ | Q-18 ($R_2$ = H, $R_7$ = H, $R_8$ = H) | H | 5-$SCH_2F$ | $OCH_3$ |
| J-2 | $CH_2C{\equiv}CH$ | Q-18 ($R_2$ = H, $R_7$ = H, $R_8$ = H) | H | H | $OCH_3$ |
| J-3 | $CH_3$ | Q-29 ($R_7$ = H, $R_8$ = H) | H | 3-$SCH_2CH_2Br$ | $OCH_3$ |
| J-4 | $CH_3$ | Q-29 ($R_7$ = H, $R_8$ = H) | H | H | $OCH_3$ |
| J-1 | $CH_3$ | Q-30 ($R_7$ = H, $R_8$ = H) | H | 5-$SCH(CH_3)(CH_2Cl)$ | $OCH_3$ |
| J-2 | $CH_3$ | Q-30 ($R_7$ = H, $R_8$ = H) | H | H | $OCH_3$ |
| J-3 | $CH_3$ | Q-32 ($R_3$ = $CH_3$, ($R_7$ = H, $R_8$ = H) | H | 3-$SOCH_3$ | $OCH_3$ |
| J-4 | $CH_3$ | Q-32 ($R_3$ = $CH_3$, $R_7$ = H, $R_8$ = H) | H | H | $OCH_3$ |
| J-1 | $CH_3$ | Q-36 ($R_2$ = H, $R_7$ = H, $R_8$ = H) | H | 5-$SO_2CH_3$ | $OCH_3$ |
| J-2 | $CH_3$ | Q-36 ($R_2$ = H, $R_7$ = H, $R_8$ = H) | H | H | $OCH_3$ |
| J-3 | $CH_3$ | Q-51 ($R_7$ = H, $R_8$ = H, $R_9$ = H) | H | 3-$SO_2N(CH_3)_2$ | $OCH_3$ |
| J-4 | $CH_3$ | Q-51 ($R_7$ = H, $R_8$ = H, $R_9$ = H) | H | H | $OCH_3$ |
| J-1 | $CH_3$ | Q-52 ($R_7$ = H, $R_8$ = H, $R_9$ = H) | H | 5-$CO_2CH_3$ | $OCH_3$ |
| J-2 | $C_6H_5$ | Q-52 ($R_7$ = H, $R_8$ = H, $R_9$ = H) | H | H | $OCH_3$ |
| J-3 | $CH_3$ | Q-55 ($R_3$ = $CH_3$, $R_7$ = H, $R_8$ = H, $R_9$ = H) | H | 3-$CO_2CH_2CH_3$ | $OCH_3$ |

TABLE 7-continued

| | | General Formula 7 | | | |
|---|---|---|---|---|---|
| J | M | Q | R | $R_1$ | $X_3$ |
| J-4 | $CH_3$ | Q-55 ($R_3$ = $CH_3$, $R_7$ = H, $R_8$ = H, $R_9$ = H) | H | H | $OCH_3$ |
| J-1 | $CH_3$ | Q-59 ($R_7$ = H, $R_8$ = H, $R_9$ = H, $R_{10}$ = H) | H | 5-$CO_2CH_3$ | $OCH_3$ |
| J-2 | $CH_3$ | Q-59 ($R_7$ = H, $R_8$ = H, $R_9$ = H, $R_{10}$ = H) | H | H | $OCH_3$ |
| J-3 | $CH_3$ | Q-60 ($R_2$ = H, $R_7$ = H, $R_8$ = H, $R_9$ = H) | H | 3-$CO_2CH_3$ | $OCH_3$ |
| J-4 | $CH_3$ | Q-60 ($R_2$ = H, $R_7$ = H, $R_8$ = H, $R_9$ = H) | H | H | $OCH_3$ |
| J-1 | $CH_3$ | Q-69 ($R_3$ = $CH_3$, $R_7$ = H, $R_8$ = H, $R_9$ = H) | H | 5-Cl | $OCH_3$ |
| J-2 | $CH_3$ | Q-69 ($R_3$ = $CH_3$, $R_7$ = H, $R_8$ = H, $R_9$ = H) | H | H | $OCH_3$ |
| J-3 | $CH_3$ | Q-70 ($R_3$ = $CH_3$, $R_7$ = H, $R_8$ = H, $R_9$ = H) | H | 3-Br | $OCH_3$ |
| J-4 | $CH_3$ | Q-70 ($R_3$ = $CH_3$, $R_7$ = H, $R_8$ = H, $R_9$ = H) | H | H | $OCH_3$ |
| J-1 | $CH_3$ | Q-71 ($R_7$ = H, $R_8$ = H, $R_9$ = H, $R_{10}$ = H) | H | 5-F | $OCH_3$ |
| J-2 | $CH_3$ | Q-71 ($R_7$ = H, $R_8$ = H, $R_9$ = H, $R_{10}$ = H) | H | H | $OCH_3$ |
| J-3 | $CH_3$ | Q-72 ($R_2$ = H, $R_7$ = H, $R_8$ = H, $R_9$ = H) | H | 3-1 | $OCH_3$ |
| J-4 | $C(CH_3)_3$ | Q-72 ($R_2$ = H, $R_7$ = H, $R_8$ = H, $R_9$ = H) | H | H | $OCH_3$ |
| J-1 | $CH_3$ | Q-74 ($R_2$ = H, $R_7$ = H, $R_8$ = H, $R_9$ = H) | H | 5-$CH_3$ | $OCH_3$ |
| J-2 | $CH_3$ | Q-74 ($R_2$ = H, $R_7$ = H, $R_8$ = H, $R_9$ = H) | H | H | $OCH_3$ |
| J-3 | $CH_3$ | Q-95 ($R_7$ = H, $R_8$ = H, $R_9$ = H) | H | 3-$CF_3$ | $OCH_3$ |
| J-4 | $CH_3$ | Q-95 ($R_7$ = H, $R_8$ = H, $R_9$ = H) | H | H | $OCH_3$ |
| J-1 | $CH_3$ | Q-104 ($R_2$ = H, $R_7$ = H, $R_8$ = H, $R_9$ = H) | H | 5-$OCF_2H$ | $OCH_3$ |
| J-2 | $CH_3$ | Q-104 ($R_2$ = H, $R_7$ = H, $R_8$ = H, $R_9$ = H) | H | H | $OCH_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 8

| | Active | Weight Percent* | |
|---|---|---|---|
| | Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

In the following examples, all parts are by weight unless otherwise indicated.

EXAMPLE 3

| Wettable Powder | |
|---|---|
| N—[(4,6-dimethoxypyrimidin-2-yl)aminocarbonyl]-1-methyl-4-(tetrahydro-2-oxofuran-3-yl)-pyrazole-3-sulfonamide | 50% |
| sodium alkynaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

| Granule | |
|---|---|
| Wettable Powder of Example 3 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 5

| Extruded Pellet | |
|---|---|
| N—[(4 methoxy-6-methyltriazin-2-yl)aminocarbonyl]-1-methyl-4-tetrahydro-2-oxofuran-3-yl)pyrazole-3 sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

| Low Strength Granule | |
|---|---|
| N—[(4,6-dimethoxypyrimidin-2-yl)aminocarbonyl]-1-methyl-4-(tetrahydro-2-oxofuran-3-yl)-pyrazole-3-sulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 7

| Aqueous Suspension | |
|---|---|
| N—[(4-methoxy-6-methyltriazin-2-yl)aminocarbonyl]-1-methyl-4-tetrahydro-2-oxofuran-3-yl)pyrazole-3 sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 8

| Oil Suspension | |
|---|---|
| N—[(4,6-dimethoxypyrimidin-2-yl)aminocarbonyl]-1-methyl-4-(tetrahydro-2-oxofuran-3-yl)-pyrazole-3-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 9

| Granule | |
|---|---|
| N—[(4-methoxy-6-methyltriazin-2-yl)aminocarbonyl]-1-methyl-4-tetrahydro-2-oxofuran-3-yl)pyrazole-3 sulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 10

| High Strength Concentrate | |
|---|---|
| N—[(4,6-dimethoxypyrimidin-2-yl)aminocarbonyl]-1-methyl-4-(tetrahydro-2-oxofuran-3-yl)-pyrazole-3-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 11

| Wettable Powder | |
|---|---|
| N—[(4,6-dimethoxypyrimidin-2-yl)aminocarbonyl]-1-methyl-4-(tetrahydro-2-oxofuran-3-yl)-pyrazole-3-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 12

| Wettable Powder | |
|---|---|
| N—[(4-methoxy-6-methyltriazin-2-yl)aminocarbonyl]-1-methyl-4-tetrahydro-2-oxofuran-3-yl)pyrazole-3 sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 13

| Dust | |
|---|---|
| N—[(4,6-dimethoxypyrimidin-2-yl)aminocarbonyl]-1-methyl-4-(tetrahydro-2-oxofuran-3-yl)-pyrazole-3-sulfonamide | 10% |
| attapulgite | 10% |
| talc | 80% |

The active ingredient is blended with attapulgite and then passed through a hammer-mill to produce particles substantially all below 200 microns. The ground concentrate is then blended with powdered talc until homogeneous.

EXAMPLE 14

| | |
|---|---|
| N—[(4-methoxy-6-methyltriazin-2-yl)aminocarbonyl]-1-methyl-4-tetrahydro-2-oxofuran-3-yl)pyrazole-3 sulfonamide | 30% |
| dimethylformamide | 70% |

The ingredients are combined and stirred to produce a solution, which can be used for low volume applications.

Utility

Compounds of the present invention are highly active preemergent or postemergent herbicides or plant growth regulants. Many of them should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, some of the compounds may have utility for selective weed control, or may be useful to modify plant growth.

The rates of application for the compounds of the invention will be determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types. The herbicidal properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), cheatgrass (*Bromus secalinus*), velvetleaf (*Abutilon theophrasti*), morningglory (*Ipomoea* spp.), cocklebur (*Xanthium pensylvanicum*), sorghum, corn, soybean, sugarbeet, cotton, rice, wheat and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

COMPOUNDS

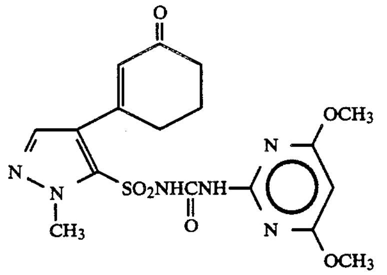

Compound 1

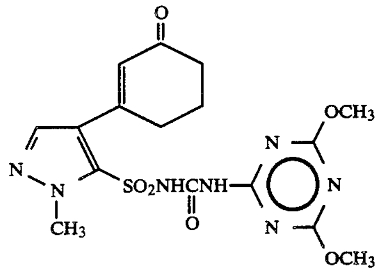

Compound 2

TABLE A

| | Cmpd. 1 | Cmpd. 2 | |
|---|---|---|---|
| Rate kg/ha | 0.05 | 0.4 | 0.05 |
| POST-EMERGENCE | | | |
| Morningglory | 5G | 0 | 0 |
| Cocklebur | 6H | 0 | 0 |
| Velvetleaf | 5G | 0 | 0 |
| Nutsedge | 4G | 0 | 0 |
| Crabgrass | 2G | 0 | 0 |
| Barnyardgrass | 2H | 0 | 0 |
| Cheatgrass | 2G | 0 | 0 |
| Wild Oats | 0 | 0 | 0 |
| Wheat | 0 | 0 | 0 |
| Corn | 8H | 0 | 0 |
| Soybean | 3C,7G | 0 | 0 |
| Rice | 5G | 0 | 0 |
| Sorghum | 3C,5G | 0 | 0 |
| Sugar beet | 3C,7G | 0 | 0 |
| Cotton | 2C,2H | 0 | 0 |
| PRE-EMERGENCE | | | |
| Rate kg/ha | 0.05 | 0.4 | 0.05 |
| Morningglory | 0 | 0 | 2G |
| Cocklebur | 5G | 0 | 0 |
| Velvetleaf | 0 | 0 | 0 |
| Nutsedge | 0 | 0 | 0 |

TABLE A-continued

| | Cmpd. 1 | | Cmpd. 2 | |
|---|---|---|---|---|
| Crabgrass | 2G | 0 | 0 | |
| Barnyardgrass | 2G | 0 | 0 | |
| Cheatgrass | 0 | 0 | 0 | |
| Wild Oats | 0 | 0 | 0 | |
| Wheat | 0 | 0 | 0 | |
| Corn | 2C,5G | 0 | 0 | |
| Soybean | 2C | 0 | 0 | |
| Rice | 2G | 0 | 0 | |
| Sorghum | 2C,5G | 0 | 0 | |
| Sugar beet | 2C,7G | 0 | 0 | |
| Cotton | 2G | 0 | 0 | |

What is claimed is:

1. A compound of the formula:

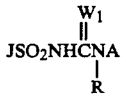

I wherein

J is 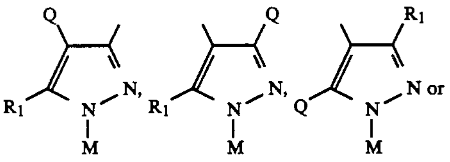

J-1 J-2 J-3

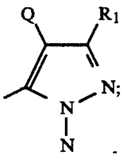

J-4

$W_1$ is O or S;

R is H or $CH_3$;

$R_1$ is H, $C_1$-$C_3$ alkyl, $C_1$-$C_3$ haloalkyl, halogen, nitro, $C_1$-$C_3$ alkoxy, $SO_2NR^IR^{II}$, $C_1$-$C_3$ alkylthio, $C_1$-$C_3$ alkylsulfinyl, amino, $C_1$-$C_3$ alkylsulfonyl, $CO_2R^{III}$, $C_1$-$C_3$ haloalkoxy, $C_1$-$C_3$ haloalkylthio, $CH_2CN$, $CH_2OCH_3$ or $CH_2SCH_3$;

$R^I$ is H, $C_1$-$C_4$ alkyl, $C_2$-$C_3$ cyanoalkyl, methoxy or ethoxy;

$R^{II}$ is H, $C_1$-$C_4$ alkyl or $C_3$-$C_4$ alkenyl; or $R^I$ and $R^{II}$ may be taken together as $-(CH_2)_3-$, $-(CH_2)_4-$, $-(CH_2)_5-$ or $-CH_2CH_2OCH_2CH_2-$;

$R^{III}$ is $C_1$-$C_4$ alkyl, $C_3$-$C_4$ alkenyl, $C_3$-$C_4$ alkynyl, $C_2$-$C_4$ haloalkyl, $C_2$—$C_3$ cyanoalkyl, $C_5$-$C_6$ cycloalkyl, $C_4$—$C_7$ cycloalkylalkyl or $C_2$-$C_4$ alkoxyalkyl;

M is H, $C_1$-$C_4$ alkyl, $C_3$-$C_4$ alkenyl, $C_3$-$C_4$ alkynyl, phenyl, phenyl substituted with Cl, $NO_2$, $CH_3$ or $OCH_3$, $C_2$-$C_3$ alkoxycarbonyl, $C_1$-$C_3$ alkylsulfonyl or $SO_2NR_4R_5$;

Q is 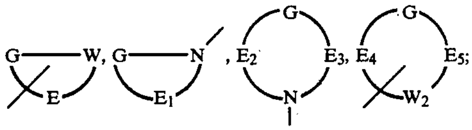

$Q_1$ $Q_2$ $Q_3$ $Q_4$

G is C=O or $SO_2$;

W is O, S, $CHR_2$ or $NR_3$;

$W_2$ is O, S, $SO_2$, $CHR_2$ or $NR_3$;

$R_2$ is H, $C_1$-$C_2$ alkyl, Cl, F or Br;

$R_3$ is H, $C_1$-$C_4$ alkyl, $C_1$-$C_4$ haloalkyl, $C_2$-$C_4$ alkoxyalkyl, $C_2$-$C_4$ cyanoalkyl, $C_3$-$C_4$ alkenyl or $C_3$-$C_4$ alkynyl;

E and $E_1$ are independently $C_3$-$C_4$ alkylene, $C_3$-$C_4$ alkenylene or $C_4$ alkenyldienyl;

$E_2$ and $E_4$ are independently $C_1$-$C_2$ alkylene or $C_2$ alkenylene;

$E_3$ and $E_5$ independently are $C_2$-$C_3$ alkylene or $C_2$-$C_3$ alkenylene; and E, $E_1$, $E_2$, $E_3$, $E_4$ and $E_5$ may optionally be substituted by 1-4 groups selected from $C_1$-$C_4$ alkyl, $C_1$-$C_4$ alkoxy, $C_1$-$C_4$ alkenyl, OH, halogen or $C_1$-$C_4$ haloalkoxy; further, when W is O, $CHR_2$ or $NR_3$, one of the carbon atoms of E may be in the form of a carbonyl group, and when $W_2$ is O, $CHR_2$ or $NR_3$, one of the carbon atoms of $E_4$ or $E_5$ may be in the form of a carbonyl group, provided that said carbonyl groups are not bonded directly to G;

A is 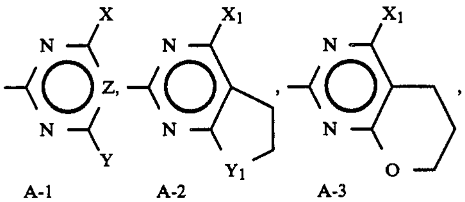

A-1 A-2 A-3

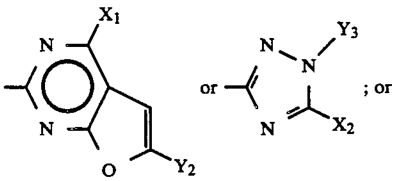

; or

A-4 A-5

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_3$-$C_5$ cycloalkyl, $C_2$-$C_4$ alkynyl, $C(O)R_6$,

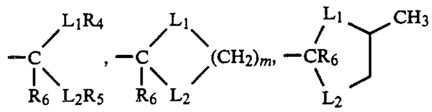

or $N(OCH_3)CH_3$;

m is 2 or 3;

$L_1$ and $L_2$ are independently O or S;

$R_4$ and $R_5$ are independently $C_1$-$C_2$ alkyl;

$R_6$ is H or $CH_3$;

Z is CH;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$; and $Y_3$ is $CH_3$, $CH_2Ch_3$ or $CH_2CF_3$;

and their agriculturally suitable salts; provided that a. when G is $SO_2$, then W is O, $CHR_2$ or $NR_3$;

b. when $E_2$ or $E_4$ is $C_2$ alkylene or $C_2$ alkenylene then $E_3$ or $E_5$ is $C_2$ alkylene or $C_2$ alkenylene;

c. when X is Cl, F, Br or I, then Y is $OCH_3$, $OC_2H_5$, $N(OCH_3)CH_3$, $NHCH_3$, $N(CH_3)_2$ or $OCF_2H$;

d. when M is other than H, alkyl, alkenyl, alkynyl or phenyl, optionally substituted, then $R_1$ is H, alkyl, haloalkyl or halogen;

e. when the total number of carbon atoms of X and Y is greater than four, then the number of carbons of $R_1$ is less than or equal to two and the number of carbons of Q is less than or equal to eight; and f. when $W_1$ is S, then R is H, A is A-1, and Y is $CH_3$, $OCH_3$, $OC_2H_5$, $CH_2OCh_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or 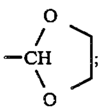;

2. Compounds of claim 1 wherein $W_1$ is O; and R is H.

3. Compounds of claim 2 wherein Q is as defined in claim 1; $R_1$ is H, Cl, Br, $CH_3$, or $OCF_2H$; M is $C_1$-$C_3$ alkyl; X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$; and Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH{=}CH_2$, $OCH_2C{\equiv}CH$, $CH_2OCH_2CH_3$.

4. Compounds of claim 3 wherein Q is $Q_1$.

5. Compounds of claim 3 wherein Q is $Q_2$.

6. Compounds of claim 3 wherein Q is $Q_3$.

7. Compounds of claim 3 wherein Q is $Q_4$.

8. Compounds of claim 3 where Q is

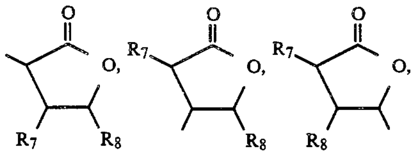

Q-1 Q-2 Q-3

-continued

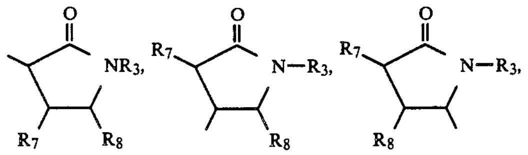

Q-4 Q-5 Q-6

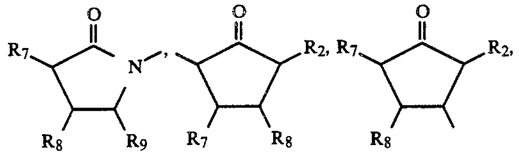

Q-7 Q-8 Q-9

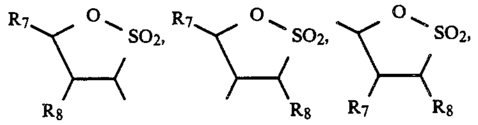

Q-10 Q-11 Q-12

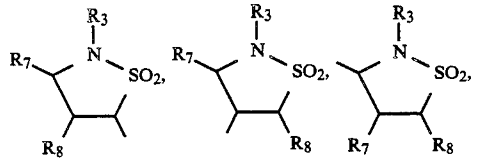

Q-13 Q-14 Q-15

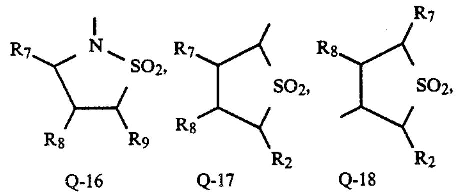

Q-16 Q-17 Q-18

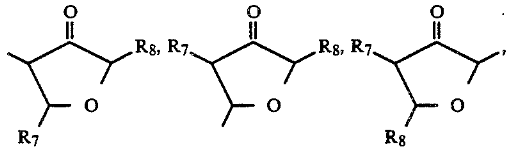

Q-19 Q-20 Q-21

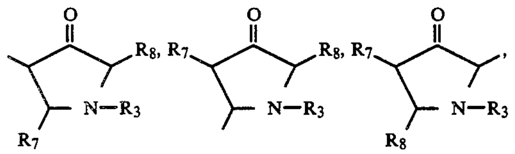

Q-22 Q-23 Q-24

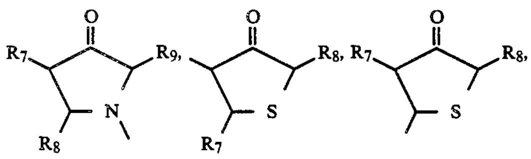

Q-25 Q-26 Q-27

-continued
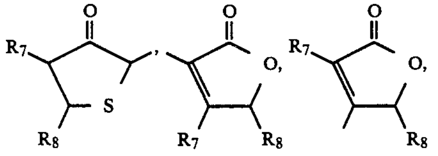
Q-28 Q-29 Q-30
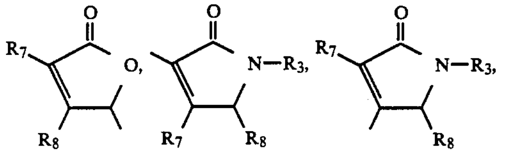
Q-31 Q-32 Q-33
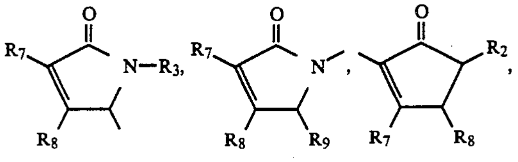
Q-34 Q-35 Q-36
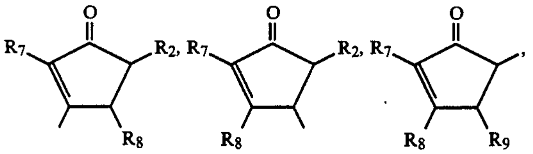
Q-37 Q-38 Q-39
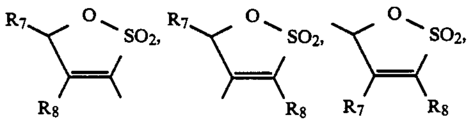
Q-40 Q-41 Q-42
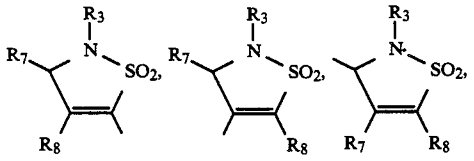
Q-43 Q-44 Q-45
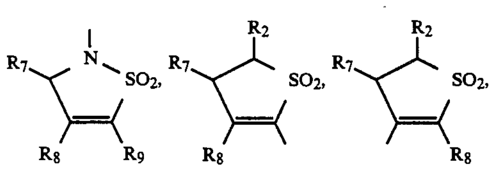
Q-46 Q-47 Q-48
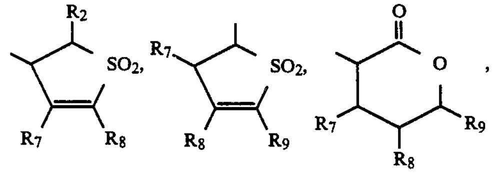
Q-49 Q-50 Q-51
-continued
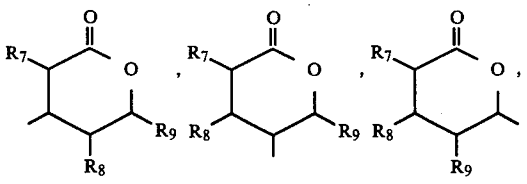
Q-52 Q-53 Q-54
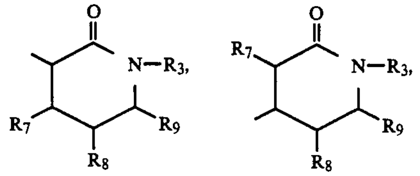
Q-55 Q-56
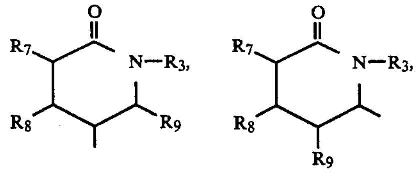
Q-57 Q-58
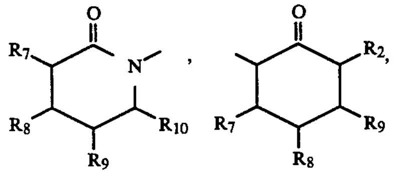
Q-59 Q-60
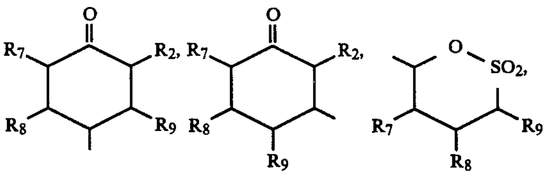
Q-61 Q-62 Q-63
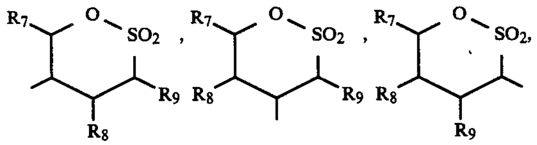
Q-64 Q-65 Q-66
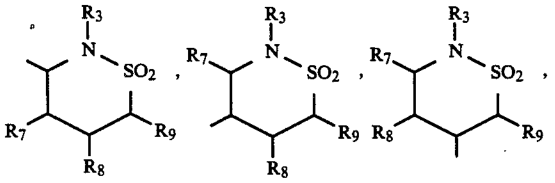
Q-67 Q-68 Q-69

-continued
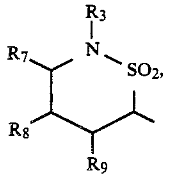
Q-70
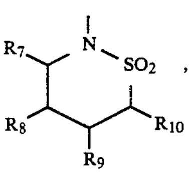
Q-71
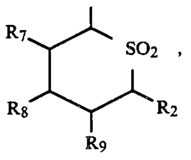
Q-72
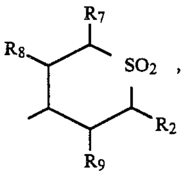
Q-73
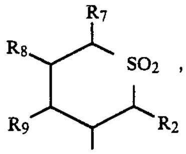
Q-74
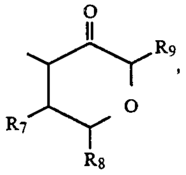
Q-75
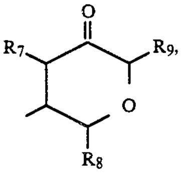
Q-76
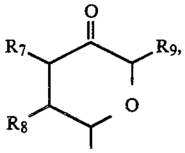
Q-77
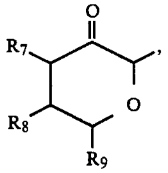
Q-78
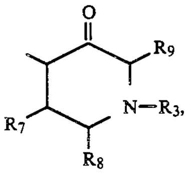
Q-79
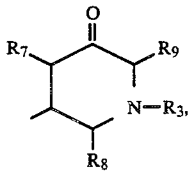
Q-80
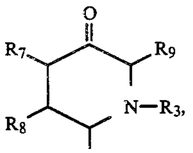
Q-81
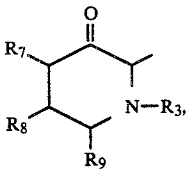
Q-82
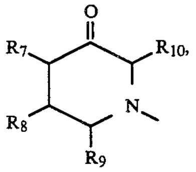
Q-83
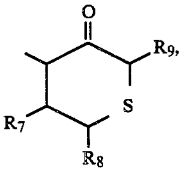
Q-84
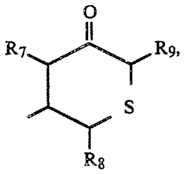
Q-85
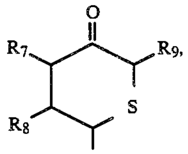
Q-86
-continued
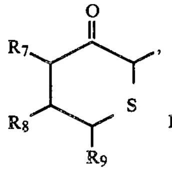
Q-87
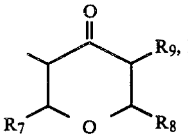
Q-88
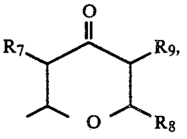
Q-89
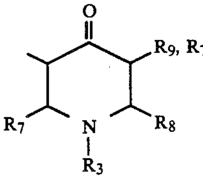
Q-90
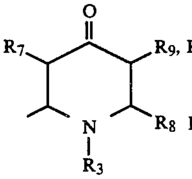
Q-91
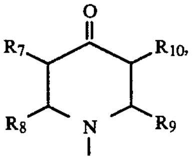
Q-92
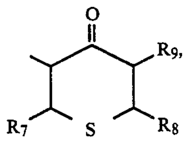
Q-93
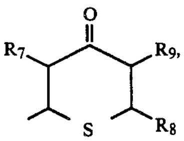
Q-94
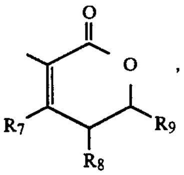
Q-95
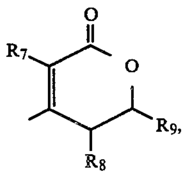
Q-96
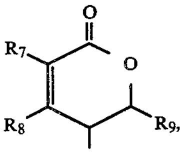
Q-97
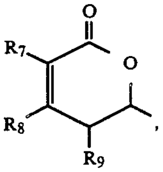
Q-98
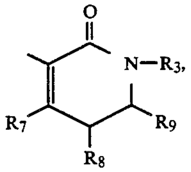
Q-99
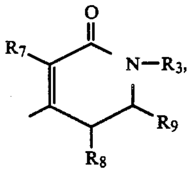
Q-100
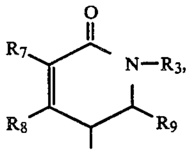
Q-101
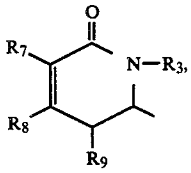
Q-102
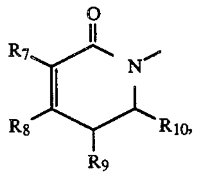
Q-103
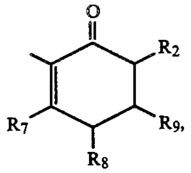
Q-104

-continued
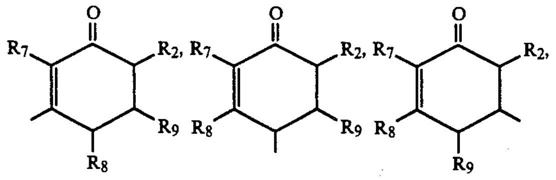
Q-105 Q-106 Q-107
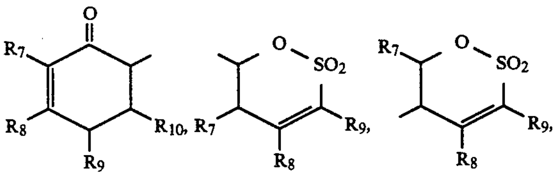
Q-108 Q-109 Q-110
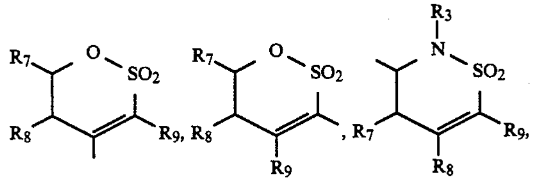
Q-111 Q-112 Q-113
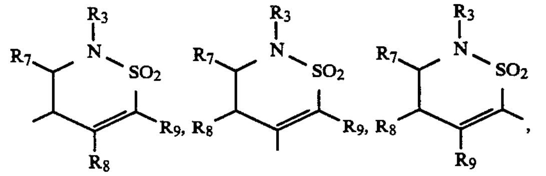
Q-114 Q-115 Q-116
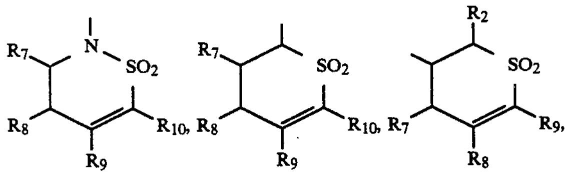
Q-117 Q-118 Q-119
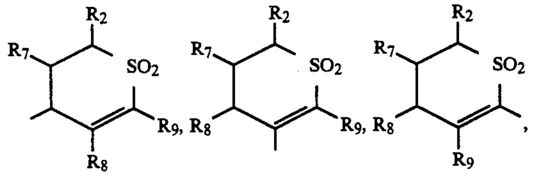
Q-120 Q-121 Q-122
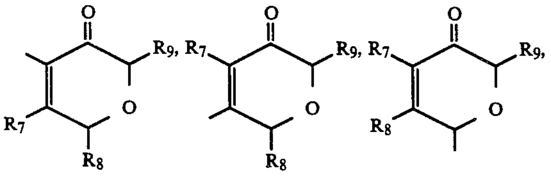
Q-123 Q-124 Q-125
-continued
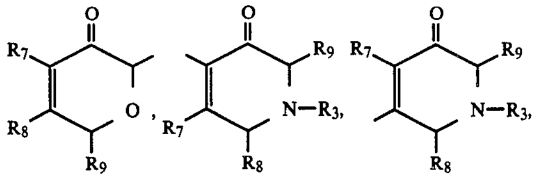
Q-126 Q-127 Q-128
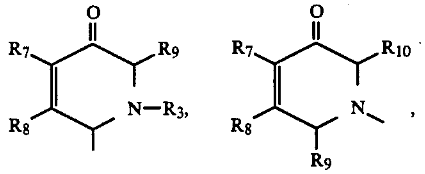
Q-129 Q-130
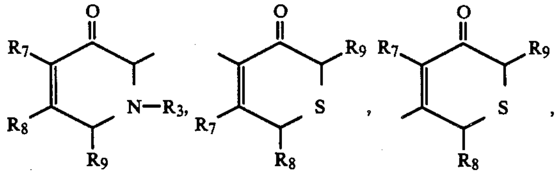
Q-131 Q-132 Q-133
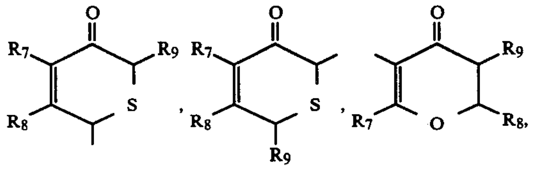
Q-134 Q-135 Q-136
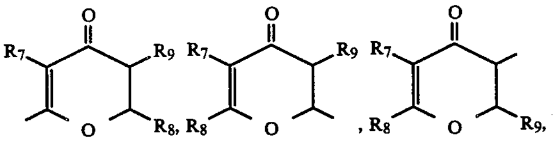
Q-137 Q-138 Q-139
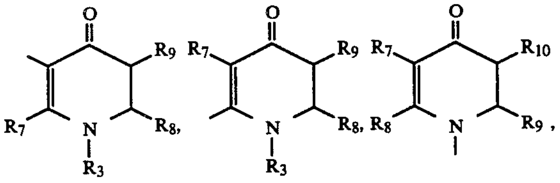
Q-140 Q-141 Q-142
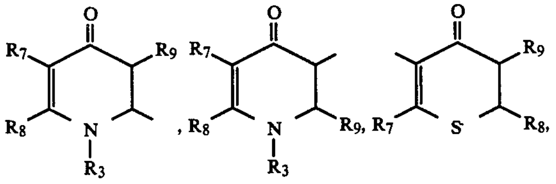
Q-143 Q-144 Q-145

-continued

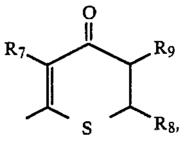
Q-146

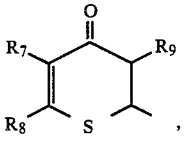
Q-147

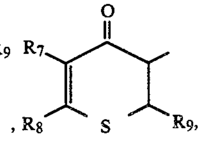
Q-148

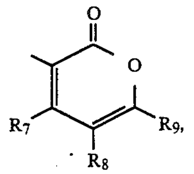
Q-149

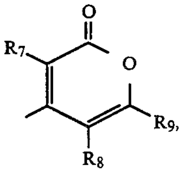
Q-150

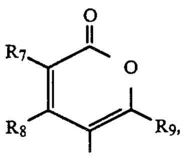
Q-151

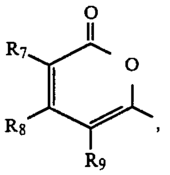
Q-152

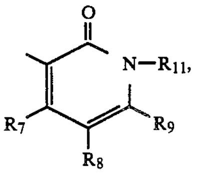
Q-153

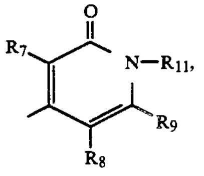
Q-154

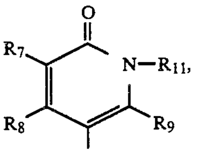
Q-155

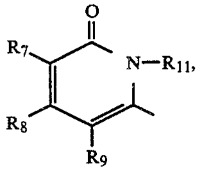
Q-156

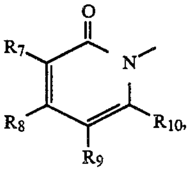
Q-157

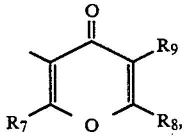
Q-158

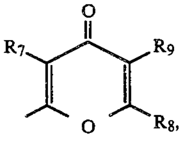
Q-159

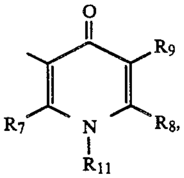
Q-160

-continued

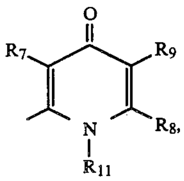
Q-161

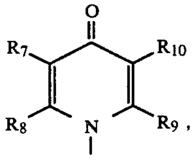
Q-162

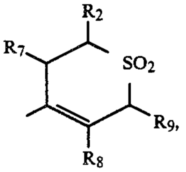
Q-163

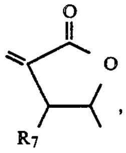
Q-164

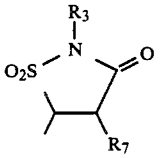
Q-165 or

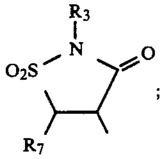
Q-166

;

$R_7$, $R_8$, $R_9$ and $R_{10}$ are independently H or $CH_3$; and $R_{11}$ is H, $CH_3$ or $CH_2CH_3$.

9. Compounds of claim 8 wherein $R_1$ is H, $CH_3$ or Cl; and Y is $CH_3$, $OCH_3$, $C_2H_5$, $OC_2H_5$, $CH_2OCH_3$, $NHCH_3$, $CH(OCH_3)_2$ or cyclopropyl.

10. Compounds of claim 9 wherein $R_2$ is H or $CH_3$; and $R_3$ is H, $CH_3$ or $C_2H_5$.

11. Compounds of claim 10 wherein A is A-1; and X is $CH_3$, $OCH_3$, Cl or $OCF_2H$.

12. Compounds of claim 11 wherein Q is Q-1, Q-2, Q-3 or Q-4.

13. Compounds of claim 11 wherein Q is Q-13, Q-14, Q-17, Q-18, Q-29, Q-37, Q-51, Q-60 or Q-105.

14. A compound of claim 1 which is N-[(4,6-dimethoxypyrimidin-2-yl)aminocarbonyl]-1-methyl-4-(tetrahydro-2-oxofuran-3-yl)pyrazole-3-sulfonamide.

15. A compound of claim 1 which is N-[(4-methoxy-6-methyltriazin-2-yl)aminocarbonyl]-1-methyl-4-(tetrahydro-2-oxofuran-3-yl)pyrazole-3-sulfonamide.

16. A compound of claim 1 which is N-[(4,6-dimethoxypyrimidin-2-yl)aminocarbonyl]-1-methyl-4-(3-oxo-1-cyclohexenyl)-1H-pyrazole-5-sulfonamide.

17. A composition suitable for controlling the growth of undesired vegetation which comprises an effective amount of a compound of claim 1 and at least one of the following: surfactant, solid or liquid diluent.

18. A composition suitable for controlling the growth of undesired vegetation which comprises an effective amount of a compound of claim 2 and at least one of the following: surfactant, solid or liquid diluent.

19. A composition suitable for controlling the growth of undesired vegetation which comprises an effective amount of a compound of claim 3 and at least one of the following: surfactant, solid or liquid diluent.

20. A composition suitable for controlling the growth of undesired vegetation which comprises an effective amount of a compound of claim 4 and at least one of the following: surfactant, solid or liquid diluent.

21. A composition suitable for controlling the growth of undesired vegetation which comprises an effective amount of a compound of claim 5 and at least one of the following: surfactant, solid or liquid diluent.

22. A composition suitable for controlling the growth of undesired vegetation which comprises an effective amount of a compound of claim 6 and at least one of the following: surfactant, solid or liquid diluent.

23. A composition suitable for controlling the growth of undesired vegetation which comprises an effective amount of a compound of claim 7 and at least one of the following: surfactant, solid or liquid diluent.

24. A composition suitable for controlling the growth of undesired vegetation which comprises an effective amount of the compound of claim 8 and at least one of the following: surfactant, solid or liquid diluent.

25. A composition suitable for controlling the growth of undesired vegetation which comprises an effective amount of a compound of claim 9 and at least one of the following: surfactant, solid or liquid diluent.

26. A composition suitable for controlling the growth of undesired vegetation which comprises an effective amount of a compound of claim 10 and at least one of the following: surfactant, solid or liquid diluent.

27. A composition suitable for controlling the growth of undesired vegetation which comprises an effective amount of a compound of claim 11 and at least one of the following: surfactant, solid or liquid diluent.

28. A composition suitable for controlling the growth of undesired vegetation which comprises an effective amount of a compound of claim 12 and at least one of the following: surfactant, solid or liquid diluent.

29. A composition suitable for controlling the growth of undesired vegetation which comprises an effective amount of a compound of claim 13 and at least one of the following: surfactant, solid or liquid diluent.

30. A composition suitable for controlling the growth of undesired vegetation which comprises an effective amount of a compound of claim 14 and at least one of the following: surfactant, solid or liquid diluent.

31. A composition suitable for controlling the growth of undesired vegetation which comprises an effective amount of a compound of claim 15 and at least one of the following: surfactant, solid or liquid diluent.

32. A composition suitable for controlling the growth of undesired vegetation which comprises an effective amount of a compound of claim 16 and at least one of the following: surfactant, solid or liquid diluent.

33. A method for controlling the growth of undesired vegetation which comprises applying to the locus to be protected an effective amount of a compound of claim 1.

34. A method for controlling the growth of undesired vegetation which comprises applying to the locus to be protected an effective amount of a compound of claim 2.

35. A method for controlling the growth of undesired vegetation which comprises applying to the locus to be protected an effective amount of a compound of claim 3.

36. A method for controlling the growth of undesired vegetation which comprises applying to the locus to be protected an effective amount of a compound of claim 4.

37. A method for controlling the growth of undesired vegetation which comprises applying to the locus to be protected an effective amount of a compound of claim 5.

38. A method for controlling the growth of undesired vegetation which comprises applying to the locus to be protected an effective amount of a compound of claim 6.

39. A method for controlling the growth of undesired vegetation which comprises applying to the locus to be protected an effective amount of a compound of claim 7.

40. A method for controlling the growth of undesired vegetation which comprises applying to the locus to be protected an effective amount of the compound of claim 8.

41. A method for controlling the growth of undesired vegetation which comprises applying to the locus to be protected an effective amount of a compound of claim 9.

42. A method for controlling the growth of undesired vegetation which comprises applying to the locus to be protected an effective amount of a compound of claim 10.

43. A method for controlling the growth of undesired vegetation which comprises applying to the locus to be protected an effective amount of a compound of claim 11.

44. A method for controlling the growth of undesired vegetation which comprises applying to the locus to be protected an effective amount of a compound of claim 12.

45. A method for controlling the growth of undesired vegetation which comprises applying to the locus to be protected an effective amount of a compound of claim 13.

46. A method for controlling the growth of undesired vegetation which comprises applying to the locus to be protected an effective amount of a compound of claim 14.

47. A method for controlling the growth of undesired vegetation which comprises applying to the locus to be protected an effective amount of the compound of claim 15.

48. A method for controlling the growth of undesired vegetation which comprises applying to the locus to be protected an effective amount of a compound of claim 16.

* * * * *

UNITED STATES PATENT AND TRADEMARK OFFICE

CERTIFICATE OF CORRECTION

PATENT NO. : 4,655,817

DATED : April 7, 1987

INVENTOR(S) : Mark Ewell Thompson

It is certified that error appears in the above-identified patent and that said Letters Patent is hereby corrected as shown below:

In Claim 1, lines 35 through 44, col. 177:

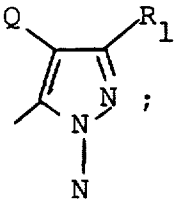 ; should be 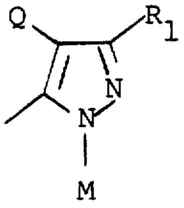 ;

J-4 J-4

In Claim 1, line 14, col. 178:

"$R_2$ is H, $C_1$-$c_2$ alkyl, Cl, F or Br;" should read "$R_2$ is H, $C_1$-$C_2$ alkyl, Cl, F or Br;".

In Claim 1, line 18, col. 179:

"$Y_3$ is $CH_3$, $CH_2Ch_3$ or $CH_2CF_3$;" should read "$Y_3$ is $CH_3$, $CH_2CH_3$ or $CH_2CF_3$;".

UNITED STATES PATENT AND TRADEMARK OFFICE
CERTIFICATE OF CORRECTION

PATENT NO. : 4,655,817

DATED : April 7, 1987

INVENTOR(S) : Mark Ewell Thompson

It is certified that error appears in the above-identified patent and that said Letters Patent is hereby corrected as shown below:

In Claim 1, line 35, col. 179:

"$OCH_3$, $OC_2H_5$, $CH_2OCh_3$, $C_2H_5$, $CF_3$, $SCH_3$," should read

"$OCH_3$, $OC_2H_5$, $CH_2OCH_3$, $C_2H_5$, $CF_3$, $SCH_3$,".

Signed and Sealed this

Fourteenth Day of June, 1988

Attest:

DONALD J. QUIGG

*Attesting Officer* *Commissioner of Patents and Trademarks*

UNITED STATES PATENT AND TRADEMARK OFFICE
CERTIFICATE OF CORRECTION

PATENT NO. : 4,655,817

DATED : April 7, 1987

INVENTOR(S) : Mark Ewell Thompson

It is certified that error appears in the above-identified patent and that said Letters Patent is hereby corrected as shown below:

In Claim 3, line 53, col. 179, add the following after "$CH_2OCH_2CH_3$":

$OCH_2CH_2OCH_3$, $CH_2SCH_3$, $C(O)R_6$, 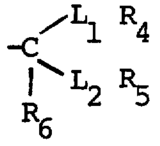 , 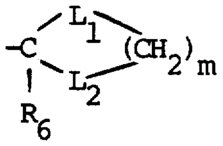 ,

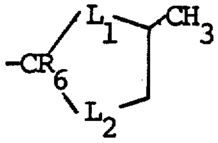 , $OCF_2H$, $SCF_2H$, cyclopropyl, $C{\equiv}CH$ or $C{\equiv}CCH_3$.

Signed and Sealed this

Thirty-first Day of January, 1989

Attest:

DONALD J. QUIGG

*Attesting Officer*

*Commissioner of Patents and Trademarks*